United States Patent
Zhang et al.

(10) Patent No.: US 11,414,661 B2
(45) Date of Patent: Aug. 16, 2022

(54) NUCLEIC ACID, COMPOSITION AND CONJUGATE CONTAINING NUCLEIC ACID, PREPARATION METHOD THEREFOR AND USE THEREOF

(71) Applicant: SUZHOU RIBO LIFE SCIENCE CO., LTD., Suzhou (CN)

(72) Inventors: Hongyan Zhang, Suzhou (CN); Shan Gao, Suzhou (CN); Daiwu Kang, Suzhou (CN); Lina Kong, Suzhou (CN)

(73) Assignee: SUZHOU RIBO LIFE SCIENCE CO., LTD., Jiangsu (CN)

( * ) Notice: Subject to any disclaimer, the term of this patent is extended or adjusted under 35 U.S.C. 154(b) by 0 days.

(21) Appl. No.: 16/764,307

(22) PCT Filed: Nov. 29, 2018

(86) PCT No.: PCT/CN2018/118191
§ 371 (c)(1),
(2) Date: May 14, 2020

(87) PCT Pub. No.: WO2019/105414
PCT Pub. Date: Jun. 6, 2019

(65) Prior Publication Data
US 2021/0032623 A1 Feb. 4, 2021

(30) Foreign Application Priority Data

Dec. 1, 2017 (CN) .......................... 201711249356.9
Dec. 29, 2017 (CN) .......................... 201711482915.0

(51) Int. Cl.
*C12N 15/113* (2010.01)
*A61P 3/06* (2006.01)

(52) U.S. Cl.
CPC .............. *C12N 15/113* (2013.01); *A61P 3/06* (2018.01); *C12N 2310/14* (2013.01)

(58) Field of Classification Search
None
See application file for complete search history.

(56) References Cited

U.S. PATENT DOCUMENTS

| | | |
|---|---|---|
| 8,344,125 B2 | 1/2013 | Manoharan et al. |
| 10,130,651 B2 | 11/2018 | Wooddell et al. |
| 10,246,708 B2 | 4/2019 | Kasperkovitz et al. |
| 2005/0246794 A1 | 11/2005 | Khvorova et al. |
| 2013/0005793 A1 | 1/2013 | Chin et al. |
| 2013/0023579 A1 | 1/2013 | Crooke et al. |
| 2013/0158021 A1 | 6/2013 | Dong et al. |
| 2014/0179768 A1 | 6/2014 | Bettencourt et al. |
| 2014/0194489 A1 | 7/2014 | Bumcrot et al. |
| 2015/0191726 A1 | 7/2015 | Manoharan et al. |
| 2015/0247143 A1 | 9/2015 | Fitzgerald et al. |
| 2015/0315584 A1 | 11/2015 | MacDonald et al. |
| 2015/0315594 A1 | 11/2015 | Prakash et al. |
| 2016/0017335 A1 | 1/2016 | Borodovsky et al. |
| 2016/0186180 A1 | 6/2016 | Bettencourt et al. |
| 2017/0000815 A1 | 1/2017 | Fitzgerald et al. |
| 2018/0087054 A1 | 3/2018 | Querbes et al. |
| 2018/0216114 A1 | 8/2018 | Fitzgerald et al. |
| 2018/0245077 A1 | 8/2018 | Chiu et al. |
| 2019/0062749 A1 | 2/2019 | Zhang |
| 2019/0202855 A1 | 7/2019 | Sakamuri et al. |
| 2019/0255091 A1 | 8/2019 | Li et al. |
| 2019/0292547 A1 | 9/2019 | Li et al. |

FOREIGN PATENT DOCUMENTS

| | | |
|---|---|---|
| AU | 2014208251 A1 | 8/2014 |
| CA | 2930393 A1 | 6/2009 |
| CN | 102083983 A | 4/2011 |
| CN | 102753186 A | 10/2012 |
| CN | 102140461 B | 12/2012 |
| CN | 102140458 B | 5/2013 |
| CN | 103380113 A | 10/2013 |
| CN | 105378082 A | 3/2014 |
| CN | 106146591 A | 11/2016 |
| CN | 106255755 A | 12/2016 |
| CN | 108220293 A | 6/2018 |

(Continued)

OTHER PUBLICATIONS

International Search Report (PCT/ISA/210) dated Mar. 6, 2019, by the State Intellectual Property Office of the P.R. China as the International Searching Authority for International Application No. PCT/CN2018/118191, and an English translation of the International Search Report.
Written Opinion (PCT/ISA/237) dated Mar. 6, 2019, by the State Intellectual Property Office of the P.R. China as the International Searching Authority for International Application No. PCT/CN2018/118191.
Wooddell et al.,"Hepatocyte-targeted RNAi Therapeutics for the Treatment of Chronic Hepatitis B Virus Infection" The American Society of Gene & Cell Therapy, 2013, doi:10.1038/mt.2013.31. (13 pages).
Rajeev et al., "Hepatocyte-Specific Delivery of siRNAs Conjugated to Novel Non-nucleosidic Trivalent N-Acetylgalactosamine Elicits Robust Gene Silencing in Vivo" ChemBioChem, 2015, vol. 16, pp. 903-908.

(Continued)

*Primary Examiner* — Brian Whiteman
(74) *Attorney, Agent, or Firm* — Buchanan Ingersoll & Rooney PC

(57) ABSTRACT

Provided are a siRNA for inhibiting the expression of an angiopoietin-like protein 3 (ANGPTL3) gene, and a pharmaceutical composition and a conjugate comprising the siRNA; wherein each nucleotide in the siRNA is independently a modified or unmodified nucleotide, and the siRNA comprises a sense strand and an antisense strand; the sense strand comprises a nucleotide sequence A, the nucleotide sequence A having the same length as the nucleotide sequence as represented by SEQ ID NO:1 with no more than 3 nucleotide differences; the antisense strand comprises a nucleotide sequence B, the nucleotide sequence B having the same length as the nucleotide sequence as represented by SEQ ID NO:2 with no more than 3 nucleotide differences.

28 Claims, 18 Drawing Sheets
Specification includes a Sequence Listing.

(56) References Cited

FOREIGN PATENT DOCUMENTS

| | | |
|---|---|---|
| EP | 2669377 A2 | 12/2013 |
| EP | 2990410 A1 | 3/2016 |
| EP | 3 315 608 A1 | 5/2016 |
| EP | 3312281 A2 | 4/2018 |
| EP | 3315608 A1 | 5/2018 |
| WO | 2009/073809 A2 | 6/2009 |
| WO | 2009/082607 A2 | 7/2009 |
| WO | 2010/012244 A1 | 2/2010 |
| WO | 2010/101951 A1 | 9/2010 |
| WO | 2011/085271 A2 | 7/2011 |
| WO | 2011/139702 A2 | 11/2011 |
| WO | 2012/024170 A2 | 2/2012 |
| WO | 2012/037254 A1 | 3/2012 |
| WO | 2012/068176 A1 | 5/2012 |
| WO | 2012/083185 A2 | 6/2012 |
| WO | 2012/177784 A2 | 12/2012 |
| WO | 2014/025805 A1 | 2/2014 |
| WO | 2014/089313 A1 | 6/2014 |
| WO | 2014/179626 A2 | 11/2014 |
| WO | 2014/179629 A2 | 11/2014 |
| WO | 2015/006740 A2 | 1/2015 |
| WO | 2015/100394 A1 | 7/2015 |
| WO | 2015/168532 A2 | 11/2015 |
| WO | 2015/188197 A2 | 12/2015 |
| WO | 2016/077321 A1 | 5/2016 |
| WO | 2016/081444 A1 | 5/2016 |
| WO | 2016/149331 A2 | 9/2016 |
| WO | 2016154127 A2 | 9/2016 |
| WO | 2016/168286 A1 | 10/2016 |
| WO | 2016/179342 A2 | 11/2016 |
| WO | 2016/206626 A1 | 12/2016 |
| WO | 2017/035340 A1 | 3/2017 |
| WO | 2017/120397 A1 | 7/2017 |
| WO | 2018/027106 A2 | 2/2018 |
| WO | 2018/140920 A1 | 8/2018 |
| WO | 2020/093053 A1 | 5/2020 |

OTHER PUBLICATIONS

Matsuda et al., "siRNA Conjugates Carrying Sequentially Assembled Trivalent N-Acetylgalactosamine Linked Through Nucleosides Elicit Robust Gene Silencing In Vivo in Hepatocytes", ACS Chemical Biology, 2015, DOI: 10.1021/cb501028c. (7 pages).

Nair et al., "Multivalent N-Acetylgalactosamine-Conjugated siRNA Localizes in Hepatocytes and Elicits Robust RNAi-Mediated Gene Silencing", Journal of the American Chemical Society, 2014, vol. 136, pp. 16958-16961.

Khvorova et al., "The chemical evolution of oligonucleotide therapies of clinical utility", Nature Biotechnology Advance Online Publication, Feb. 27, 2017; doi:10.1038/nbt.3765, (11 pages).

Love et al., "Lipid-like materials for low-dose, in vivo gene silencing", Proceedings of the National Academy of Sciences, Feb. 2, 2010, vol. 107, No. 5, pp. 1864-1869. (7 pages).

Dong et al., "Lipopeptide nanoparticles for potent and selective siRNA delivery in rodents and nonhuman primates", Proceedings of the National Academy of Sciences, Feb. 2014, www.pnas.org/cgi/doi/10.1073/pnas.1322937111 (6 pages).

Beaucage et al. "Advances in the Synthesis of Oligonucleotides by the Phosphoramidite Approach", Tetrahedron, 1992, vol. 48, No. 12, pp. 2223-2311.

Greene et al., "Protection for the Hydroxyl Group, Including 1,2- and 1,3-DIOLS", Protective Groups in Organic Synthesis, Third Edition, 1999 John Wiley & Sons, Inc. pp. 17-245, (229 pages).

Ui-Tei et al., "Functional dissection of siRNA sequence by systematic DNA substitution: modified siRNA with a DNA seed arm is a powerful tool for mammalian gene silencing with significantly reduced off-target effect", Nucleic Acids Rearch, 2008, vol. 36, No. 7, pp. 2136-2151.

Watts et al., "Chemically modified siRNA: tools and applications", Drug Discovery Today, Oct. 2008, vol. 13, Nos. 19/20, pp. 842-855.

Extended European Search Report dated Sep. 16, 2021, by the European Patent Office in corresponding European Patent Application No. 18883803.1. (10 pages).

Berthold et al., "Cellular Delivery and Antisense Effects of Peptide Nucleic Acid Conjugated to Polyethyleneimine via Disulfide Linkers," Bioconjugate Chemistry, 2010, vol. 21, No. 10, pp. 1933-1938.

Dai et al., "A vital role for Angptl3 in the PAN-induced podocyte loss by affecting detachment and apoptosis in vitro," BMC Nephrology, Biomed Central, London, GB, 2015, vol. 16, No. 1, p. 38. (10 pages).

Norata et al., "Gene silencing approaches for the management of dyslipidaemia," Trends in Pharmacological Sciences, Apr. 2013, vol. 34, No. 4, pp. 198-205. (8 pages).

Pessentheiner et al., "ANGPTL3 targeting: The power of versatile lipid-lowering," Atherosclerosis, Jan. 2018, vol. 268, pp. 185-187.

Xu et al., "Role of angiopoietin-like 3 (ANGPTL3) in regulating plasma level of low-density lipoprotein cholesterol," Atherosclerosis, 2018, vol. 268, pp. 196-206.

SEQUENCE LISTING

```
<160> NUMBER OF SEQ ID NOS: 64

<210> SEQ ID NO 1
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z, Z is A

<400> SEQUENCE: 1
```
ccaagagcac caagaacun                                                19

<210> SEQ ID NO 2
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z', Z'is U

<400> SEQUENCE: 2
naguucuugg ugcucuugg                                                19

<210> SEQ ID NO 3
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is ZA, ZA is A, U, G or C

<400> SEQUENCE: 3
ccaagagcac caagaacun                                                19

<210> SEQ ID NO 4
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z'B, Z'B is a nucleotide complementary to
      ZA, ZA is selected from A, U, G or C

<400> SEQUENCE: 4
naguucuugg ugcucuugg                                                19

<210> SEQ ID NO 5
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z'B, Z'B is a nucleotide complementary to
      ZA, ZA is selected from A, U, G or C

<400> SEQUENCE: 5
naguucuugg ugcucuuggc u                                             21

<210> SEQ ID NO 6
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (21)..(21)

```
<223> OTHER INFORMATION: n is ZA, ZA is selected from A, U, G or C

<400> SEQUENCE: 6
agccaagagc accaagaacu n                                              21

<210> SEQ ID NO 7
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z'B, Z'B is a nucleotide complementary to
      ZA, ZA is selected from A, U, G or C

<400> SEQUENCE: 7
naguucuugg ugcucuuggc uug                                            23

<210> SEQ ID NO 8
<211> LENGTH: 19
<212> TYPE: RNA
<213> ORGANISM: Artificial Sequence
<220> FEATURE:
<223> OTHER INFORMATION: siRNA

<400> SEQUENCE: 8
ccaagagcac caagaacua                                                 19

<210> SEQ ID NO 9
<211> LENGTH: 21
<212> TYPE: RNA
<213> ORGANISM: Artificial Sequence
<220> FEATURE:
<223> OTHER INFORMATION: siRNA

<400> SEQUENCE: 9
uaguucuugg ugcucuuggc u                                              21

<210> SEQ ID NO 10
<211> LENGTH: 21
<212> TYPE: RNA
<213> ORGANISM: Artificial Sequence
<220> FEATURE:
<223> OTHER INFORMATION: siRNA

<400> SEQUENCE: 10
agccaagagc accaagaacu a                                              21

<210> SEQ ID NO 11
<211> LENGTH: 23
<212> TYPE: RNA
<213> ORGANISM: Artificial Sequence
<220> FEATURE:
<223> OTHER INFORMATION: siRNA

<400> SEQUENCE: 11
uaguucuugg ugcucuuggc uug                                            23

<210> SEQ ID NO 12
<211> LENGTH: 19
<212> TYPE: RNA
<213> ORGANISM: Artificial Sequence
<220> FEATURE:
<223> OTHER INFORMATION: siRNA
```

-continued

```
<400> SEQUENCE: 12
ccaagagcac caagaacua                                              19

<210> SEQ ID NO 13
<211> LENGTH: 21
<212> TYPE: RNA
<213> ORGANISM: Artificial Sequence
<220> FEATURE:
<223> OTHER INFORMATION: siRNA

<400> SEQUENCE: 13
uaguucuugg ugcucuuggc u                                           21

<210> SEQ ID NO 14
<211> LENGTH: 21
<212> TYPE: RNA
<213> ORGANISM: Artificial Sequence
<220> FEATURE:
<223> OTHER INFORMATION: siRNA

<400> SEQUENCE: 14
agccaagagc accaagaacu a                                           21

<210> SEQ ID NO 15
<211> LENGTH: 23
<212> TYPE: RNA
<213> ORGANISM: Artificial Sequence
<220> FEATURE:
<223> OTHER INFORMATION: siRNA

<400> SEQUENCE: 15
uaguucuugg ugcucuuggc uug                                         23

<210> SEQ ID NO 16
<211> LENGTH: 21
<212> TYPE: RNA
<213> ORGANISM: Artificial Sequence
<220> FEATURE:
<223> OTHER INFORMATION: siRNA

<400> SEQUENCE: 16
uaguucuugg ugcucuuggc u                                           21

<210> SEQ ID NO 17
<211> LENGTH: 23
<212> TYPE: RNA
<213> ORGANISM: Artificial Sequence
<220> FEATURE:
<223> OTHER INFORMATION: siRNA

<400> SEQUENCE: 17
uaguucuugg ugcucuuggc uug                                         23

<210> SEQ ID NO 18
<211> LENGTH: 19
<212> TYPE: RNA
<213> ORGANISM: Artificial Sequence
<220> FEATURE:
<223> OTHER INFORMATION: siRNA

<400> SEQUENCE: 18
ccaagagcac caagaacua                                              19

<210> SEQ ID NO 19
<211> LENGTH: 21
```

<210> SEQ ID NO 19
<211> LENGTH: 21
<212> TYPE: RNA
<213> ORGANISM: Artificial Sequence
<220> FEATURE:
<223> OTHER INFORMATION: siRNA

<400> SEQUENCE: 19
agccaagagc accaagaacu a        21

<210> SEQ ID NO 20
<211> LENGTH: 19
<212> TYPE: RNA
<213> ORGANISM: Artificial Sequence
<220> FEATURE:
<223> OTHER INFORMATION: siRNA

<400> SEQUENCE: 20
ccaagagcac caagaacua        19

<210> SEQ ID NO 21
<211> LENGTH: 21
<212> TYPE: RNA
<213> ORGANISM: Artificial Sequence
<220> FEATURE:
<223> OTHER INFORMATION: siRNA

<400> SEQUENCE: 21
uaguucuugg ugcucuuggc u        21

<210> SEQ ID NO 22
<211> LENGTH: 21
<212> TYPE: RNA
<213> ORGANISM: Artificial Sequence
<220> FEATURE:
<223> OTHER INFORMATION: siRNA

<400> SEQUENCE: 22
agccaagagc accaagaacu a        21

<210> SEQ ID NO 23
<211> LENGTH: 23
<212> TYPE: RNA
<213> ORGANISM: Artificial Sequence
<220> FEATURE:
<223> OTHER INFORMATION: siRNA

<400> SEQUENCE: 23
uaguucuugg ugcucuuggc uug        23

<210> SEQ ID NO 24
<211> LENGTH: 21
<212> TYPE: RNA
<213> ORGANISM: Artificial Sequence
<220> FEATURE:
<223> OTHER INFORMATION: siRNA

<400> SEQUENCE: 24
uaguucuugg ugcucuuggc u        21

<210> SEQ ID NO 25
<211> LENGTH: 23
<212> TYPE: RNA
<213> ORGANISM: Artificial Sequence
<220> FEATURE:
<223> OTHER INFORMATION: siRNA

<400> SEQUENCE: 25
uaguucuugg ugcucuuggc uug    23

<210> SEQ ID NO 26
<211> LENGTH: 19
<212> TYPE: RNA
<213> ORGANISM: Artificial Sequence
<220> FEATURE:
<223> OTHER INFORMATION: siRNA

<400> SEQUENCE: 26
ccaagagcac caagaacua    19

<210> SEQ ID NO 27
<211> LENGTH: 21
<212> TYPE: RNA
<213> ORGANISM: Artificial Sequence
<220> FEATURE:
<223> OTHER INFORMATION: siRNA

<400> SEQUENCE: 27
agccaagagc accaagaacu a    21

<210> SEQ ID NO 28
<211> LENGTH: 21
<212> TYPE: RNA
<213> ORGANISM: Artificial Sequence
<220> FEATURE:
<223> OTHER INFORMATION: siRNA

<400> SEQUENCE: 28
uaguucuugg ugcucuuggc u    21

<210> SEQ ID NO 29
<211> LENGTH: 23
<212> TYPE: RNA
<213> ORGANISM: Artificial Sequence
<220> FEATURE:
<223> OTHER INFORMATION: siRNA

<400> SEQUENCE: 29
uaguucuugg ugcucuuggc uug    23

<210> SEQ ID NO 30
<211> LENGTH: 21
<212> TYPE: RNA
<213> ORGANISM: Artificial Sequence
<220> FEATURE:
<223> OTHER INFORMATION: siRNA

<400> SEQUENCE: 30
uaguucuugg ugcucuuggc u    21

<210> SEQ ID NO 31
<211> LENGTH: 23
<212> TYPE: RNA
<213> ORGANISM: Artificial Sequence
<220> FEATURE:
<223> OTHER INFORMATION: siRNA

<400> SEQUENCE: 31
uaguucuugg ugcucuuggc uug    23

<210> SEQ ID NO 32
<211> LENGTH: 21
<212> TYPE: RNA
<213> ORGANISM: Artificial Sequence

```
<220> FEATURE:
<223> OTHER INFORMATION: siRNA

<400> SEQUENCE: 32
uaguucuugg ugcucuuggc u                                              21

<210> SEQ ID NO 33
<211> LENGTH: 23
<212> TYPE: RNA
<213> ORGANISM: Artificial Sequence
<220> FEATURE:
<223> OTHER INFORMATION: siRNA

<400> SEQUENCE: 33
uaguucuugg ugcucuuggc uug                                            23

<210> SEQ ID NO 34
<211> LENGTH: 21
<212> TYPE: RNA
<213> ORGANISM: Artificial Sequence
<220> FEATURE:
<223> OTHER INFORMATION: siRNA

<400> SEQUENCE: 34
uaguucuugg ugcucuuggc u                                              21

<210> SEQ ID NO 35
<211> LENGTH: 23
<212> TYPE: RNA
<213> ORGANISM: Artificial Sequence
<220> FEATURE:
<223> OTHER INFORMATION: siRNA

<400> SEQUENCE: 35
uaguucuugg ugcucuuggc uug                                            23

<210> SEQ ID NO 36
<211> LENGTH: 21
<212> TYPE: RNA
<213> ORGANISM: Artificial Sequence
<220> FEATURE:
<223> OTHER INFORMATION: siRNA

<400> SEQUENCE: 36
uaguucuugg ugcucuuggc u                                              21

<210> SEQ ID NO 37
<211> LENGTH: 21
<212> TYPE: RNA
<213> ORGANISM: Artificial Sequence
<220> FEATURE:
<223> OTHER INFORMATION: siRNA

<400> SEQUENCE: 37
uaguucuugg ugcucuuggc u                                              21

<210> SEQ ID NO 38
<211> LENGTH: 21
<212> TYPE: RNA
<213> ORGANISM: Artificial Sequence
<220> FEATURE:
<223> OTHER INFORMATION: siRNA

<400> SEQUENCE: 38
uaguucuugg ugcucuuggc u                                              21
```

```
<210> SEQ ID NO 39
<211> LENGTH: 21
<212> TYPE: RNA
<213> ORGANISM: Artificial Sequence
<220> FEATURE:
<223> OTHER INFORMATION: siRNA

<400> SEQUENCE: 39
uaguucuugg ugcucuuggc u                                              21

<210> SEQ ID NO 40
<211> LENGTH: 21
<212> TYPE: RNA
<213> ORGANISM: Artificial Sequence
<220> FEATURE:
<223> OTHER INFORMATION: siRNA

<400> SEQUENCE: 40
uaguucuugg ugcucuuggc u                                              21

<210> SEQ ID NO 41
<211> LENGTH: 21
<212> TYPE: RNA
<213> ORGANISM: Artificial Sequence
<220> FEATURE:
<223> OTHER INFORMATION: siRNA

<400> SEQUENCE: 41
uaguucuugg ugcucuuggc u                                              21

<210> SEQ ID NO 42
<211> LENGTH: 21
<212> TYPE: RNA
<213> ORGANISM: Artificial Sequence
<220> FEATURE:
<223> OTHER INFORMATION: siRNA

<400> SEQUENCE: 42
uaguucuugg ugcucuuggc u                                              21

<210> SEQ ID NO 43
<211> LENGTH: 23
<212> TYPE: RNA
<213> ORGANISM: Artificial Sequence
<220> FEATURE:
<223> OTHER INFORMATION: siRNA

<400> SEQUENCE: 43
uaguucuugg ugcucuuggc uug                                            23

<210> SEQ ID NO 44
<211> LENGTH: 23
<212> TYPE: RNA
<213> ORGANISM: Artificial Sequence
<220> FEATURE:
<223> OTHER INFORMATION: siRNA

<400> SEQUENCE: 44
uaguucuugg ugcucuuggc uug                                            23

<210> SEQ ID NO 45
<211> LENGTH: 23
<212> TYPE: RNA
<213> ORGANISM: Artificial Sequence
<220> FEATURE:
<223> OTHER INFORMATION: siRNA
```

```
<400> SEQUENCE: 45
uaguucuugg ugcucuuggc uug                                            23

<210> SEQ ID NO 46
<211> LENGTH: 21
<212> TYPE: RNA
<213> ORGANISM: Artificial Sequence
<220> FEATURE:
<223> OTHER INFORMATION: siRNA

<400> SEQUENCE: 46
uaguucuugg ugcucuuggc u                                              21

<210> SEQ ID NO 47
<211> LENGTH: 21
<212> TYPE: RNA
<213> ORGANISM: Artificial Sequence
<220> FEATURE:
<223> OTHER INFORMATION: siRNA

<400> SEQUENCE: 47
agccaagagc accaagaacu a                                              21

<210> SEQ ID NO 48
<211> LENGTH: 23
<212> TYPE: RNA
<213> ORGANISM: Artificial Sequence
<220> FEATURE:
<223> OTHER INFORMATION: siRNA

<400> SEQUENCE: 48
uaguucuugg ugcucuuggc uug                                            23

<210> SEQ ID NO 49
<211> LENGTH: 19
<212> TYPE: RNA
<213> ORGANISM: Artificial Sequence
<220> FEATURE:
<223> OTHER INFORMATION: siRNA

<400> SEQUENCE: 49
ccuugaggca uacuucaaa                                                 19

<210> SEQ ID NO 50
<211> LENGTH: 21
<212> TYPE: RNA
<213> ORGANISM: Artificial Sequence
<220> FEATURE:
<223> OTHER INFORMATION: siRNA

<400> SEQUENCE: 50
uuugaaguau gccucaaggu u                                              21

<210> SEQ ID NO 51
<211> LENGTH: 21
<212> TYPE: RNA
<213> ORGANISM: Artificial Sequence
<220> FEATURE:
<223> OTHER INFORMATION: siRNA

<400> SEQUENCE: 51
acauauuuga ucagucuuuu u                                              21

<210> SEQ ID NO 52
```

```
<211> LENGTH: 23
<212> TYPE: RNA
<213> ORGANISM: Artificial Sequence
<220> FEATURE:
<223> OTHER INFORMATION: siRNA

<400> SEQUENCE: 52
aaaaagacug aucaaauaug uug                                               23

<210> SEQ ID NO 53
<211> LENGTH: 18
<212> TYPE: DNA
<213> ORGANISM: Artificial Sequence
<220> FEATURE:
<223> OTHER INFORMATION: primer

<400> SEQUENCE: 53
accaactata cgctacat                                                     18

<210> SEQ ID NO 54
<211> LENGTH: 18
<212> TYPE: DNA
<213> ORGANISM: Artificial Sequence
<220> FEATURE:
<223> OTHER INFORMATION: primer

<400> SEQUENCE: 54
cctcctgaat aaccctct                                                     18

<210> SEQ ID NO 55
<211> LENGTH: 19
<212> TYPE: DNA
<213> ORGANISM: Artificial Sequence
<220> FEATURE:
<223> OTHER INFORMATION: primer

<400> SEQUENCE: 55
ggtcggagtc aacggattt                                                    19

<210> SEQ ID NO 56
<211> LENGTH: 19
<212> TYPE: DNA
<213> ORGANISM: Artificial Sequence
<220> FEATURE:
<223> OTHER INFORMATION: primer

<400> SEQUENCE: 56
ccagcatcgc cccacttga                                                    19

<210> SEQ ID NO 57
<211> LENGTH: 23
<212> TYPE: DNA
<213> ORGANISM: Artificial Sequence
<220> FEATURE:
<223> OTHER INFORMATION: primer

<400> SEQUENCE: 57
gaggagcagc taaccaactt aat                                               23

<210> SEQ ID NO 58
<211> LENGTH: 23
<212> TYPE: DNA
<213> ORGANISM: Artificial Sequence
<220> FEATURE:
<223> OTHER INFORMATION: primer

<400> SEQUENCE: 58
```

-continued

```
tctgcatgtg ctgttgactt aat                                          23
```

<210> SEQ ID NO 59
<211> LENGTH: 24
<212> TYPE: DNA
<213> ORGANISM: Artificial Sequence
<220> FEATURE:
<223> OTHER INFORMATION: primer

<400> SEQUENCE: 59

```
aactttggca ttgtggaagg gctc                                         24
```

<210> SEQ ID NO 60
<211> LENGTH: 24
<212> TYPE: DNA
<213> ORGANISM: Artificial Sequence
<220> FEATURE:
<223> OTHER INFORMATION: primer

<400> SEQUENCE: 60

```
tggaagagtg ggagttgctg ttga                                         24
```

<210> SEQ ID NO 61
<211> LENGTH: 20
<212> TYPE: DNA
<213> ORGANISM: Artificial Sequence
<220> FEATURE:
<223> OTHER INFORMATION: primer

<400> SEQUENCE: 61

```
ctggtggtgg catgatgagt                                              20
```

<210> SEQ ID NO 62
<211> LENGTH: 21
<212> TYPE: DNA
<213> ORGANISM: Artificial Sequence
<220> FEATURE:
<223> OTHER INFORMATION: primer

<400> SEQUENCE: 62

```
ctcttctccg ctctggctta g                                            21
```

<210> SEQ ID NO 63
<211> LENGTH: 20
<212> TYPE: DNA
<213> ORGANISM: Artificial Sequence
<220> FEATURE:
<223> OTHER INFORMATION: primer

<400> SEQUENCE: 63

```
gggagccaaa agggtcatca                                              20
```

<210> SEQ ID NO 64
<211> LENGTH: 20
<212> TYPE: DNA
<213> ORGANISM: Artificial Sequence
<220> FEATURE:
<223> OTHER INFORMATION: primer

<400> SEQUENCE: 64

```
cgtggactgt ggtcatgagt                                              20
```

NUCLEIC ACID, COMPOSITION AND CONJUGATE CONTAINING NUCLEIC ACID, PREPARATION METHOD THEREFOR AND USE THEREOF

SEQUENCE LISTING

Incorporated by reference herein in its entirety is a computer-readable sequence listing submitted via EFS-Web and identified as follows: One (12305 byte ASCII (Text)) file named "16764307 amended sequence listing.txt" created on Oct. 19, 2020.

BACKGROUND ART

Dyslipidemia (hyperlipidemia) refers to a systemic disease involving a higher plasma lipid content than normal value, which is caused by abnormal metabolism and transportation of fat, and severely threatens the health of patients worldwide. The currently available medicines for treating dyslipidemia include mainly statins, cholesterol absorption inhibitor, resins, probucol, fibrates and niacins and derivatives thereof.

Angiopoietin-like protein 3 (ANGPTL3) is a secretory protein mainly expressed in liver, and is named for its genetic structure similar to angiopoietin. Existing studies prove that dyslipidemia is related to the high expression amount of ANGPTL3. ANGPTL3 regulates lipid metabolism by binding to fat tissues and inhibiting the activity of lipoprotein lipase. Low expression of ANGPTL3 could delay atherosclerosis caused by dyslipidemia. Thus, silencing gene expression at genetic level to block the production of ANGPTL3 is undoubtedly the most idealist treatment manner. Based on the mechanism of RNA interference (RNAi), small interfering RNA (siRNA) could inhibits or blocks the expression of any target gene of interest by means of sequence specificity, so as to treat diseases.

Stabilization modification of siRNA and the delivery system thereof are two crucial technologies in the development of siRNA medicines.

SUMMARY OF THE INVENTION

In some embodiments, the present disclosure provides a siRNA capable of inhibiting the expression of ANGPTL3 gene, wherein the siRNA comprises a sense strand and an antisense strand, wherein each nucleotide in the siRNA is independently a modified or unmodified nucleotide, wherein the sense strand comprises a nucleotide sequence I and the antisense strand comprises a nucleotide sequence II, wherein the nucleotide sequence I and the nucleotide sequence II are at least partly reverse complementary to form a double-stranded region, wherein the nucleotide sequence I comprises a nucleotide sequence A, which has the same length as the nucleotide sequence represented by SEQ ID NO: 1 with no more than 3 nucleotide differences, and the nucleotide sequence II comprises a nucleotide sequence B, which has the same length as the nucleotide sequence represented by SEQ ID NO:2 with no more than 3 nucleotide differences:

```
                                        (SEQ ID NO: 1)
    5'-CCAAGAGCACCAAGAACUZ-3';

(SEQ ID NO: 2)
    5'-Z'AGUUCUUGGUGCUCUUGG-3',
``` wherein, Z is A and Z' is U;

the nucleotide sequence A comprises a nucleotide $Z_A$ at the corresponding position of Z, the nucleotide sequence B comprises a nucleotide $Z'_B$ which is at the corresponding position of Z', wherein $Z'_B$ is the first nucleotide at the 5' terminal of the antisense strand.

In some embodiments, the present disclosure provides a pharmaceutical composition, which comprises the siRNA of the present disclosure and a pharmaceutically acceptable carrier.

In some embodiments, the present disclosure provides a siRNA conjugate, which comprises the siRNA of the present disclosure and a conjugating group conjugated to the siRNA.

In some embodiments, the present disclosure provides use of the siRNA and/or the pharmaceutical composition and/or the siRNA conjugate of the present disclosure in the manufacture of a medicament for treating and/or preventing dyslipidemia caused by abnormal expression of the ANGPTL3 gene.

In some embodiments, the present disclosure provides a method for treating and/or preventing dyslipidemia, which method comprises administering an effective amount of the siRNA and/or the pharmaceutical composition and/or the siRNA conjugate of the present disclosure to a subject suffering from dyslipidemia.

In some embodiments, the present disclosure provides a method for inhibiting the expression of ANGPTL3 gene in liver cells, which method comprises contacting an effective amount of the siRNA and/or the pharmaceutical composition and/or the siRNA conjugate of the present disclosure with the liver cells.

In some embodiments, the present disclosure provides a kit, which comprises the siRNA and/or the pharmaceutical composition and/or the siRNA conjugate of the present disclosure.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BENEFICIAL EFFECTS

The siRNA or the siRNA conjugate of the present disclosure has good stability, higher gene inhibitory effect and very low off-target effects, and could remarkably reduce plasma lipid level.

In some embodiments, the siRNA, the composition comprising the siRNA, or the siRNA conjugate of the present disclosure could exhibit higher stability and/or higher activity in vivo. In some embodiments, the siRNA, the composition comprising the siRNA, or the siRNA conjugate of the present disclosure exhibits an in vivo inhibition rate against target gene expression of at least 20%, 30%, 40%, 50%, 60%, 70%, 80%, 90% or 95%. In some embodiments, the siRNA, the composition comprising the siRNA, or the siRNA conjugate of the present disclosure exhibits an in vivo inhibition rate of ANGPTL3 gene expression of at least 20%, 30%, 40%, 50%, 60%, 70%, 80%, 90%, or 95%. In some embodiments, the siRNA, the composition comprising the siRNA or, the siRNA conjugate of the present disclosure exhibits an in vivo inhibition rate of ANGPTL3 gene expression in liver of at least 20%, 30%, 40%, 50%, 60%, 70%, 80%, 90%, or 95%. In some embodiments, the siRNA, the composition comprising the siRNA, or the siRNA conjugate of the present disclosure exhibits an in vivo inhibition rate of ANGPTL3 gene expression in liver in an animal model of at least 20%, 30%, 40%, 50%, 60%, 70%, 80%, 90%, or 95%. In some embodiments, the siRNA, the composition comprising the siRNA, or the siRNA conjugate of the present disclosure exhibits an in vivo inhibition rate of ANGPTL3 gene expression in liver in a human subject of at least 20%, 30%, 40%, 50%, 60%, 70%, 80%, 90%, or 95%. In some embodiments, the siRNA, the composition comprising the siRNA, or the siRNA conjugate of the present disclosure exhibits no significant off-target effect. An off-target effect may be for example inhibition on normal expression of a gene which is not the target gene. It is considered that the off-target effect is not significant if the binding/inhibition of off-target gene expression is at a level of lower than 50%, 40%, 30%, 20%, or 10% of the on-target effect.

In some embodiments, the siRNA of the present disclosure exhibits excellent performance in inhibiting the expression of ANGPTL3 gene. The siRNA has an $IC_{50}$ of 3-30 pM, as measured in a psiCHECK system. Even at 5 nM, the modified siRNA of the present disclosure exhibits no off-target effects. Moreover, the modified siRNA of the present disclosure remains good stability in the lysosome lysate in vitro, and remains undegraded for at least 24 hours.

In some embodiments, the siRNA of the present disclosure has good stability, and keeps unified stability in the lysosome lysate in vitro, in human plasma or monkey plasma.

In some embodiments, the siRNA conjugate of the present disclosure exhibits excellent inhibitory efficiency against ANGPTL3, and could significantly reduce blood lipid level. For example, in some embodiments, 14 days after subcutaneous administration of a single dose, the inhibition rate against ANGPTL3 mRNA in mice is 95% or higher. In some embodiments, after subcutaneous administration of a single dose, the inhibition rate against triglyceride (TG) is up to 93%, and the inhibition rate against total cholesterol (CHO) is up to 83%. 154 days after administration, the inhibition rate against TG maintains 55% or higher, and the inhibition rate against CHO maintains 40% or higher. In particular, compared with the conjugates formed from conjugating molecules as provided in the prior art, the siRNA conjugate of the present disclosure exhibits more excellent gene inhibition rate and stronger ability of reducing blood lipid. Moreover, the siRNA conjugate of the present disclosure continuously shows excellent inhibitory effect against blood lipid over a period of up to 189 days under the conditions of low administration dosage and low administration frequency.

This shows that the siRNA, the pharmaceutical composition and the siRNA conjugate of the present disclosure could inhibit the expression of ANGPTL3 gene, effectively treat and/or prevent dyslipidemia caused by overexpression of ANGPTL3, and thus have good application prospect.

Additional features and advantages of the present disclosure will be illustrated in detail in the following part of detailed description of the invention.

BRIEF DESCRIPTION OF THE DRAWINGS

In order to clarify the inventive examples and the technical solutions of the prior art more clearly, a brief introduction is made to the figures that are required to be used in the examples and the prior art in the following text. Obviously, the figures described below represent only some examples of the present invention. In view of these figures, those skilled in the art could obtain other figures without paying inventive labor.

DETAILED DESCRIPTION OF THE INVENTION

Figure 1A:
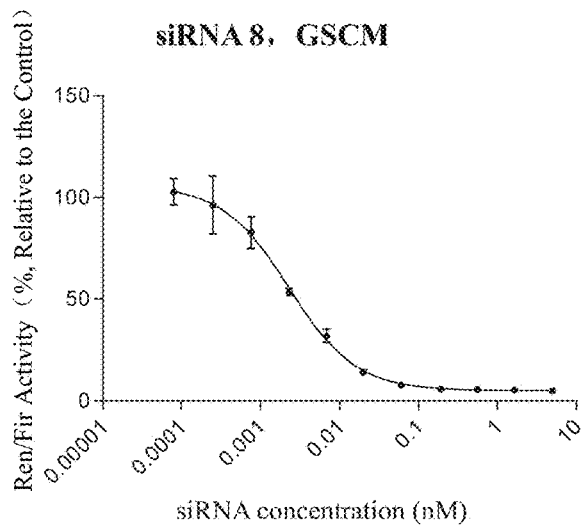
FIGS. 1A-1D show the on-target activity and off-target effect of siRNA 8 in a psiCHECK system in vitro.
Figure 1B:
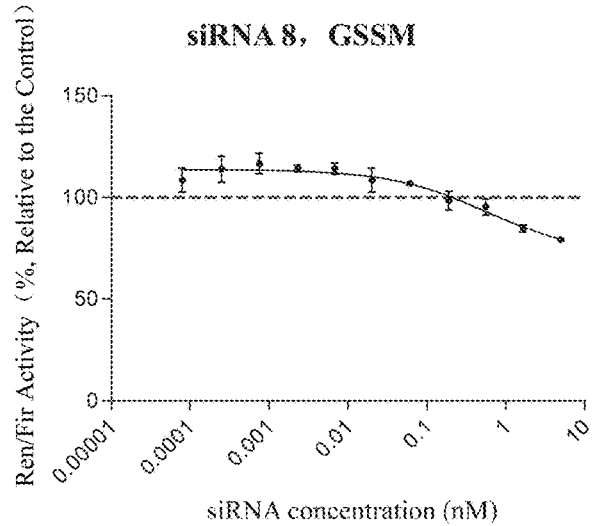
Figure 1C:
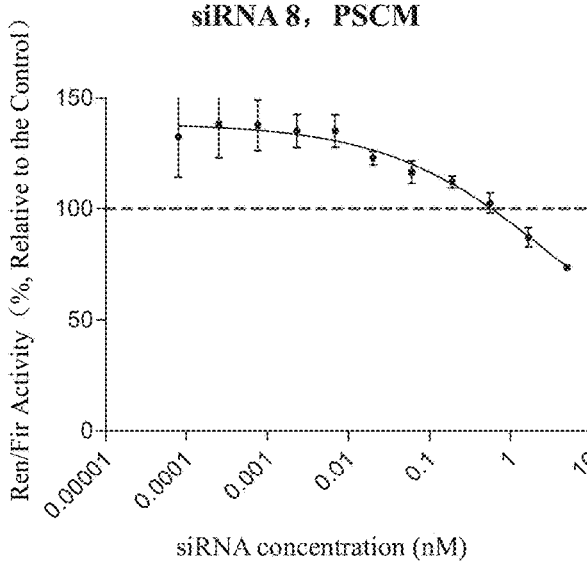
Figure 1D:
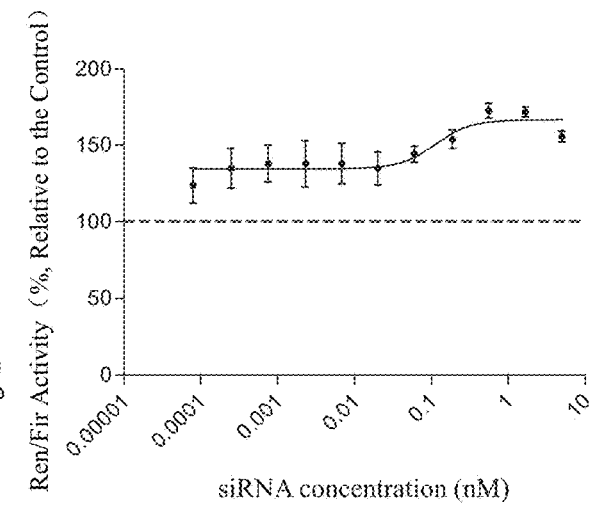
Figure 2A:
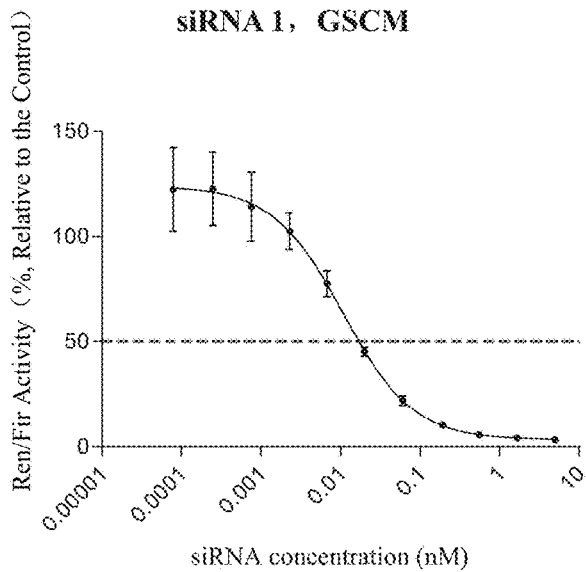
FIGS. 2A-2D show the on-target activity and off-target effect of siRNA 1 in a psiCHECK system in vitro.
Figure 2B:
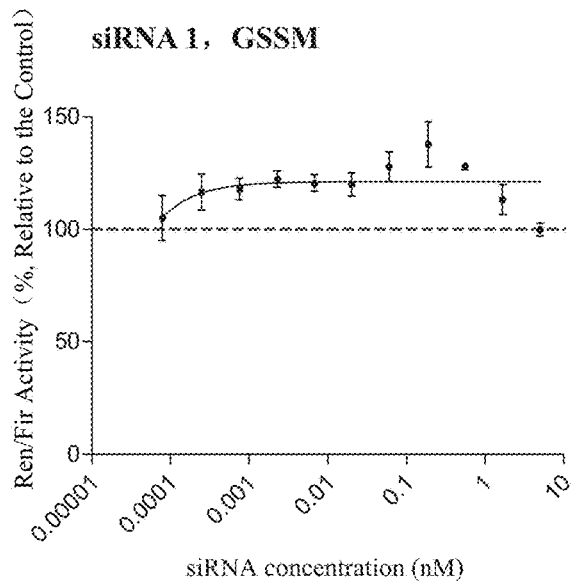
Figure 2C:
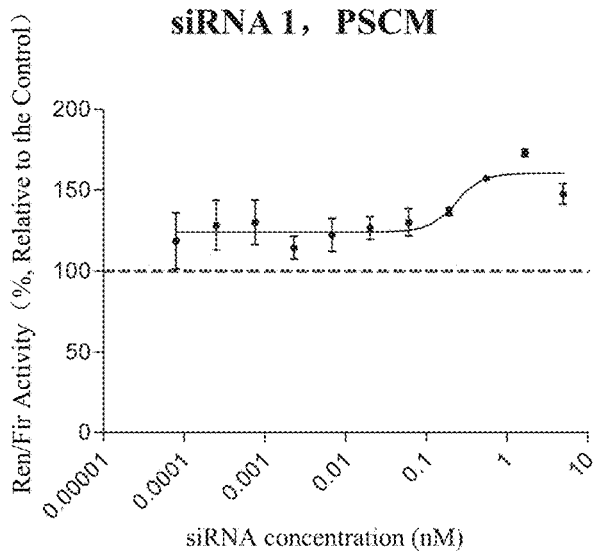
Figure 2D:
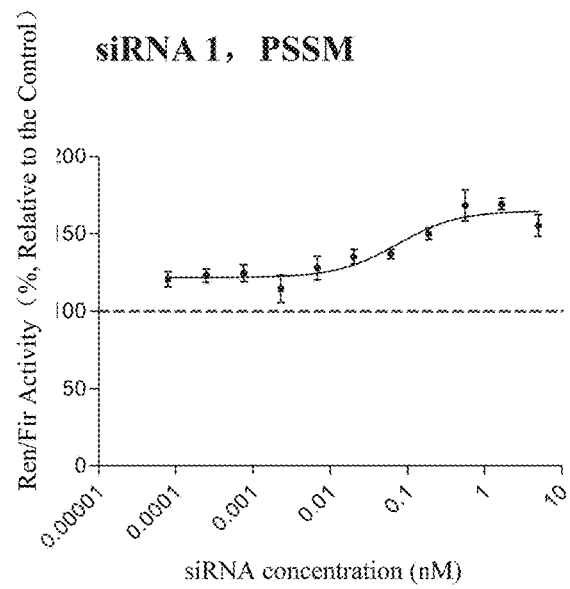

The detailed embodiments of the present disclosure are described in detail as below. It should be understood that the detailed embodiments described herein are only used to illustrate and explain the present disclosure and are not intended to limit the present disclosure.

In the present disclosure, ANGPTL3 gene refers to a gene having an mRNA sequence, as shown in Genbank Accession No. NM_014495.3.

DEFINITIONS

In the context of the present disclosure, unless otherwise specified, C, G, U, and A represent the base composition of the nucleotides; m represents that the nucleotide adjacent to the left side of the letter m is a methoxy modified nucleotide; f represents that the nucleotide adjacent to the left side of the letter f is a fluoro modified nucleotide; s represents the two nucleotides adjacent to both sides of the letter s are linked by a thiophosphate linkage; P1 represents that the nucleotide adjacent to the right side of P1 is a 5'-phosphate nucleotide or a 5'-phosphate analogue modified nucleotide; VP represents that the nucleotide adjacent to the right side of the monogram VP is a vinyl phosphate modified nucleotide; Ps represents that the nucleotide adjacent to the right side of the monogram Ps is a thiophosphate modified nucleotide; and P represents that the nucleotide adjacent to the right side of the letter P is a 5'-phosphate nucleotide.

In the context of the present disclosure, a "fluoro modified nucleotide" refers to a nucleotide formed by replacing 2'-hydroxy of the ribose group with a fluorine atom. A "non-fluoro modified nucleotide" refers to a nucleotide formed by replacing 2'-hydroxy of the ribose group with a non-fluoro group, or a nucleotide analogue. A "nucleotide analogue" refers to a group that can replace a nucleotide in the nucleic acid, while differs from an adenine ribonucleotide, a guanine ribonucleotide, a cytosine ribonucleotide, a uracil ribonucleotide or thymine deoxyribonucleotide in terms of structure, such as an isonucleotide, a bridged nucleic acid (BNA) nucleotide or a acyclic nucleotide. The "methoxy modified nucleotide" refers to a nucleotide formed by replacing 2'-hydroxy of the ribose group with a methoxy group.

In the context of the present disclosure, expressions "complementary" and "reverse complementary" are interchangeably used herein, and have a meaning well-known in the art, namely, bases in one strand are each paired in complementary with those in another strand in a double-stranded nucleic acid molecule. In DNAs, a purine base adenine (A) is always paired with a pyrimidine base thymine (T) (or a uracil (U) in RNAs); and a purine base guanine (C) is always paired with a pyrimidine base cytosine (G). Each base pair comprises a purine and a pyrimidine. While adenines in a strand are always paired with thymines (or uracils) in another strand, and guanines are always paired with cytosines, these two strands are considered as being complementary with each other; and the sequence of a strand may be deduced from the sequence of its complementary strand. Correspondingly, a "mispairing" means that the bases at corresponding positions are not present in a manner of being complementary paired in a double-stranded nucleic acid.

In the context of the present disclosure, unless otherwise specified, "basically reverse complementary" means that there are no more than 3 base mispairings between two nucleotide sequences. "Substantially reverse complementary" means that there is no more than 1 base mispairing between two nucleotide sequences. "Completely reverse complementary" means that there is no base mispairing between two nucleotide sequences.

In the context of the present disclosure, a "nucleotide difference" between a nucleotide sequence and another nucleotide sequence refers to a change in the type of the nucleotide base at the same position therebetween. For example, in the case that a nucleotide base in the later sequence is A while the nucleotide base at the same position in the former sequence is U, C, G or T, it is considered that a nucleotide difference is present at this position between these two nucleotide sequences. In some embodiments, while a nucleotide at a position is replaced with an abasic nucleotide or a nucleotide analogue, it is also considered that there is a nucleotide difference at the position.

In the context of the present disclosure, particularly in the description of the method for preparing the siRNA, the composition comprising the siRNA, or the siRNA conjugate of the present disclosure, unless otherwise specified, the "nucleoside monomer" refers to, according to the type and sequence of the nucleotides in the siRNA or siRNA conjugate to be prepared, unmodified or modified RNA phosphoramidites used in the solid phase synthesis of phosphoramidites (sometimes the RNA phosphoramidites are referred to as Nucleoside phosphoramidites). Solid phase synthesis of phosphoramidites is a method well known by those skilled in the art to be used in the synthesis of RNA. Nucleoside monomers used in the present disclosure are all commercially available.

In the context of the present disclosure, unless otherwise specified, "conjugating" refers to two or more chemical moieties each having specific function being covalently linked with each other. Correspondingly, "conjugate" refers to a compound formed by covalent linkage of individual chemical moieties. Furthermore, "siRNA conjugate" represents a compound formed by covalently attaching one or more chemical moieties each with specific functions to siRNA. In the following text, the siRNA conjugate of the present disclosure is sometimes abbreviated as "conjugate". According to the context of the present disclosure, the siRNA conjugate should be understood as the general term of siRNA conjugates, the general name of siRNA conjugates represented by Formula (305) and Formula (307), or siRNA conjugates represented by Formula (305), Formula (307) or and Formula (308). In the context of the present disclosure, "conjugating molecule" should be interpreted as a specific compound capable of being conjugated to a siRNA via reactions, thus finally forming the siRNA conjugate of the present disclosure.

As used herein, a dash ("-") that is not between two letters or symbols is used to indicate the position that is an attachment point for a substituent. For example, —$C_1$-$C_{10}$alkyl-$NH_2$ is attached through the $C_1$-$C_{10}$alkyl.

As used herein, "optional" or "optionally" is meant that the subsequently described event or circumstance may or may not occur, and that the description includes instances wherein the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically infeasible and/or inherently unstable.

As used herein, "alkyl" refers to straight chain and branched chain having the indicated number of carbon atoms, usually from 1 to 20 carbon atoms, for example 1 to 10 carbon atoms, such as 1 to 8 or 1 to 6 carbon atoms. For example $C_1$-$C_6$ alkyl encompasses both straight and branched chain alkyl of from 1 to 6 carbon atoms. When an alkyl residue having a specific number of carbons is named, all branched and straight chain forms having that number of carbons are intended to be encompassed; thus, for example, "butyl" is meant to include n-butyl, sec-butyl, isobutyl and t-butyl; "propyl" includes n-propyl and isopropyl. Alkylene is a subset of alkyl, referring to the same residues as alkyl, but having two attachment points.

As used herein, "alkenyl" refers to an unsaturated branched or straight-chain alkyl group having at least one carbon-carbon double bond obtained by respectively removing one hydrogen molecule from two adjacent carbon atoms of the parent alkyl. The group may be in either the cis or trans configuration of the double bond(s). Typical alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl; and the like. In certain embodiments, an alkenyl group has from 2 to 20 carbon atoms and in other embodiments, from 2 to 10, 2 to 8, or 2 to 6 carbon atoms. Alkenylene is a subset of alkenyl, referring to the same residues as alkenyl, but having two attachment points.

As used herein, "alkynyl" refers to an unsaturated branched or straight-chain alkyl group having at least one carbon-carbon triple bond obtained by respectively removing two hydrogen molecules from two adjacent carbon atoms of the parent alkyl. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 2 to 10, 2 to 8, or 2 to 6 carbon atoms. Alkynylene is a subset of alkynyl, referring to the same residues as alkynyl, but having two attachment points.

As used herein, "alkoxy" refers to an alkyl group of the indicated number of carbon atoms attached through an oxygen bridge such as, for example, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy groups will usually have from 1 to 10, 1 to 8, 1 to 6, or 1 to 4 carbon atoms attached through oxygen bridge.

As used herein, "aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon, including from 6 to 18 carbon atoms, where at least one ring in the ring system is fully unsaturated, i.e., it contains a cyclic, delocalized (4n+2)π-electron system in accordance with the Hückel theory. Aryl groups include, but are not limited to, groups such as phenyl, fluorenyl, and naphthyl. Arylene is a subset of aryl, referring to the same residues as aryl, but having two attachment points.

As used herein, "cycloalkyl" refers to a non-aromatic carbon ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbornane.

As used herein, "halo substituent" or "halo" refers to fluoro, chloro, bromo, and iodo, and the term "halogen" includes fluorine, chlorine, bromine, and iodine.

As used herein, "haloalkyl" refers to alkyl as defined above having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl. "Heterocyclyl" refers to a stable 3 to 18 membered non-aromatic ring radical that comprises two to twelve carbon atoms and one to six heteroatoms selected from nitrogen, oxygen or sulfur. Unless stated otherwise specifically in the specification, the heterocyclyl is a monocyclic, bicyclic, tricyclic or tetracyclic ring system, which may include fused or bridged ring system(s). The heteroatom(s) in the heterocyclyl free radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxapiperazinyl, 2-oxapiperidinyl, 2-oxapyrimidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxathiomorpholinyl, and 1,1-dioxa thiomorpholinyl.

"Heteroaryl" refers to a radical derived from a 3 to 18 membered aromatic ring radical that comprises two to seventeen carbon atoms and one to six heteroatoms selected from nitrogen, oxygen or sulfur. As used herein, the heteroaryl radical may be a monocyclic, bicyclic, tricyclic or tetracyclic ring system, wherein at least one ring in the ring system is fully unsaturated, i.e., it contains a cyclic, delocalized (4n+2)π-electron system in accordance with the Hückel theory. Heteroaryl includes fused or bridged ring system(s). The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryl include, but are not limited to, azepinyl, acridinyl, benzimidazolyl, benzindolyl, 1,3-benzodioxazolyl, benzofuranyl, benzoxazolyl, benzo[d]thiazolyl, benzothiadiazolyl, benzo[b][1,4]dioxazoly, benzo[b][1,4]oxazolyl, 1,4-benzodioxazoyl, benzonaphthofuranyl, benzodiazolyl, benzodioxaphenyl, benzopyranyl, benzopyranonyl, benzofuranyl, benzofuranonyl, benzothienyl, benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro 5H-cyclopenta[4,5]thieno[2,3-d]pyrimidinyl, 5,6-dihydrobenzo[h]quinazolinyl, 5,6 dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10 hexahydrocycloocta[d]pyrimidinyl, 5,6,7,8,9,10-hexahydrocyclohepta[d]pyridazinyl, 5,6,7,8,9,10-hexahydrocycloocta[d]pyridinyl, isothiazolyl, indazolyl, imidazolyl, indolyl, isoindolyl, indolinyl, isoindolinyl, isoquinolyl, indolizinyl, isoxazolyl, 5,8-methano-5,6,7,8-tetrahydroquinazolinyl, naphthyridinonyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta [4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3 c]pridinyl and thienyl.

Various hydroxyl protecting groups may be used in the present disclosure. In general, protecting groups render chemical functionalities inert to specific reaction conditions, and may be appended to and removed from such functionalities in a molecule without substantially damaging the remainder of the molecule. Representative hydroxyl protecting groups are disclosed in Beaucage, et al., Tetrahedron 1992, 48, 2223-2311, and also in Greene and Wuts, Protective Groups in Organic Synthesis, Chapter 2, 2d ed, John Wiley & Sons, New York, 1991, each of which is hereby incorporated by reference in their entirety. In some embodiments, the protecting group is stable under basic conditions but may be removed under acidic conditions. In some embodiments, non-exclusive examples of the hydroxyl protecting groups that may be used herein include dimethoxytrityl (DMT), monomethoxytrityl, 9-phenylxanthen-9-yl (Pixyl) and 9-(p-methoxyphenyl)xanthen-9-yl (Mox). In some embodiments, non-exclusive examples of the hydroxyl protecting groups that may be used herein comprises Tr (trityl), MMTr (4-methoxytrityl), DMTr (4,4'-dimethoxytrityl), and TMTr (4,4',4''-trimethoxytrityl).

The term "subject", as used herein, refers to any animal, e.g., a mammal or marsupial. Subject of the present disclosure includes but are not limited to human, non-human primate (e.g., rhesus or other types of macaques), mouse, pig, horse, donkey, cow, sheep, rat and any kind of poultry.

As used herein, "treatment" or "treating," or "alleviating" or "ameliorating" are used interchangeably herein. These terms refers to an approach for obtaining beneficial or desired results including but not limited to therapeutic benefit. By "therapeutic benefit" is meant eradication or amelioration of the underlying disorder being treated. Also, a therapeutic benefit is achieved by eradicating or ameliorating one or more of the physiological symptoms associated with the underlying disorder such that amelioration is observed in the subject, notwithstanding that the subject may still be afflicted with the underlying disorder.

As used herein, "prevention" and "preventing" are used interchangeably. These terms refer to an approach for obtaining beneficial or desired results including but not limited to a prophylactic benefit. For "prophylactic benefit", the conjugates or compositions may be administered to a subject at risk of developing a particular disease, or to a subject reporting one or more of the physiological symptoms of a disease, even though a diagnosis of this disease may not have been made.

siRNA

The present disclosure provides a siRNA capable of inhibiting the expression of ANGPTL3 gene.

The siRNA of the present disclosure comprises nucleotide groups as basic structural units. It is well known to those skilled in the art that the nucleotide group, in turn, comprises a phosphate group, a ribose group and a base. Detailed illustrations relating to such groups are omitted herein.

The siRNA of the present disclosure comprises a sense strand and an antisense strand, wherein each nucleotide in the siRNA is independently a modified or unmodified nucleotide, wherein the sense strand comprises a nucleotide sequence I and the antisense strand comprises a nucleotide sequence II, wherein the nucleotide sequence I and the nucleotide sequence II are at least partly reverse complementary to form a double-stranded region, wherein the nucleotide sequence I comprises a nucleotide sequence A, which has the same length as the nucleotide sequence represented by SEQ ID NO: 1 with no more than 3 nucleotide differences, and the nucleotide sequence II comprises a nucleotide sequence B, which has the same length as the nucleotide sequence represented by SEQ ID NO:2 with no more than 3 nucleotide differences:

(SEQ ID NO: 1)
5'-CCAAGAGCACCAAGAACUZ-3';

(SEQ ID NO: 2)
5'-Z'AGUUCUUGGUGCUCUUGG-3', wherein, Z is A and Z' is U;

the nucleotide sequence A comprises nucleotide $Z_A$ at the corresponding position of Z, the nucleotide sequence B comprises nucleotide $Z'_B$ at the corresponding position of Z', wherein $Z'_B$ is the first nucleotide at the 5' terminal of the antisense strand.

In the context of the present disclosure, "corresponding position" refers to the same position in the nucleotide sequence by counting from the same terminal of the nucleotide sequence. For example, the first nucleotide at the 3' terminal of nucleotide sequence A is a nucleotide at the corresponding position of the first nucleotide at the 3' terminal of SEQ ID NO:1.

In some embodiments, the sense strand comprises only nucleotide sequence I, and the antisense strand comprises only nucleotide sequence II.

In some embodiments, there is no more than 1 nucleotide difference between the nucleotide sequence A and the nucleotide sequence represented by SEQ ID NO: 1, and/or there is no more than 1 nucleotide difference between the nucleotide sequence B and the nucleotide sequence represented by SEQ ID NO:2.

In some embodiments, the nucleotide difference between the nucleotide sequence B and the nucleotide sequence represented by SEQ ID NO:2 includes a difference at the position of $Z'_B$, wherein $Z'_B$ is selected from A, C or G. In some embodiments, the nucleotide difference is a difference at the position of $Z'_B$, wherein $Z'_B$ is selected from A, C or G. In some embodiments, $Z_A$ is a nucleotide complementary to $Z'_B$.

These nucleotide differences will not significantly reduce the ability of the siRNA conjugates to inhibit the target gene, and thus these siRNA conjugates comprising the nucleotide differences are within the scope of the present disclosure.

In some embodiments, the nucleotide sequence A is basically reverse complementary, substantially reverse complementary, or completely reverse complementary with the nucleotide sequence B. "Basically reverse complementary" means that there is no more than 3 base mispairings between two nucleotide sequences. "Substantially reverse complementary" means that there is no more than 1 base mispairing between two nucleotide sequences. "Completely reverse complementary" means that there is no mispairing between two nucleotide sequences.

In some embodiments, the nucleotide sequence A is a nucleotide sequence represented by SEQ ID NO:3, and the nucleotide sequence B is a nucleotide sequence represented by SEQ ID NO: 4:

```
                                              (SEQ ID NO: 3)
        5'-CCAAGAGCACCAAGAACUZ_A-3';

(SEQ ID NO: 4)
        5'-Z'_BAGUUCUUGGUGCUCUUGG-3',
``` wherein, $Z'_B$ is the first nucleotide at the 5'terminal of the antisense strand, $Z_A$ is selected from A, U, G, or C, and $Z'_B$ is a nucleotide complementary to $Z_A$. In some embodiments, $Z_A$ is A, and $Z'_B$ is U.

Moreover, the sense strand and the antisense strand have the same or different length, wherein the sense strand has a length of 19 to 23 nucleotides, and the antisense strand has a length of 20 to 26 nucleotides. Thus, the sense strand and antisense strand of the siRNA of the present disclosure may have a length ratio of 19/20, 19/21, 19/22, 19/23, 19/24, 19/25, 19/26, 20/20, 20/21, 20/22, 20/23, 20/24, 20/25, 20/26, 21/20, 21/21, 21/22, 21/23, 21/24, 21/25, 21/26, 22/20, 22/21, 22/22, 22/23, 22/24, 22/25, 22/26, 23/20, 23/21, 23/22, 23/23, 23/24, 23/25 or 23/26. In some embodiments, the sense strand and the antisense strand of the siRNA have a length ratio of 19/21, 21/23 or 23/25.

In some embodiments, the present disclosure provides a siRNA capable of inhibiting the expression of ANGPTL3 gene, wherein the siRNA comprises a sense strand and an antisense strand, wherein each nucleotide in the siRNA is independently a modified or unmodified nucleotide, wherein the sense strand comprises a nucleotide sequence I and the antisense strand comprises a nucleotide sequence II, the nucleotide sequence I and nucleotide sequence II are at least partly reverse complementary to form a double-stranded region, wherein the nucleotide sequence I comprises a nucleotide sequence represented by SEQ ID NO:3, and the nucleotide sequence II comprises a nucleotide sequence represented by SEQ ID NO:4:

```
                                              (SEQ ID NO: 3)
        5'-CCAAGAGCACCAAGAACUZ_A-3';

(SEQ ID NO: 4)
        5'-Z'_BAGUUCUUGGUGCUCUUGG-3',
``` wherein, $Z'_B$ is the first nucleotide at the 5'terminal of the antisense strand, $Z_A$ is selected from A, U, G, or C, and $Z'_B$ is a nucleotide complementary to $Z_A$; in some embodiments, $Z_A$ is A, and $Z'_B$ is U;

the sense strand and the antisense strand have the same or different length, wherein the sense strand has a length of 19 to 23 nucleotides, and the antisense strand has a length of 20 to 26 nucleotides. Thus, the sense strand and the antisense strand of the siRNA of the present disclosure may have a length ratio of 19/20, 19/21, 19/22, 19/23, 19/24, 19/25, 19/26, 20/20, 20/21, 20/22, 20/23, 20/24, 20/25, 20/26, 21/20, 21/21, 21/22, 21/23, 21/24, 21/25, 21/26, 22/20, 22/21, 22/22, 22/23, 22/24, 22/25, 22/26, 23/20, 23/21, 23/22, 23/23, 23/24, 23/25 or 23/26. In some embodiments, the sense strand and the antisense strand of the siRNA have a length ratio of 19/21, 21/23 or 23/25.

In some embodiments, the sense strand and the antisense strand have the same length. The nucleotide sequence I further comprises nucleotide sequence III, the nucleotide sequence II further comprises nucleotide sequence IV, and the nucleotide sequence III and the nucleotide sequence IV each independently have a length of 1 to 4 nucleotides; the nucleotide sequence III is linked to the 5' terminal of the nucleotide sequence A, the nucleotide sequence IV is linked to the 3' terminal of the nucleotide sequence B, and the nucleotide sequence III and the nucleotide sequence IV have the same length. The nucleotide sequence III and the nucleotide sequence IV may be complementary or non-complementary. In order to enhance the stability of siRNA, in some embodiments, the nucleotide sequence III and the nucleotide sequence IV are at least partially complementary; in some embodiments, the nucleotide sequence III is complementary to more than 80% or 90% of the bases in the nucleotide sequence IV; in some embodiments, the nucleotide sequence III and the nucleotide sequence IV are substantially reverse complementary or completely reverse complementary. "Substantially reverse complementary" means that there is no more than 1 base mispairing between two nucleotide sequences. "Completely reverse complementary" means that there is no pairing between two nucleotide sequences. In some embodiments, the nucleotide sequence III and the nucleotide sequence IV are completely reverse complementary. In this case, the sense strand and the antisense strand of the siRNA have the same length, and have a length ratio of 20/20, 21/21, 22/22 or 23/23. In some embodiments, the sense strand and the antisense strand of the siRNA have a length ratio of 21/21 or 23/23.

In some embodiments, the nucleotide sequence III and the nucleotide sequence IV both have a length of one nucleotide, and the nucleotide sequence III has a base of G, and the nucleotide sequence IV has a base of C; in this case, the length ratio of the sense strand and the antisense strand thereof is 20/20; or, the nucleotide sequence III and the nucleotide sequence IV both have a length of 2 nucleotides, and in the direction from 5' terminal to 3' terminal, the nucleotide sequence III has a base composition of AG, and the nucleotide sequence IV has a base composition of CU; in this case, the length ratio of the sense strand and the antisense strand thereof is 21/21; or, the nucleotide sequence III and the nucleotide sequence IV both have a length of 3 nucleotides, and in the direction from 5' terminal to 3' terminal, the nucleotide sequence III has a base composition of AAG, and the nucleotide sequence IV has a base composition of CUU; in this case, the length ratio of the sense strand and the antisense strand thereof is 22/22; or, the nucleotide sequence III and the nucleotide sequence IV both have a length of 4 nucleotides, and in the direction from 5' terminal to 3' terminal, the nucleotide sequence III has a base composition of CAAG, and the nucleotide sequence IV has a base composition of CUUG; in this case, the length ratio of the sense strand and the antisense strand thereof is 23/23. In some embodiments, the nucleotide sequence III and the nucleotide sequence IV have a length of 2 nucleotides, and in the direction from 5' terminal to 3' terminal, the nucleotide sequence III has a base composition of AG, and the nucleotide sequence IV has a base composition of CU; in this case, the length ratio of the sense strand and the antisense strand thereof is 21/21.

In some embodiments, the nucleotide sequence III and the nucleotide sequence IV have the same length, and are completely reverse complementary. Hence, where the base(s) of nucleotide III is(are) provided, the base(s) of nucleotide IV is(are) determined.

In some embodiments, the sense strand and the antisense strand have different lengths. The nucleotide sequence II comprises nucleotide sequence V. The nucleotide sequence V has a length of 1 to 3 nucleotides and is linked to the 3' terminal of the antisense strand, thereby forming a 3' overhang terminal of the antisense strand. In this case, the length ratio of the sense strand and the antisense strand of the siRNA of the present disclosure is 19/20, 19/21, 19/22, 20/21, 20/22, 20/23, 21/22, 21/23, 21/24, 22/23, 22/24, 22/25, 23/24, 23/25 or 23/26. In some embodiments, the nucleotide sequence V has a length of two nucleotides. In this case, the length ratio of the sense strand and the antisense strand of the siRNA of the present disclosure is 19/21, 21/23 or 23/25.

Each nucleotide in the nucleotide sequence V may be any nucleotide. In order to facilitate the synthesis and to save synthesis cost, the nucleotide sequence V is 2 continuous thymine deoxyribonucleotides (TT) or 2 continuous uridine ribonucleotides (UU); in order to enhance the affinity of the antisense strand of the siRNA to the target mRNA, the nucleotide sequence V is complementary to the nucleotides at the corresponding positions of the target mRNA. Thus, in some embodiments, the length ratio of the sense strand and the antisense strand of the siRNA is 19/21 or 21/23. In this case, the siRNA of the present disclosure has better activity for silencing mRNA.

In some embodiments, the sense strand of the siRNA comprises nucleotide sequence represented by SEQ ID NO:3, and the antisense strand of the siRNA comprises nucleotide sequence represented by SEQ ID NO:5:

```
                                    (SEQ ID NO: 3)
5'-CCAAGAGCACCAAGAACUZ_A-3';

(SEQ ID NO: 5)
5'-Z'_BAGUUCUUGGUGCUCUUGGCU-3';
``` or, the sense strand of the siRNA comprises nucleotide sequence represented by SEQ ID NO:6, and the antisense strand of the siRNA comprises nucleotide sequence represented by SEQ ID NO:7:

```
                                    (SEQ ID NO: 6)
5'-AGCCAAGAGCACCAAGAACUZ_A-3';

(SEQ ID NO: 7)
5'-Z'_BAGUUCUUGGUGCUCUUGGCUUG-3';
``` wherein, $Z'_B$ is the first nucleotide at the 5' terminal of the antisense strand, $Z_A$ is selected from A, U, G or C, and $Z'_B$ is a nucleotide complementary to $Z_A$.

In some embodiments, the siRNA of the present disclosure is siAN1 or siAN2:

```
siAN1
Sense strand:
                                    (SEQ ID NO: 8)
5'-CCAAGAGCACCAAGAACUA-3'

Antisense strand:
                                    (SEQ ID NO: 9)
5'-UAGUUCUUGGUGCUCUUGGCU-3' siAN2
Sense strand:
                                    (SEQ ID NO: 10)
5'-AGCCAAGAGCACCAAGAACUA-3'

Antisense strand:
                                    (SEQ ID NO: 11)
5'-UAGUUCUUGGUGCUCUUGGCUUG-3'.
```

As mentioned above, the nucleotides in the siRNA of the present disclosure are each independently a modified or unmodified nucleotide. In some embodiments, the nucleotides in the siRNA of the present disclosure are unmodified nucleotides; in some embodiments, partial or all nucleotides in the siRNA of the present disclosure are modified nucleotides. These modifications on the nucleotide groups would not lead to significant impair or loss of functions of the siRNA conjugate of the present disclosure in inhibiting the expression of ANGPTL3 gene.

In some embodiments, the siRNA of the present disclosure comprises at least 1 modified nucleotide. In the context of the present disclosure, the used term "modified nucleotide" refers to a nucleotide formed by replacing 2'-hydroxy of the ribose group with other groups, or a nucleotide analogue, or a nucleotide on which the base is a modified base. The modified nucleotide would not lead to significant impair or loss of functions of the siRNA in inhibiting gene expression. For example, modified nucleotides disclosed in Watts, J. K., G. F. Deleavey and M. J. Damha, Chemically Modified siRNA: tools and applications. Drug Discov Today, 2008.13(19-20): p. 842-55 may be selected.

In some embodiments, at least one nucleotide in the sense strand or the antisense strand of the siRNA of the present disclosure is a modified nucleotide, and/or at least one phosphate group is a phosphate group with modified group(s). In other words, at least a portion of the phosphate groups and/or the ribose groups in phosphate-ribose backbone of at least one single strand in the sense strand and the antisense strand are a phosphate and/or ribose group with modified group(s).

In some embodiments, all nucleotides in the sense strand and/or the antisense strand are modified nucleotides. In some embodiments, each nucleotide in the sense strand and the antisense strand of the siRNA of the present disclosure is independently a fluoro modified nucleotide or a non-fluoro modified nucleotide.

The inventors of the present disclosure surprisingly found that the siRNA of the present disclosure achieves highly balanced stability and gene silencing efficiency in plasma in the animal experiment.

In some embodiments, the fluoro modified nucleotide is present in the nucleotide sequence A and nucleotide sequence B. Moreover, in the direction from 5' terminal to 3' terminal, the nucleotides at positions 7, 8, 9 of the nucleotide sequence A is fluoro modified nucleotides; in the direction from 5' terminal to 3' terminal, the nucleotides at positions 2, 6, 14 and 16 of the nucleotide sequence B is fluoro modified nucleotides.

In some embodiments, the fluoro modified nucleotide is present in the nucleotide sequence A and nucleotide sequence B. There is no more than 5 fluoro modified nucleotides present in the nucleotide sequence A. Moreover, in the direction from 5' terminal to 3' terminal, the nucleotides at positions 7, 8 and 9 of the nucleotide sequence A is fluoro modified nucleotides; there is no more than 7 fluoro modified nucleotides present in the nucleotide sequence B. Moreover, the nucleotides at the positions 2, 6, 14 and 16 of the nucleotide sequence B is fluoro modified nucleotides. In some embodiments, in the direction from 5' terminal to 3' terminal, the nucleotides at positions 7, 8 and 9 or at positions 5, 7, 8 and 9 of the nucleotide sequence A in the sense strand are fluoro modified nucleotides, and the nucleotides at the other positions in the sense strand are non-fluoro modified nucleotides; in the direction from 5' terminal to 3' terminal, the nucleotides at positions 2, 6, 14 and 16 or at positions 2, 6, 8, 9, 14 and 16 of the nucleotide sequence B in the antisense strand are fluoro modified nucleotides, and the nucleotides at the other positions in the antisense strand are non-fluoro modified nucleotides.

Fluoro modified nucleotide refers to a nucleotide formed by replacing 2'-hydroxy of the ribose group with fluoro, and has the structures represented by the following Formula (7). A non-fluoro modified nucleotide refers to a nucleotide formed by replacing 2'-hydroxy of the ribose group with a non-fluoro group, or a nucleotide analogue. In some embodiments, each non-fluoro modified nucleotide is independently selected from a nucleotide formed by replacing 2'-hydroxy of the ribose group thereof with a non-fluoro group, or a nucleotide analogue.

A nucleotide formed by replacing 2'-hydroxy of the ribose group with a non-fluoro group is well-known in the art, such as one selected from the group consisting of 2'-alkoxy modified nucleotides, 2'-substituted alkoxy modified nucleotides, 2'-alkyl modified nucleotides, 2'-substituted alkyl modified nucleotides, 2'-amino modified nucleotides, 2'-substituted amino modified nucleotides and 2'-deoxy nucleotides. In some embodiments, the 2'-alkoxy modified nucleotide is a methoxy modified nucleotide (2'-OMe), represented by Formula (8). In some embodiments, the 2'-substituted alkoxy modified nucleotide is for example a 2'-O-methoxyethyl modified nucleotide (2'-MOE), represented by Formula (9). In some embodiments, the 2'-amino modified nucleotide (2'-NH$_2$) is represented by Formula (10). In some embodiments, the 2'-deoxy nucleotide (DNA) is represented by Formula (11).

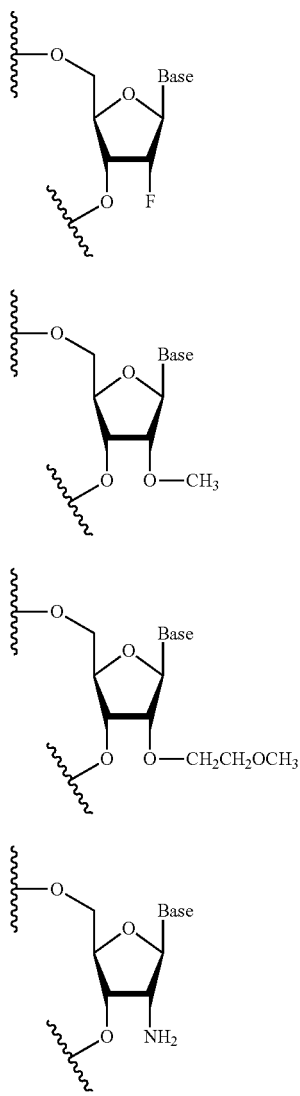

Formula (7)

Formula (8)

Formula(9)

Formula(10)

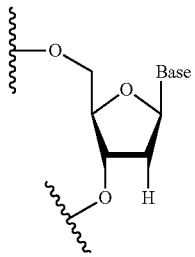

Formula (11)

A nucleotide analogue refers to a group that can replace a nucleotide in the nucleic acid, while differs from an adenine ribonucleotide, a guanine ribonucleotide, a cytosine ribonucleotide, a uracil ribonucleotide or thymine deoxyribonucleotide in terms of structure. In some embodiments, the nucleotide analogue may be an isonucleotide, a bridged nucleic acid (BNA) nucleotide or an acyclic nucleotide.

A BNA nucleotide is a nucleotide that is constrained or inaccessible. BNA can contain a 5-, 6-membered or even a 7-membered ring bridged structure with a "fixed" C3'-endo sugar puckering. The bridge is typically incorporated at the 2'- and 4'-position of the ribose to afford a 2', 4'-BNA nucleotide. In some embodiments, BNA may be LNA, ENA and cET BNA which is represented by Formulae (12), (13) and (14), respectively.

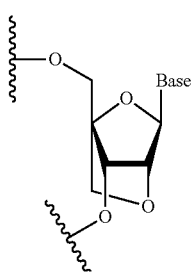

Formula (12)

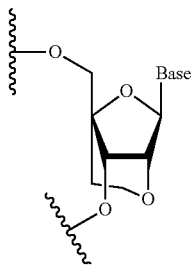

Formula (13)

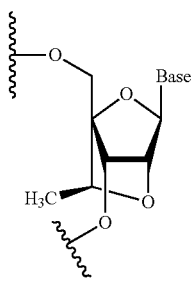

Formula (14)

An acyclic nucleotide is a category of nucleotides in which the ribose ring is opened. In some embodiments, the acrylic nucleotide is an unlocked nucleic acid (UNA) and a glycerol nucleic acid (GNA), which are represented by Formulae (15) and (16), respectively.

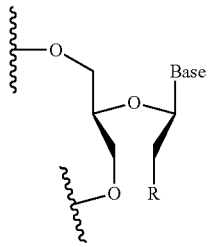

Formula (15)

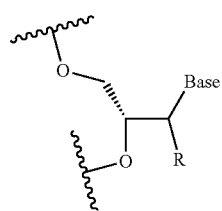

Formula (16)

In the above Formulae (15) and (16), R is selected from H, OH or alkoxy (O-alkyl). An isonucleotide is a compound in which the position of the base on the ribose ring in the nucleotide is changed. In some embodiments, the isonucleotide is a compound formed by transposing the base from position-1' to position-2' or position-3' on the ribose ring, as represented by Formula (17) or (18), respectively.

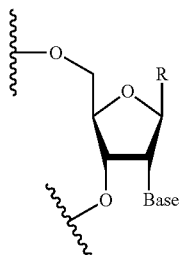

Formula (17)

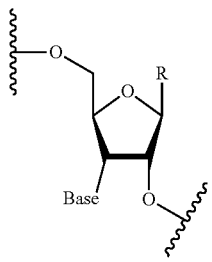

Formula (18)

In the compounds of formulae (17)-(18), Base represents a base, such as A, U, G, C or T; R is selected from H, OH, F or a non-fluoro group described above.

In some embodiments, a nucleotide analogue is one selected from isonucleotide, LNA, ENA, cET, UNA or GNA. In some embodiments, each non-fluoro modified nucleotide is a methoxy modified nucleotide. In the context of the present disclosure, the methoxy modified nucleotide refers to a nucleotide formed by replacing 2'-hydroxy of the ribose group with a methoxy group.

In the context of the disclosure, a "fluoro modified nucleotide", a "2'-fluoro modified nucleotide", a "nucleotide in which 2'-hydroxy of a ribose group is replaced with fluoro" and a "2'-fluororibosyl" have the same meaning, referring to a compound in which 2'-hydroxy of the nucleotide is replaced with fluoro, having a structure represented by Formula (7). A "methoxy modified nucleotide", a "2'-methoxy modified nucleotide", a "nucleotide in which 2'-hydroxy of a ribose group is replaced with methoxy" and a "2'-methoxyribosyl" have the same meaning, referring to a compound in which 2'-hydroxy of the ribose group in the nucleotide is replaced with methoxy, having a structure represented by Formula (8).

In some embodiments, the siRNA of the present disclosure is a siRNA with the following modifications: in the direction from 5' terminal to 3' terminal, the nucleotides at positions 7, 8 and 9 or at positions 5, 7, 8 and 9 of the nucleotide sequence A in the sense strand are fluoro modified nucleotides, and the nucleotides at the other positions in the sense strand are methoxy modified nucleotides; the nucleotides at positions 2, 6, 14 and 16 or at positions 2, 6, 8, 9, 14 and 16 of the nucleotide sequence B in the antisense strand are fluoro modified nucleotides, and the nucleotides at the other positions in the antisense strand are methoxy modified nucleotides.

In some embodiments, the siRNA of the present disclosure is a siRNA with the following modifications: in the direction from 5' terminal to 3' terminal, the nucleotides at positions 5, 7, 8 and 9 of the nucleotide sequence A in the sense strand of the siRNA are fluoro modified nucleotides, and the nucleotides at the other positions of the sense strand of the siRNA are methoxy modified nucleotides; and in the direction from 5' terminal to 3' terminal, the nucleotides at positions 2, 6, 8, 9, 14 and 16 of the nucleotide sequence B in the antisense strand of the siRNA are fluoro modified nucleotides, and the nucleotides at the other positions in the antisense strand are methoxy modified nucleotides;

or, in the direction from 5' terminal to 3' terminal, the nucleotides at positions 5, 7, 8 and 9 of the nucleotide sequence A in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 14 and 16 of the nucleotide sequence B in the antisense strand of the siRNA are fluoro modified nucleotides, and the nucleotides at the other positions in the antisense strand of the siRNA are methoxy modified nucleotides;

or, in the direction from 5' terminal to 3' terminal, the nucleotides at positions 7, 8 and 9 of the nucleotide sequence A in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 14 and 16 of the nucleotide sequence B in the antisense strand of the siRNA are fluoro modified nucleotides, and the nucleotides at the other positions in the antisense strand of the siRNA are methoxy modified nucleotides.

In other words, the ribose groups in phosphate-ribose backbone of the siRNA respectively have the following modifying groups: in the direction from 5' terminal to 3' terminal, the ribose groups at positions 5, 7, 8 and 9 of the nucleotide sequence A in the sense strand of the siRNA is 2'-fluororibosyl, and the ribose groups of the nucleotides at the other positions in the sense strand of the siRNA is 2'-methoxyribosyl; and in the direction from 5' terminal to 3' terminal, the ribose groups at positions 2, 6, 8, 9, 14 and 16 of the nucleotide sequence B in the antisense strand of the siRNA is 2'-fluororibosyl, and the ribose groups of the nucleotides at the other positions in the antisense strand of the siRNA is 2'-methoxyribosyl; or, in the direction from 5' terminal to 3' terminal, the ribose groups at positions 5, 7, 8 and 9 of the nucleotide sequence A in the sense strand of the siRNA is 2'-fluororibosyl, and the ribose groups of the nucleotides at the other positions in the sense strand of the siRNA is 2'-methoxyribosyl; and in the direction from 5' terminal to 3' terminal, the ribose groups at positions 2, 6, 14 and 16 of the nucleotide sequence B in the antisense strand of the siRNA is 2'-fluororibosyl, and the ribose groups of the nucleotides at the other positions in the antisense strand of the siRNA is 2'-methoxyribosyl;

or, in the direction from 5' terminal to 3' terminal, the ribose groups at positions 7, 8 and 9 of the nucleotide sequence A in the sense strand of the siRNA is 2'-fluororibosyl, and the ribose groups of the nucleotides at the other positions in the sense strand of the siRNA is 2'-methoxyribosyl; and in the direction from 5' terminal to 3' terminal, the ribose groups at positions 2, 6, 14 and 16 of the nucleotide sequence B in the antisense strand of the siRNA is 2'-fluororibosyl, and the ribose groups of the nucleotides at the other positions in the antisense strand of the siRNA is 2'-methoxyribosyl.

In some embodiments, the siRNA of the present disclosure is any one selected from siAN1-M1, siAN2-M1, siAN1-M2, siAN2-M2, siAN1-M3, or siAN2-M3:

siAN1-M1
sense strand:
(SEQ ID NO: 12)
5'-CmCmAmAmGfAmGfCfAfCmCmAmAmGmAmAmCmUmAm-3' antisense strand:
(SEQ ID NO: 13)
5'-UmAfGmUmUmCfUmUfGfGmUmGmCmUfCmUfUmGmGmCmUm-3' siAN2-M1
sense strand:
(SEQ ID NO: 14)
5'-AmGmCmCmAmAmGfAmGfCfAfCmCmAmAmGmAmAmCmUmAm-3' antisense strand:
(SEQ ID NO: 15)
5'-UmAfGmUmUmCfUmUfGfGmUmGmCmUfCmUfUmGmGmCmUmUmGm-3' siAN1-M2
sense strand:
(SEQ ID NO: 12)
5'-CmCmAmAmGfAmGfCfAfCmCmAmAmGmAmAmCmUmAm-3' antisense strand:
(SEQ ID NO: 16)
5'-UmAfGmUmUmCfUmUmGmGmUmGmCmUfCmUfUmGmGmCmUm-3' siAN2-M2
sense strand:
(SEQ ID NO: 14)
5'-AmGmCmCmAmAmGfAmGfCfAfCmCmAmAmGmAmAmCmUmAm-3' antisense strand:
(SEQ ID NO: 17)
5'-
UmAfGmUmUmCfUmUmGmGmUmGmCmUfCmUfUmGmGmCmUmUmGm-3' siAN1-M3
sense strand:
(SEQ ID NO: 18)
5'-CmCmAmAmGmAmGfCfAfCmCmAmAmGmAmAmCmUmAm-3' antisense strand:
(SEQ ID NO: 16)
5'-UmAfGmUmUmCfUmUmGmGmUmGmCmUfCmUfUmGmGmCmUm-3' siAN2-M3
sense strand:
(SEQ ID NO: 19)
5'-AmGmCmCmAmAmGmAmGfCfAfCmCmAmAmGmAmAmCmUmAm-3' antisense strand:
(SEQ ID NO: 17)
5'-
UmAfGmUmUmCfUmUmGmGmUmGmCmUfCmUfUmGmGmCmUmUmGm-3'

The siRNA with said modifications not only has a low cost, but also allow the ribonuclease in the blood to be less liable to cleaving the nucleic acid, thus increasing the stability of the nucleic acid and making the nucleic acid more resistant to the hydrolysis using nuclease.

In some embodiments, at least a portion of the phosphoester groups in phosphate-ribose backbone of at least one single strand in the sense strand and the antisense strand of the siRNA of the present disclosure is a phosphate group with modified group(s). In some embodiments, the phosphoester group with modified groups is a phosphorothioate group formed by replacing at least one oxygen atom in a phosphodiester bond in the phosphate groups with a sulfur atom. In some embodiments, the phosphoester group with modified group(s) is a phosphorothioate group having a structure represented by Formula (1):

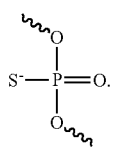

Formula (1)

This modification stabilizes the double-strand structure of the siRNA and maintains high specificity and high affinity for base pairing.

In some embodiments, in the siRNA of the present disclosure, a phosphorothioate linkage is present at at least one position selected from the group consisting of the following positions: the position between the first and the second nucleotides at either terminal of the sense or antisense strand, the position between the second and the third nucleotides at either terminal of the sense strand or antisense strand, or any combination thereof. In some embodiments, a phosphorothioate linkage is present at all the above positions except for 5' terminal of the sense strand. In some embodiments, a phosphorothioate linkage is present at all the above positions except for 3' terminal of the sense strand. In some embodiments, a phosphorothioate linkage is present at at least one of the following positions:
  the position between the first and second nucleotides at 5' terminal of the sense strand;
  the position between the second and third nucleotides at 5' terminal of the sense strand;
  the position between the first and second nucleotides at 3' terminal of the sense strand;

the position between the second and third nucleotides at 3' terminal of the sense strand;
the position between the first and second nucleotides at 5' terminal of the antisense strand;
the position between the second and third nucleotides at 5' terminal of the antisense strand;
the position between the first and second nucleotides at 3' terminal of the antisense strand; and
the position between the second and third nucleotides at 3' terminal of the antisense strand.

In some embodiments, the siRNA of the present disclosure is any one of siAN1-M1S, siAN2-M1S, siAN1-M2S, siAN2-M2S, siAN1-M3S, and siAN2-M3S:

siAN1-M1S
sense strand:
(SEQ ID NO: 20)
5'-CmsCmsAmAmGfAmGfCfAfCmCmAmAmGmAmAmCmUmAm-3'
antisense strand:
(SEQ ID NO: 21)
5'-UmsAfsGmUmUmCfUmUfGfGmUmGmCmUfCmUfUmGmGmsCmsUm-3' siAN2-M1S
sense strand:
(SEQ ID NO: 22)
5'-AmsGmsCmCmAmAmGfAmGfCfAfCmCmAmAmGmAmAmCmUmAm-3'
antisense strand:
(SEQ ID NO: 23)
5'-UmsAfsGmUmUmCfUmUfGfGmUmGmCmUfCmUfUmGmGmCmUmsUmsGm-3' siAN1-M2S
sense strand:
(SEQ ID NO: 20)
5'-CmsCmsAmAmGfAmGfCfAfCmCmAmAmGmAmAmCmUmAm-3'
antisense strand:
(SEQ ID NO: 24)
5'-UmsAfsGmUmUmCfUmUmGmGmUmGmCmUfCmUfUmGmGmsCmsUm-3' siAN2-M2S
sense strand:
(SEQ ID NO: 22)
5'-AmsGmsCmCmAmAmGfAmGfCfAfCmCmAmAmGmAmAmCmUmAm-3'
antisense strand:
(SEQ ID NO: 25)
5'-UmsAfsGmUmUmCfUmUmGmGmUmGmCmUfCmUfUmGmGmCmUmsUmsGm-3' siAN1-M3S
sense strand:
(SEQ ID NO: 26)
5'-CmsCmsAmAmGmAmGfCfAfCmCmAmAmGmAmAmCmUmAm-3'
antisense strand:
(SEQ ID NO: 24)
5'-UmsAfsGmUmUmCfUmUmGmGmUmGmCmUfCmUfUmGmGmsCmsUm-3' siAN2-M3S
sense strand:
(SEQ ID NO: 27)
5'-AmsGmsCmCmAmAmGmAmGfCfAfCmCmAmAmGmAmAmCmUmAm-3'
antisense strand:
(SEQ ID NO: 25)
5'-UmsAfsGmUmUmCfUmUmGmGmUmGmCmUfCmUfUmGmGmCmUmsUmsGm-3'

In some embodiments, the nucleotide at 5' terminal of the antisense strand of the siRNA is a 5'-phosphate nucleotide or a 5'-phosphate analogue modified nucleotide. Common 5'-phosphate nucleotides or the 5'-phosphate analogue modified nucleotides are well known to those skilled in the art, for example, 5'-phosphate nucleotide may have the following structure:

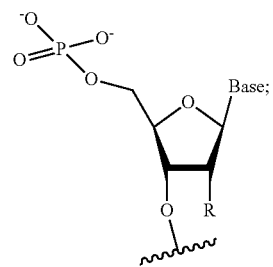

Formula (2)

as another example, the following four 5'-phosphate analogue modified nucleotides represented by Formulae (3)-(6) are disclosed in Anastasia Khvorova and Jonathan K. Watts, The chemical evolution of oligonucleotide therapies of clinical utility. Nature Biotechnology, 2017, 35(3): 238-48:

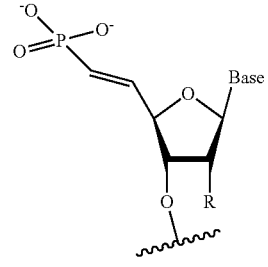

Formula (3)

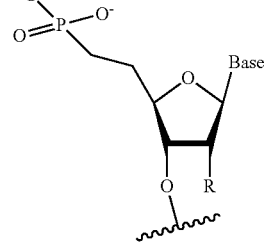

Formula (4)

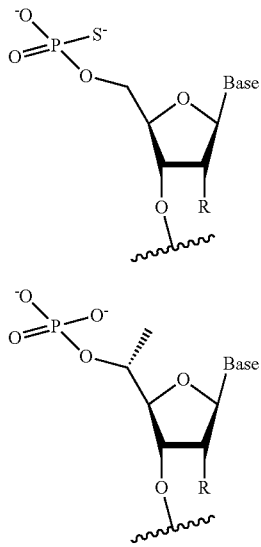

Formula (5)

Formula (6)

wherein, R represents a group selected from the group consisting of H, OH, methoxy, and F; "Base" represents a base selected from A, U, C, G, or T.

In some embodiments, 5'-phosphate nucleotide is 5'-phosphate modified nucleotide represented by Formula (2), the 5'-phosphate analogue modified nucleotide is a nucleotide modified with a vinyl phosphate (5'-(E)-vinylphosphonate, E-VP) as represented by Formula (3), or phosphorothioate modified nucleotide represented by Formula (5).

In some embodiments, the siRNA of the present disclosure is any one of siAN1-M1P1, siAN2-M1P1, siAN1-M2P1, siAN2-M2P1, siAN1-M3P1, siAN2-M3P1, siAN1-M1SP1, siAN2-M1SP1, siAN1-M2SP1, siAN2-M2SP1, siAN1-M3SP1, and siAN2-M3SP1:

```
siAN1-M1P1
sense strand:
                                        (SEQ ID NO: 12)
5'-CmCmAmAmGfAmGfCfAfCmCmAmAmGmAmAmCmUmAm-3' antisense strand:
                                        (SEQ ID NO: 28)
5'-P1-UmAfGmUmUmCfUmUfGfGmUmGmCmUfCmUfUmGmGmCmUm-
3' siAN2-M1P1
sense strand:
                                        (SEQ ID NO: 14)
5'-AmGmCmCmAmAmGfAmGfCfAfCmCmAmAmGmAmAmCmUmAm-3' antisense strand:
                                        (SEQ ID NO: 29)
5'-P1-
UmAfGmUmUmCfUmUfGfGmUmGmCmUfCmUfUmGmGmCmUmUmGm-3' siAN1-M2P1
sense strand:
                                        (SEQ ID NO: 12)
5'-CmCmAmAmGfAmGfCfAfCmCmAmAmGmAmAmCmUmAm-3' antisense strand:
                                        (SEQ ID NO: 30)
5'-P1-UmAfGmUmUmCfUmUmGmGmUmGmCmUfCmUfUmGmGmCmUm-
3' siAN2-M2P1
sense strand:
                                        (SEQ ID NO: 14)
5'-AmGmCmCmAmAmGfAmGfCfAfCmCmAmAmGmAmAmCmUmAm-3' antisense strand:
                                        (SEQ ID NO: 31)
5'-P1-
UmAfGmUmUmCfUmUmGmGmUmGmCmUfCmUfUmGmGmCmUmUmGm-3' siAN1-M3P1
sense strand:
                                        (SEQ ID NO: 18)
5'-CmCmAmAmGmAmGfCfAfCmCmAmAmGmAmAmCmUmAm-3' antisense strand:
                                        (SEQ ID NO:30)
5'-P1-
UmAfGmUmUmCfUmUmGmGmUmGmCmUfCmUfUmGmGmCmUm-3' siAN2-M3P1
sense strand:
                                        (SEQ ID NO: 19)
5'-AmGmCmCmAmAmGmAmGfCfAfCmCmAmAmGmAmAmCmUmAm-3' antisense strand:
                                        (SEQ ID NO: 31)
5'-P1-
UmAfGmUmUmCfUmUmGmGmUmGmCmUfCmUfUmGmGmCmUmUmGm-3' siAN1-M1SP1
sense strand:
                                        (SEQ ID NO: 20)
5'-CmsCmsAmAmGfAmGfCfAfCmCmAmAmGmAmAmCmUmAm-3' antisense strand:
                                        (SEQ ID NO: 32)
5'-P1-
UmsAfsGmUmUmCfUmUfGfGmUmGmCmUfCmUfUmGmGmsCmsUm-3' siAN2-M1SP1
sense strand:
                                        (SEQ ID NO: 22)
5'-
AmsGmsCmCmAmAmGfAmGfCfAfCmCmAmAmGmAmAmCmUmAm-3' antisense strand:
                                        (SEQ ID NO: 33)
5'-P1-
UmsAfsGmUmUmCfUmUfGfGmUmGmCmUfCmUfUmGmGmCmUmsUms
Gm-3' siAN1-M2SP1
sense strand:
                                        (SEQ ID NO: 20)
5'-CmsCmsAmAmGfAmGfCfAfCmCmAmAmGmAmAmCmUmAm-3' antisense strand:
                                        (SEQ ID NO: 34)
5'-P1-
UmsAfsGmUmUmCfUmUmGmGmUmGmCmUfCmUfUmGmGmsCmsUm-3' siAN2-M2SP1
sense strand:
                                        (SEQ ID NO: 22)
5'-
AmsGmsCmCmAmAmGfAmGfCfAfCmCmAmAmGmAmAmCmUmAm-3'
```

```
                                  -continued
antisense strand:
                                         (SEQ ID NO: 35)
5'-P1-

UmsAfsGmUmUmCfUmUmGmGmUmGmCmUfCmUfUmGmGmCmUmsUms

Gm-3' siAN1-M3SP1
sense strand:
                                         (SEQ ID NO: 26)
5'-CmsCmsAmAmGmAmGfCfAfCmCmAmAmGmAmAmCmUmAm-3' antisense strand:
                                         (SEQ ID NO: 34)
5'-P1-

UmsAfsGmUmUmCfUmUmGmGmUmGmCmUfCmUfUmGmGmsCmsUm-3' siAN2-M3SP1
sense strand:
                                         (SEQ ID NO: 27)
5'-

AmsGmsCmCmAmAmGmAmGfCfAfCmCmAmAmGmAmAmCmUmAm-3' antisense strand:
                                         (SEQ ID NO: 35)
5'-P1-

UmsAfsGmUmUmCfUmUmGmGmUmGmCmUfCmUfUmGmGmCmUmsUms

Gm-3'
```

The inventors of the present disclosure have unexpectedly discovered that the siRNA of the present disclosure not only have significantly enhanced stability in plasma and lysosome, but also maintain very high activity of suppressing gene.

The siRNAs of the present disclosure may be obtained by conventional processes for preparing siRNA in the art, such as solid phase synthesis process and liquid phase synthesis process. Among them, commercial customized services have already been available for solid phase synthesis. A modified nucleotide group can be introduced into the siRNA of the present disclosure by using the nucleoside monomer with corresponding modification. The process for preparing the nucleotide monomer with corresponding modification and the process for introducing the modified nucleotide group into the siRNA are also well known to those skilled in the art.

Pharmaceutical Composition

The present disclosure provides a pharmaceutical composition comprising the siRNA described above as an active ingredient and a pharmaceutically acceptable carrier. The pharmaceutically acceptable carrier may be a carrier conventionally used in the field of siRNA administration, for example, but not limited to, one or more of magnetic nanoparticles, such as $Fe_3O_4$ or $Fe_2O_3$-based nanoparticles, carbon nanotubes, mesoporous silicon, calcium phosphate nanoparticles, polyethylenimine (PEI), polyamidoamine (PAMAM) dendrimer, poly(L-lysine) (PLL), chitosan, 1,2-dioleoyl-3-trimethylammonium-propane (DOTAP), poly (D&L-lactic/glycolic acid)copolymer (PLGA), poly(2-aminoethyl ethylene phosphate) (PPEEA), and poly(2-dimethylaminoethyl methacrylate) (PDMAEMA), and derivatives thereof. In some embodiments, in the pharmaceutical composition, there are no special requirements for the contents of the siRNA and the pharmaceutically acceptable carrier. In some embodiments, the weight ratio of the siRNA and the pharmaceutically acceptable carrier is 1: (1-500). In some embodiments, the weight ratio is 1:(1-50).

In some embodiments, the pharmaceutical composition further contains other pharmaceutically acceptable excipients, which may be one or more of various formulations or compounds conventionally employed in the art. For example, said other pharmaceutically acceptable excipients may include at least one of a pH buffer, a protective agent and an osmotic pressure regulator.

The pH buffer may be tris(hydroxymethyl) aminomethane hydrochloride buffer solution with a pH of 7.5-8.5, and/or phosphate buffer solution with a pH of 5.5-8.5, for example phosphate buffer solution with a pH of 5.5-8.5.

The protective agent may be at least one of inositol, sorbitol, sucrose, trehalose, mannose, maltose, lactose and glucose. The content of the protective agent may be from 0.01 wt % to 30 wt % on the basis of the total weight of the pharmaceutical composition.

The osmotic pressure regulator may be sodium chloride and/or potassium chloride. The content of the osmotic pressure regulator allows the osmotic pressure of the pharmaceutical composition to be 200-700 mOsm/kg. Depending on the desired osmotic pressure, those skilled in the art can readily determine the content of the osmotic pressure regulator.

In some embodiments, the pharmaceutical composition may be a liquid formulation, for example, an injection solution; or a lyophilized powder for injection, which is mixed with a liquid excipient to form a liquid formulation upon administration. The liquid formulation may be administered by, but is not limited to, subcutaneous, intramuscular or intravenous injection, and also may be administrated to, but is not limited to, lung by spray, or to other organ tissues (such as liver) via lung by spray. In some embodiments, the pharmaceutical composition is administered by intravenous injection.

In some embodiments, the pharmaceutical composition may be in the form of a liposome formulation. In some embodiments, the pharmaceutically acceptable carrier used in the liposome formulation comprises an amine-containing transfection compound (hereinafter also referred to as an amine-containing compound), a helper lipid and/or a PEGylated lipid. Among others, the organic amine, the helper lipid and the PEGylated lipid may be respectively selected from one or more of the amine-containing transfection compounds or pharmaceutically acceptable salts or derivatives thereof, the helper lipids and the PEGylated lipids described in CN103380113A, which is incorporated herein by reference in its entirety.

In some embodiments, the organic amine is a compound represented by Formula (201) or a pharmaceutically acceptable salt thereof described in CN103380113A:

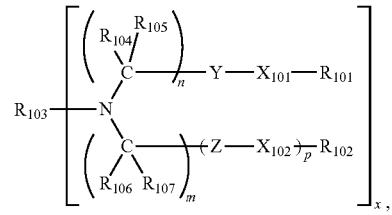

Formula (201)

wherein:

each of $X_{101}$ and $X_{102}$ is independently selected from O, S, N-A or C-A, wherein A is hydrogen or a $C_1$-$C_{20}$ hydrocarbon chain;

each of Y and Z is independently selected from C=O, C=S, S=O, CH—OH or SO$_2$; each of R$_{101}$, R$_{102}$, R$_{103}$, R$_{104}$, R$_{105}$, R$_{106}$ and R$_{107}$ is independently selected from hydrogen; a cyclic or an acyclic, substituted or unsubstituted, branched or linear aliphatic group; a cyclic or an acyclic, substituted or unsubstituted, branched or linear heteroaliphatic group; a substituted or unsubstituted, branched or linear acyl group; a substituted or unsubstituted, branched or linear aryl group; a substituted or unsubstituted, branched or linear heteroaryl group;

x is an integer of 1-10;

n is an integer of 1-3, m is an integer of 0-20, p is an integer of 0 or 1, wherein if m=p=0, then R$_{102}$ is hydrogen, and if at least one of n or m is 2, then R$_{103}$ and nitrogen in Formula (201) form a structure as represented by Formula (202) or Formula (203):

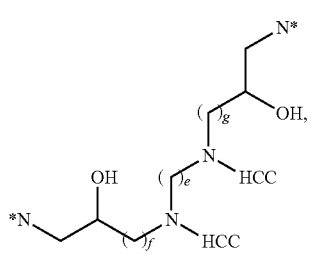

Formula (202)

Formula (203)

wherein, each of g, e and f is independently an integer of 1-6, "HCC" represents a hydrocarbon chain, and each *N represents nitrogen atom in Formula (201).

In some embodiments, R$_{103}$ is polyamine. In other embodiments, R$_{103}$ is ketal. In some embodiments, each of R$_{101}$ and R$_{102}$ in Formula (201) is independently any substituted or unsubstituted, branched or linear alkyl or alkenyl, wherein the alkyl or alkenyl has 3 to about 20 carbon atoms, such as 8 to about 18 carbon atoms, and 0 to 4 double bonds, such as 0 to 2 double bonds.

In some embodiments, if each of n and m is independently a value of 1 or 3, R$_{103}$ may be any one of the following formulae (204) to (213):

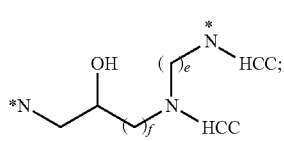

Formula (204)

formula (205)

Formula (206)

Formula (207)

Formula (208)

Formula (209)

Formula (210)

Formula (211)

Formula (212) and

Formula (213)

wherein, in formulae (204) to (213), each of g, e and f is independently an integer of 1-6, each "HCC" represents a hydrocarbon chain, and each * represents a possible attachment point of R$_{103}$ to the nitrogen atom in Formula (201), wherein each H at any * position may be replaced to achieve the attachment to the nitrogen atom in Formula (201).

The compound represented by Formula (201) may be prepared according to the description of CN103380113A.

In some embodiments, the organic amine is the organic amine represented by Formula (214) and/or the organic amine represented by Formula (215):

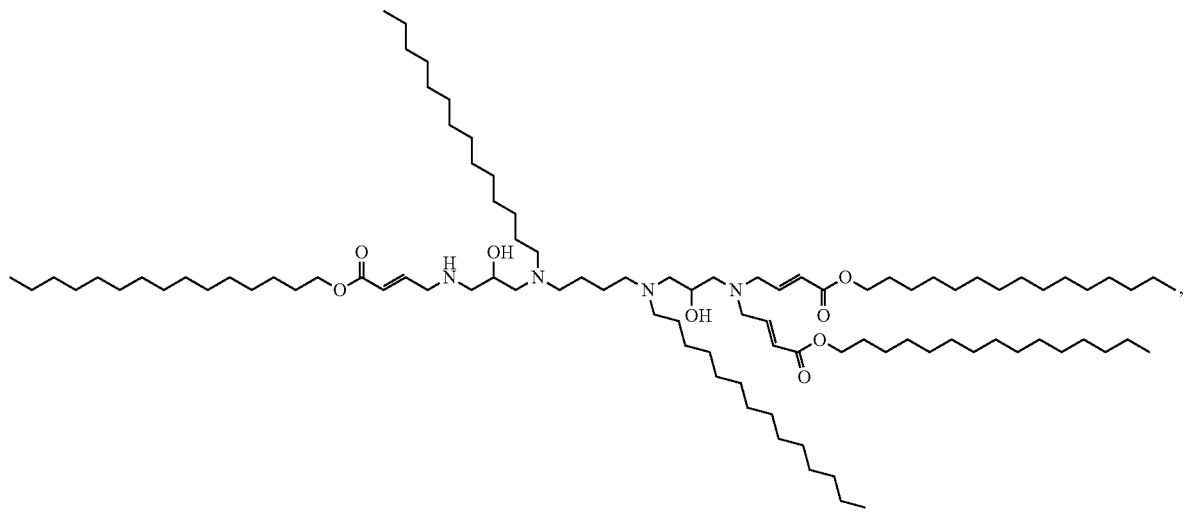

Formula (214)

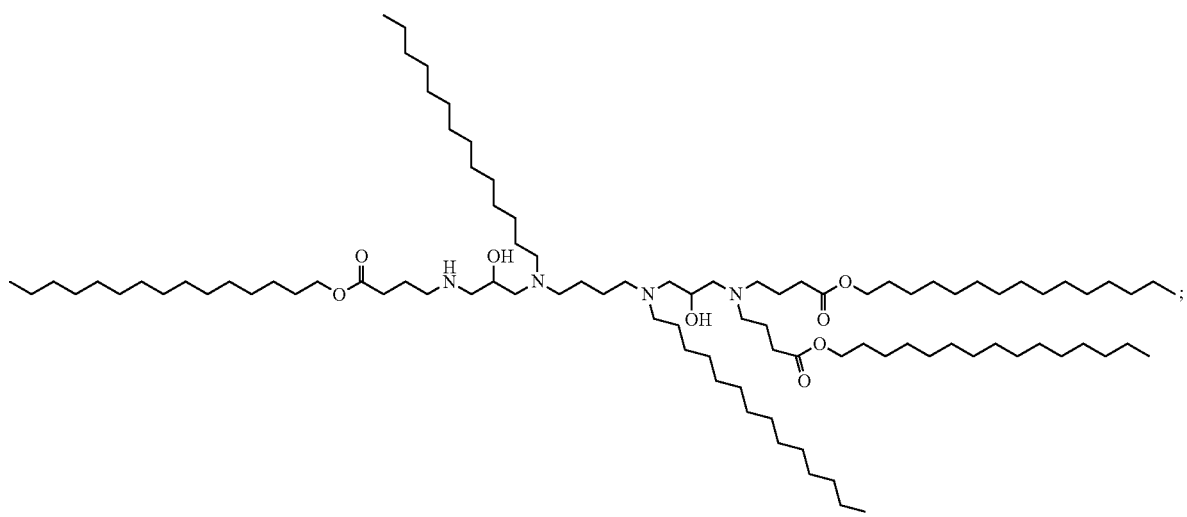

Formula (215)

the helper lipid is cholesterol, cholesterol analogues and/or cholesterol derivatives;

the PEGylated lipid is 1,2-dipalmitoyl-sn-glycero-3-phosphatidylethanolamine-N-[methoxy(polyethylene glycol)-2000].

In some embodiments, the molar ratio of the organic amine, the helper lipid and the PEGylated lipid in the pharmaceutical compositions is (19.7-80): (19.7-80): (0.3-50), for example (50-70): (20-40): (3-20).

In some embodiments, the particles of the pharmaceutical composition formed by the siRNA of the present disclosure and the above amine-containing transfection agent have an average diameter from about 30 nm to about 200 nm, typically from about 40 nm to about 135 nm, and more typically, the average diameter of the liposome particles is from about 50 nm to about 120 nm, from about 50 nm to about 100 nm, from about 60 nm to about 90 nm, or from about 70 nm to about 90 nm, for example, the average diameter of the liposome particles is about 30, 40, 50, 60, 70, 75, 80, 85, 90, 100, 110, 120, 130, 140, 150 or 160 nm.

In some embodiments, in the pharmaceutical composition formed by the siRNA of the present disclosure and the above amine-containing transfection agent, the weight ratio (weight/weight ratio) of the siRNA to total lipids, e.g., the organic amines, the helper lipids and/or the PEGylated lipids, ranges from about 1:1 to about 1:50, from about 1:1 to about 1:30, from about 1:3 to about 1:20, from about 1:4 to about 1:18, from about 1:5 to about 1:17, from about 1:5 to about 1:15, from about 1:5 to about 1:12, from about 1:6 to about 1:12, or from about 1:6 to about 1:10, for example, the weight ratio of the siRNA of the present disclosure to total lipids is about 1:5, 1:6, 1:7, 1:8, 1:9, 1:10, 1:11, 1:12, 1:13, 1:14, 1:15, 1:16, 1:17 or 1:18.

In some embodiments, the pharmaceutical compositions may be marketed with each component being separate, and used in the form of liquid formulation. In some embodiments, the pharmaceutical composition formed by the siRNA of the present disclosure and the above pharmaceutically acceptable carrier may be prepared according to various known processes, except replacing the existing siRNA with the siRNA of the present disclosure. In some embodiments, it may be prepared according to the following process:

The organic amines, the helper lipids and the PEGylated lipids in the molar ratio as described above are suspended in alcohol and mixed uniformly to afford a lipid solution; the alcohol is used in such an amount that the afforded lipid solution has a total mass concentration of 2 to 25 mg/mL, for example, 8 to 18 mg/mL. The alcohol is selected from a pharmaceutically acceptable alcohol, for example an alcohol that is in liquid form at about room temperature, such as one or more of ethanol, propylene glycol, benzyl alcohol, glycerol, polyethylene glycol 200, polyethylene glycol 300, and polyethylene glycol 400, e.g. ethanol.

The siRNA of the present disclosure is dissolved in a buffer salt solution to produce a siRNA aqueous solution. The buffer salt solution is in a concentration of 0.05 to 0.5 M, for example 0.1 to 0.2 M. The pH of the buffer salt solution is adjusted to 4.0 to 5.5, for example 5.0 to 5.2. The buffer salt solution is used in an amount to make the concentration of siRNA no more than 0.6 mg/ml, for example 0.2 to 0.4 mg/mL. The buffer salt solution may be one or more selected from the group consisting of soluble acetate and soluble citrate, for example sodium acetate and/or potassium acetate.

The lipid solution and the siRNA aqueous solution are mixed. The obtained mixture is incubated at a temperature of 40 to 60° C. for at least 2 minutes, for example 5 to 30 minutes, to produce a incubated liposome formulation. The lipid solution and the aqueous solution of the siRNA is in a volume ratio of 1:(2-5), for example 1:4.

The incubated liposome formulation is concentrated or diluted, and then subjected to impurity removal and sterilization to obtain the pharmaceutical composition of the present disclosure, of which the physical and chemical parameters are as follows: a pH of 6.5 to 8, an encapsulation percentage of not lower than 80%, a particle size of 40 to 200 nm, a polydispersity index of no greater than 0.30, and an osmotic pressure of 250 to 400 mOsm/kg; for example, the physical and chemical parameters may be as follows: a pH of 7.2 to 7.6, an encapsulation percentage of not lower than 90%, a particle size of 60 to 100 nm, a polydispersity index of no greater than 0.20, and an osmotic pressure of 300 to 400 mOsm/kg.

In particular, concentration or dilution may be performed before, after or simultaneously with the step of removing impurities. The methods for removing impurities may be various existing methods, for example, ultrafiltration under 100K Da using a hollow fiber column, a phosphate buffer (PBS) at pH 7.4 as ultrafiltration exchange solution, and a tangential flow system. The methods for sterilization may be various existing methods, such as filtration sterilization on a 0.22 μm filter.

siRNA Conjugates

The present disclosure provides a siRNA conjugate, which comprises the siRNA and a conjugating group linked to the siRNA by conjugation.

Generally speaking, the conjugating group comprises at least one pharmaceutically acceptable targeting group and an optional linker. Moreover, the siRNA, the linker and the targeting group are sequentially linked. In some embodiments, the number of the targeting group is 1 to 6. In some embodiments, the number of target groups is 2 to 4. The siRNA molecule may be non-covalently or covalently conjugated to the conjugating group, for example the siRNA molecule may be covalently conjugated to the conjugating group. The conjugating site between the siRNA and the conjugating group can be at the 3' terminal or 5' terminal of the sense strand of the siRNA, or at the 5' terminal of the antisense strand, and can be within the internal sequence of the siRNA. In some embodiments, the conjugating site between the siRNA and the conjugating group is at the 3' terminal of the sense strand of the siRNA.

In some embodiments, the conjugating group may be linked to a phosphate group, 2'-hydroxy or a base in the nucleotide. In some embodiments, the conjugating group may be linked to 3'-hydroxyl when the nucleotides are linked via 2'-5' phosphoramidite bond. Where the conjugating group is linked to a terminal of the siRNA strand, the conjugating group is usually linked to a phosphate group of the nucleotide. Where the conjugating group is linked to an internal sequence of the siRNA, the conjugating group is usually linked to a ribose ring or a base. For various linking manners, reference shall be made to the document: Muthiah Manoharan et.al. siRNA conjugates carrying sequentially assembled trivalent N-acetylgalactosamine linked through nucleosides elicit robust gene silencing in vivo in hepatocytes. ACS Chemical biology, 2015, 10 (5): 1181-7.

In some embodiments, the siRNA and the conjugating group may be linked through acid-unstable or reducible chemical bonds, and these chemical bonds may be degraded under acidic environment of cell inclusions, thereby rendering the siRNA to be in free state. With respect to undegradable conjugating manner, the conjugating group may be linked to the sense strand of siRNA, thereby reducing the influence of conjugation on the siRNA activity as low as possible.

In some embodiments, the pharmaceutically acceptable targeting group may be a ligand conventionally used in the field of siRNA administration, for example, all the ligands described in WO 2009082607A2, which is incorporated herein by reference in its entirety.

In some embodiments, the pharmaceutically acceptable targeting group may be selected from one or more of the ligands formed by the following targeting molecules or derivatives thereof: lipophilic molecules, such as cholesterol, bile acids, vitamins such as vitamin E, lipid molecules of different chain lengths; polymers, such as polyethylene glycol; polypeptides, such as cell-penetrating peptide; aptamers; antibodies; quantum dots; saccharides, such as lactose, polylactose, mannose, galactose, N-acetylgalactosamine (GalNAc); folate; or receptor ligands expressed in hepatic parenchymal cells, such as asialoglycoprotein, asialo-sugar residue, lipoproteins (such as high density lipoprotein, low density lipoprotein and the like), glucagon, neurotransmitters (such as adrenaline), growth factors, transferrin and the like.

In some embodiments, each ligand is independently selected from a ligand capable of binding to a cell surface receptor. In some embodiments, at least one ligand is a lingand capable of binding to a receptor on the surface of a hepatocyte. In some embodiments, at least one ligand is a ligand capable of binding to a surface receptor on the surface of a mammalian cell. In some embodiments, at least one ligand is a ligand capable of binding to a surface receptor on the surface of a human hepatocyte. In some embodiments, at least one ligand is a ligand capable of binding to an asialoglycoprotein receptor (ASGPR) on the surface of liver. The kinds of these ligands are well-known to those skilled in the art, and they generally serve the function of binding to specific receptor on the surface of the target cells, thereby mediating the delivery of the siRNA linked to the ligands into target cells.

In some embodiments, the pharmaceutically acceptable targeting group may be any ligand that binds to the ASGPR on the surface of mammalian hepatocytes. In some embodiments, each ligand is independently an asialoglycoprotein, such as asialoorosomucoid (ASOR) or asialofetuin (ASF). In some embodiments, the ligand is a saccharide or derivatives thereof.

In some embodiments, at least one ligand is a saccharide. In some embodiments, each ligand is a saccharide. In some embodiments, at least one ligand is a monosaccharide, polysaccharide, modified saccharide, modified polysaccharide or saccharide derivatives. In some embodiments, at least one ligand is a monosaccharide, disaccharide or trisaccharide. In some embodiments, at least one ligand is a modified saccharide. In some embodiments, each ligand is a modified saccharide. In some embodiments, each ligand is independently selected from polysaccharides, modified polysaccharides, monosaccharides, modified monosaccharides, polysaccharide derivatives or monosaccharide derivatives. In some embodiments, each or at least one ligand is selected from a group consisting of glucose and its derivatives, mannose and its derivatives, galactose and its derivatives, xylose and its derivatives, ribose and its derivatives, fucose and its derivatives, lactose and its derivatives, maltose and its derivatives, arabinose and its derivatives, fructose and its derivatives, and sialic acid. In some embodiments, each ligand may be independently selected from the group consisting of D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, β-D-mannopyranose, α-D-glucopyranose, β-D-glucopyranose, α-D-glucofuranose, β-D-glucofuranose, α-D-fructofuranose, α-D-fructopyranose, α-D-galactopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-n-butyrylgalactosamine, N-isobutyrylgalactosamine, 2-amino-3-O—[(R)-1-carboxyethyl]-2-deoxy-β-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-α-neuraminic acid, 5-thio-β-D-glucopyranose, methyl 2,3,4-tris-O-acetyl-1-thio-6-O-trityl-α-D-glucopyranoside, 4-thio-β-D-galactopyranose, ethyl 3,4,6,7-tetra-O-acetyl-2-deoxy-1,5-dithio-α-D-glucoheptopyranoside, 2,5-anhydro-D-allononitrile, ribose, D-ribose, D-4-thioribose, L-ribose, and L-4-thioribose. Other selections of the ligand may be found, for example, in the disclosure of CN105378082A, which is incorporated herein by reference in its entirety.

In some embodiments, the pharmaceutically acceptable targeting group in the siRNA conjugate may be galactose or N-acetylgalactosamine, which may be of monovalence, divalence, trivalence or tetravalence. It should be understood that the monovalence, divalence, trivalence and tetravalence mean that the molar ratio of the siRNA molecule to the galactose or N-acetylgalactosamine in the siRNA conjugate is 1:1, 1:2, 1:3 or 1:4, wherein the siRNA conjugate is formed from the siRNA molecule and the conjugating group containing galactose or N-acetylgalactosamine molecule as the targeting group. In some embodiments, the pharmaceutically acceptable targeting group is N-acetylgalactosamine. In some embodiments, where the siRNA of the present disclosure is conjugated to the conjugating group containing N-acetylgalactosamine, the N-acetylgalactosamine molecule is of trivalence or tetravalence. In some embodiments, where the siRNA of the present disclosure is conjugated to the conjugating group containing N-acetylgalactosamine, the N-acetylgalactosamine molecule is of trivalence.

The targeting group may be linked to the siRNA molecule via an appropriate linker. Those skilled in the art could select appropriate linkers according to the specific kind of the targeting group. These linkers, the kind of the targeting group and the manner of linking to siRNA may be referred to the contents disclosed in WO 2015006740A2, which is incorporated herein by reference in its entirety.

In some embodiments, where the targeting group is N-acetylgalactosamine, the appropriate linker has the structure represented by Formula (301):

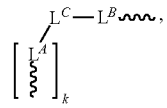

Formula (301)

wherein, k is an integer of 1-3;

$L^A$ is an amide bond-comprising chain moiety having the structure represented by Formula (302), each $L^A$ is respectively linked to a targeting group and the $L^C$ moiety through an ether bond at its two terminals;

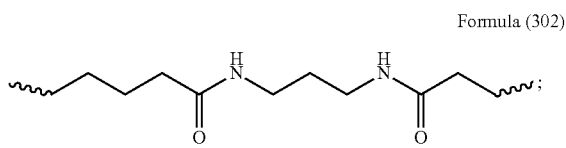

Formula (302)

$L^B$ is an N-acylpyrrolidine-comprising chain moiety having the structure represented by Formula (303), wherein the chain moiety has a carbonyl at its one terminal and is linked to the $L^C$ moiety through an amide bond, and has an oxy group at the other terminal and is linked to the siRNA through a phosphoester bond;

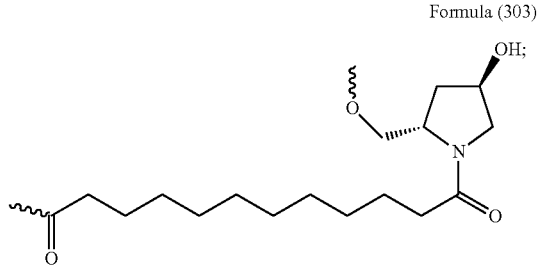

Formula (303)

$L^C$ is a bivalent to tetravalent linking group based on hydroxymethyl aminomethane, dihydroxymethyl aminomethane or trihydroxymethyl aminomethane, and is linked to each $L^A$ moiety through ether bond via oxygen atom, and is linked to the $L^B$ moiety through amide bond via nitrogen atom.

In some embodiments, when n=3 and $L^C$ is a tetravalent linking group based on trihydroxymethyl aminomethane, the siRNA conjugate formed by linking N-acetylgalactosamine molecule(s) with a siRNA molecule via -($L^A$)$_3$-trihydroxymethyl aminomethane-$L^B$- as a linker has the structure as represented by Formula (304):

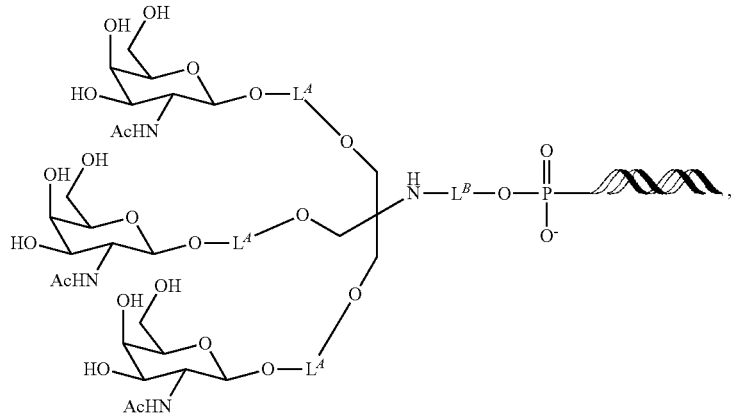

Formula (304)

wherein the double helix structure represents a siRNA.

Likewise, the conjugating site between the siRNA and the conjugating group can be at the 3' terminal or 5'-terminal of the sense strand of the siRNA, or at the 5' terminal of the antisense strand, or within the internal sequence of the siRNA.

In some embodiments, the 3' terminal of the sense strand of the siRNA of the present disclosure is covalently conjugated to three N-acetylgalactosamine (GalNAc) molecules via a linker -$(L^A)_3$-trihydroxymethyl aminomethane-$L^B$- to afford a siRNA conjugate in which the molar ratio of the siRNA molecule to the GalNAc molecule is 1:3 (hereinafter this siRNA conjugate may be referred to as (GalNAc)$_3$-siRNA), and this siRNA conjugate has the structure represented by Formula (305):

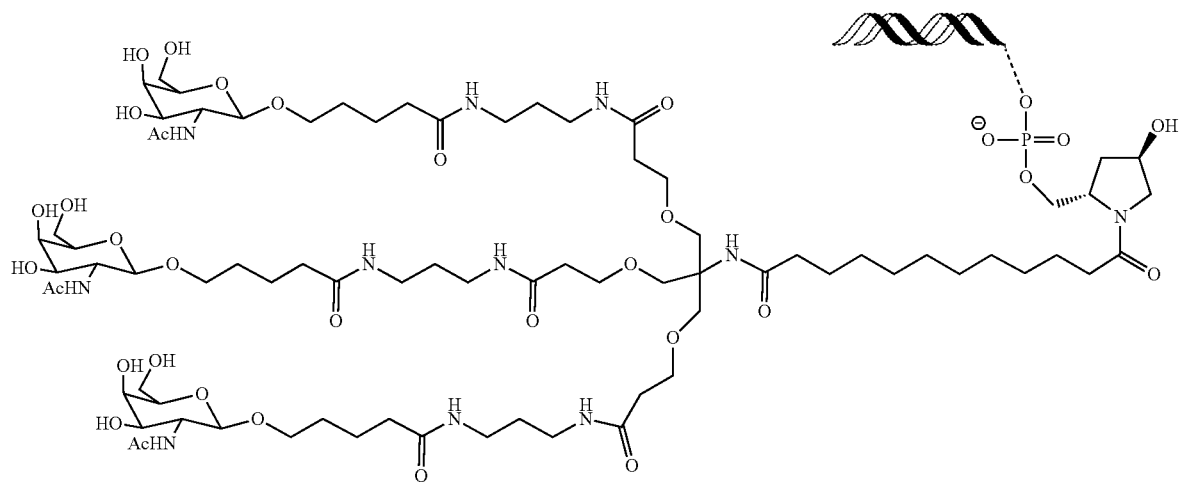

Formula (305)

wherein, the double helix structure represents a siRNA, and the linker is linked to the 3' terminal of the sense strand of the siRNA.

In some embodiments, when the targeting group is N-acetylgalactosamine, the appropriate linker has the structure represented by Formula (306):

Formula (306)

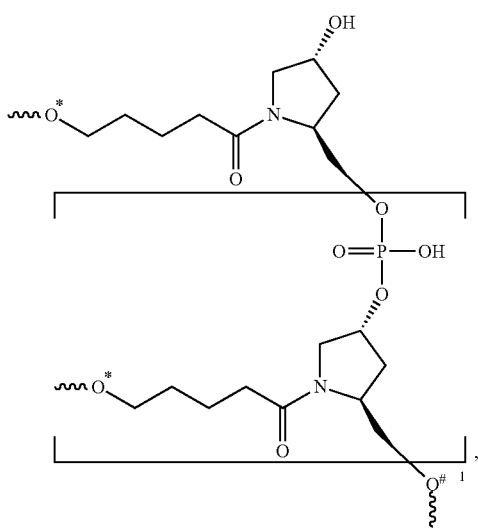

wherein,
l is an integer of 0-3;
* represents the site on the linker where the targeting group is linked through ether bond; and
# represents the site on the linker where the siRNA is linked through phosphoester bond.

In some embodiments, when l=2, the siRNA conjugate has the structure represented by Formula (307):

wherein the double helix structure represents a siRNA, and the linker is linked to the 3' terminal of the sense strand of the siRNA.

The above mentioned conjugate may be synthesized by the process that has been described in detail in the prior art. For example, WO2015006740A2 describes in detail the process for preparing various conjugates. The siRNA conjugate of the present disclosure may be obtained by the process well-known to those skilled in the art. For example, WO 2014025805A1 discloses the process for preparing the structure represented by Formula (305). Rajeev et al. in ChemBioChem 2015, 16, 903-908 describes the process for preparing the structure represented by Formula (307).

In some embodiments, the siRNA conjugate has the structure represented by Formula (308):

Formula (308)

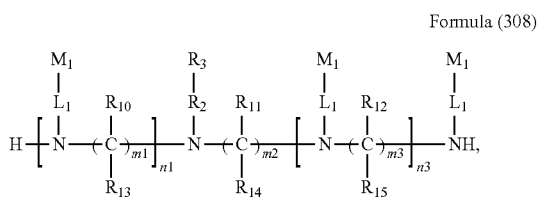

wherein,
n1 is an integer of 1-3, and n3 is an integer of 0-4;
each of m1, m2, and m3 is independently an integer of 2-10;

Formula (307)

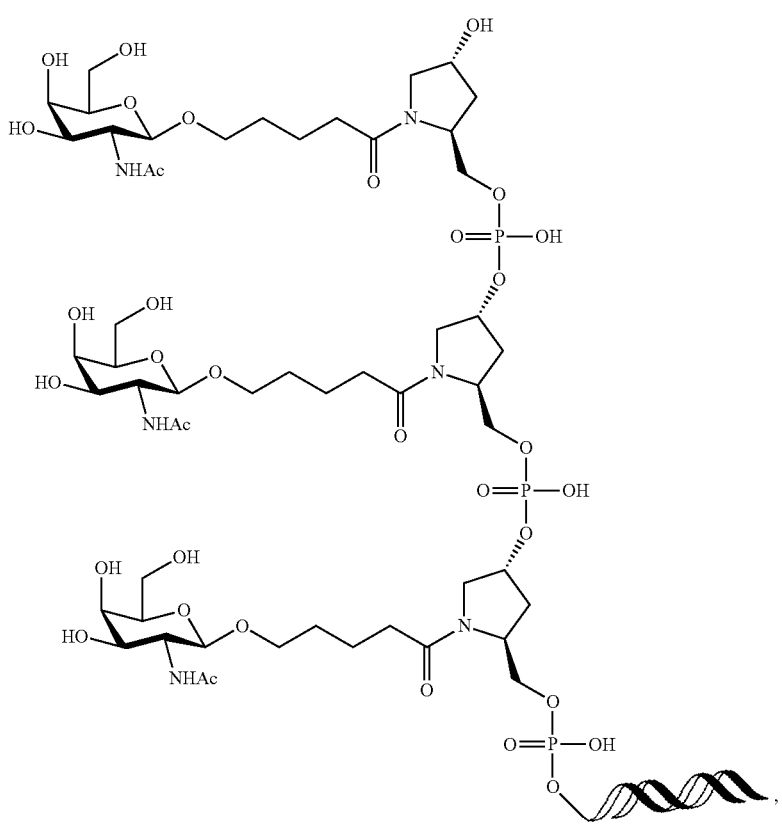

each of $R_{10}$, $R_{11}$, $R_{12}$, $R_{13}$, $R_{14}$ and $R_{15}$ is independently H, or selected from the group consisting of $C_1$-$C_{10}$ alkyl, $C_1$-$C_{10}$ haloalkyl, and $C_1$-$C_{10}$ alkoxy;

$R_3$ is a group having the structure represented by Formula A59:

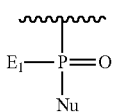
(A59)

wherein $E_1$ is OH, SH or $BH_2$, and Nu is the siRNA of the present disclosure;

$R_2$ is a linear alkylene of 1 to 20 carbon atoms in length, wherein one or more carbon atoms are optionally replaced with one or more groups selected from the group consisting of: C(O), NH, O, S, CH=N, S(O)$_2$, $C_2$-$C_{10}$ alkeylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $R_2$ is optionally substituted by any one or more groups selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, alkylphenyl, —$C_1$-$C_{10}$ alkyl-SH, haloalkyl, halo, —OH, —SH, —NH$_2$, alkyl-NH$_2$, —N($C_1$-$C_{10}$ alkyl)($C_1$-$C_{10}$ alkyl), —NH($C_1$-$C_{10}$ alkyl), cyano, nitro, —CO$_2$H, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —CONH$_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —SO$_2$($C_1$-$C_{10}$ alkyl), —SO$_2$(phenyl), —SO$_2$($C_1$-$C_{10}$ haloalkyl), —SO$_2$NH$_2$, —SO$_2$NH($C_1$-$C_{10}$ alkyl), —SO$_2$NH(phenyl), —NHSO$_2$($C_1$-$C_{10}$ alkyl), —NHSO$_2$(phenyl), and —NHSO$_2$($C_1$-$C_{10}$ haloalkyl);

each $L_1$ is a linear alkylene having a length of 1 to 70 carbon atoms, wherein one or more carbon atoms are optionally replaced with one or more groups selected from the group consisting of: C(O), NH, O, S, CH=N, S(O)$_2$, $C_2$-$C_{10}$ alkeylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $L_1$ is optionally substituted by any one or more groups selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, alkyl-SH, —S$C_1$-$C_{10}$ haloalkyl, halo, —OH, —SH, —NH$_2$, —$C_1$-$C_{10}$ alkyl-NH$_2$, —N($C_1$-$C_{10}$ alkyl)($C_1$-$C_{10}$ alkyl), —NH($C_1$-$C_{10}$ alkyl), cyano, nitro, —CO$_2$H, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —CONH$_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —SO$_2$($C_1$-$C_{10}$ alkyl), —SO$_2$(phenyl), —SO$_2$($C_1$-$C_{10}$ haloalkyl), —SO$_2$NH$_2$, —SO$_2$NH($C_1$-$C_{10}$ alkyl), —SO$_2$NH(phenyl), —NHSO$_2$($C_1$-$C_{10}$ alkyl), —NHSO$_2$(phenyl), and —NHSO$_2$($C_1$-$C_{10}$ haloalkyl).

In some embodiments, $L_1$ may be selected from the group consisting of groups A1-A26 and any combination thereof, wherein the groups A1-A26 have the following structures and definitions:

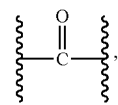
(A1)

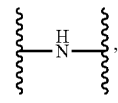
(A2)

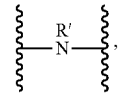
(A3)

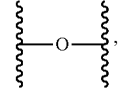
(A4)

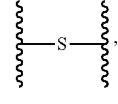
(A5)

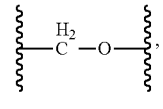
(A6)

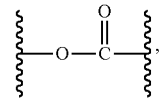
(A7)

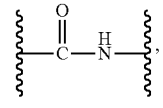
(A8)

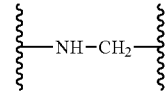
(A9)

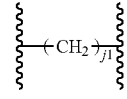
(A10)

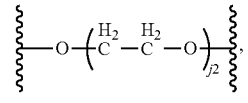
(A11)

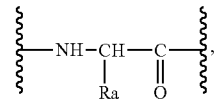
(A12)

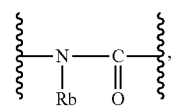
(A13)

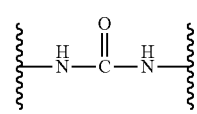
(A14)

-continued
(A15) 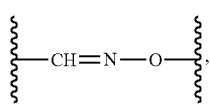
(A16) 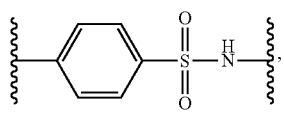
(A17) 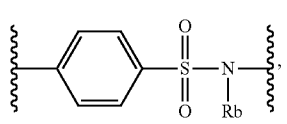
(A18) 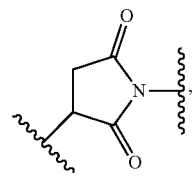
(A19) 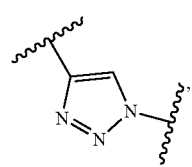
(A20) 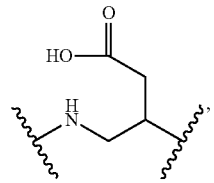
(A21) 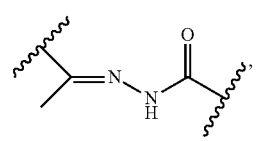
(A22) 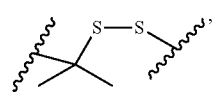
(A23) 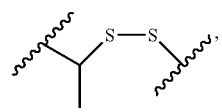
(A24) 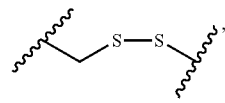
(A25) 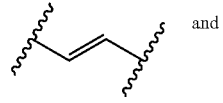 and
-continued
(A26) 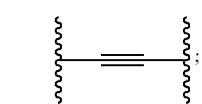;
wherein, j1 is an integer of 1-20; j2 is an integer of 1-20; R' is a $C_1$-$C_{10}$ alkyl;
Ra is selected from the group consisting of Formulae A27-A45 and any combination thereof:
(A27) 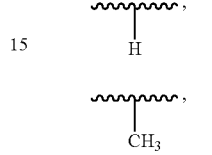
(A28) 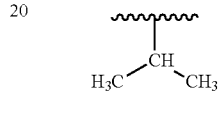
(A29) 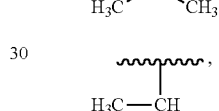
(A30) 
(A31) 
(A32) 
(A33) 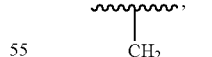
(A34) 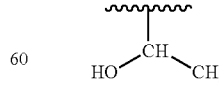
(A35) 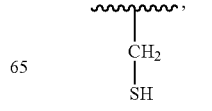
(A36)

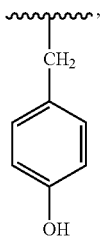
(A37)

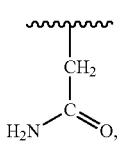
(A38)

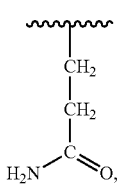
(A39)

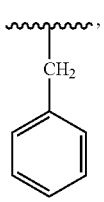
(A40)

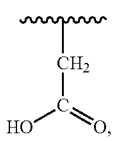
(A41)

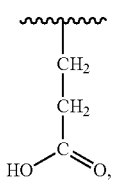
(A42)

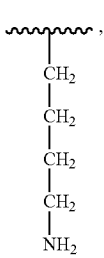
(A43)

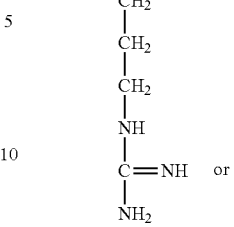
(A44)

or

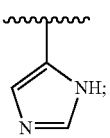
(A45)

Rb is a $C_1$-$C_{10}$ alkyl; and

~~~ represents a site where a group is attached to the rest of the molecule.

Those skilled in the art would understand that, though $L_1$ is defined as a linear alkyl for convenience, it may not be a linear group or be named differently, such as an amine or alkenyl as a result of the above replacement and/or substitution. For the purpose of the present disclosure, the length of $L_1$ is the atom number in the chain connecting the two attachment points. For this purpose, a ring resulted from replacement of a carbon atom of the linear alkylene, such as a heterocyclylene or heteroarylene, is counted as one atom.

$M_1$ represents a targeting group, of which the definitions and options are the same as the above-mentioned targeting groups. In some embodiments, each M1 is independently selected from one of the ligands that have affinity to the asialoglycoprotein receptor on the surface of mammalian hepatocytes.

When $M_1$ is a ligand having affinity to the asialoglycoprotein receptor on the surface of mammalian hepatocytes, in some embodiments, n1 may be an integer of 1-3, and n3 may be an integer of 0-4 to ensure that there are at least two $M_1$ targeting groups in the conjugate. In some embodiments, n1+n3≥2, so that the number of the $M_1$ targeting groups may be at least 3, thereby allowing the $M_1$ targeting group to more conveniently bind to the asialoglycoprotein receptor on the surface of liver, which may facilitate the endocytosis of the conjugate into cells. Experiments have shown that when the number of the $M_1$ targeting groups is greater than 3, the feasibility of binding the M1 targeting groups to the asialoglycoprotein receptor on the surface of liver is not significantly increased. Therefore, in view of various aspects such as the synthesis convenience, structure/process costs and delivery efficiency, in some embodiments, n1 is an integer of 1-2, n3 is an integer of 0-1, and n1+n3=2–3.

In some embodiments, when m1, m2, and m3 are each independently selected from an integer of 2-10, the steric position among a plurality of the $M_1$ targeting groups may be fit for binding the $M_1$ targeting groups to the asialoglycoprotein receptor on the surface of liver. In order to make the conjugate of the present disclosure have simpler structure, easier synthesis and/or reduced cost, in some embodiments, m1, m2 and m3 are each independently an integer of 2-5, in some embodiments, m1=m2=m3.

It may be understood by those skilled in the art that when each of $R_{10}$, $R_{11}$, $R_{12}$, $R_{13}$, $R_{14}$, and $R_{15}$ is independently one selected from H, $C_1$-$C_{10}$ alkyl, $C_1$-$C_{10}$ haloalkyl, or $C_1$-$C_{10}$ alkoxy, the purpose of the present disclosure may be achieved without changing the properties of the conjugates of the present disclosure. In some embodiments, $R_{10}$, $R_{11}$, $R_{12}$, $R_{13}$, $R_{14}$, and $R_{15}$ are each independently selected from H, methyl or ethyl. In some embodiments, $R_{10}$, $R_{11}$, $R_{12}$, $R_{13}$, $R_{14}$, and $R_{15}$ are all H.

$R_3$ is a group having the structure represented by Formula A59, wherein $E_1$ is OH, SH or BH$_2$. Considering the easy accessibility of the starting materials, in some embodiments, $E_1$ is OH or SH.

$R_2$ is selected to achieve the linkage of N on the nitrogenous backbone to A59. In the context of the present disclosure, a "nitrogenous backbone" refers to a chain structure in which the carbon atom to which $R_{10}$, $R_{11}$, $R_{12}$, $R_{13}$, $R_{14}$, and $R_{15}$ are attached and the N atom are linked to each other. Thus, $R_2$ is a linking group capable of attaching group A59 to the N atom on a nitrogenous backbone in an appropriate manner. In some embodiments, in the case where the siRNA conjugate represented by Formula (308) is prepared by the solid phase process, it is required that $R_2$ group comprises both a site linking to the N atom on the nitrogenous backbone and a site linking to the P atom in $R_3$. In some embodiments, in $R_2$, the site linking to the N atom on the nitrogenous backbone forms an amide bond with the N atom, and the site linking to the P atom in $R_3$ forms a phosphoester bond with the P atom. In some embodiments, $R_2$ is B5, B6, B5' or B6':

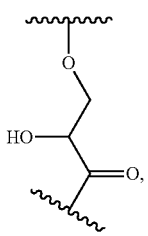

(B5)

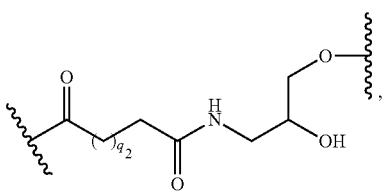

(B6)

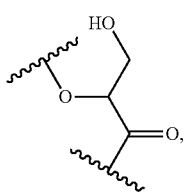

(B5')

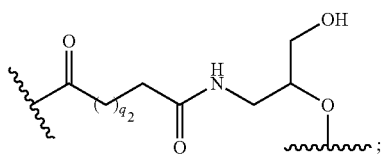

(B6')

wherein, ⁓⁓ represents the site where a group is covalently linked.

$q_2$ may be an integer of 1-10, and in some embodiments, $q_2$ is an integer of 1-5.

$L_1$ is used to link the $M_1$ targeting group to the N atom on the nitrogenous backbone, thereby providing liver targeting function for the siRNA conjugate represented by Formula (308). In some embodiments, $L_1$ is selected from connection combinations of one or more groups having Formulae A1-A26. In some embodiments, $L_1$ is selected from connection combinations of one or more of A1, A4, A5, A6, A8, A10, A11, and A13. In some embodiments, $L_1$ is selected from connection combinations of at least two of A1, A4, A8, A10, and A11. In some embodiments, $L_1$ is selected from connection combinations of at least two of A1, A8, and A10.

In some embodiments, the length of $L_1$ may be 3 to 25, 3 to 20, 4 to 15, or 5 to 12 atoms. In some embodiments, $L_1$ is 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 atoms in length.

Those skilled in the art would understand that, though $L_1$ is defined as a linear alkyl for convenience, it may not be a linear group or be named differently, such as an amine or alkenyl as a result of the above replacement and/or substitution. For the purpose of the present disclosure, the length of $L_1$ is the atom number in the chain connecting two attachment points. For this purpose, a ring resulted from replacement of a carbon atom of the linear alkylene, such as a heterocyclylene or heteroarylene, is counted as one atom.

In some embodiments, j1 is an integer of 2-10, and in some embodiments is an integer of 3-5. In some embodiments, j2 is an integer of 2-10, and in some embodiments is an integer of 3-5. R' is a $C_1$-$C_4$ alkyl, and in some embodiments is one of methyl, ethyl, and isopropyl. Ra is one of A27, A28, A29, A30, and A31, and in some embodiments is A27 or A28. Rb is a $C_1$-$C_5$ alkyl, and in some embodiments is one of methyl, ethyl, isopropyl, and butyl. In some embodiments, j1, j2, R', Ra, and Rb in Formulae A1-A26 are respectively selected to achieve the linkage between the $M_1$ targeting group and the N atom on the nitrogenous backbone, and to make the steric position among the $M_1$ targeting group more suitable for binding the $M_1$ targeting group to the asialoglycoprotein receptor on the surface of liver.

In some embodiments, the conjugate has the structure represented by Formula (403), (404), (405), (406), (407), (408), (409), (410), (411), (412), (413), (414), (415), (416), (417), (418), (419), (420), (421) or (422):

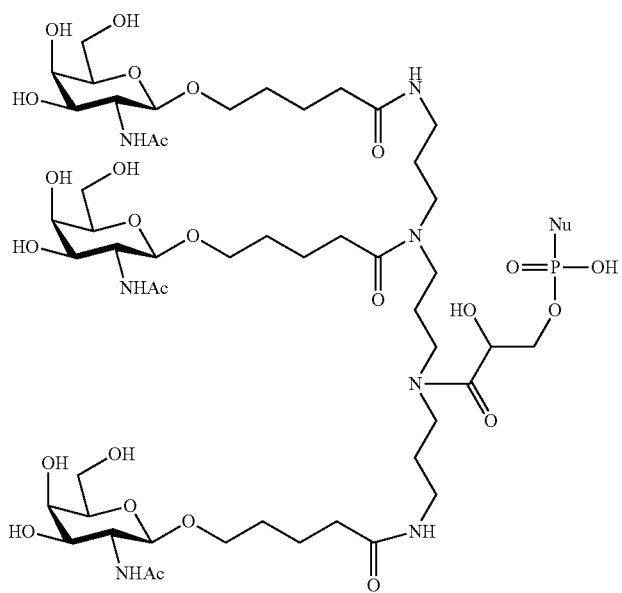
Formula (403)
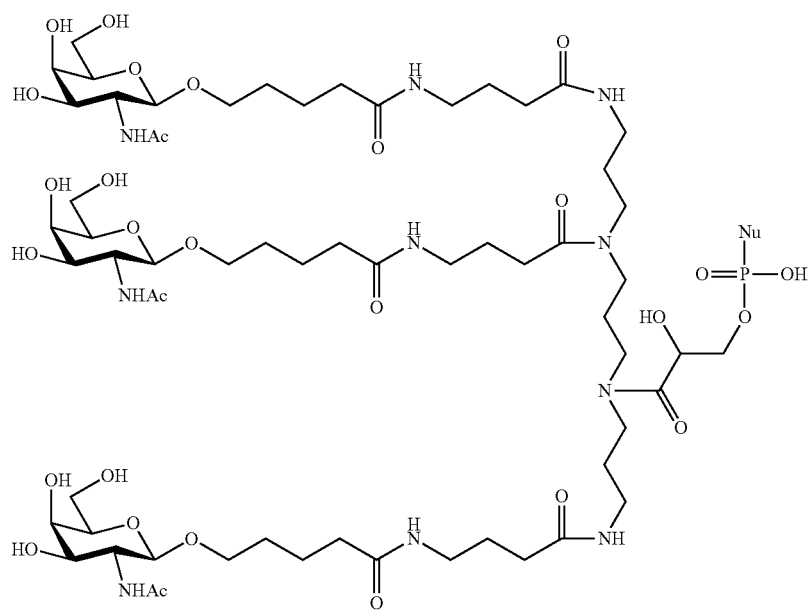
Formula (404)

Formula (405)
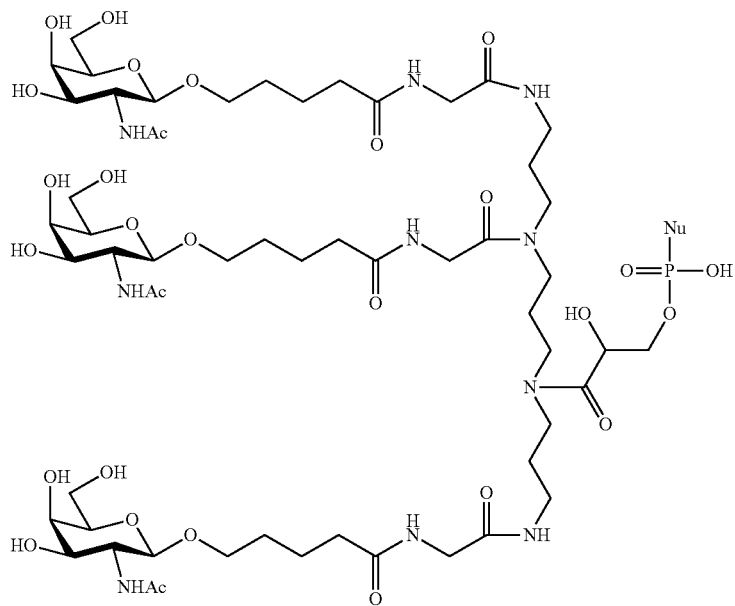
Formula (406)
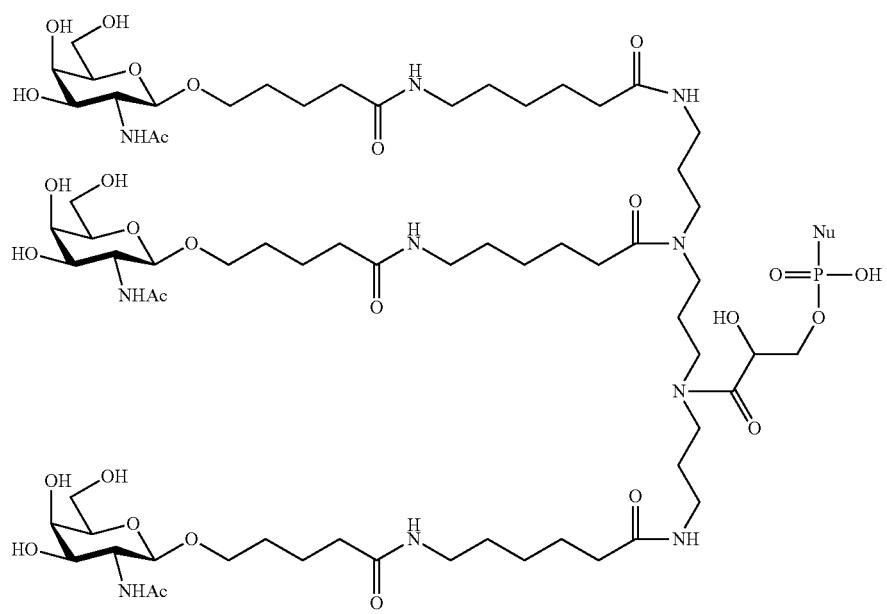

-continued
Formula (407)
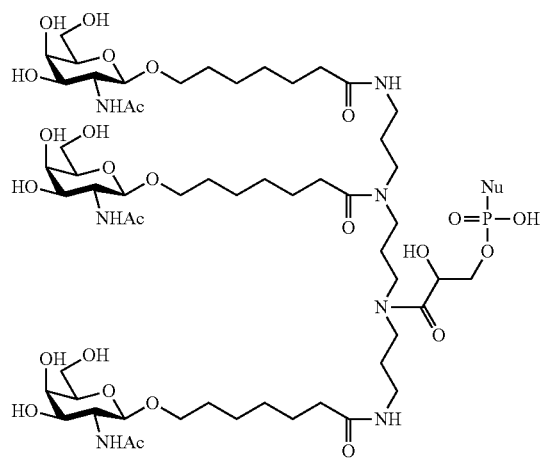
Formula (408)
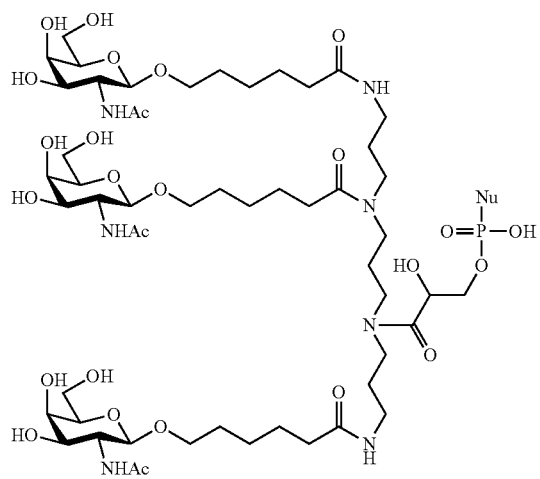
Formula (409)
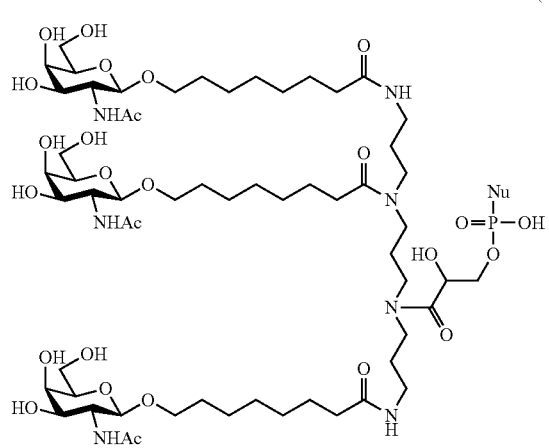
Formula (410)
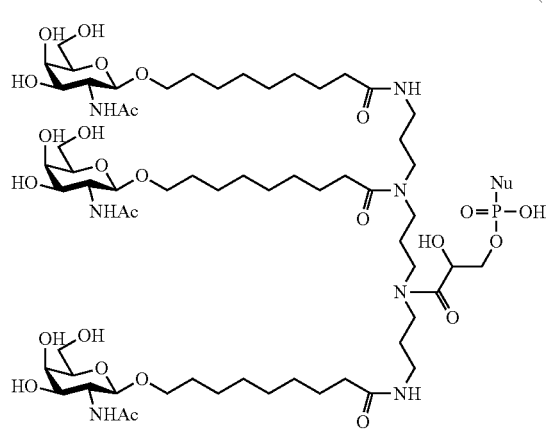
Formula (411)
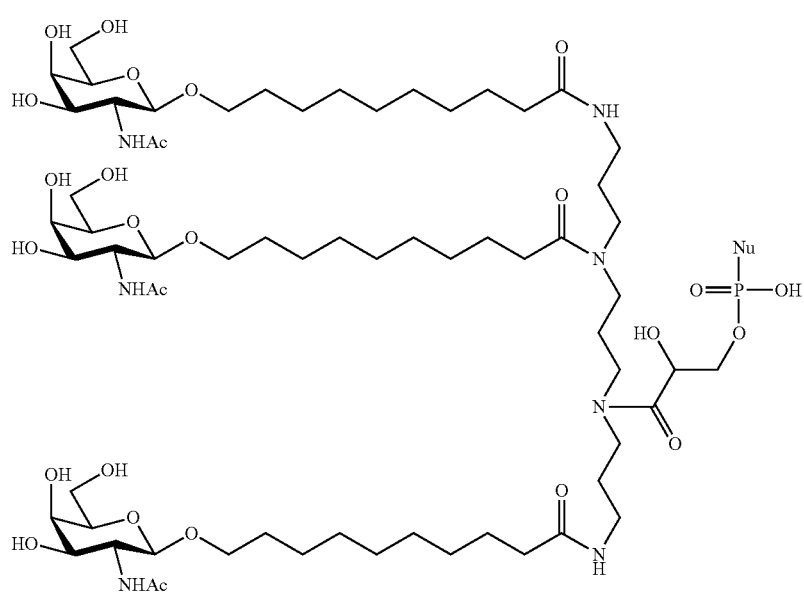

-continued
Formula (412)
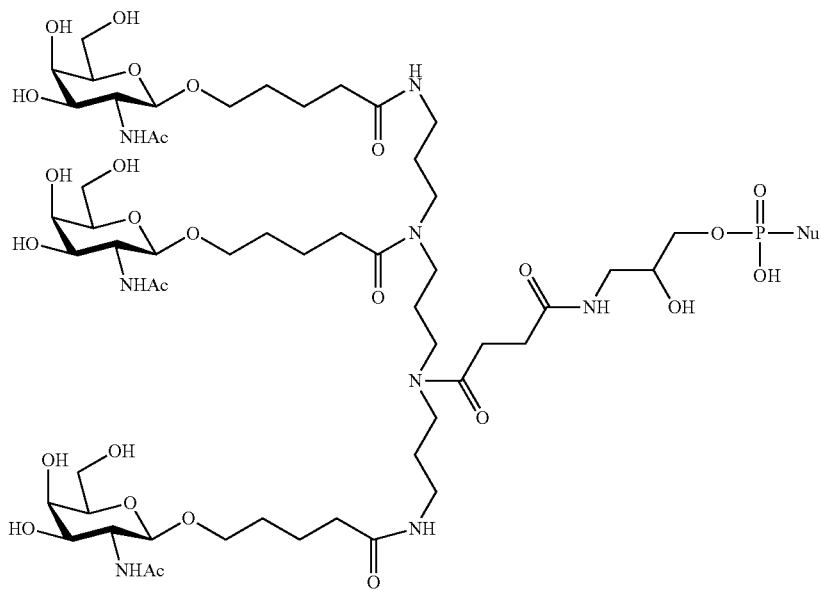
Formula (413)
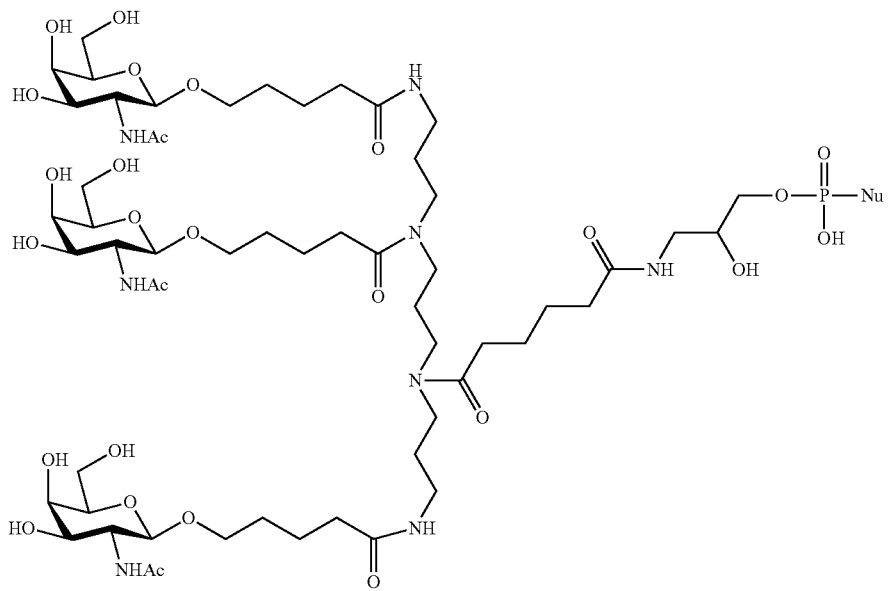

-continued
Formula (414)
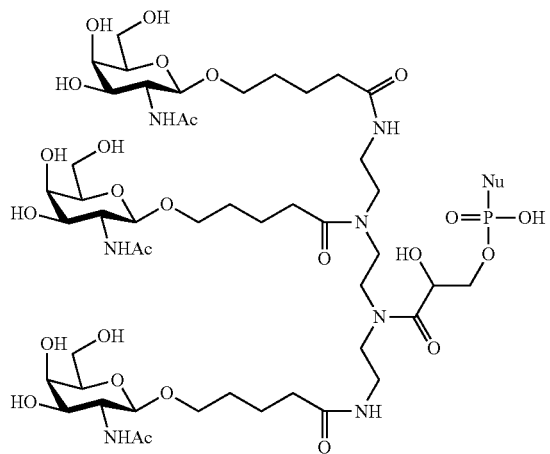
Formula (415)
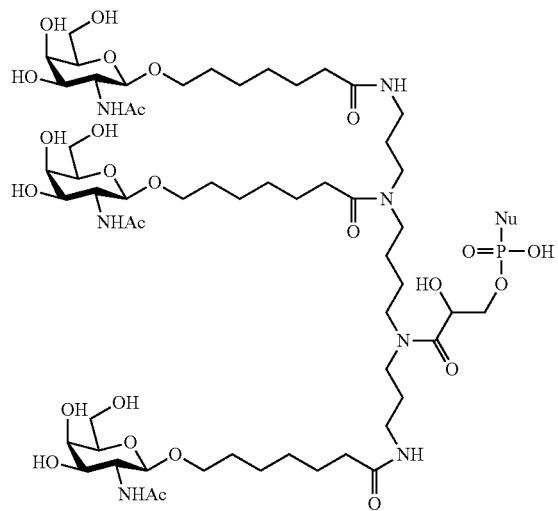
Formula (416)
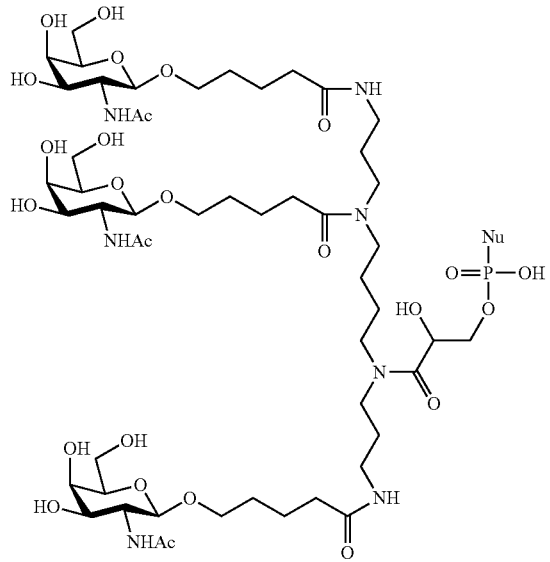
Formula (417)
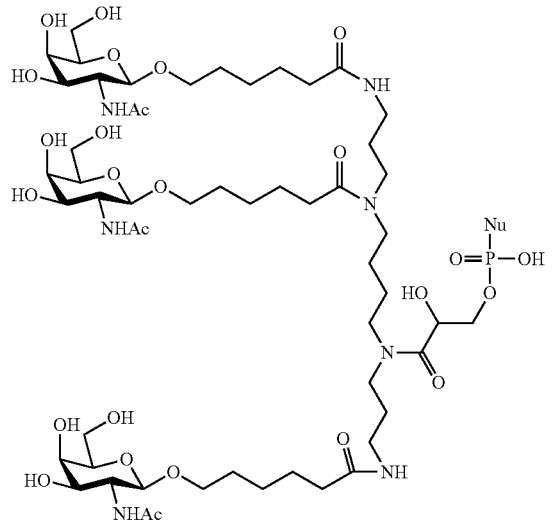
Formula (418)
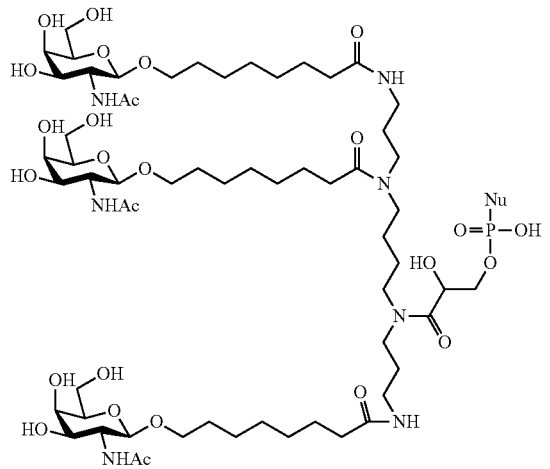
Formula (419)
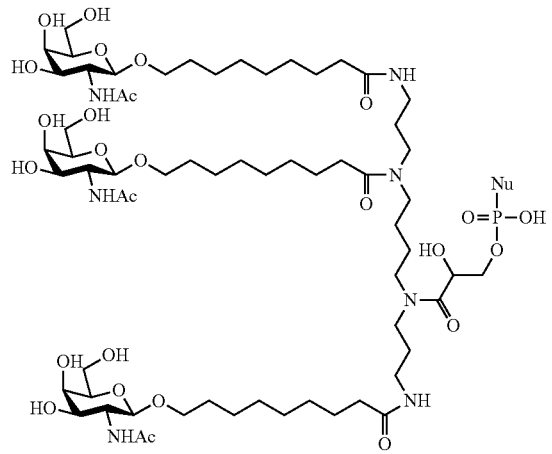

Formula (420)

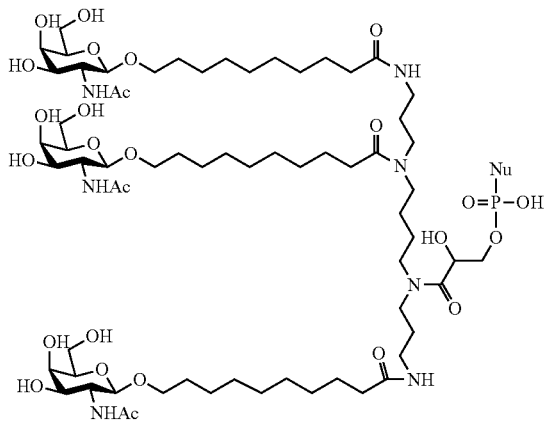

Formula (421)

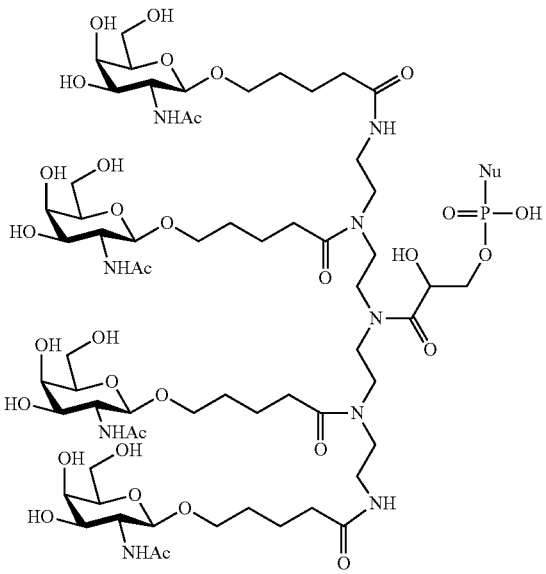

Formula (422)

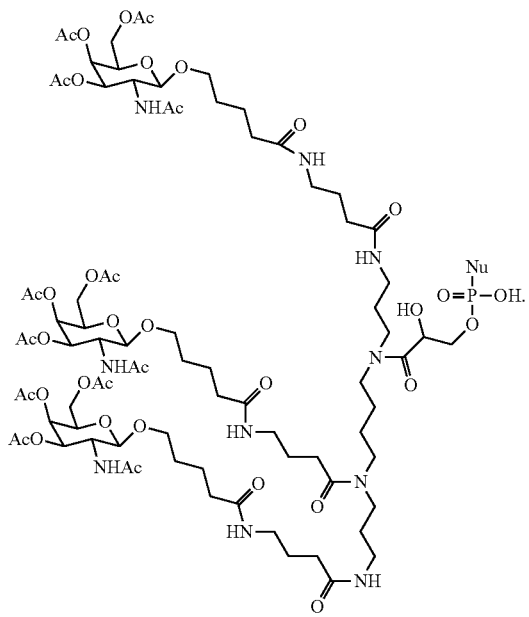

In some embodiments, the P atom in Formula A59 may be linked to any possible position in the siRNA sequence, for example, to any nucleotide in the sense strand or the antisense strand of the siRNA; in some embodiments, the P atom in the Formula A59 is linked to any nucleotide in the sense strand of siRNA. In some embodiments, the P atom in Formula A59 is linked to a terminal of the sense strand or the antisense strand of the siRNA; in some embodiments, the P atom in the A59 is linked to a terminal of the sense strand of the siRNA. The terminal refers to the first 4 nucleotides counted from a terminal of the sense strand or the antisense strand. In some embodiments, the P atom in Formula A59 is linked to a terminal of the sense strand or the antisense strand of siRNA; in some embodiments, the P atom in Formula A59 is linked to the 3' terminal of the sense strand of the siRNA. In the case where the P atom in Formula A59 is linked to the above position in the sense strand of the siRNA, after entering into cells, the siRNA conjugate represented by Formula (308) can release a separate antisense strand of the siRNA during unwinding thereby blocking the translation of ANGPTL3 mRNA into a protein and inhibiting the expression of ANGPTL3 gene.

In some embodiments, the P atom in Formula A59 may be linked to any possible position of the nucleotide in the siRNA, for example, to position 5', 2' or 3', or to the base of the nucleotide. In some embodiments, the P atom in Formula A59 may be linked to position 5', 2' or 3' of the nucleotide in the siRNA by forming a phosphodiester bond. In some embodiments, the P atom in Formula A59 is linked to an oxygen atom formed by dehydrogenation of 3'-hydroxy of the nucleotide at 3' terminal of the sense strand of siRNA, or linked to a nucleotide by substituting a hydrogen atom in 2'-hydroxy of a nucleotide of the sense strand of the siRNA, or linked to a nucleotide by substituting a hydrogen atom in 5'-hydroxy of the nucleotide at 5' terminal of the nucleotide in the sense strand of the siRNA.

The inventors of the present disclosure have unexpectedly discovered that the siRNA conjugate of the present disclosure exhibits a significantly improved plasma stability, low off-target effect without significantly reduced ANGPTL3 mRNA silencing activity, and relatively high effect in inhibiting blood lipid. Thus, in some embodiments, the siRNA in the siRNA conjugate of the present disclosure may be one of siAN1, siAN2, siAN1-M1, siAN2-M1, siAN1-M2, siAN2-M2, siAN1-M3, siAN2-M3, siAN1-M1 S, siAN2-M1 S, siAN1-M2 S, siAN2-M2S, siAN1-M3 S, siAN2-M3 S, siAN1-M1P1, siAN2-M1P1, siAN1-M2P1, siAN2-M2P1, siAN1-M3P1, siAN2-M3P1, siAN1-M1 SP1, siAN2-M1 SP1, siAN1-M2 SP1, siAN2-M2 SP1, siAN1-M3 SP1, and siAN2-M3 SP1, as shown in Table 1.

TABLE 1 siRNA sequence of the conjugate of the present disclosure

| siRNA NO. | SEQ ID NO: | Sequence Direction 5' - 3' |
|---|---|---|
| siAN1 | 8 | CCAAGAGCACCAAGAACUA |
|  | 9 | UAGUUCUUGGUGCUCUUGGCU |
| siAN2 | 10 | AGCCAAGAGCACCAAGAACUA |
|  | 11 | UAGUUCUUGGUGCUCUUGGCUUG |
| siAN1-M1 | 12 | CmCmAmAmGfAmGfCfAfCmCmAmAmGmAmAmCmUmAm |
|  | 13 | UmAfGmUmUmCfUmUfGfGmUmGmCmUfCmUfUmGmGmCmUm |
| siAN2-M1 | 14 | AmGmCmCmAmAmGfAmGfCfAfCmCmAmAmGmAmAmCmUmAm |
|  | 15 | UmAfGmUmUmCfUmUfGfGmUmGmCmUfCmUfUmGmGmCmUmUmGm |
| siAN1-M2 | 12 | CmCmAmAmGfAmGfCfAfCmCmAmAmGmAmAmCmUmAm |
|  | 16 | UmAfGmUmUmCfUmUmGmGmUmGmCmUfCmUfUmGmGmCmUm |
| siAN2-M2 | 14 | AmGmCmCmAmAmGfAmGfCfAfCmCmAmAmGmAmAmCmUmAm |
|  | 17 | UmAfGmUmUmCfUmUmGmGmUmGmCmUfCmUfUmGmGmCmUmUmGm |
| siAN1-M3 | 18 | CmCmAmAmGmAmGfCfAfCmCmAmAmGmAmAmCmUmAm |
|  | 16 | UmAfGmUmUmCfUmUmGmGmUmGmCmUfCmUfUmGmGmCmUm |
| siAN2-M3 | 19 | AmGmCmCmAmAmGmAmGfCfAfCmCmAmAmGmAmAmCmUmAm |
|  | 17 | UmAfGmUmUmCfUmUmGmGmUmGmCmUfCmUfUmGmGmCmUmUmGm |
| siAN1-M1S | 20 | CmsCmsAmAmGfAmGfCfAfCmCmAmAmGmAmAmCmUmAm |
|  | 21 | UmsAfsGmUmUmCfUmUfGfGmUmGmCmUfCmUfUmGmGmsCmsUm |
| siAN2-M1S | 22 | AmsGmsCmCmAmAmGfAmGfCfAfCmCmAmAmGmAmAmCmUmAm |
|  | 23 | UmsAfsGmUmUmCfUmUfGfGmUmGmCmUfCmUfUmGmGmCmUmsUmsGm |
| siAN1-M2S | 20 | CmsCmsAmAmGfAmGfCfAfCmCmAmAmGmAmAmCmUmAm |
|  | 24 | UmsAfsGmUmUmCfUmUmGmGmUmGmCmUfCmUfUmGmGmsCmsUm |
| siAN2-M2S | 22 | AmsGmsCmCmAmAmGfAmGfCfAfCmCmAmAmGmAmAmCmUmAm |
|  | 25 | UmsAfsGmUmUmCfUmUmGmGmUmGmCmUfCmUfUmGmGmCmUmsUmsGm |
| siAN1-M3S | 26 | CmsCmsAmAmGmAmGfCfAfCmCmAmAmGmAmAmCmUmAm |
|  | 24 | UmsAfsGmUmUmCfUmUmGmGmUmGmCmUfCmUfUmGmGmsCmsUm |
| siAN2-M3S | 27 | AmsGmsCmCmAmAmGmAmGfCfAfCmCmAmAmGmAmAmCmUmAm |
|  | 25 | UmsAfsGmUmUmCfUmUmGmGmUmGmCmUfCmUfUmGmGmCmUmsUmsGm |
| siAN1-M1P1 | 12 | CmCmAmAmGfAmGfCfAfCmCmAmAmGmAmAmCmUmAm |
|  | 28 | P1-UmAfGmUmUmCfUmUfGfGmUmGmCmUfCmUfUmGmGmCmUm |
| siAN2-M1P1 | 14 | AmGmCmCmAmAmGfAmGfCfAfCmCmAmAmGmAmAmCmUmAm |
|  | 29 | P1-UmAfGmUmUmCfUmUfGfGmUmGmCmUfCmUfUmGmGmCmUmUmGm |
| siAN1-M2P1 | 12 | CmCmAmAmGfAmGfCfAfCmCmAmAmGmAmAmCmUmAm |
|  | 30 | P1-UmAfGmUmUmCfUmUmGmGmUmGmCmUfCmUfUmGmGmCmUm |
| siAN1-M2P1 | 14 | AmGmCmCmAmAmGfAmGfCfAfCmCmAmAmGmAmAmCmUmAm |
|  | 31 | P1-UmAfGmUmUmCfUmUmGmGmUmGmCmUfCmUfUmGmGmCmUmUmGm |
| siAN2-M3P1 | 18 | CmCmAmAmGmAmGfCfAfCmCmAmAmGmAmAmCmUmAm |
|  | 30 | P1-UmAfGmUmUmCfUmUmGmGmUmGmCmUfCmUfUmGmGmCmUm |
| siAN2-M3P1 | 19 | AmGmCmCmAmAmGmAmGfCfAfCmCmAmAmGmAmAmCmUmAm |
|  | 31 | P1-UmAfGmUmUmCfUmUmGmGmUmGmCmUfCmUfUmGmGmCmUmUmGm |
| siAN1-M1SP1 | 20 | CmsCmsAmAmGfAmGfCfAfCmCmAmAmGmAmAmCmUmAm |
|  | 32 | P1-UmsAfsGmUmUmCfUmUfGfGmUmGmCmUfCmUfUmGmGmsCmsUm |
| siAN2-M1SP1 | 22 | AmsGmsCmCmAmAmGfAmGfCfAfCmCmAmAmGmAmAmCmUmAm |
|  | 33 | P1-UmsAfsGmUmUmCfUmUfGfGmUmGmCmUfCmUfUmGmGmCmUmsUmsGm |
| siAN1-M2SP1 | 20 | CmsCmsAmAmGfAmGfCfAfCmCmAmAmGmAmAmCmUmAm |
|  | 34 | P1-UmsAfsGmUmUmCfUmUmGmGmUmGmCmUfCmUfUmGmGmsCmsUm |
| siAN2-M2SP1 | 22 | AmsGmsCmCmAmAmGfAmGfCfAfCmCmAmAmGmAmAmCmUmAm |
|  | 35 | P1-UmsAfsGmUmUmCfUmUmGmGmUmGmCmUfCmUfUmGmGmCmUmsUmsGm |
| siAN1-M3SP1 | 26 | CmsCmsAmAmGmAmGfCfAfCmCmAmAmGmAmAmCmUmAm |
|  | 34 | P1-UmsAfsGmUmUmCfUmUmGmGmUmGmCmUfCmUfUmGmGmsCmsUm |

TABLE 1-continued siRNA sequence of the conjugate of the present disclosure

| siRNA NO. | SEQ ID NO: | Sequence Direction 5' - 3' |
|---|---|---|
| siAN2-M3SP1 | 27 | AmsGmsCmCmAmAmGmAmGfCfAfCmCmAm AmGmAmAmCmUmAm |
|  | 35 | P1-UmsAfsGmUmUmCfUmUmGmGmUmGmCm UfCmUfUmGmGmCmUmsUmsGm |

In the siRNA or siRNA conjugate of the present disclosure, each pair of adjacent nucleotides are linked by a phosphodiester bond or a phosphorothioate diester bond. The non-bridging oxygen or sulfur atom in the phosphodiester bond or a phosphorothioate diester bond has negative charges, and may be present in the form of hydroxy or sulfydryl. Moreover, the hydrogen ion in the hydroxy or sulfydryl may be partially or completely replaced with a cation. The cation may be any cation, such as one of a metal cation, an ammonium cation $NH_4^+$ or an organic ammonium cation. In order to increase solubility, in one embodiment, the cation is selected from one or more of alkali metal cation, an ammonium cation formed by a tertiary amine or a quaternary ammonium cation. The alkali metal ion may be $K^+$ and/or $Na^+$, and the cation formed by a tertiary amine may be ammonium cation formed by triethylamine and/or N,N-diisopropylethylamine. Thus, the siRNA or the siRNA conjugate of the present disclosure may be at least partially present in the form of salt. In one embodiments, the non-bridging oxygen or sulfur atom in the phosphodiester bond or a phosphorothioate diester bond at least partly binds to sodium ion. The siRNA or the siRNA conjugate of the present disclosure is present or partially present in the form of sodium salt.

It is well known to those skilled in the art that a modified nucleotide group may be introduced into the siRNA of the present disclosure by a nucleoside monomer with a corresponding modification. Methods for preparing a nucleoside monomer having a corresponding modification and for introducing a modified nucleotide group into a siRNA are also well known to those skilled in the art. All modified nucleoside monomers may be either commercially available or prepared by known methods.

Preparation of the siRNA Conjugate Represented by Formula (308)

The siRNA conjugate represented by Formula (308) may be prepared by any appropriate synthetic routes.

In some embodiments, the siRNA conjugate represented by Formula (308) may be prepared by a method which comprises successively linking nucleoside monomers in 3' to 5' direction according to the nucleotide type and sequence of the sense strand and the antisense strand of the siRNA, under a condition of phosphoramidite solid phase synthesis, wherein the linking of each nucleoside monomer includes a four-step reaction of deprotection, coupling, capping, and oxidation or sulfurization; isolating the sense strand and antisense strand of the siRNA; and annealing; wherein the siRNA is the siRNA of the present disclosure are described as above;

and, wherein the method further comprises contacting the compound represented by Formula (321) with a nucleoside monomer or a nucleotide sequence linked to a solid phase support under a coupling reaction condition in the presence of a coupling reagent, thereby linking the compound represented by Formula (321) to the nucleotide sequence via a coupling reaction. In the following text, the compound represented by Formula (321) is also referred to as a conjugating molecule.

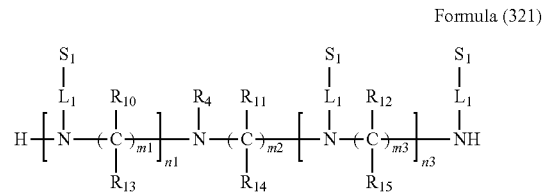

Formula (321)

wherein:

$R_4$ is a moiety capable of binding to the siRNA represented by Nu. In some embodiments, $R_4$ is a moiety capable of binding to the siRNA represented by Nu via a covalent bond. In some embodiments, $R_4$ is a moiety capable of being conjugated to any functional group of siRNA represented by Nu via a phosphodiester bond by a reaction;

each $S_1$ is independently a group formed by replacing all the active hydroxyl groups in $M_1$ with YCOO— group, wherein each Y is independently one selected from the group consisting of methyl, trifluoromethyl, difluoromethyl, monofluoromethyl, trichloromethyl, dichloromethyl, monochloromethyl, ethyl, n-propyl, isopropyl, phenyl, halophenyl and alkylphenyl; in some embodiments, Y is methyl;

the definitions and options of n1, n3, m1, m2, m3, $R_{10}$, $R_{11}$, $R_{12}$, $R_{13}$, $R_{14}$, $R_{15}$, $L_1$, and $M_1$ are respectively described as above.

$R_4$ is selected to achieve the linkage to N on the nitrogenous backbone, and to provide a appropriate reaction site for the synthesis of the siRNA conjugate represented by Formula (308). In some embodiments, $R_4$ comprises a $R_2$ linking group or a protected $R_2$ linking group, and functional group(s) that can form the structure represented by Formula A59 with siRNA via reaction.

In some embodiments, $R_4$ comprises a first functional group that can react with a group on the siRNA represented by Nu or the nucleoside monomer to form a phosphite ester, and a second functional group that can react with hydroxy or amino to form a covalent bond, or comprises a solid phase support linked by a covalent bond.

In some embodiments, the first functional group is a phosphoramidite, a hydroxy or a protected hydroxy. In some embodiments, the second functional group is a phosphoramidite, a carboxylic acid or a carboxylate salt. In some embodiments, the second functional group is a solid phase support linked to the rest of the molecule via a covalent bond, wherein the covalent bond is formed by hydroxy or amino. In some embodiments, the solid phase support is linked via a phosphoester bond, a carboxyl ester bond, or an amide bond. In some embodiments, the solid phase support is a resin.

In some embodiments, the first functional group comprises hydroxy, —$OR_k$ or a group represented by Formula (C3); and/or the second functional group has a structure represented by Formula (C1), (C2), (C3), (C1'), or (C3'):

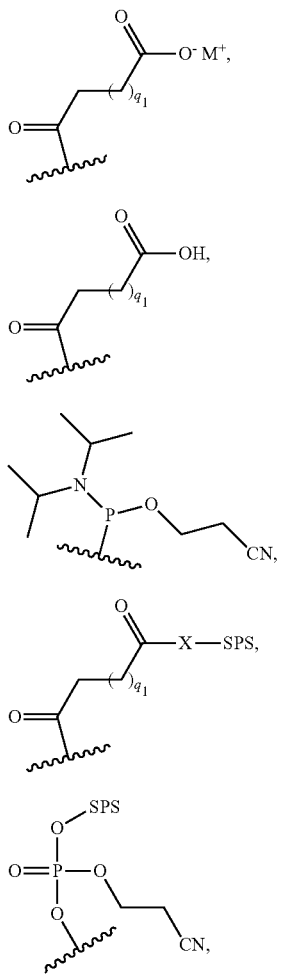

wherein $q_1$ is an integer of 1-4, X is O or NH, $M^+$ is a cation, $R_k$ is a hydroxyl protecting group, SPS represents a solid phase support, and ∼∼∼ represents the site where the group is linked to the rest of the molecule.

In some embodiments, the first functional group comprises a phosphoramidite group, such as the group represented by Formula (C3). The phosphoramidite group can form a phosphite ester with a hydroxy at any position (such as a 2'- or 3'-hydroxyl) on a nucleotide by a coupling reaction, and the phosphite ester can form a phosphodiester bond or a phosphorothioate bond represented by Formula A59 via oxydation or sulfuration, so as to conjugate the conjugating molecule to siRNA. Thus, even if the second functional group is not present, the compound represented by Formula (321) will be able to be conjugated with the nucleotide, while not affecting the acquisition of the siRNA conjugate represented by Formula (308). Under such circumstances, after obtaining a sense strand or an antisense strand of the siRNA via a method such as phosphoramidite solid phase synthesis, the compound of Formula (321) reacts with the hydroxy on the nucleotide at the terminal of the nucleotide sequence, and a phosphodiester bond linkage or thiophosphoester bond linkage is formed in the following oxydization or sulfurization process, so as to conjugate the compound of Formula (321) to the siRNA.

In some embodiments, the first functional group comprises a protected hydroxy. In some embodiments, the second functional group comprises a group that can react with a solid phase support to provide a conjugating molecule comprising a solid phase support. In some embodiments, the second functional group comprises a carboxyl, a carboxylate salt or a phosphoramidite, such as represented by Formula (C1), (C2) or (C3). When the second functional group comprises a carboxyl or a carboxylate salt, the compound of Formula (321) can react via an esterification or an amidation with a hydroxy or an amino group on a solid phase support, such as a resin, to form a conjugating molecule comprising a solid phase support linked via a carboxylate ester bond. When the second functional group comprises a phosphoramidite functional group, the compound of Formula (321) can couple with a hydroxy group on a universal solid phase support, such as a resin, and form a conjugating molecule comprising a solid phase support linked via a phosphodiester bond by subsequent oxidation. Next, starting from the above product linked to a solid phase support, the nucleoside monomers are successively linked according to the phosphoramidite solid phase synthesis, so as to obtain a sense strand or an antisense strand of the siRNA linked to a conjugating group. In the process of phosphoramidite solid phase synthesis, the first functional group is deprotected, and then coupled with a phosphoramidite group on a nucleoside monomer under a coupling condition.

In some embodiments, the first functional group comprises a hydroxy or a protected hydroxy group; the second functional group comprises a solid phase support linked via a carboxylate ester bond, an amide bond, or a phosphodiester bond, as represented by Formula (C1') or (C3'). Thus, starting from the compound of Formula (321) instead of a solid phase support, the nucleoside monomers are successively linked according to the phosphoramidite solid phase synthesis, so as to obtain a sense strand or an antisense strand of the siRNA linked to a conjugating group.

In some embodiments, the carboxylate may be represented by $—COO^-M^+$, wherein $M^+$ is a cation such as one of a metal cation, an ammonium cation NH' and an organic ammonium cation. In some embodiments, the metal cation may be an alkali metal cation, such as $K^+$ or $Na^+$. In order to increase solubility and facilitate the reaction, in some embodiments, the organic ammonium cation is an ammonium cation formed by a tertiary amine or a quaternary ammonium cation, such as an ammonium cation formed by triethylamine or N,N-diisopropylethylamine. In some embodiments, the carboxylate is a triethylamine carboxylate or an N,N-diisopropylethylamine carboxylate.

In some embodiments, $R_4$ has the structure represented by (B9), (B10), (B9'), (B10'), (B11), (B12), (B11') or B(12'):

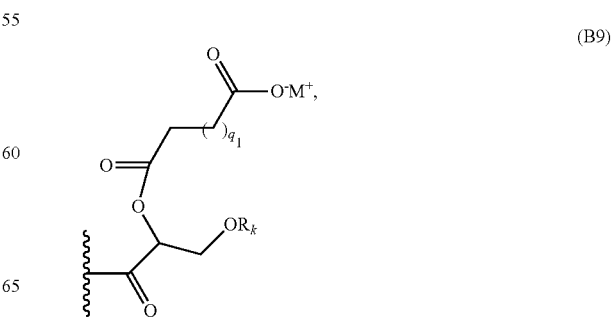

(B10)
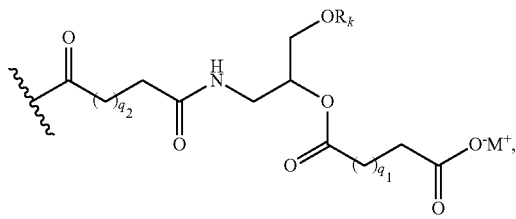

(B9')
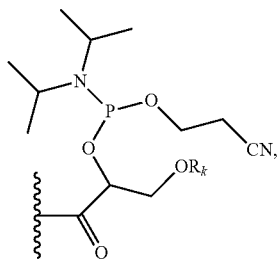

(B10')
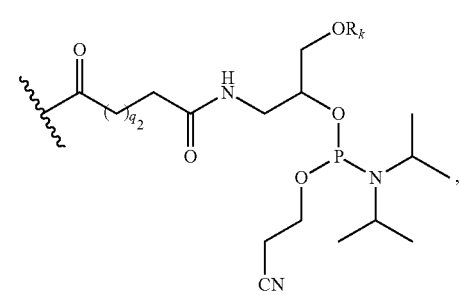

(B11)
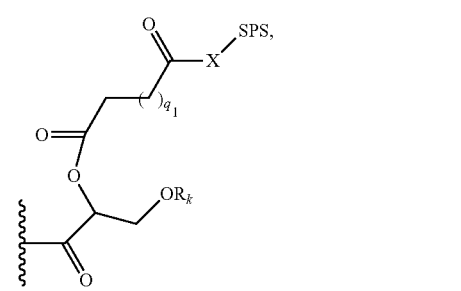

(B12)
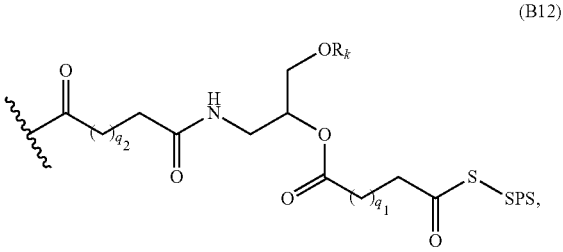

(B11')
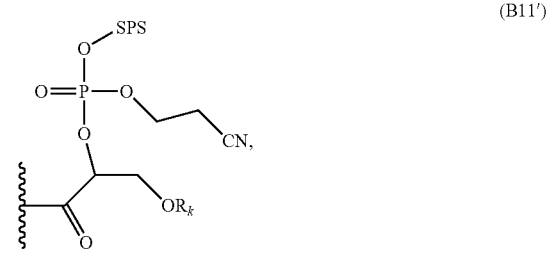

(B12')
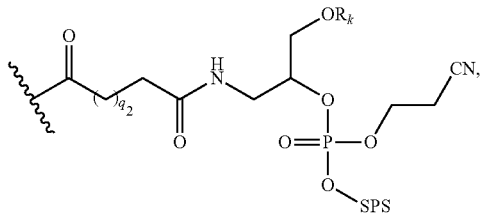

wherein $q_1$ is an integer of 1-4, $q_2$ is an integer of 1-10, X is O or NH, $M^+$ is a cation, $R_k$ is a hydroxy protecting group, SPS represents a solid phase support, and ∿∿∿ represents the site where the group is linked to the rest of the molecule. In some embodiments, $q_1$ is 1 or 2. In some embodiments, $q_2$ is an integer of 1-5. In some embodiments, $R_4$ comprises a structure represented by Formula (B9) or (B10). In some embodiments, $R_4$ comprises a group represented by Formula (B11) or (B12). In some embodiments, $R_k$ is one or more of Tr (trityl), MMTr (4-methoxytrityl), DMTr (4,4'-dimethoxytrityl), and TMTr (4,4',4''-trimethoxytrityl). In some embodiments, $R_k$ may be DMTr, i.e. 4,4'-dimethoxytrityl.

$L_1$ is defined as above.

In some embodiments, $L_1$ is used to link the $M_1$ targeting group to the N atom on the nitrogenous backbone, thereby providing liver targeting function for the siRNA conjugate represented by Formula (308). In some embodiments, $L_1$ comprises any one of Formulae A1-A26, and any combination thereof.

It will be readily understood by those skilled in the art that, as compared with the phosphoramidite solid phase synthesis method well-known in the art, the siRNA conjugate represented by Formula (308) in which the conjugating molecule is linked to any possible position of the nucleotide sequence can be obtained by using the first functional group and optional second functional group. For example, the conjugating molecule is linked to a terminal of the nucleotide sequence, and the conjugating molecule is linked to either terminal of the nucleotide sequence. Correspondingly, unless otherwise indicated, in the following description regarding conjugation preparation, when the reactions such as "deprotection", "coupling", "capping", "oxidation" and "sulfurization" are mentioned, it should be understood that the reaction conditions and agents involved in the phosphoramidite nucleotide solid phase synthesis well-known in the art would also apply to these reactions. Exemplary reaction conditions and agents would be detailed in the following text.

In some embodiments, each $S_1$ is independently a $M_1$. In some embodiments, each $S_1$ is independently a group formed by protecting at least one active hydroxyl group in $M_1$ with a hydroxyl protecting group. In some embodiments, each $S_1$ is independently a group formed by protecting all active hydroxyl groups in $M_1$ with hydroxyl protecting groups. In some embodiments, any hydroxyl protecting group known to a skilled one may be used to protect the active hydroxyl group in $M_1$. In some embodiments, the protected hydroxy is represented by the formula YCOO—, wherein each Y is independently selected from the group consisting of $C_1$-$C_{10}$ alkyl and $C_6$-$C_{10}$ aryl, which is optionally substituted with one or more substituents selected from the group consisting of halo and $C_1$-$C_6$ alkyl. In some embodiments, each Y is independently selected from the group consisting of methyl, trifluoromethyl, difluoromethyl, monofluoromethyl, trichloromethyl, dichloromethyl, monochloromethyl, ethyl, n-propyl, isopropyl, phenyl, halophenyl, and $C_1$-$C_6$ alkylphenyl.

In some embodiments, each $S_1$ is independently selected from the group consisting of Formulae A46-A54:

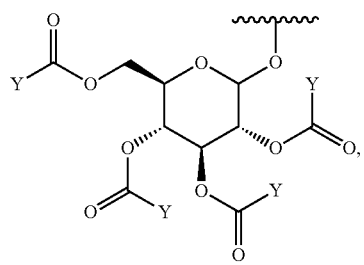
(A46)

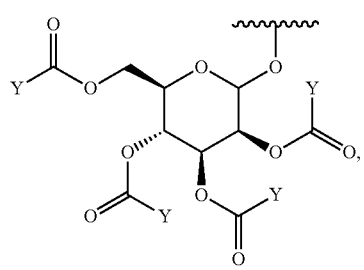
(A47)

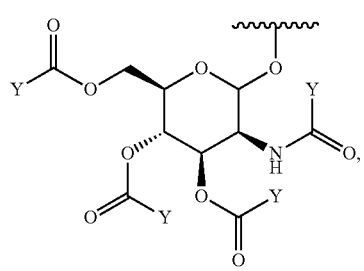
(A48)

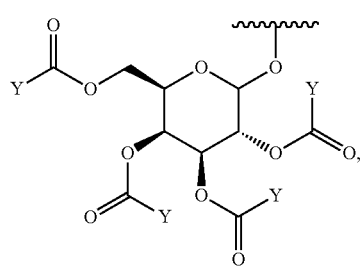
(A49)

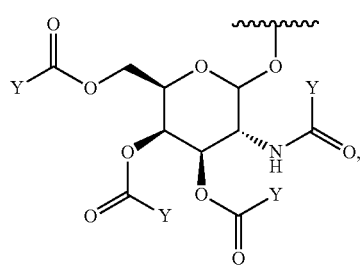
(A50)

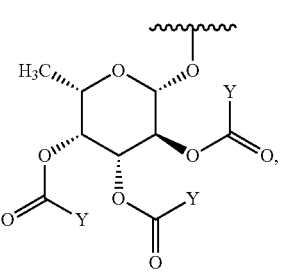
(A51)

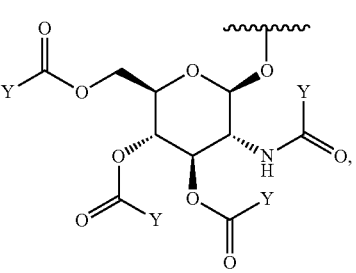
(A52)

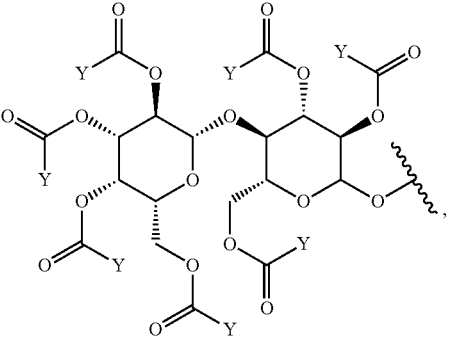
(A53)

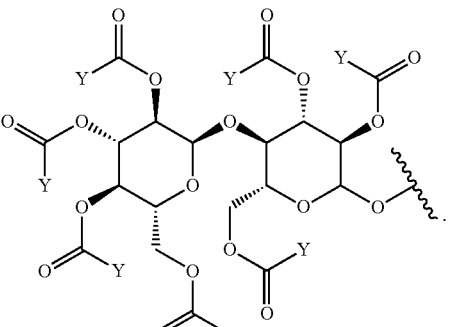
(A54)

In some embodiments, $S_1$ is A49 or A50.

In some embodiments, each Y is independently selected from one of methyl, trifluoromethyl, difluoromethyl, monofluoromethyl, trichloromethyl, dichloromethyl, monochloromethyl, ethyl, n-propyl, isopropyl, phenyl, halophenyl, and alkylphenyl. In some embodiments, Y is methyl.

As mentioned above, the method for preparing the siRNA conjugate represented by Formula (308) further comprises the following steps: synthesizing the other strand of the siRNA (for example, when a sense strand of the siRNA linked to a conjugating molecule is synthesized in the above step, the method further comprises synthesizing an antisense strand of the siRNA according to the solid phase synthesis method, vice versa), isolating the sense strand and the antisense strand, and annealing. In particular, in the step of isolating, the solid phase support linked to the nucleotide sequence and/or a conjugating molecule is cleaved, and meanwhile the necessary protecting group is removed (in this case, each S1 group in the compound of Formula (321) is converted to the corresponding $M_1$ targeting group), to afford a sense strand (or an antisense strand) of the siRNA linked to a conjugating molecule and the corresponding antisense strand (or sense strand), wherein the sense strand and the antisense strand are annealed to form a double-strand RNA structure, thereby affording the siRNA conjugate represented by Formula (308).

In some embodiments, the method for preparing the siRNA conjugate represented by Formula (308) comprises the following steps: contacting the compound represented by Formula (321) with the first nucleoside monomer at 3' terminal of the sense strand or the antisense strand under a coupling reaction condition in the presence of a coupling reagent, thereby linking the compound represented by Formula (321) to the first nucleotide in the sequence; successively linking nucleoside monomers in 3' to 5' direction to synthesize a sense or antisense strand of siRNA under the phosphoramidite solid phase synthesis conditions according to the kind and sequence of nucleotides in the desired sense or antisense strand, wherein, the compound of Formula (321) is a compound in which $R_4$ comprises a first functional group that comprises a protected hydroxy and a second functional group having the structure represented by Formula (C1') or (C3'), and the compound of (321) is deprotected before being linked to the first nucleoside monomer, and the linking of each nucleoside monomer comprising a four-step reaction of deprotection, coupling, capping, and oxidation or sulfurization, thus obtaining a sense or antisense strand of nucleotide linked to a conjugating group; successively linking nucleoside monomers in 3' to 5' direction to synthesize the antisense or sense strand of the nucleotide under the phosphoramidite solid phase synthesis conditions according to the kind and sequence of nucleotides in the sense or antisense strand, wherein the linking of each nucleoside monomer includes a four-step reaction of deprotection, coupling, capping, and oxidation or sulfurization; removing the protecting groups and cleaving the solid phase support; obtaining the sense strand and the antisense strand of nucleotide via isolation and purification; and annealing.

In some embodiments, the method for preparing the siRNA conjugate represented by Formula (308) comprises the following steps: successively linking nucleoside monomers in 3' to 5' direction to synthesize the antisense and sense strand according to the kind and sequence of nucleotides in the sense or antisense strand of the double-strand siRNA, wherein the linking of each nucleoside monomer includes a four-step reaction of deprotection, coupling, capping, and oxidation or sulfurization, to obtain the sense strand linked to the solid phase support and the antisense strand linked to the solid phase support; contacting the compound represented by Formula (321) with the sense strand linked to the solid phase support or the antisense strand linked to the solid phase support under a coupling reaction condition in the presence of a coupling reagent, so as to link the compound represented by Formula (321) to the sense strand or antisense strand, wherein the compound represented by Formula (321) is a compound in which $R_4$ comprises a first functional group that is a phosphoramidite group; removing the protecting group and cleaving the solid phase support; obtaining the sense strand or the antisense strand of the siRNA via isolation and purification; and annealing, wherein the sense or antisense strand of the siRNA is linked to a conjugating group.

In some embodiments, the P atom in the Formula A59 is linked to the 3' terminal of the sense strand in the siRNA, and the method for preparing the siRNA conjugate as represented by Formula (308) comprises:

(1) removing the hydroxyl protecting group $P_k$ in the compound of Formula (321) (wherein, the compound of Formula (321) is a compound wherein $R_4$ comprises a first functional group comprising a protected hydroxyl $OR_k$, and a second functional group having the structure represented by Formulas (C1') or (C3')); contacting the deprotected product with a nucleoside monomer to obtain a nucleoside monomer linked to a solid phase support via a conjugating molecule under a coupling reaction condition in the presence of a coupling reagent;

(2) synthesizing a sense strand of the siRNA in 3' to 5' direction by a phosphoramidite solid phase synthesis method, starting from the nucleoside monomer linked to a solid phase support via the conjugating molecule; and (3) synthesizing an antisense strand of the siRNA by a phosphoramidite solid phase synthesis method; and (4) isolating the sense strand and the antisense strand of the siRNA and annealing the same to obtain the siRNA conjugate represented by the Formula (308).

In particular, in step (1), the method for removing the protecting group $R_k$ in the compound represented by Formula (321) comprises contacting the compound of Formula (321) with a deprotection agent under a deprotection condition. The deprotection condition comprises a temperature of 0-50° C., and in some embodiments of 15-35° C., and a reaction time of 30-300 seconds, and in some embodiments of 50-150 seconds. The deprotection agent may be selected from one or more of trifluoroacetic acid, trichloroacetic acid, dichloroacetic acid, and monochloroacetic acid, and in some embodiments is dichloroacetic acid. The molar ratio of the deprotection agent to the compound represented by Formula (321) is 10:1 to 1000:1, and in some embodiments is 50:1 to 500:1.

The coupling reaction condition and the coupling agent may be any conditions and agents appropriate for the above coupling reaction. In some embodiments, the same condition and agent as the coupling reaction in the solid phase synthesis method employed can be used.

In some embodiments, the coupling reaction condition comprises a reaction temperature of 0-50° C., and in some embodiments, 15-35° C. The molar ratio of the compound of Formula (321) to the nucleoside monomer may be 1:1 to 1:50, and in some embodiments is 1:2 to 1:5. The molar ratio of the compound of Formula (321) to the coupling agent may be 1:1 to 1:50, and in some embodiments is 1:3 to 1:10. The reaction time may be 200-3000 seconds, and in some embodiments is 500-1500 seconds. The coupling agent may be selected from one or more of 1H-tetrazole, 5-ethylthio-1H-tetrazole and 5-benzylthio-1H-tetrazole, and in some embodiments is 5-ethylthio-1H-tetrazole. The coupling reaction may be performed in an organic solvent. The organic solvent may be selected from one or more of anhydrous acetonitrile, anhydrous DMF and anhydrous dichloromethane, and in some embodiments is anhydrous acetonitrile. The amount of the organic solvent may be 3-50 L/mol, and in some embodiments is 5-20 L/mol with respect to the compound represented by Formula (321).

In step (2), a sense strand S of the second siRNA conjugate is synthesized in 3' to 5' direction by the phosphoramidite solid phase synthesis method, starting from the nucleoside monomer linked to a solid phase support via a conjugating molecule prepared in the above steps. In this case, the conjugating group is linked to the 3' terminal of the resulting sense strand.

Other conditions for solid phase synthesis described in steps (2) and (3), including the deprotection condition for the nucleoside monomer, type and amount of the deprotection agent, the coupling reaction condition, type and amount of the coupling agent, the capping reaction condition, type and amount of the capping agent, the oxidation reaction condition, type and amount of the oxidation agent, the sulfuration reaction condition, and type and amount of the sulfuration agent, are various agents, amounts, and conditions conventionally used in the art.

In some embodiments, for example, the solid phase synthesis described in steps (2) and (3) may be performed by using the following conditions:

The deprotection condition for the nucleoside monomer comprises a temperature of 0-50° C., and in some embodiments, 15-35° C., and a reaction time of 30-300 seconds, and in some embodiments, 50-150 seconds. The deprotection agent may be selected from one or more of trifluoroacetic acid, trichloroacetic acid, dichloroacetic acid, and monochloroacetic acid, and in some embodiments is dichloroacetic acid. The molar ratio of the deprotection agent to the protecting group 4,4'-dimethoxytrityl on the solid phase support may be 2:1 to 100:1, and in some embodiments is 3:1 to 50:1.

The coupling reaction condition comprises a temperature of 0-50° C., and in some embodiments, 15-35° C. The molar ratio of the nucleic acid sequence linked to the solid phase support to the nucleoside monomer may be 1:1 to 1:50, and in some embodiments is 1:5 to 1:15. The molar ratio of the nucleic acid sequence linked to the solid phase support to the coupling agent may be 1:1 to 1:100, and in some embodiments is 1:50 to 1:80. The reaction time and the coupling agent are selected as above.

The capping reaction condition comprises a temperature of 0-50° C., and in some embodiments, 15-35° C., and a reaction time of 5-500 seconds, and in some embodiments, 10-100 seconds. The capping agent is selected as above. The molar ratio of the total amount of the capping agent to the nucleic acid sequence linked to the solid phase support is 1:100 to 100:1, and in some embodiments is 1:10 to 10:1. In the case where equimolar acetic anhydride and N-methylimidazole are used as a capping agent, the molar ratio of acetic anhydride, N-methylimidazole, and the nucleic acid sequence linked to the solid phase support is 1:1:10-10:10:1, and in some embodiments is 1:1:2-2:2:1.

The oxidation reaction condition comprises a temperature of 0-50° C., and in some embodiments 15-35° C., and a reaction time of 1-100 seconds, and in some embodiments, 5-50 seconds. In some embodiments, the oxidation agent is iodine (and in some embodiments provided as iodine water). The molar ratio of the oxidation agent to the nucleic acid sequence linked to the solid phase support in the coupling step may be 1:1 to 100:1, and in some embodiments is 5:1 to 50:1. In some embodiments, the oxidation reaction is performed in a mixed solvent of tetrahydrofuran:water:pyridine=3:1:1-1:1:3. The sulfuration reaction condition comprises a temperature of 0-50° C., and in some embodiments, 15-35° C., and a reaction time of 50-2000 seconds, and in some embodiments, 100-1000 seconds. In some embodiments, the sulfuration agent is xanthane hydride. The molar ratio of the sulfuration agent to the nucleic acid sequence linked to the solid phase support in the coupling step is 10:1 to 1000:1, and in some embodiments is 10:1 to 500:1. In some embodiments, the sulfuration reaction is performed in a mixed solvent of acetonitrile:pyridine=1:3-3:1.

The method further comprises isolating the sense strand and the antisense strand of the siRNA after linking all nucleoside monomers and before the annealing. Methods for isolation are well known to those skilled in the art and generally comprise cleaving the synthesized nucleotide sequence from the solid phase support, removing the protecting groups on the bases, phosphate groups and ligands, purifying and desalting. The synthesized nucleotide sequence may be cleaved from the solid phase support, and the protecting groups on the bases, phosphate groups and ligands are removed, according to conventional cleavage and deprotection methods in the synthesis of siRNA. For example, the resulting nucleotide sequence linked to the solid phase support is contacted with concentrated aqueous ammonia; during deprotection, the protecting group YCOO— in groups A46-A54 is converted to a hydroxyl group, thus the $S_1$ groups are converted to corresponding $M_1$ groups, providing the conjugate represented by Formula (308). Here, the concentrated aqueous ammonia may be aqueous ammonia of a concentration of 25-30% by weight. The amount of the concentrated aqueous ammonia may be 0.2 ml/μmol-0.8 ml/μmol with respect to the target siRNA sequence.

When there is at least one 2'-TBDMS protection on the synthesized nucleotide sequence, the method further comprises contacting the nucleotide sequence removed from the solid phase support with triethylamine trihydrofluoride to remove the 2'-TBDMS protection. Here, the resulting target siRNA sequence comprises the corresponding nucleoside having a free 2'-hydroxy. The amount of pure triethylamine trihydrofluoride with respect to the target siRNA sequence may be 0.4 ml/μmol-1.0 ml/μmol. As such, the siRNA conjugate represented by Formula (308) may be obtained.

Methods for purification and desalting are well known to those skilled in the art. For example, nucleic acid purification may be performed by using a preparative ion chromatography purification column with a gradient elution of NaBr or NaCl; after collection and combination of the product, a reversed phase chromatography purification column may be used for desalting.

In the resulting siRNA conjugate represented by Formula (308), the non-bridging oxygen atom or sulfur atom in the phosphodiester bond or thiophosphate diester bond between the nucleotides substantially binds to a sodium ion, and the siRNA conjugate represented by Formula (308) is substantially present in the form of a sodium salt. Other forms of the siRNA conjugate represented by Formula (308) may be obtained by using a well-known ion exchange method in which said sodium ion is replaced with a hydrogen ion and/or another cation. The cation ion is described as above. During synthesis, the purity and molecular weight of the nucleic acid sequence may be determined at any time, in order to control the synthesis quality more conveniently. Such determination methods are well known to those skilled in the art. For example, the purity of the nucleic acid may be determined by ion exchange chromatography, and the molecular weight may be determined by liquid chromatography-mass spectrometry (LC-MS).

Methods for annealing are also well known to those skilled in the art. For example, the synthesized sense strand (S strand) and antisense strand (AS strand) may be simply mixed in water for injection in an equimolar ratio, heated to 70-95° C., and then cooled at room temperature to form a double stranded structure via hydrogen bond. As such, the siRNA conjugate of formula (308) is thus obtained.

After obtaining the conjugate of the present disclosure, in some embodiments, the siRNA conjugate of formula (308) thus synthesized may also be characterized by using a method such as LC-MS by the means such as molecular weight detection, to confirm that the synthesized siRNA conjugate is the siRNA conjugate of formula (308) as a designed target and the synthesized siRNA sequence is the desired siRNA sequence, for example, is one of the sequences listed in Table 1.

The compound represented by Formula (321) is prepared by the following method comprising: contacting a compound represented by Formula (313) with a cyclic anhydride under esterification reaction condition in the presence of a base and an esterification catalyst in an organic solvent; ion exchanging and isolating the compound represented by Formula (321):

Formula (313)

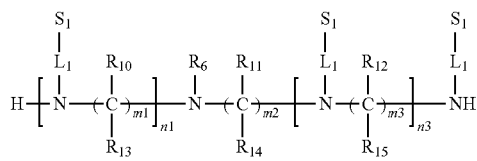

wherein the definitions and options of n1, n3, m1, m2, m3, $R_{10}$, $R_{11}$, $R_{12}$, $R_{13}$, $R_{14}$, $R_{15}$, $L_1$, $S_1$ are respectively described as above;

$R_6$ is a group for providing $R_4$ of Formula (321). In some embodiments, for example, $R_6$ has a structure represented by Formula (A61):

(A61)

wherein, Ri is any group capable of linking to the N atom on the nitrogenous backbone, linking to $R_kO$ and linking to a free hydroxy group; $R_k$ is a hydroxy protecting group. In this case, a compound represented by Formula (321) is obtained, where $R_4$ comprises a first functional group as a hydroxy protecting group and a second functional group having the structure represented by Formula (C1) or (C2). The esterification reaction condition includes a reaction temperature of 0-100° C. and a reaction time of 8-48 hours. In some embodiments, the esterification reaction condition comprises a reaction temperature of 10-40° C. and a reaction time of 20-30 hours.

In some embodiments, the organic solvent comprises one or more of an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran, the ether solvent is diethyl ether and/or methyl tert-butyl ether, and the haloalkane solvent is one or more of dichloromethane, trichloromethane and 1,2-dichloroethane. In some embodiments, the organic solvent is dichloromethane. The amount of the organic solvent is 3-50 L/mol, and in some embodiments, 5-20 L/mol with respect to the compound represented by Formula (313).

In some embodiments, the cyclic anhydride is one of succinic anhydride, glutaric anhydride, adipic anhydride or pimelic anhydride, and in some embodiments is succinic anhydride. The molar ratio of the cyclic anhydride to the compound represented by Formula (313) is 1:1 to 10:1, and in some embodiments is 2:1 to 5:1. The esterification catalyst may be any catalyst capable of catalyzing the esterification, such as 4-dimethylaminopyridine. The molar ratio of the catalyst to the compound represented by Formula (313) is 1:1 to 10:1, and in some embodiments is 2:1 to 5:1. In some embodiments, the base may be any inorganic base, organic base or combination thereof. Considering the solubility as well as the product stability, the base may be, for example, an organic base of tertiary amine. In some embodiments, the organic base of tertiary amine is triethylamine or N,N-diisopropylethylamine. The molar ratio of the tertiary amine to the compound represented by Formula (313) is 1:1 to 20:1, and in some embodiments is 3:1 to 10:1.

The ion exchange serves to convert the compound represented by Formula (321) to a desired form of carboxylic acid or salt thereof. The method of ion exchange is well known to those skilled in the art, and the above conjugating molecule in which the cation is M$^+$ may be obtained by using suitable ion exchange solution and ion exchange condition, which is not described here in detail. In some embodiments, a triethylamine phosphate solution is employed in the ion exchange reaction. The concentration of the triethylamine phosphate solution is 0.2-0.8 M, and in some embodiments is 0.4-0.6 M. In some embodiments, the amount of the triethylamine phosphate solution is 3-6 L/mol, and in further embodiment is 4-5 L/mol with respect to the compound represented by Formula (313).

The compound represented by Formula (321) may be isolated from the reaction mixture using any suitable isolation method. In some embodiments, the compound represented by Formula (321) may be isolated by removal of solvent via evaporation followed by chromatography, for example, using the following two chromatographic conditions for the isolation: (1) normal phase purification of silica gel: 200-300 mesh silica gel filler, with gradient elution of 1 wt ‰ triethylamine-containing dichloromethane:methanol=100:18-100:20; or (2) reverse phase purification: $C_{18}$ and $C_8$ reverse phase filler, with gradient elution of methanol: acetonitrile=0.1:1-1:0.1. In some embodiments, the solvent may be removed directly to obtain a crude product of the compound represented by Formula (321), which may be used directly in subsequent reactions.

In some embodiments, the method for preparing the compound represented by Formula (321) further comprises: further contacting the product obtained from the above ion exchange with a solid phase support with an amino or hydroxy group under a condensation reaction condition in the presence of a condensing agent and an organic base of tertiary amine in an organic solvent. In this case, a compound represented by Formula (321) is obtained, wherein $R_4$ comprises a first functional group containing a hydroxy protecting group and a second functional group having a structure represented by Formula (C1').

The solid phase support is one of the supports used in solid phase synthesis of siRNA, some of which are well known to those skilled in the art. For example, the solid phase support may be selected from solid phase supports having an active hydroxy or amino functional group. In some embodiments, the solid phase support is an amino or hydroxy resin. In some embodiments, the amino or hydroxy resin has a particle size of 100-400 mesh, and surface amino or hydroxy loading of 0.2-0.5 mmol/g. The ratio of the compound represented by Formula (321) to the solid phase support is 10 μmol compound per gram of the solid phase support (μmol/g) to 400 μmol/g. In some embodiments, the ratio of compound of Formula (321) to the solid phase support is 50 μmol/g to 200 μmol/g.

The organic solvent may be any suitable solvent or mixture of solvents known to those skilled in the art. In some embodiments, the organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran, the ether solvent is diethyl ether and/or methyl tert-butyl ether, the haloalkane solvent is one or more of dichloromethane, trichloromethane and 1,2-dichloroethane. In some embodiments, the organic solvent is acetonitrile. The amount of the organic solvent is 20-200 L/mol, in some embodiments is 50-100 L/mol with respect to the compound represented by Formula (321).

In some embodiments, the condensing agent may be benzotriazol-1-yl-oxytripyrrolidinophosphonium hexafluorophosphate, 3-diethoxyphosphoryl-1,2,3-benzotriazol-4(3H)-one and/or O-benzotriazol-tetramethyluronium hexafluorophosphate. In some embodiments, the condensing agent is O-benzotriazol-tetramethyluronium hexafluorophosphate. The molar ratio of the condensing agent to the compound represented by Formula (321) is 1:1 to 20:1, and in further embodiments, 1:1 to 5:1.

In some embodiments, the organic base of tertiary amine is triethylamine and/or N,N-diisopropylethylamine, and in some embodiments is N,N-diisopropylethylamine. The molar ratio of the organic base of tertiary amine to the compound represented by Formula (321) is 1:1 to 20:1, and in some embodiments is 1:1 to 5:1.

In some embodiments, the method for preparing the compound represented by Formula (321) further comprises: contacting the obtained product of condensation reaction with a capping reagent and an acylation catalyst under a capping reaction condition in an organic solvent, and isolating the compound represented by Formula (321). The capping reaction serves to remove any active functional groups that are not completely reacted, so as to avoid unnecessary by-products in subsequent reactions. The capping reaction condition comprises a reaction temperature of 0-50° C., and in some embodiments, 15-35° C., and a reaction time of 1-10 hours, and in some embodiments, 3-6 hours. The capping reagent may be a capping reagent used in solid phase synthesis of siRNA, which are well known to those skilled in the art.

In some embodiments, the capping reagent is composed of capping reagent 1 (cap1) and capping reagent 2 (cap2). The capping reagent 1 is N-methylimidazole, and in some embodiments provided as a mixed solution of N-methylimidazole in pyridine/acetonitrile, wherein the volume ratio of pyridine to acetonitrile is 1:10 to 1:1, and in some embodiments is 1:3 to 1:1. The ratio of the total volume of pyridine and acetonitrile to the volume of N-methylimidazole is 1:1 to 10:1, and in some embodiments is 3:1 to 7:1. The capping reagent 2 is acetic anhydride. In some embodiments, the capping reagent 2 is provided as a solution of acetic anhydride in acetonitrile, wherein the volume ratio of acetic anhydride to acetonitrile is 1:1 to 1:10, and in further embodiments is 1:2 to 1:6.

In some embodiments, the ratio of the volume of the mixed solution of N-methylimidazole in pyridine/acetonitrile to the mass of the compound of Formula (321) is 5 ml/g-50 ml/g, and in some embodiments is 15 ml/g-30 ml/g.

The ratio of the volume of the solution of acetic anhydride in acetonitrile to the mass of the compound of Formula (321) is 0.5 ml/g-10 ml/g, and in some embodiments is 1 ml/g-5 ml/g.

In some embodiments, the capping reagent is equimolar acetic anhydride and N-methylimidazole. In some embodiments, the organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the organic solvent is acetonitrile. In some embodiments, the amount of the organic solvent is 10-50 L/mol, and in some embodiments 5-30 L/mol with respect to the compound represented by Formula (321).

In some embodiments, the acylation catalyst may be selected from any catalyst that can be used for esterification condensation or amidation condensation, such as alkaline heterocyclic compounds. In some embodiments, the acylation catalyst is 4-dimethylaminopyridine. The ratio of the mass of the catalyst to the mass of the compound represented by Formula (321) may be 0.001:1 to 1:1, and in some embodiments is 0.01:1 to 0.1:1.

In some embodiments, the compound represented by Formula (321) may be isolated from the reaction mixture by any suitable isolation methods. In some embodiments, the compound of Formula (321) may be obtained by thoroughly washing with an organic solvent and filtering to remove unreacted reactants, excess capping reagent and other impurities, wherein the organic solvent is selected from acetonitrile, dichloromethane, or methanol, and in some embodiments is acetonitrile.

In some embodiments, the method for preparing the conjugating molecule represented by Formula (321) comprises contacting a compound represented by Formula (313) with a phosphorodiamidite under a coupling reaction condition in the presence of a coupling agent in an organic solvent, and isolating the compound represented by Formula (321). In this case, a compound represented by Formula (321) is obtained, wherein $R_4$ comprises a first functional group containing a hydroxy protecting group and a second functional group comprising the structure represented by Formula (C3). In some embodiments, the coupling reaction condition comprises a reaction temperature of 0-50° C., such as 15-35° C. The molar ratio of the compound of Formula (313) to the phosphorodiamidite may be 1:1 to 1:50, such as 1:5 to 1:15. The molar ratio of the compound of Formula (313) to the coupling agent may be 1:1 to 1:100, such as 1:50 to 1:80. The reaction time may be 200-3000 seconds, for example, 500-1500 seconds. The phosphorodiamidite may be, such as bis(biisopropylamino)(2-cyanoethoxy)phosphine, which may be commercially available or prepared according to methods well-known in the art. The coupling agent is selected from one or more of 1H-tetrazole, 5-ethylthio-1H-tetrazole and 5-benzylthio-1H-tetrazole, such as 5-ethylthio-1H-tetrazole. The coupling reaction may be performed in an organic solvent. The organic solvent is selected from one or more of anhydrous acetonitrile, anhydrous DMF and anhydrous dichloromethane, for example, anhydrous acetonitrile. In some embodiments, the amount of the organic solvent may be 3-50 L/mol, such as 5-20 L/mol with respect to the compound represented by Formula (313). By the coupling reaction, the hydroxy group in the compound (313) reacts with the phosphorodiamidite to form a phosphoramidite group. In some embodiments, the solvent may be removed directly to obtain a crude product of the compound represented by Formula (321), which may be used directly in subsequent reactions.

In some embodiments, the method for preparing the compound represented by Formula (321) further comprises the following steps: further contacting the isolated product with a solid phase support with hydroxy group(s) under a coupling reaction condition in the presence of a coupling agent in an organic solvent, followed by capping, oxidation, and isolation, to obtain the compound represented by Formula (321), wherein $R_4$ comprises a first functional group containing a hydroxy protecting group and a second functional group comprising the structure represented by Formula (C3').

In some embodiments, the solid phase support is a solid phase support used in solid phase synthesis of nucleic acid, such as a deprotected universal solid phase support, which is commercially available (such as NittoPhase®HL UnyLinker™ 300 Oligonucleotide Synthesis Support, Kinovate Life Sciences, represented by Formula B80):

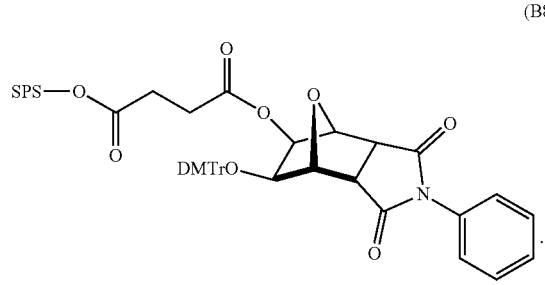

(B80)

A deprotection reaction is well known in the art. In some embodiments, the deprotection condition comprises a temperature of 0-50° C., such as 15-35° C., and a reaction time of 30-300 seconds, such as 50-150 seconds. The deprotection agent may be selected from one or more of trifluoroacetic acid, trichloroacetic acid, dichloroacetic acid, and monochloroacetic acid, and in some embodiments is dichloroacetic acid. The molar ratio of the deprotection agent to the protecting group -DMTr (4,4'-dimethoxytrityl) on the solid phase support may be 2:1 to 100:1, such as 3:1 to 50:1. By such deprotection, reactive free hydroxy groups are obtained on the surface of the solid phase support, for facilitating the subsequent coupling reaction. The coupling reaction condition and the coupling agent may be selected as above. By such coupling, the free hydroxy group formed in the deprotection reacts with the phosphoramidite group, so as to form a phosphite ester linkage.

In some embodiments, the capping reaction condition comprises a temperature of 0-50° C., such as 15-35° C., and a reaction time of 5-500 seconds, such as 10-100 seconds. The capping reaction is performed in the presence of capping agent. The selection and the amount of the capping agent may be described above.

The oxidation reaction condition may comprise a temperature of 0-50° C., such as 15-35° C., and a reaction time of 1-100 seconds, such as 5-50 seconds. The oxidation agent may be, for example, iodine (in some embodiments, provided as iodine water). In some embodiments, the molar ratio of the oxidation agent to the phosphite group is 1:1 to 100:1, for example, 5:1 to 50:1. In some embodiments, the oxidation reaction is performed in a mixed solvent of tetrahydrofuran:water:pyridine=3:1:1-1:1:3.

In some embodiments, $R_6$ is B7 or B8:

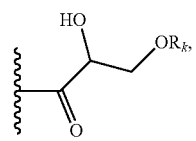

(B7)

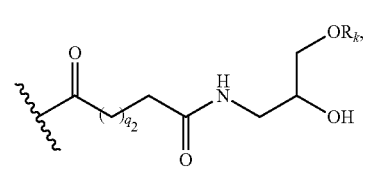

(B8)

wherein $q_2$ is defined as above.

In this case, the compound of Formula (313) may be obtained by the following preparation method comprising: contacting the compound represented by Formula (314) with a compound represented by Formula (A-1) or (A-2) under an amidation reaction condition in the presence of an condensing agent for amidation reaction and an organic base of tertiary amine, in an organic solvent, and followed by isolation:

Formula (314)

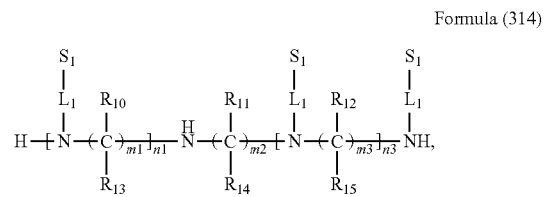

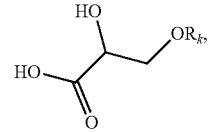

(A-1)

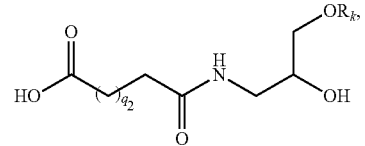

(A-2)

wherein, the definitions and options of n1, n3, m1, m2, m3, $R_{10}$, $R_{11}$, $R_{12}$, $R_{13}$, $R_{14}$, $R_{15}$, $L_1$, $S_1$, $q_2$ and $R_k$ are respectively described above.

The amidation reaction condition may comprise a reaction temperature of 0-100° C. and a reaction time of 1-48 hours. In some embodiments, the amidation reaction condition is a reaction temperature of 10-40° C. and a reaction time of 2-16 hours. In some embodiments, the organic solvent is one or more of an alcohol solvent, an epoxy solvent, an ether solvent, an haloalkane solvent, dimethyl sulfoxide, N,N-dimethylformamide, and N,N-diisopropylethylamine. In some embodiments, the alcohol solvent is one or more of methanol, ethanol and propanol, and in some embodiments is ethanol. In some embodiments, the epoxy solvent is dioxane and/or tetrahydrofuran. In some embodiments, the ether solvent is diethyl ether and/or methyl tert-butyl ether. In some embodiments, the haloalkane solvent is one or more of dichloromethane, trichloromethane and 1,2-dichloroethane. In some embodiments, the organic solvent is dichloromethane. The amount of the organic solvent is 3-50 L/mol, and in further embodiments is 3-20 L/mol with respect to the compound represented by Formula (314).

In some embodiments, the condensing agent for amidation reaction is benzotriazol-1-yl-oxytripyrrolidinophosphonium hexafluorophosphate, 3-(diethoxyphosphoryloxy)-1,2,3-benzotrizin-4(3H)-one, 4-(4,6-dimethoxytriazin-2-yl)-4-methylmorpholine hydrochloride, 2-ethoxy-1-ethoxycarbonyl-1,2-dihydroquinoline (EEDQ) or O-benzotriazol-tetramethyluronium hexafluorophosphate, and in further embodiments is 3-(diethoxyphosphoryloxy)-1,2,3-benzotrizin-4(3H)-one. The molar ratio of the condensing agent for amidation reaction to the compound represented by Formula (314) may be 1:1 to 10:1, and in some embodiments is 2.5:1 to 5:1.

In some embodiments, the organic base of tertiary amine is triethylamine or N,N-diisopropylethylamine, and in further embodiments is N,N-diisopropylethylamine. The molar ratio of the organic base of tertiary amine to the compound represented by Formula (314) may be 3:1 to 20:1, and in some embodiments is 5:1 to 10:1.

In some embodiments, the compounds of Formulae (A-1) and (A-2) may be prepared by any suitable means. For example, when Rk is a DMTr group, the compound of Formula (A-1) may be prepared by reacting calcium glycerate with DMTrCl. Similarly, the compound of Formula (A-2) may be prepared by firstly contacting 3-amino-1,2-propanediol with a cyclic anhydride which may have 4-13 carbon atoms, and in some embodiments 4-8 carbon atoms, followed by reacting with DMTrCl. It will be readily understood by those skilled in the art that the selection of different cyclic anhydride corresponds to different values for $q_2$ in the compound of Formula (A-2). For example, when the cyclic anhydride is succinic anhydride, $q_2=1$; when the cyclic anhydride is glutaric anhydride, $q_2=2$, and so on.

In some variations, the compound of Formula (313) can also be prepared by successively reacting the compound represented by Formula (314) with the cyclic anhydride, 3-amino-1,2-propanediol, and DMTrCl. It will be readily understood by those skilled in the art that these variations would not affect the structure and function(s) of the compound of Formula (313), and these variations are readily achieved by those skilled in the art on the basis of the above methods.

Similarly, the compound represented by Formula (313) may be isolated from the reaction mixture by any suitable isolation methods. In some embodiments, the compound represented by Formula (313) may be isolated by removal of solvent via evaporation followed by chromatography. For example, the following two sets of chromatographic conditions may be employed for isolation, (1) normal phase purification of silica gel: 200-300 mesh silica gel filler, with gradient elution of petroleum ether: ethyl acetate: dichloromethane: N,N-dimethylformamide=1:1:1:0.5-1:1:1:0.6; and (2) reverse phase purification: $C_{18}$ and $C_8$ reverse phase fillers, with gradient elution of methanol: acetonitrile=0.1:1-1:0.1. In some embodiments, the solvent may be removed directly to obtain a crude product of the compound represented by Formula (313), which may be directly used in subsequent reactions. In some embodiments, the compound represented by Formula (314) may be obtained by the following preparation method comprising: contacting the compound represented by Formula (315) with haloacetic acid under a deprotection reaction condition in an organic solvent, and followed by isolation:

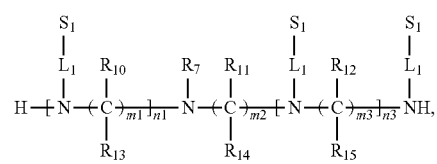

Formula (315)

wherein, $R_7$ is selected from the group represented by Formula (330), (331), (332) or (333), and in some embodiments, $R_7$ has the structure represented by Formula (330):

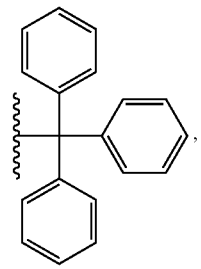

Formula (330)

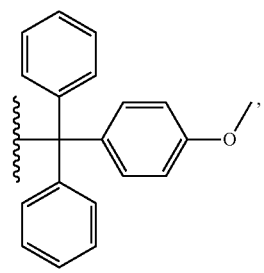

Formula (331)

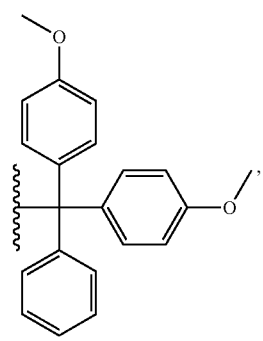

Formula (332)

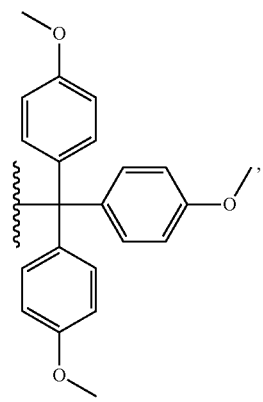

Formula (333)

wherein the definitions and options of n1, n3, m1, m2, m3, $R_{10}$, $R_{11}$, $R_{12}$, $R_{13}$, $R_{14}$, $R_{15}$, $L_1$ and $S_1$ are respectively described as above.

The haloacetic acid may be selected from one or more of dichloroacetic acid, trichloroacetic acid, monochloroacetic acid and trifluoroacetic acid, and in some embodiments is dichloroacetic acid.

The deprotection reaction condition may comprise a reaction temperature of 0-100° C. and a reaction time of 0.1-24 hours, and in some embodiments comprises a reaction temperature of 10-40° C. and a reaction time of 0.5-16 hours.

In some embodiments, the organic solvent is one or more of an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tert-butyl ether. In some embodiments, the haloalkane solvent is one or more of dichloromethane, trichloromethane and 1,2-dichloroethane. In some embodiments, the organic solvent is dichloromethane. The amount of the organic solvent is 3-50 L/mol, and in further embodiments 5-20 L/mol with respect to the compound represented by Formula (315).

The molar ratio of the haloacetic acid to the compound represented by Formula (315) may be 5:1 to 100:1, and in some embodiments is 10:1 to 50:1.

Similarly, the compound represented by Formula (314) may be isolated from the reaction mixture by any suitable isolation method. In some embodiments, the compound represented by Formula (314) may be isolated by removal of solvent via evaporation followed by chromatography, for example, using the following two sets of chromatographic conditions for isolation: (1) normal phase purification of silica gel: 200-300 mesh silica gel filler, with gradient elution of dichloromethane:methanol=100:30-100:40; and (2) reverse phase purification: $C_{18}$ and $C_8$ reverse phase fillers, with gradient elution of methanol: acetonitrile=0.1:1-1:0.1. In some embodiments, the solvent may be removed directly to obtain a crude product of the compound represented by Formula (314), which may be directly used in subsequent reactions. The compound represented by Formula (315) may be obtained by the following preparation method comprising: contacting the compound represented by Formula (317) with the compound represented by Formula (316) under a condensation reaction condition in the presence of a condensing agent for amidation reaction and an organic base of tertiary amine, in an organic solvent, and followed by isolation:

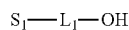

Formula (316)

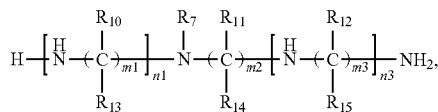

Formula (317)

wherein the definitions and options of n1, n3, m1, m2, m3, $R_7$, $R_{10}$, $R_{11}$, $R_{12}$, $R_{13}$, $R_{14}$, $R_{15}$, $L_1$ and $S_1$ are respectively described as above.

The compound of Formula (316) may be compounds disclosed in J. Am. Chem. Soc. 2014, 136, 16958-16961. Alternatively, the compound of Formula (316) may be prepared by those skilled in the art by various methods. For example, some compounds of Formula (316) may be prepared according to the disclosed method in Example 1 of U.S. Pat. No. 8,106,022 B2, which is incorporated herein by reference in its entirety.

In some embodiments, the condensation reaction condition comprises a reaction temperature of 0-100° C. and a reaction time of 0.1-24 hours. In some embodiments, the reaction temperature is 10-40° C. and the reaction time is 0.5-16 hours.

The molar ratio of the compound represented by Formula (316) to the compound represented by Formula (317) may be 2:1 to 10:1, and in some embodiments is 2.5:1 to 5:1.

In some embodiments, the organic solvent is one or more of acetonitrile, an epoxy solvent, an ether solvent, an haloalkane solvent, dimethyl sulfoxide, N,N-dimethylformamide and N,N-diisopropylethylamine. In some embodiments, the epoxy solvent is dioxane and/or tetrahydrofuran. In some embodiments, the ether solvent is diethyl ether and/or methyl tert-butyl ether. In some embodiments, the haloalkane solvent is one or more of dichloromethane, trichloromethane and 1,2-dichloroethane. In some embodiments, the organic solvent is acetonitrile. The amount of the organic solvent may be 3-50 L/mol, and in some embodiments is 5-20 L/mol with respect to the compound represented by Formula (317).

In some embodiments, the condensing agent for amidation reaction is benzotriazol-1-yl-oxytripyrrolidinophosphonium hexafluorophosphate, 3-(diethoxyphosphoryloxy)-1,2,3-benzotrizin-4(3H)-one (DEPBT), O-benzotriazol-tetramethyluronium hexafluorophosphate or 4-(4,6-dimethoxytriazin-2-yl)-4-methylmorpholine hydrochloride, and in further embodiments is 4-(4,6-dimethoxytriazin-2-yl)-4-methylmorpholine hydrochloride. The molar ratio of the condensing agent for amidation reaction to the compound represented by Formula (317) may be 2:1 to 10:1, and in some embodiments is 2.5:1 to 5:1.

The organic base of tertiary amine may be N-methylmorpholine, triethylamine or N,N-diisopropylethylamine, and in some embodiments is N-methylmorpholine. The molar ratio of the organic base of tertiary amine to the compound represented by Formula (317) may be 3:1 to 20:1, and in some embodiments is 5:1 to 10:1. Similarly, the compound represented by Formula (315) may be isolated from the reaction mixture by any suitable isolation method. In some embodiments, the compound represented by Formula (315) is isolated by removal of solvent via evaporation followed by chromatography, for example, using the following two sets of chromatographic conditions for isolation: (1) normal phase purification of silica gel: 200-300 mesh silica gel filler, with gradient elution of dichloromethane:methanol=100:5-100:7; (2) reverse phase purification: $C_{18}$ and $C_8$ reverse phase fillers, with gradient elution of methanol: acetonitrile=0.1:1-1:0.1. In some embodiments, the solvent may be removed directly to obtain a crude product of the compound represented by Formula (315), which may be used directly in subsequent reactions. In some embodiments, the compound of Formula (317) is reacted with a sufficient amount of one compound of Formula (316) in one batch to obtain the desired compound of Formula (315), wherein all $S_1$-$L_1$ moieties are identical. In some embodiments, the compound of Formula (317) is reacted in batches with different compounds of Formula (316), i.e., the compounds of Formula (316) having different $L_1$ and/or $S_1$, as desired, so as to obtain the compound of Formula (315) having two or more types of $S_1$ and/or $L_1$ therein. For example, 1 eq of the compound of Formula (317) may be firstly contacted with 2 eq of a first compound of Formula (316) so that a first S₁-L₁ moiety is linked to the two terminal primary amine groups in the compound of Formula (317), and then contacted with the (n3+n1-1) eq of a second compound of Formula (316) so that a second S₁-L₁ moiety is linked to the (n3+n1-1) secondary amine groups (wherein the definition and scope of n3 and n1 are defined above) in the compound of Formula (317).

In some embodiments, the compound represented by Formula (317) may be obtained by the following preparation method comprising: contacting the compound represented by Formula (318) with methylamine aqueous solution under a deprotection reaction condition in the presence of an organic solvent, and follow by isolation:

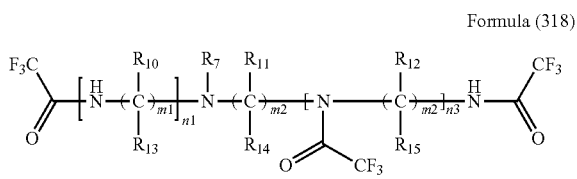

Formula (318)

wherein the definitions and options of n1, n3, m1, m2, m3, R₇, R₁₀, R₁₁, R₁₂, R₁₃, R₁₄ and R₁₅ are respectively defined above.

The deprotection reaction condition may comprise a reaction temperature of 0-150° C. and a reaction time of 5-72 hours, and in some embodiments comprises a reaction temperature of 20-80° C. and a reaction time of 10-30 hours.

The organic solvent may be selected from alcohols, and in some embodiments is one of methanol, ethanol and isopropanol, and in further embodiments is methanol. The amount of the organic solvent may be 1-20 L/mol, and in some embodiments is 1.5-10 L/mol with respect to the compound represented by Formula (318).

The concentration of the methylamine aqueous solution may be 30%-40% by mass, and the molar ratio of methylamine to the compound represented by Formula (318) may be 10:1 to 500:1, and in some embodiments is 50:1 to 200:1.

Similarly, the compound represented by Formula (317) may be isolated from the reaction mixture using any suitable isolation method. In some embodiments, the compound represented by Formula (317) may be isolated by removal of solvent via evaporation followed by chromatography, for example, using the following two sets of chromatographic conditions for isolation: (1) normal phase purification of silica gel: 200-300 mesh silica gel filler, with gradient elution of dichloromethane: methanol: aqueous ammonia (25 wt %)=1:1:0.05-1:1:0.25; and (2) reverse phase purification: C₁₈ and C₈ reverse phase fillers, with gradient elution of methanol: acetonitrile=0.1:1-1:0.1. In some embodiments, the solvent may be removed directly to obtain a crude product of the compound represented by Formula (317), which may be used directly in subsequent reactions.

The compound represented by Formula (318) may be obtained by the following preparation method comprising: contacting the compound represented by Formula (319) with triphenylchloromethane (TrCl), diphenylethylphenylchloromethane, phenyldiethylphenylchloromethane or triethylphenylchloromethane, and in some embodiments with triphenylchloromethane (TrCl), under a substitution reaction condition in the presence of an organic solvent, and followed by isolation:

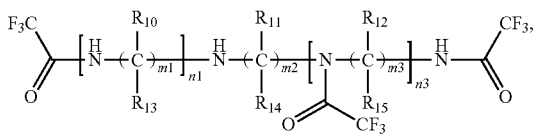

Formula (319)

wherein the definitions and options of n1, n3, m1, m2, m3, R₁₀, R₁₁, R₁₂, R₁₃, R₁₄ and R₁₅ are respectively defined as above.

The substitution reaction condition may comprise a reaction temperature of 0-100° C. and a reaction time of 5-72 hours, and in some embodiments comprises a reaction temperature of 10-40° C. and a reaction time of 10-30 hours. Triphenylchloromethane (TrCl), diphenylethylphenylchloromethane, phenyldiethylphenylchloromethane or triethylphenylchloromethane are commercially available. The molar ratio of triphenylchloromethane (TrCl), diphenylethylphenylchloromethane, phenyldiethylphenylchloromethane or triethylphenylchloromethane to the compound represented by Formula (319) may be 1:1 to 10:1, and in some embodiments is 1:1 to 3:1.

The organic solvent may be one or more of an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tert-butyl ether. In some embodiments, the haloalkane solvent is one or more of dichloromethane, trichloromethane and 1,2-dichloroethane. In some embodiments, the organic solvent is dichloromethane. The amount of the organic solvent may be 3-50 L/mol, and in some embodiments is 5-20 L/mol with respect to the compound represented by Formula (319).

Similarly, the compound represented by Formula (318) may be isolated from the reaction mixture by any suitable isolation method. In some embodiments, the compound represented by Formula (318) may be isolated by removal of solvent via evaporation followed by chromatography, for example, using the following two sets of chromatographic conditions for isolation: (1) normal phase purification of silica gel: 200-300 mesh silica gel filler, with gradient elution of methanol: dichloromethane=0.01:1-0.5:1 or gradient elution of methanol:dichloromethane:ethyl acetate: petroleum ether=0.1:1:1:1-1:1:1:1; and (2) reverse phase purification: C₁₈ and C₈ reverse phase fillers, with gradient elution of methanol: acetonitrile=0.1:1-1:0.1. In some embodiments, the solvent may be removed directly to obtain a crude product of the compound represented by Formula (318), which may be used directly in subsequent reactions.

In some embodiments, the compound represented by Formula (319) may be obtained by the following preparation method comprising: contacting the compound represented by Formula (320) with ethyl trifluoroacetate under a substitution reaction condition in an organic solvent, and followed by isolation:

Formula (320)

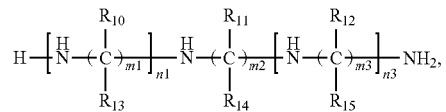

wherein the definitions and options of n1, n3, m1, m2, m3, $R_{10}$, $R_{11}$, $R_{12}$, $R_{13}$, $R_{14}$ and $R_{15}$ are respectively defined as above.

In some embodiments, the organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tert-butyl ether. In some embodiments, the haloalkane solvent is one or more of dichloromethane, trichloromethane and 1,2-dichloroethane. In some embodiments, the organic solvent is acetonitrile. The amount of the organic solvent may be 1-50 L/mol, and in some embodiments is 1-20 L/mol with respect to the compound represented by Formula (320).

The substitution reaction condition may comprise a reaction temperature of 0-100° C. and a reaction time of 5-72 hours, and in some embodiments comprises a reaction temperature of 10-40° C. and a reaction time of 10-30 hours.

The compound represented by Formula (320) may be commercially purchased, or obtained by methods known to the skilled in the art. For example, in the case that m1=m2=m3=3, n1=1, n3=2, and each of $R_{10}$, $R_{11}$, $R_{12}$, $R_{13}$, $R_{14}$ and $R_{15}$ is H, the compound represented by Formula (320) is commercially available from Alfa Aesar Inc.

The molar ratio of ethyl trifluoroacetate to the compound represented by Formula (320) may be 2:1 to 10:1, and in some embodiments is 3:1 to 5:1.

Similarly, the compound represented by Formula (319) may be isolated from the reaction mixture using any suitable isolation method. In some embodiments, the compound represented by Formula (319) may be isolated by removal of solvent via evaporation followed by chromatography, for example, using the following two sets of chromatographic conditions for isolation: (1) normal phase purification of silica gel: 200-300 mesh silica gel filler, with gradient elution of methanol: dichloromethane=0.01:1-0.5:1 or gradient elution of methanol:dichloromethane:ethyl acetate: petroleum ether=0.1:1:1:1-1:1:1:1; and (2) reverse phase purification: $C_{18}$ and $C_8$ reverse phase fillers, with gradient elution of methanol: acetonitrile=0.1:1-1:0.1. In some embodiments, the solvent may be removed directly to obtain a crude product of the compound represented by Formula (319), which may be used directly in subsequent reactions.

For the siRNA conjugate of the present disclosure, it may also be used in combination with other pharmaceutically acceptable excipients, which may be one or more of various formulations or compounds conventionally employed in the art. Please see the above description of the pharmaceutical composition of the present disclosure for details.

Use of the siRNA, the Pharmaceutical Composition Comprising siRNA and the siRNA Conjugate of the Present Disclosure In some embodiments, the present disclosure provides the use of the siRNA and/or the pharmaceutical composition and/or the siRNA conjugate in the preparation of a medicament for treating and/or preventing dyslipidemia.

In some embodiments, the present disclosure provides a method for treating and/or preventing dyslipidemia, wherein the method comprises administering an effective amount of the siRNA and/or the pharmaceutical composition and/or the siRNA conjugate of the present disclosure to a subject in need thereof.

The purpose of preventing and/or treating dyslipidemia may be achieved through the mechanism of RNA interference by administering the siRNA active ingredient to a subject in need thereof. Therefore, the siRNA and/or the pharmaceutical composition and/or the siRNA conjugate of the present disclosure may be used for preventing and/or treating dyslipidemia, or for preparing a medicament for preventing and/or treating dyslipidemia.

The dyslipidemia refers to abnormal blood lipid caused by over-expression of ANGPTL 3 gene in hepatocytes, and generally manifests itself as increased level(s) of any one or more of lipids such as triglyceride and cholesterol and/or lipoprotein in blood. A high level of blood lipid is highly associated with hypertension, cardiovascular disease, diabetes and other pathological conditions. Hypertriglyceridemia is related to atherosclerosis, and would lead to pancreatitis. The dyslipidemia of the present disclosure includes, but not limited to, hypercholesteremia, hypertriglyceridemia or atherosclerosis.

As used herein, the term "administration/administrate" refers to placing the siRNA, the pharmaceutical composition and/or the siRNA conjugate into a subject by a method or route that at least partly locates the siRNA, the pharmaceutical composition and/or the siRNA conjugate at a desired site to achieve a desired effect. The administration routes suitable for the method of the present disclosure include topical administration and systemic administration. In general, topical administration results in the delivery of more siRNA conjugate to a particular site as compared to the whole body of the subject; while systemic administration results in the delivery of the siRNA, the pharmaceutical composition and/or the siRNA conjugate of the present disclosure to basically the whole body of the subject. Considering that the present disclosure is intended to provide means for the prevention and/or treatment of dyslipidemia, in some embodiments, an administration mode that can deliver drugs to the liver is employed.

The administration to a subject may be achieved by any suitable route known in the art, including, but is not limited to, oral or parenteral route, including intravenous administration, intramuscular administration, subcutaneous administration, transdermal administration, endotracheal administration (aerosol), pulmonary administration, nasal administration, rectal administration and topical administration (including buccal administration and sublingual administration). The administration frequency may be once or more times daily, weekly, biweekly, monthly, or yearly.

The used dosage of the siRNA, the pharmaceutical composition or the siRNA conjugate of the present disclosure may be a conventional dose in the art, which may be determined according to various parameters, especially the age, weight and gender of the subject. Toxicity and therapeutic efficacy can be determined by standard pharmaceutical procedures in cell cultures or experimental animals, e.g., by determining LD50 (the dose that is lethal to 50% of the population) and ED50 (the dose that can cause 50% of the maximum response intensity in the quantitative response, or the dose that can cause a positive response in 50% of the experimental subjects in the qualitative response). The dose range for human may be derived based on the data obtained from cell culture assays and animal studies.

When administrating the siRNA, the pharmaceutical composition and/or the siRNA conjugate of the present disclosure is administered, for example, to C57BL/6J mice having a weight of 18 to 25 g or to ob/ob mice having a weight of 30 to 45 g, either male or female, with an age of 6 to 12 weeks, on the basis of the amount of the siRNA: (i) for a siRNA conjugate, the dose of siRNA thereof may be from 0.001 to 100 mg/kg body weight, in further embodiments 0.01 to 50 mg/kg body weight, in more further embodiments from 0.05 to 20 mg/kg body weight, and in still more further embodiments from 0.1 to 10 mg/kg body weight; (ii) for a pharmaceutical composition formed from a siRNA and a pharmaceutically acceptable support, the dosage of siRNA thereof may be from 0.001 to 50 mg/kg body weight, in further embodiments from 0.01 to 10 mg/kg body weight, in more further embodiments from 0.05 to 5 mg/kg body weight, and in still more further embodiments from 0.1 to 3 mg/kg body weight.

In some embodiments, the present disclosure provides a method of inhibiting the expression of ANGPTL3 gene in hepatocytes, which comprises contacting an effective amount of the siRNA and/or the pharmaceutical composition and/or the siRNA conjugate of the present disclosure with the hepatocytes, and introducing the siRNA and/or the pharmaceutical composition and/or the siRNA conjugate of the present disclosure into the hepatocytes, so as to achieve the object of inhibiting the expression of ANGPTL3 gene in hepatocytes through the mechanism of RNA interference. The hepatocytes may be selected from hepatoma cell lines such as Hep3B, HepG2 or Huh7, and isolated liver primary cells. In some embodiments, the hepatocytes are Huh7 hepatoma cells.

In the case where the expression of ANGPTL3 gene in a cell is inhibited by using the method of the present disclosure, the amount of siRNA in the modified siRNA, the pharmaceutical composition and/or the siRNA conjugate of the present disclosure is generally an amount sufficient to reduce the expression of the target gene and result in an extracellular concentration of 1 pM to 1 µM, or 0.01 nM to 100 nM, or 0.05 nM to 50 nM, or 0.05 nM to about 5 nM on the surface of the target cells. The amount required to achieve this local concentration will vary with various factors, including the delivery method, the delivery site, the number of cell layers between the delivery site and the target cells or tissue, the delivery route (topical or systemic), etc. The concentration at the delivery site may be significantly higher than that on the surface of the target cells or tissue.

Kit

The present disclosure provides a kit, which comprises an effective amount of at least one of the modified siRNA, the pharmaceutical composition and the siRNA conjugate of the present disclosure.

In some embodiments, the kit of the present disclosure may provide a modified siRNA in a container. In some embodiments, the kit of the present disclosure may comprise a container comprising a pharmaceutically acceptable excipient. In some embodiments, the kit of the present disclosure further comprises other ingredients, such as stabilizers or preservatives. In some embodiments, the kit of the present disclosure may comprise at least one additional therapeutic agent in a container different than the container comprising the modified siRNA of the present disclosure. In some embodiments, the kit may comprise an instruction for mixing the modified siRNA with a pharmaceutically acceptable carrier and/or excipient or other ingredients (if present).

In the kit of the present disclosure, the modified siRNA and the pharmaceutically acceptable carrier and/or excipient as well as the modified siRNA, the pharmaceutical composition and/or the siRNA conjugate and/or the conjugate, and/or the pharmaceutically acceptable excipient may be provided in any form, such as in a liquid form, a dried form or a lyophilized form. In some embodiments, the modified siRNA and the pharmaceutically acceptable carrier and/or excipient and the pharmaceutical composition and/or conjugate and optional pharmaceutically acceptable excipient(s) are substantially pure and/or sterilized. In some embodiments, sterilized water may be provided in the kit of the present disclosure.

The present disclosure will be further illustrated by way of examples, but will not be limited to them.

EXAMPLES

Hereinafter, the present disclosure will be described in detail by way of examples. Unless otherwise specified, the reagents and culture media used in following examples are all commercially available, and operations used such as nucleic acid electrophoresis and real-time PCR are all performed according to methods described in Molecular Cloning (Cold Spring Harbor Laboratory Press (1989)).

HEK293A cells were provided by Nucleic acid technology laboratory, Institute of Molecular Medicine, Peking University and cultured in DMEM complete media (Hyclone company) containing 20% fetal bovine serum (FBS, Hyclone company) and 0.2% by volume of Penicillin-Streptomycin (Gibco, Invitrogen company) at 37° C. in an incubator containing 5% $CO_2$/95% air.

Huh7 cells were purchased from the Stem Cell Bank of Chinese Academy of Science and cultured in DMEM complete media (Hyclone company) containing 10% fetal bovine serum (FBS, Hyclone company) and 1% nonessential amino acid (NEAA, Corning company) at 37° C. in an incubator containing 5% $CO_2$/95% air.

When the siRNA or the siRNA conjugate against ANGPTL3 gene synthesized in the present disclosure or the siRNA or the siRNA conjugate as negative control was used to transfect cells, Lipofectamine™2000 (Invitrogen) was used as a transfection reagent. The specific procedures thereof may refer to the instruction provided by the manufacturer.

Unless otherwise specified, ratios of reagents provided below are all calculated by volume ratio (v/v).

The animal models used are as follows:
C57BL/6N mice: 6-8 week old, purchased from Beijing Vital River Laboratory Animal Technology Co., Ltd., and hereinafter referred to as C57 mice;
BALB/c mice: 6-8 week old, purchased from Beijing Vital River Laboratory Animal Technology Co., Ltd.;
ob/ob mice: 6-8 week old, purchased from Changzhou Cavens Laboratory Animal Co., Ltd.;
Human APOC3 transgenic mice: B6; CBA-Tg(APOC3) 3707Bres/J, purchased from Jackson Lab in the United States of America;
Monkey with metabolic syndrome: provided by Nonhuman primate research center, Institute of Molecular Medicine, Peking University.

All the experimental data are expressed as $\overline{X}\pm SEM$, and the data are analyzed by using Graphpad prism 5.0 statistical analysis software. The data are initially tested for normal distribution and homogeneity of variance. If the data meet normal distribution ($p>0.20$) and homogeneity of variance ($p>0.10$), comparison among groups would be performed by LSD method using one-way analysis of variance for multiple comparisons. $P<0.05$ is considered statistically significant. If the data fail to meet normal distribution or homogeneity of variance, differences among groups would be performed by using Krushkal-Wallis H Method for Nonparametric Test. If the results obtained by Krushkal-Wallis H test are significant ($p<0.05$), pairwise comparisons among groups would be conducted after rank transformation of the data. P<0.05 is considered to be statistically significant. In the figures, "*" indicates p<0.05, "" indicates p<0.01, and "*" indicates p<0.001.

Preparation Example 1. The Preparations of Conjugates 1-4

In this preparation example, conjugate 1, conjugate 2 and conjugate 4 (hereinafter also referred to as L10-siAN1M3SVP, L10-siAN1M3SP and L10-siAN1M3S conjugate respectively) were synthesized, and conjugate 3 (referred to as L10-siAN1M3SPs conjugate) was expected to be synthesized. The above-mentioned conjugates were those formed by conjugating L-9 conjugating molecule with the siRNA No. siAN1M3SVP, siAN1M3SP, siAN1M3S or siAN1M3SPs. The sequences of the conjugated siRNAs in said conjugates were shown in Table 3.

(1-1) Synthesis of Compound L-10:

Compound L-10 was synthesized according to the following method.

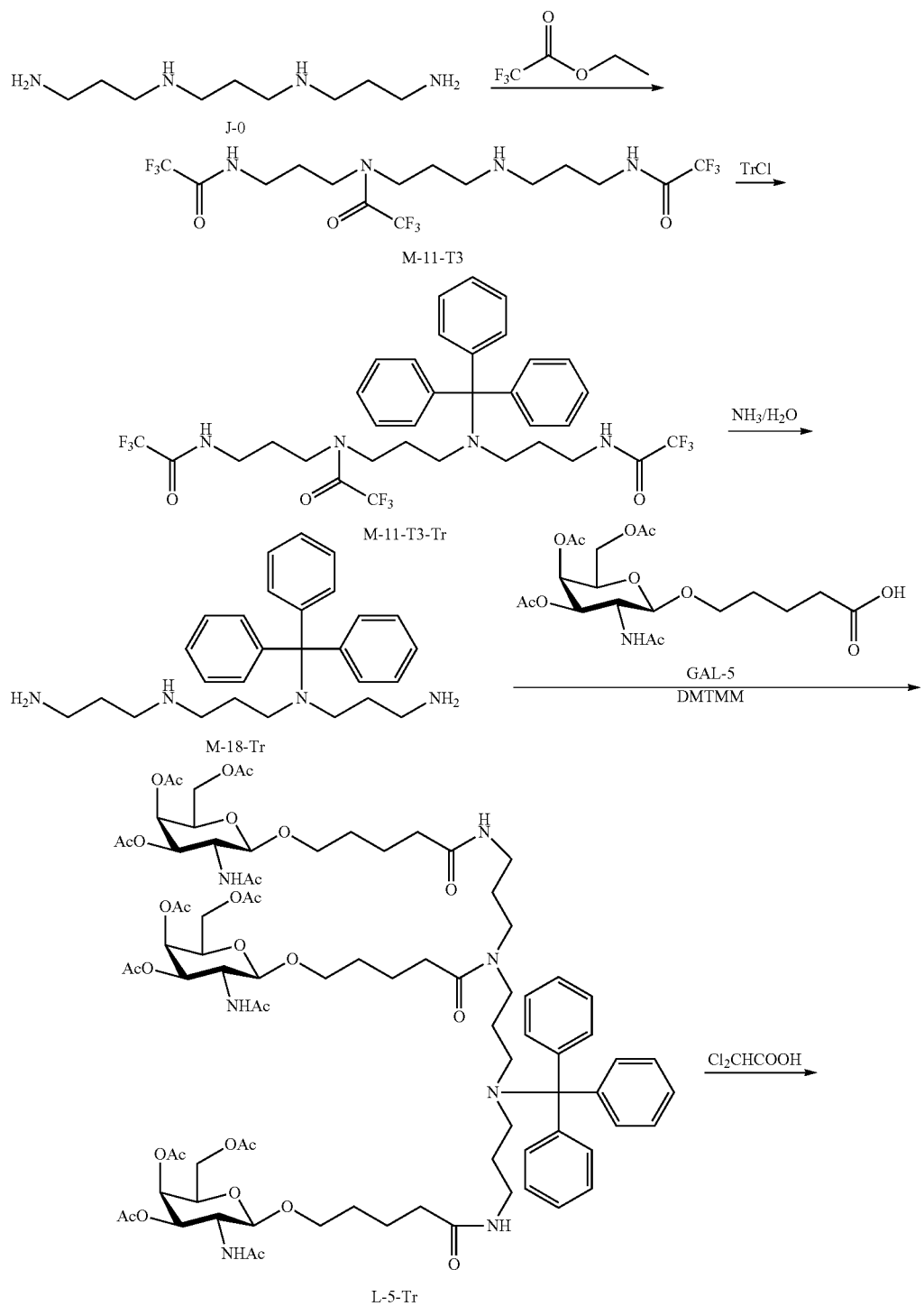

-continued
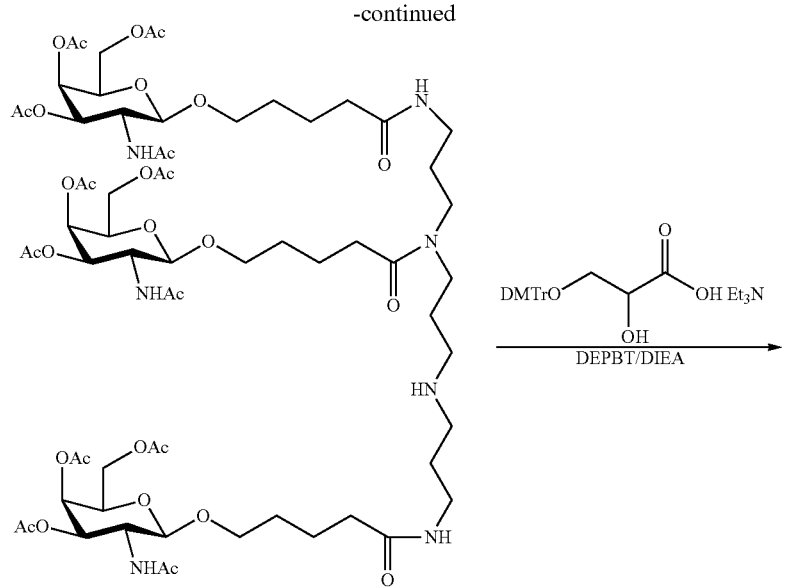
L-8
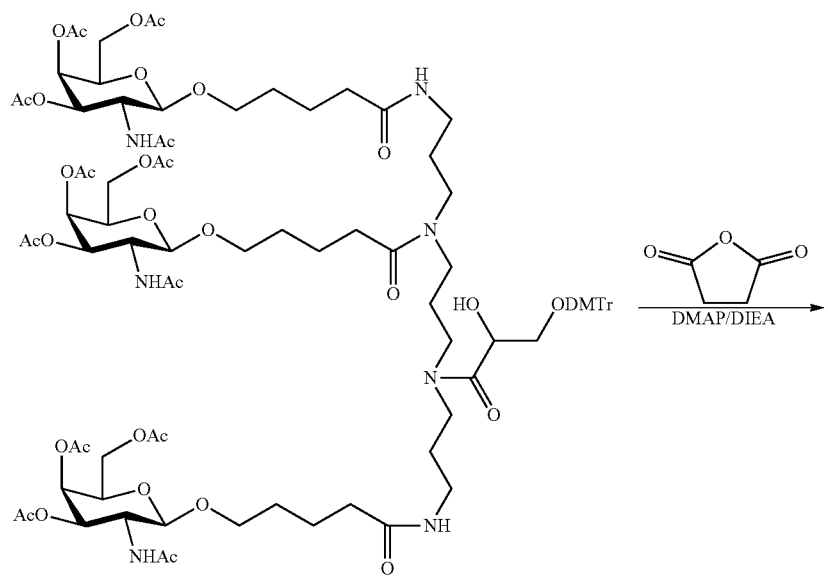
L-7

-continued
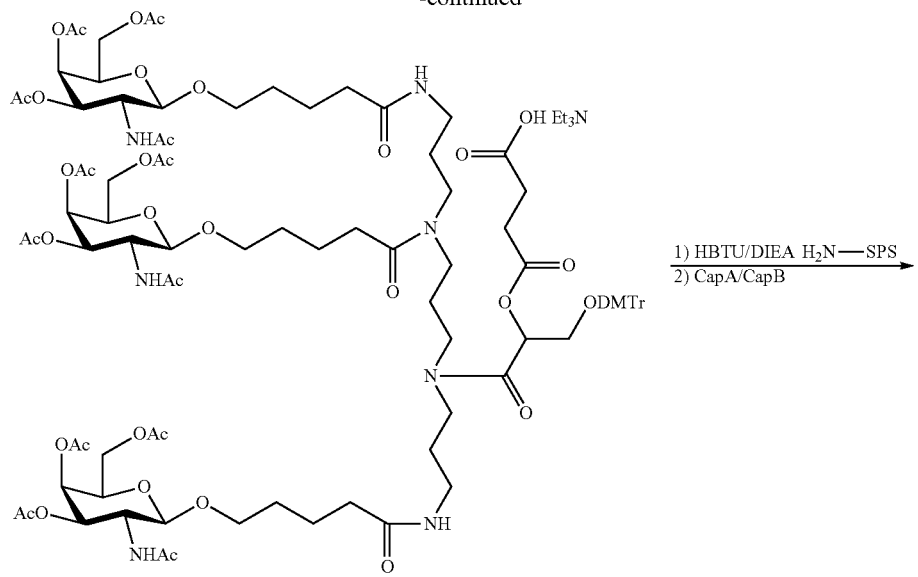
L-9
1) HBTU/DIEA H$_2$N—SPS
2) CapA/CapB
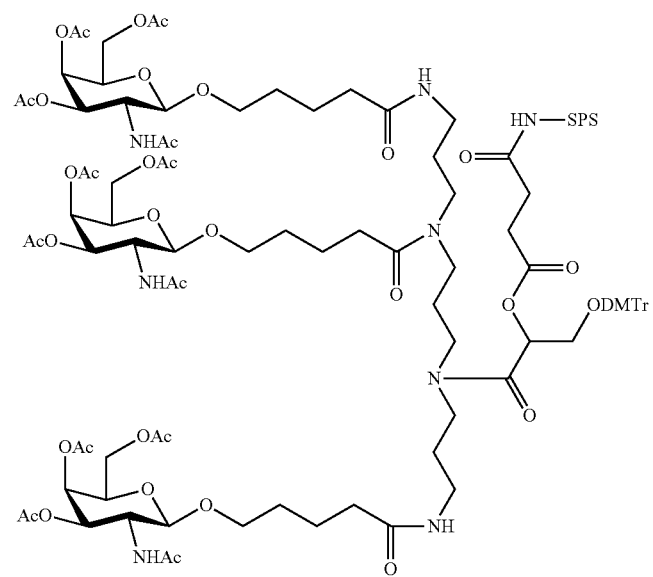
L-10

(1-1-1) Synthesis of the Conjugating Terminal Segment GAL-5:

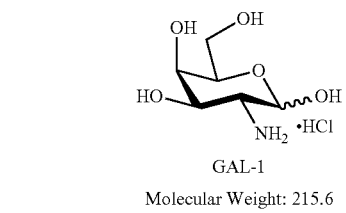

GAL-1

Molecular Weight: 215.6

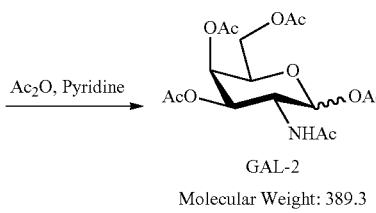

GAL-2

Molecular Weight: 389.3

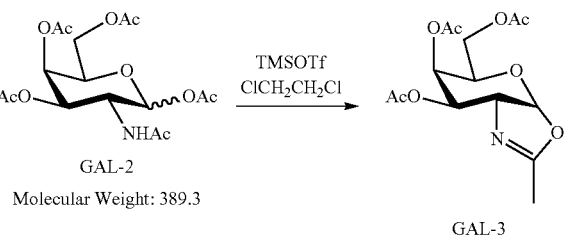

GAL-3

Molecular Weight: 329.3

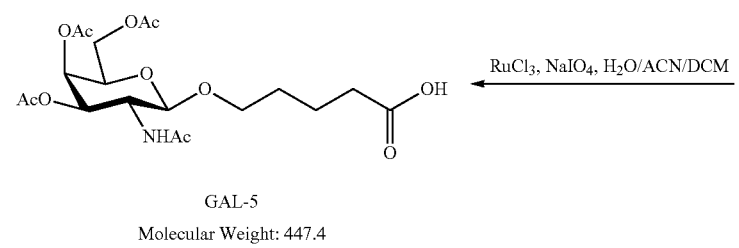

GAL-5

Molecular Weight: 447.4

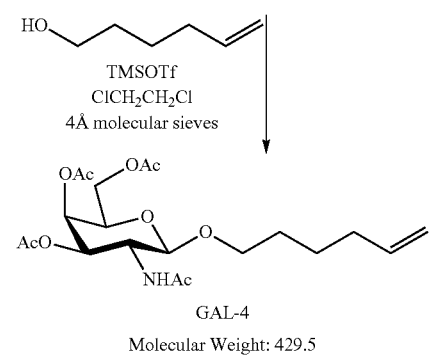

GAL-4

Molecular Weight: 429.5

(1-1-1a) Synthesis of GAL-2:

100.0 g of GAL-1 (N-acetyl-D-galactosamine hydrochloride, CAS No.: 1772-03-8, purchased from Ning Bo hongxiang bio-chem Co., Ltd., 463.8 mmol) was dissolved in 1000 ml of anhydrous pyridine, to which 540 ml of acetic anhydride (purchased from Enox Inc., 5565.6 mmol) was added in an ice water bath to react for 1.5 hours under stirring at room temperature. The resulting reaction solution was poured into 10 L of ice water and was subjected to suction filtration under reduced pressure. The residue was washed with 2 L of ice water, and then added with a mixed acetonitrile/toluene solvent (v/v ratio of acetonitrile:toluene=1:1) until complete dissolution. The solvent was evaporated to give 130.0 g of product GAL-2 as a white solid.

(1-1-1b) Synthesis of GAL-3:

GAL-2 (35.1 g, 90.0 mmol) obtained in step (1-1-1a) was dissolved in 213 ml of anhydrous 1,2-dichloroethane, to which 24.0 g of TMSOTf (CAS No.: 27607-77-8, purchased from Macklin Inc., 108.0 mmol) was added in an ice water bath and under nitrogen atmosphere to react overnight at room temperature.

400 ml dichloromethane was added to the reaction solution for dilution, filtered with diatomite, and then 1 L saturated aqueous sodium bicarbonate solution was added to the resulting reaction solution and stirred evenly. The organic phase was isolated. The aqueous phase was extracted twice, each with 300 ml of dichloroethane, and the organic phases were combined and washed with 300 ml of saturated aqueous sodium bicarbonate solution and 300 ml of saturated brine, respectively. The organic phase was isolated and dried with anhydrous sodium sulfate. The solvent was evaporated under reduced pressure to give 26.9 g of product GAL-3 as a light yellow viscous syrup.

(1-1-1c) Synthesis of GAL-4:

GAL-3 (26.9 g, 81.7 mmol) obtained in step (1-1-1b) was dissolved in 136 ml of anhydrous 1,2-dichloroethane, added with 30 g of 4 Å molecular sieve as a dry powder followed by 9.0 g of 5-hexen-1-ol (CAS No.: 821-41-0, purchased from Adamas-beta Inc., 89.9 mmol), and stirred for 30 minutes at room temperature. 9.08 g of TMSOTf (40.9 mmol) was added in an ice bath and nitrogen atmosphere to react overnight under stirring at room temperature. The 4 Å molecular sieve powder was removed by filtration. 300 ml dichloroethane was added to the filtrate for dilution, filtered with diatomite, and then 500 ml of saturated aqueous sodium bicarbonate solution was added to the resulting reaction solution and stirred for 10 minutes for washing. The organic phase was isolated. The aqueous phase was extracted once with 300 ml of dichloroethane. The organic phases were combined and washed with 300 ml of saturated aqueous sodium bicarbonate solution and 300 ml of saturated brine respectively. The organic phase was isolated and dried with anhydrous sodium sulfate. The solvent was evaporated under reduced pressure to give 41.3 g of product GAL-4 as a yellow syrup, which was directly used in the next oxidation reaction without purification.

(1-1-1d) Synthesis of GAL-5:

GAL-4 (14.9 g, 34.7 mmol) obtained according to the method described in step (1-1-1c) was dissolved in a mixed solvent of 77 ml of dichloromethane and 77 ml of acetonitrile, added with 103 ml of deionized water and 29.7 g of sodium periodate (CAS No.: 7790-28-5, purchased from Aladdin Inc., 138.8 mmol) respectively, and stirred in an ice bath for 10 minutes. Ruthenium trichloride (CAS No.: 14898-67-0, available from Energy Chemical, 238 mg, 1.145 mmol) was added to react overnight at room temperature. The resulting reaction solution was diluted by adding 300 ml of water, stirred, and adjusted to a pH of about 7.5 by adding saturated sodium bicarbonate. The organic phase was isolated and discarded. The aqueous phase was extracted three times, each with 200 ml of dichloromethane, and the organic phase resulted from the extraction was discarded. The aqueous phase resulted from the extraction was adjusted to a pH of about 3 with citric acid solid and extracted three times, each with 200 ml of dichloromethane, and the organic phases were combined and dried with anhydrous sodium sulfate. The solvent is evaporated under reduced pressure to give 6.85 g of product GAL-5 as a white foamy solid. $^1$H NMR (400 MHz, DMSO) δ 12.01 (br, 1H), 7.83 (d, J=9.2 Hz, 1H), 5.21 (d, J=3.2 Hz, 1H), 4.96 (dd, J=11.2, 3.2 Hz, 1H), 4.49 (d, J=8.4 Hz, 1H), 4.07-3.95 (m, 3H), 3.92-3.85 (m, 1H), 3.74-3.67 (m, 1H), 3.48-3.39 (m, 1H), 2.20 (t, J=6.8 Hz, 2H), 2.11 (s, 3H), 2.00 (s, 3H), 1.90 (s, 3H), 1.77 (s, 3H), 1.55-1.45 (m, 4H).

(1-1-2) Synthesis of M-11-T3:

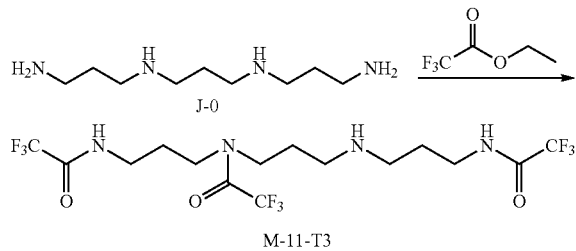

J-0 (1.883 g, 10 mmol, purchased from Alfa Aesar) was dissolved in 25 ml of acetonitrile, added with triethylamine (4.048 g, 40 mmol), and cooled to 0° C. in an ice water bath. Ethyl trifluoroacetate (5.683 g, 40 mmol) was added to react for 22 hours at room temperature. The solvent was evaporated under reduced pressure, and the residue was foam-dried with a vacuum oil pump for 18 hours to give 5.342 g of crude solid product M-11-T3, which was directly used in subsequent reaction without further purification. MS m/z: $C_{15}H_{22}F_9N_4O_3$, [M+H]$^+$, calcd: 477.35, measured: 477.65.

(1-1-3) Synthesis of M-11-T3-Tr:

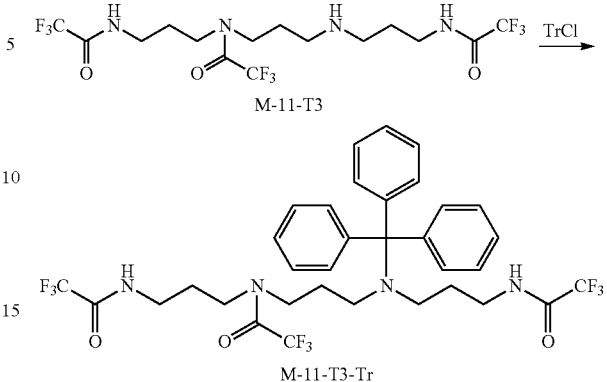

The crude product M-11-T3 (5.342 g, 10 mmol) was dissolved in 50 ml of dichloromethane. The resulting reaction solution was added with TrCl (3.345 g, 12 mmol) and triethylamine (1.518 g, 15 mmol) to react for 20 hours under stirring at room temperature. The reaction solution was washed twice, each with 20 ml of saturated sodium bicarbonate and once with 20 ml of saturated brine. The organic phase was dried with anhydrous sodium sulfate and filtered. The solvent was evaporated under reduced pressure, and the residue was foam-dried with a vacuum oil pump overnight to give 7.763 g of crude solid product M-11-T3-Tr. MS m/z: $C_{34}H_{36}F_9N_4O_3$, [M+Na]$^+$, calcd: 741.25, measured: 741.53. The crude solid product M-11-T3-Tr was then used in the next step for synthesis of M-18-Tr without purification.

(1-1-4) Synthesis of M-18-Tr:

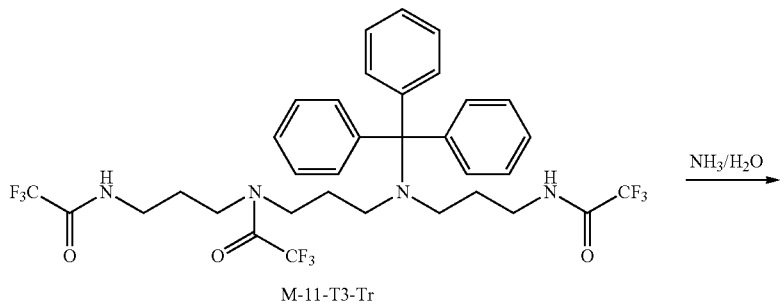

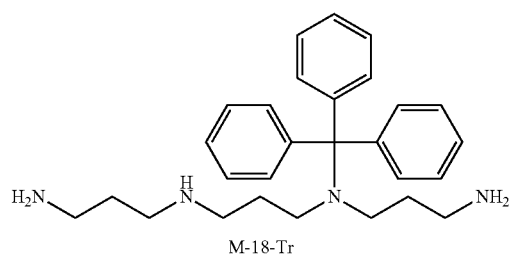

The crude product M-11-T3-Tr (7.763 g, 10 mmol) obtained in step (1-1-3) was dissolved in 100 ml of methanol, and added with 100 ml of aqueous methylamine solution (40 mass %) to react for 23 hours under stirring at 50° C. Insoluble particles were removed by filtration. The solvent was evaporated under reduced pressure, and the residue was added with 200 ml of mixed solvent of DCM: methanol in a volume ratio of 1:1, washed with 50 ml of saturated sodium bicarbonate. The aqueous phase was extracted three times, each with 50 ml of dichloromethane. The organic phases were combined, dried with anhydrous sodium sulfate and filtered. The solvent was evaporated under reduced pressure, and the residue was foam-dried with a vacuum oil pump overnight, and purified by using a normal phase silica gel column having 200-300 mesh. The column was packed with petroleum ether, added with 1 wt % triethylamine for neutralizing the acidity of silica gel, and eluted with a gradient elution of dichloromethane: methanol: aqueous ammonia (25 wt %)=1:1:0.05-1:1:0.25. The eluate of product was collected, the solvent was evaporated to dryness under reduced pressure, and the residue was foam-dried with a vacuum oil pump to give 2.887 g of pure product M-18-Tr. $^1$H NMR (400 MHz, DMSO) δ7.47-7.39 (m, 6H), 7.32-7.24 (m, 6H), 7.19-7.12 (m, 3H), 2.60-2.47 (m, 4H), 2.46-2.19 (m, 13H), 1.70-1.55 (m, 4H), 1.40 (p, J=6.8 Hz, 2H). MS m/z: $C_{28}H_{39}N_4$, [M+H]$^+$, calcd: 431.65, measured: 432.61.

(1-1-5) Synthesis of L-5-Tr:

M-18-Tr (2.02 g, 4.69 mmol) obtained in step (1-1-4) and GAL-5 (6.93 g, 15.48 mmol) obtained in step (1-1-1) were mixed and dissolved in 47 ml of acetonitrile, and added with N-methylmorpholine (3.13 g, 30.96 mmol) and 4-(4,6-dimethoxytriazin-2-yl)-4-methylmorpholine hydrochloride (DMTMM, 4.28 g, 15.48 mmol) to react for 2 hours under stirring at room temperature. The resulting reaction solution was diluted with 200 ml of dichloromethane. The organic phase was washed with 100 ml of a saturated sodium bicarbonate solution and 100 ml of saturated brine, dried with anhydrous sodium sulfate, and filtered. Then the solvent was evaporated under reduced pressure to give a crude product. The crude product was purified by using a normal phase silica gel column having 200-300 mesh. The column was packed with petroleum ether, added with 1 wt % triethylamine for neutralizing the acidity of silica gel, and eluted with a gradient elution of dichloromethane:methanol=100:5-100:7. The eluate of product was collected, and the solvent was evaporated under reduced pressure to give 7.49 g of pure product L-5-Tr. $^1$H NMR (400 MHz, DMSO) δ7.83-7.10 (m, 4H), 7.67-7.60 (m, 1H), 7.44-7.34 (m, 6H), 7.33-7.24 (m, 6H), 7.20-7.15 (m, 3H), 5.22 (s, 3H), 4.97 (d, J=11.3 Hz, 3H), 4.49 (d, J=8.4 Hz, 3H), 4.06-3.07 (m, 9H), 3.95-3.83 (m, 3H), 3.77-3.64 (m, 3H), 3.45-3.35 (m, 3H), 3.12-2.87 (m, 8H), 2.30-2.15 (m, 3H), 2.11-1.98 (m, 22H), 1.95-1.84 (m, 11H), 1.81-1.61 (m, 14H), 1.54-1.36 (m, 14H). MS m/z: $C_{85}H_{119}N_7O_{30}$, [M+H]$^+$, calcd: 1718.81, measured: 1718.03.

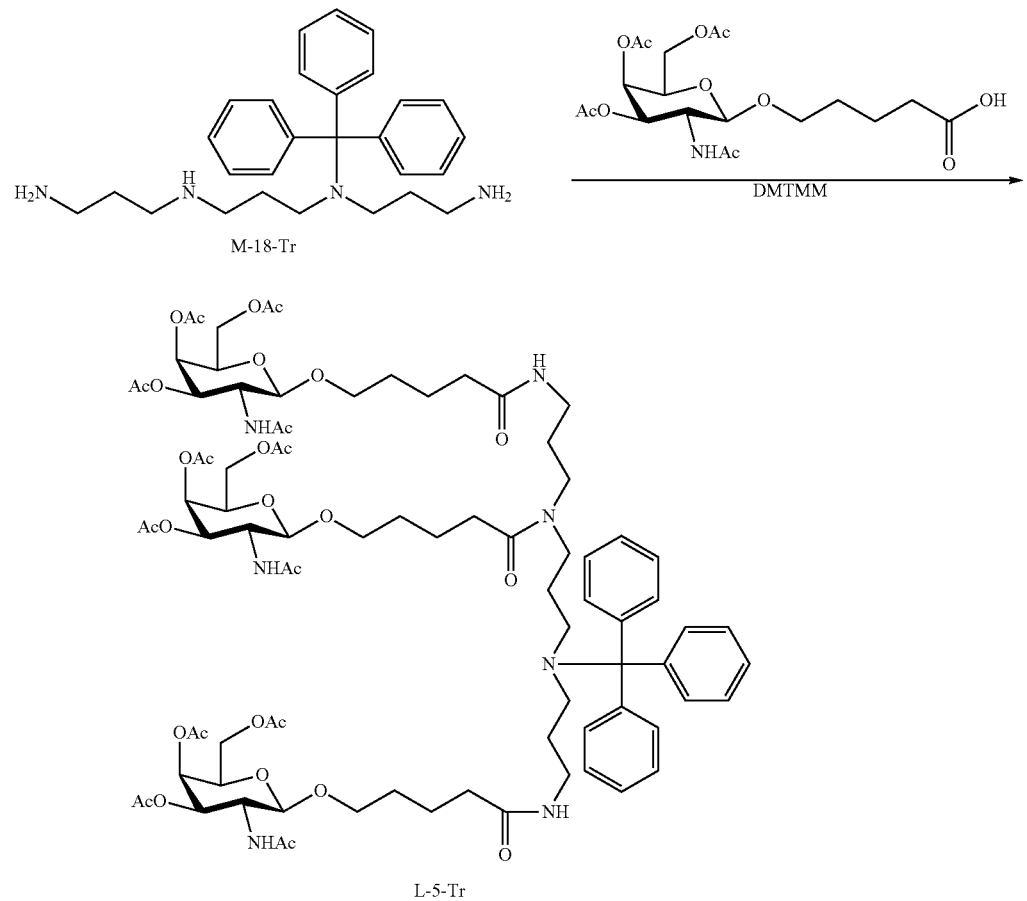

(1-1-6) Synthesis of L-8:
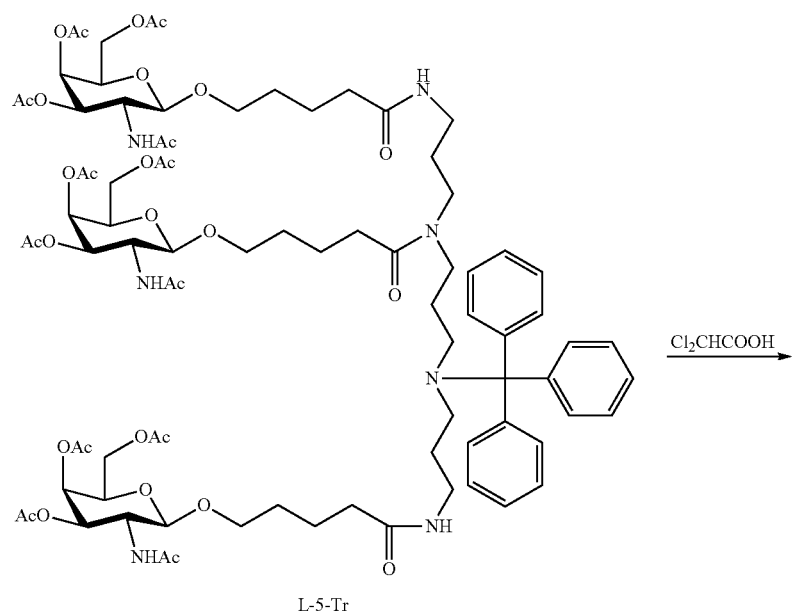
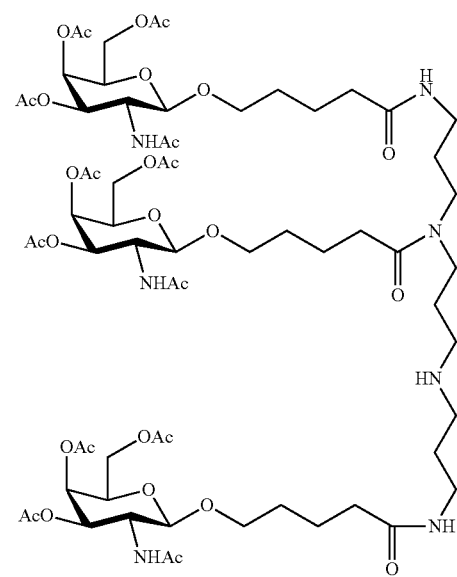

L-5-Tr (5.94 g, 3.456 mmol) obtained in step (1-1-5) was dissolved in 69 ml of dichloromethane, and added with dichloroacetic acid (13.367 g, 103.67 mmol) to react for 2 hours at room temperature. The resulting reaction solution was diluted by adding 100 ml of dichloromethane, washed and adjusted to pH 7-8 with saturated sodium bicarbonate solution. The aqueous phase was extracted six times, each with 30 ml of dichloromethane. The organic phases were combined, dried with anhydrous sodium sulfate, and filtered. Then the solvent was evaporated to dryness under reduced pressure to give a crude product. The crude product was purified by using a normal phase silica gel column having 200-300 mesh. The column was added with 10 wt % triethylamine for neutralizing the acidity of silica gel, equilibrated with 1 wt ‰ triethylamine, and eluted with a gradient elution of dichloromethane:methanol=100:30-100:40. The eluate of product was collected, and the solvent was evaporated under reduced pressure to give 4.26 g of pure product L-8. $^1$H NMR (400 MHz, DMSO) δ 7.84 (d, J=9.0 Hz, 3H), 7.27-7.23 (m, 1H), 7.13-7.18 (m, 1H), 5.22 (d, J=3.1 Hz, 3H), 4.97 (dd, J=11.3, 3.1 Hz, 3H), 4.48 (d, J=8.4 Hz, 3H), 4.09-3.98 (m, 9H), 3.88 (dd, J=19.3, 9.3 Hz, 3H), 3.75-3.66 (m, 3H), 3.44-3.38 (m, 3H), 3.17-3.30 (m, 4H), 3.10-2.97 (m, 4H), 2.35-2.20 (m, 6H), 2.15-2.08 (m, 9H), 2.07-1.98 (m, 13H), 1.94-1.87 (m, 9H), 1.81-1.74 (m, 9H), 1.65-1.42 (m, 18H). MS m/z: $C_{85}H_{119}N_7O_{30}$, $[M+H]^+$, calcd: 1477.59, measured: 1477.23.

(1-1-7a) Synthesis of A-1:

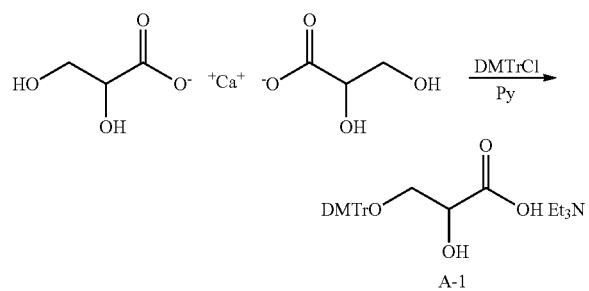

DMTrCl (4,4'-dimethoxytrityl chloride, 38.12 g, 112.5 mmol) was dissolved in 450 ml of anhydrous pyridine, and added with calcium DL-glycerate hydrate (12.88 g, 45.0 mmol) to react for 22 hours at 45° C. The resulting reaction solution was filtered. The filter cake was rinsed with 200 ml of DCM, and the filtrate was concentrated under reduced pressure. The residue was redissolved in 500 ml of dichloromethane and washed twice, each with 200 ml of 0.5 M triethylamine phosphate (pH=7-8). The aqueous phase was extracted twice, each with 200 ml of dichloromethane. The organic phases were combined, dried with anhydrous sodium sulfate, and filtered. The solvent was evaporated under reduced pressure, and the residue was purified by using a normal phase silica gel column having 200-300 mesh, eluted with a gradient elution of petroleum ether:ethyl acetate:dichloromethane:methanol=1:1:1:0.35-1:1:1:0.55.

The eluate of product was collected, and the solvent was evaporated to dryness under reduced pressure. The residue was redissolved in 500 ml of dichloromethane, and washed once with 200 ml of 0.5 M triethylamine phosphate. The aqueous phase was extracted twice, each with 200 ml of dichloromethane. The organic phases were combined, dried with anhydrous sodium sulfate, and filtered. The solvent was evaporated under reduced pressure, and the residue was subject to a reduced pressure with a vacuum oil pump overnight to give 20.7 g of product A-1 as a white solid. $^1$H NMR (400 MHz, DMSO-d6) δ 7.46 (ddd, J=6.5, 2.3, 1.1 Hz, 1H), 7.40-7.28 (m, 7H), 6.89-6.81 (m, 4H), 4.84 (d, J=5.0 Hz, 1H), 4.36-4.24 (m, 1H), 4.29 (s, 6H), 3.92 (dd, J=12.4, 7.0 Hz, 1H), 3.67 (dd, J=12.3, 7.0 Hz, 1H), 2.52 (q, J=6.3 Hz, 6H), 1.03 (t, J=6.3 Hz, 9H). MS m/z: $C_{24}H_{23}O_6$, $[M-H]^-$, calcd: 407.15, measured: 406.92.

(1-1-7b) Synthesis of L-7:

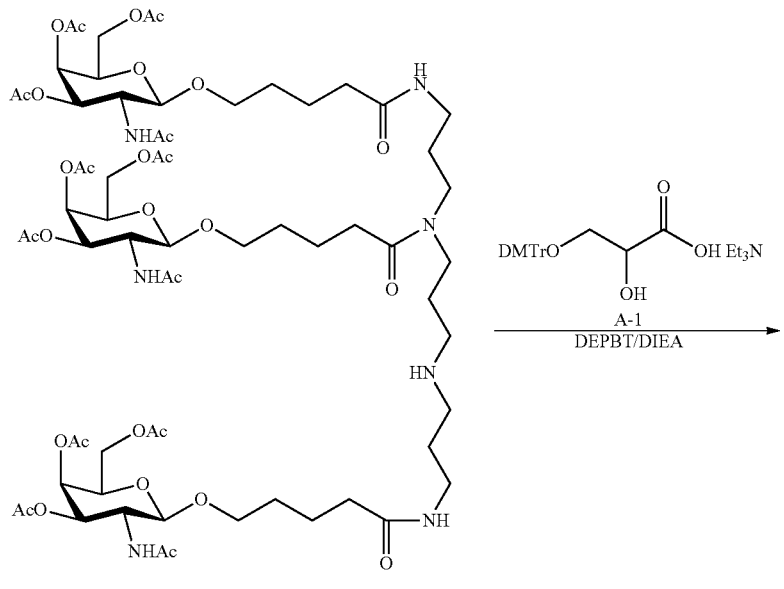

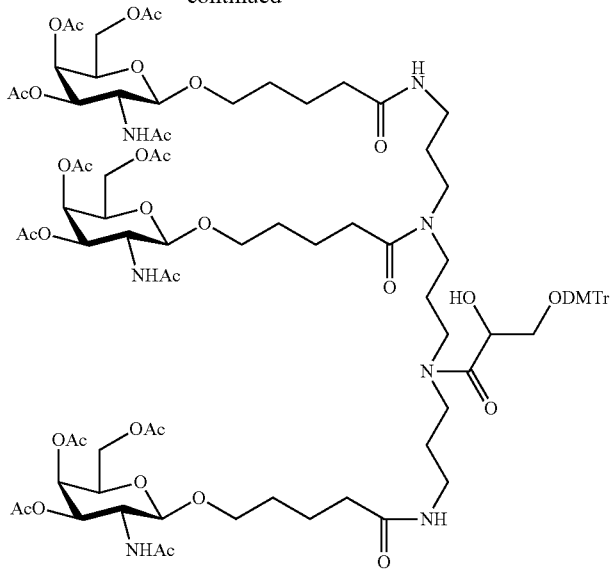

L-7

L-8 (2.262 g, 1.532 mmol) obtained in step (1-1-6) and A-1 (2.342 g, 4.596 mmol) obtained in step (1-1-7a) were mixed and dissolved in 16 ml of dichloromethane, added with 3-(diethoxyphosphoryloxy)-1,2,3-benzotrizin-4(3H)-one (DEPBT, 1.375 g, 4.596 mmol), and further added with diisopropylethylamine (1.188 g, 9.191 mmol) to react for 2 hours under stirring at 25° C.'. The organic phase was washed with 10 ml of saturated sodium bicarbonate. The aqueous phase was extracted three times, each with 10 ml of dichloromethane. The organic phases was washed with 10 ml of saturated brine, and the aqueous phase isolated was extracted twice, each with 10 ml of dichloromethane, and the obtained organic phases were combined, dried with anhydrous sodium sulfate and filtered. The solvent was evaporated under reduced pressure, and the residue was foam-dried overnight with a vacuum oil pump to give 4.900 g of crude product. The crude product was subjected to a column purification. The column was filled with 120 g of normal phase silica gel having 200-300 mesh, and added with 20 ml triethylamine for neutralizing the acidity of silica gel. The column was equilibrated with petroleum ether containing 1 wt % triethylamine and eluted with a gradient elution of petroleum ether: ethyl acetate: dichloromethane: N,N-dimethylformamide=1:1:1:0.5-1:1:1:0.6. The eluate of product was collected, and the solvent was evaporated under reduced pressure to give 2.336 g of pure product L-7. $^1$H NMR (400 MHz, DMSO) δ7.90-7.78 (m, 4H), 7.75-7.64 (m, 1H), 7.38-7.18 (m, 9H), 6.91-6.83 (m, 4H), 5.25-5.10 (m, 4H), 4.97 (dd, J=11.2, 3.2 Hz, 3H), 4.48-4.30 (m, 4H), 4.02 (s, 9H), 3.93-3.84 (m, 3H), 3.76-3.66 (m, 9H), 3.45-3.35 (m, 3H), 3.24-2.98 (m, 10H), 2.30-2.20 (m, 2H), 2.11-1.88 (m, 31H), 1.80-1.40 (m, 28H). MS m/z: $C_{90}H_{128}N_7O_{35}$, [M-DMTr]$^+$, calced: 1564.65, measured: 1564.88.

(1-1-8) Synthesis of L-9:

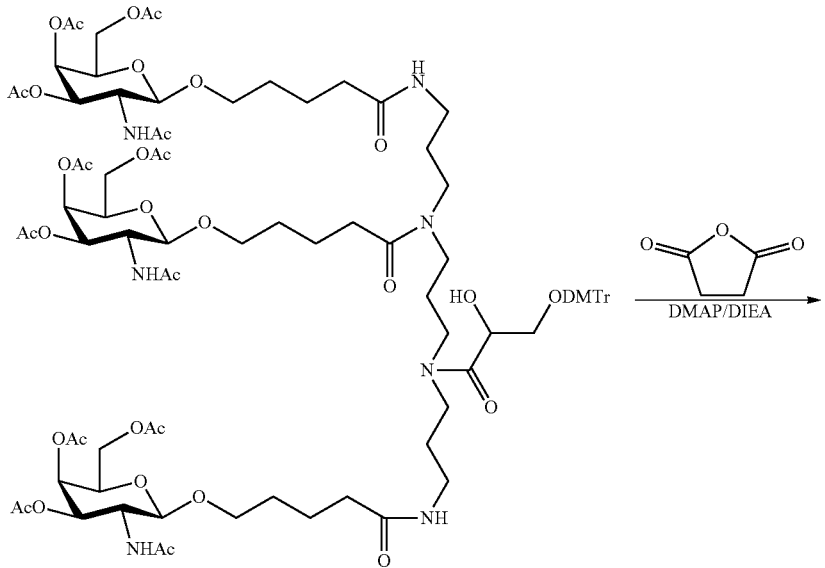

L-7

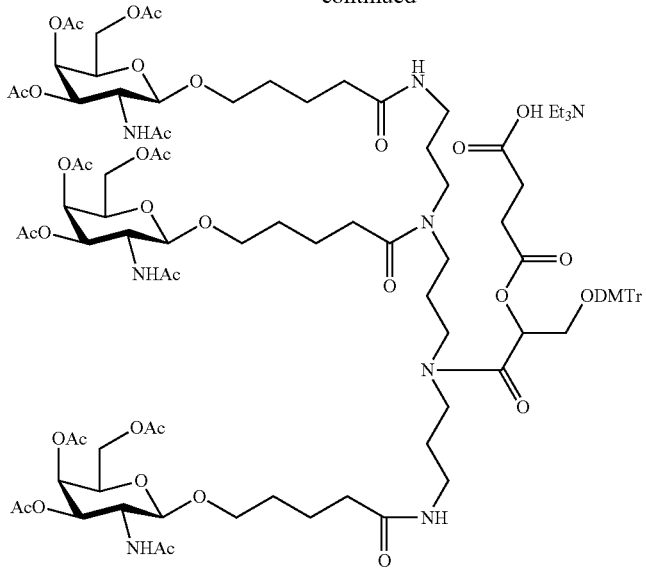

L-9

L-7 (2.300 g, 1.26 mmol) obtained in step (1-1-7b), succinic anhydride (0.378 g, 3.78 mmol) and 4-dimethylaminopyridine (DMAP, 0.462 g, 3.78 mmol) were mixed and dissolved in 13 ml of dichloromethane, then added with diisopropylethylamine (DIPEA, 0.814 g, 6.30 mmol), and stirred for 24 hours at 25° C. The resulting reaction solution was washed with 5 ml of 0.5 M triethylamine phosphate. The aqueous phase was extracted three times, each with 5 ml of dichloromethane. The organic phases were combined, and evaporated under reduced pressure to give 2.774 g of crude product. The crude product was subjected to a column purification. The column was filled with 60 g of normal phase silica gel having 200-300 mesh, and added with 1 wt % triethylamine for neutralizing the acidity of silica gel. The column was equilibrated with dichloromethane and eluted with a gradient elution of 1 wt ‰ triethylamine-containing dichloromethane:methanol=100:18-100:20. The eluate of product was collected, and the solvent was evaporated under reduced pressure to give 1.874 g of pure L-9 conjugating molecule. $^1$H NMR (400 MHz, DMSO) δ 8.58 (d, J=4.2 Hz, 1H), 7.94-7.82 (m, 3H), 7.41-7.29 (m, 5H), 7.22 (d, J=8.1 Hz, 5H), 6.89 (d, J=8.3 Hz, 4H), 5.49-5.37 (m, 1H), 5.21 (d, J=3.0 Hz, 3H), 4.97 (d, J=11.1 Hz, 3H), 4.49 (d, J=8.2 Hz, 3H), 4.02 (s, 9H), 3.88 (dd, J=19.4, 9.4 Hz, 3H), 3.77-3.65 (m, 9H), 3.50-3.39 (m, 6H), 3.11-2.90 (m, 5H), 2.61-2.54 (m, 4H), 2.47-2.41 (m, 2H), 2.26-2.17 (m, 2H), 2.15-1.95 (m, 22H), 1.92-1.84 (m, 9H), 1.80-1.70 (m, 10H), 1.65-1.35 (m, 17H), 1.31-1.19 (m, 4H), 0.96 (t, J=7.1 Hz, 9H). MS m/z: $C_{94}H_{132}N_7O_{38}$, [M-DMTr]$^+$, calcd: 1664.72, measured: 1665.03.

(1-1-9) Synthesis of Compound L-10:

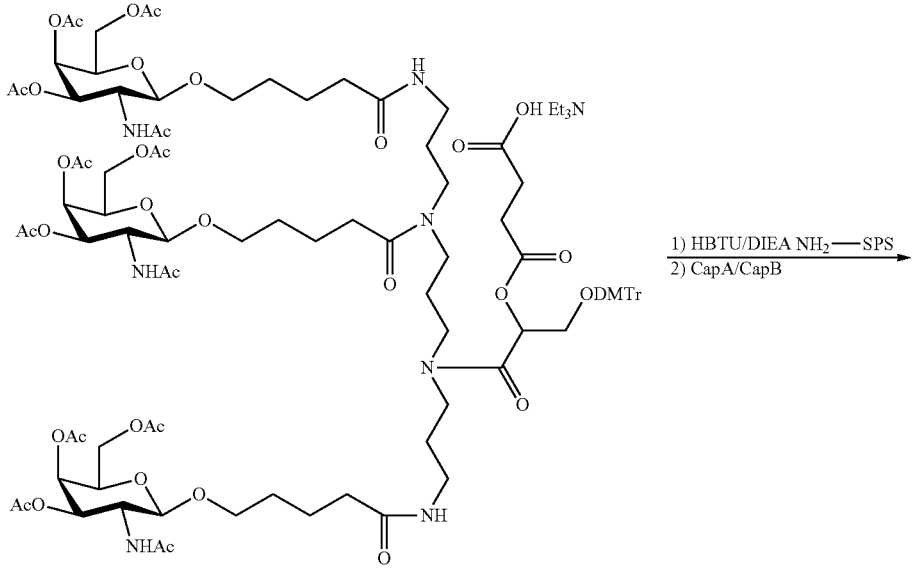

L-9

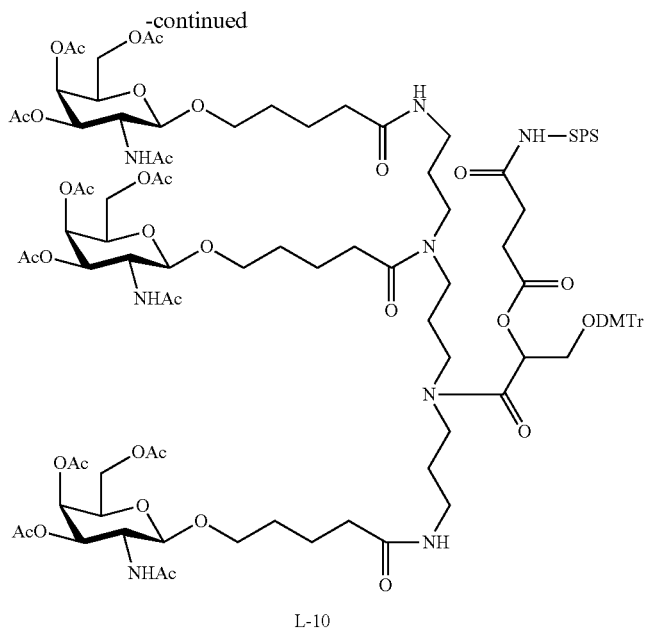

L-10

In this step, compound L-10 was prepared by linking the L-9 conjugating molecule to a solid phase support.

The L-9 conjugating molecule (0.233 g, 0.1126 mmol) obtained in step (1-1-8), O-benzotriazol-tetramethyluronium hexafluorophosphate (HBTU, 0.064 g, 0.1689 mmol) and diisopropylethylamine (DIPEA, 0.029 g, 0.2252 mmol) were mixed and dissolved in 19 ml of acetonitrile, and stirred at room temperature for 5 minutes. Aminomethyl resin (0.901 g, 100-200 mesh, amino loading: 400 μmol/g, purchased from Tianjin Nankai HECHENG S&T Co., Ltd.) was added into the reaction solution.

The reaction was performed on a shaker at 25° C. and 220 rpm/min for 15 hours, followed by filtration. The filter cake was rinsed twice, each with 30 ml of DCM; three times, each with 30 ml of acetonitrile; and once with 30 ml of ethyl ether; and then dried for 2 hours with a vacuum oil pump. Then a capping reaction was performed by adding starting-materials (CapA, CapB, 4-dimethylaminopyridine (DMAP) and acetonitrile) according to the feeding ratio shown in Table 2. The reaction was placed on a shaker at 25° C. and 200 rpm/min for 5 hours. The reaction solution was filtered. The filter cake was rinsed three times, each with 30 ml of acetonitrile, and was subjected to suction filtration to dryness, and then was dried overnight under a reduced pressure with a vacuum oil pump to give 1.100 g of compound L-10 (i.e., L-9 conjugating molecule linked to a solid phase support), with a loading of 90.8 μmol/g.

TABLE 2

The feeding ratio of capping reaction

| Starting materials | Amount | grade | Lot No. | Manufacturer |
|---|---|---|---|---|
| CapA | 20 ml | — | — | — |
| CapB | 2.3 ml | — | — | — |
| DMAP | 0.01 g | analytical pure | I1422139 | Aladdin |
| acetonitrile | 2.3 ml | spectroscopic pure | O15161001 | CINC (Shanghai) Co., Ltd |

In the above table, Cap A and Cap B are solutions of capping reagents. Cap A is a solution of 20% by volume of N-methylimidazole in a mixture of pyridine/acetonitrile, wherein the volume ratio of pyridine to acetonitrile is 3:5. Cap B is a solution of 20% by volume of acetic anhydride in acetonitrile.

(1-2) Synthesis of Sense Strands of Conjugates 1-4

Since the sense strands of conjugates 1-4 have the same sequence, they were prepared by the same method.

Nucleoside monomers were linked one by one in 3' to 5' direction according to the sequence of nucleotides in the sense strand by the phosphoramidite solid phase synthesis method, starting the cycles from the compound L-10 prepared in the above step. The linking of each nucleoside monomer included a four-step reaction of deprotection, coupling, capping, and oxidation or sulfuration. In particular, when a phosphoester linkage was present between two nucleotides, a four-step reaction of deprotection, coupling, capping, and oxidation was included during linking of the later nucleoside monomer; and when a phosphorothioate linkage was present between two nucleotides, a four-step reaction of deprotection, coupling, capping, and sulfurization was included during linking of the later nucleoside monomer. The synthesis condition was given as follows:

The nucleoside monomers were provided in a 0.1 M solution in acetonitrile. The conditions were the same for each deprotection reaction, i.e., a temperature of 25° C., a reaction time of 70 seconds, a solution of dichloroacetic acid in dichloromethane (3% v/v) as a deprotection reagent, and a molar ratio of dichloroacetic acid to the protecting group 4,4'-dimethoxytrityl on the solid phase support of 5:1.

The conditions were the same for each coupling reaction, including a temperature of 25° C., a molar ratio of the nucleic acid sequence linked to the solid phase support to nucleoside monomers of 1:10, a molar ratio of the nucleic acid sequence linked to the solid phase support to a coupling reagent of 1:65, a reaction time of 600 seconds, and a coupling reagent of 0.5 M solution of 5-ethylthio-1H-tetrazole in acetonitrile.

The conditions were the same for each capping reaction, including a temperature of 25° C. and a reaction time of 15 seconds. The capping reagent was a mixed solution of Cap A and Cap B in a molar ratio of 1:1; and a molar ratio of the capping reagent to the nucleic acid sequence linked to the solid phase support was acetic anhydride: N-methylimidazole: the nucleic acid sequence linked to the solid phase support=1:1:1.

The conditions were the same for each oxidation reaction, including a temperature of 25° C., a reaction time of 15 seconds, and 0.05 M iodine water as an oxidation reagent; and a molar ratio of iodine to the nucleic acid sequence linked to the solid phase support in the coupling step was 30:1. The reaction was carried out in a mixed solvent of tetrahydrofuran:water:pyridine=3:1:1.

The conditions were the same for each sulfuration reaction, including a temperature of 25° C., a reaction time of 300 seconds, and xanthane hydride as a sulfurization reagent. The molar ratio of the sulfurization reagent to the nucleic acid sequence linked to the solid phase support in the coupling step was 120:1. The reaction was carried out in a mixed solvent of acetonitrile:pyridine=1:1.

The conditions for cleavage and deprotection were as follows: The synthesized nucleotide sequence linked to the support was added to 25 wt % aqueous ammonia to react for 16 hours at 55° C., and the aqueous ammonia was used in an amount of 0.5 ml/μmol. The liquid was removed, and the residue was concentrated in vacuum to dryness.

Purification and desalination: purification of the nucleic acid was achieved by using a preparative ion chromatography column (Source 15Q) with a gradient elution of NaCl. Specifically, eluent A: 20 mM sodium phosphate (pH 8.1), solvent: water/acetonitrile=9:1 (v/v); eluent B: 1.5 M sodium chloride, 20 mM sodium phosphate (pH 8.1), solvent: water/acetonitrile=9:1 (v/v); elution gradient: the ratio of eluent A:eluent B=100:0-50:50. The eluate of product was collected, combined and desalted by using a reversed phase chromatography column. The specific condition included that a Sephadex column was used for desalination, with Sephadex-G25 as the filler and deionized water for eluting.

Detection: The purity was determined by ion exchange chromatography (IEX-HPLC), and the molecular weight was analyzed by Liquid Chromatography-Mass Spectrometry (LC-MS), with a calculated value of 7584.5 and a measured value of 7584.0. The measured value was in conformity with the calculated value, indicating that a sense strand S conjugated with L-9 conjugating molecule at 3' terminal was synthesized.

(1-3) Synthesis of an Antisense Strand
(1-3A) Preparation of Antisense Strand of Conjugate 1

The antisense strand AS of the conjugate 1 is synthesized by using a universal solid phase support (UnyLinker™ loaded NittoPhase®HL Solid Supports, Kinovate Life Sciences Inc.) according to a solid phase phosphoramidite method. Deprotection, coupling, capping, and oxidization or sulfuration reaction in the solid phase synthesis method, cleavage and deprotection, and purification and desalting are conducted under the same conditions as those in the synthesis of sense strand.

Detection: The purity was determined by ion exchange chromatography (IEX-HPLC), and the molecular weight was analyzed by Liquid Chromatography-Mass Spectrometry (LC-MS), with a calculated value of 7007.46 and a measured value of 7006.2. The measured value was in conformity with the calculated value, indicating that antisense strand AS having target sequence was synthesized.

In particular, vinyl phosphate modified 2'-methoxy modified uracil nucleoside monomer (VP-Um) was synthesized according to the following method:

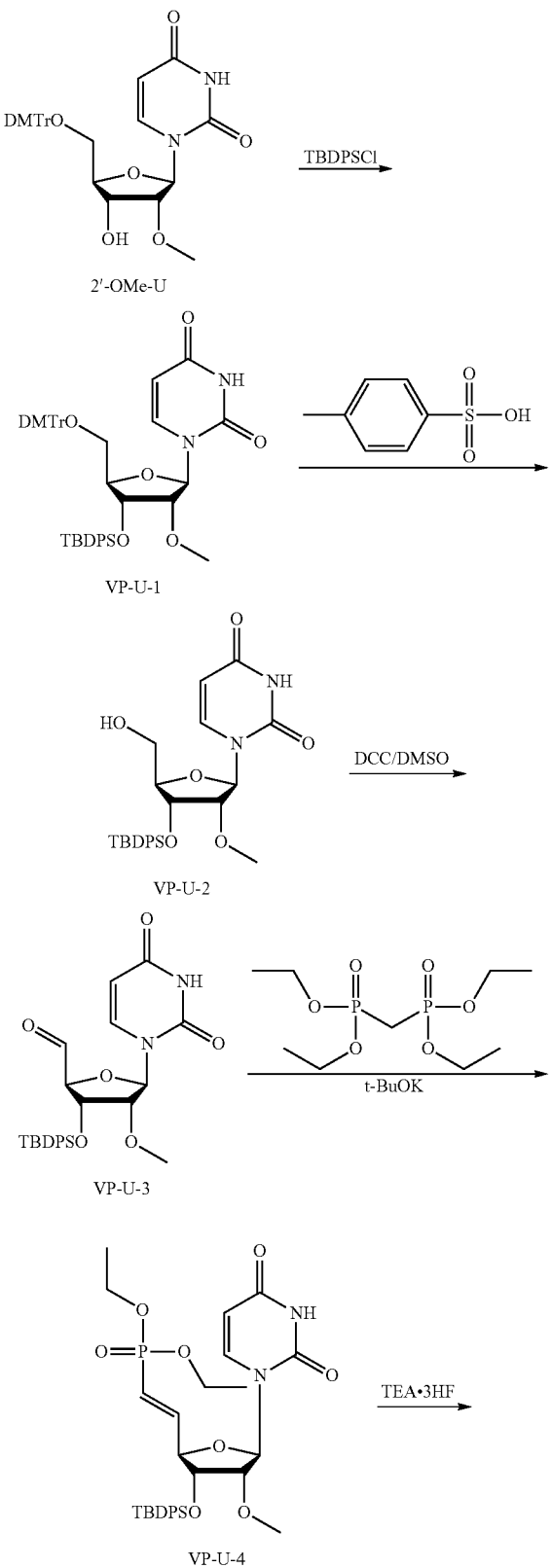

-continued

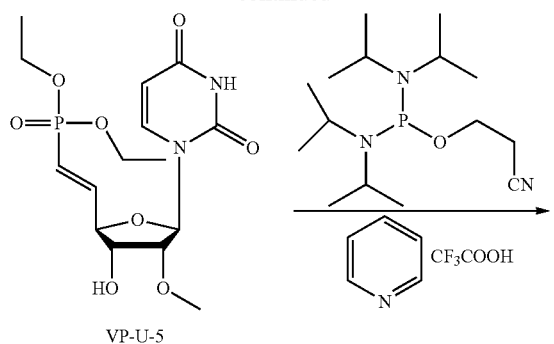

VP-U-5

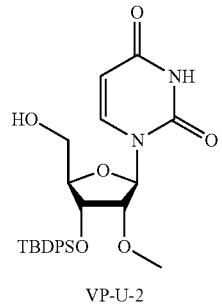

VP-U-2

A 2'-methoxy modified uracil nucleoside (2'-OMe-U, 51.30 g, 91.6 mmol), tert-butyl diphenylchlorosilane (TBDPSCl, 50.35 g, 183.2 mmol), and imidazole (12.47 g, 183.2 mmol) were mixed and dissolved in 450 ml of N,N-dimethylformamide (DMF) to react for 20 hours under stirring at room temperature. DMF was removed by evaporation, and the residue was dissolved with 600 ml of dichloromethane and washed with 300 ml of saturated sodium bicarbonate. The aqueous phase was extracted three times, each with 300 ml of dichloromethane. The organic phases were combined, washed with 5% oxalic acid until an aqueous phase of pH<5 was obtained. The solvent was evaporated to give a crude product VP-U-1, which was directly used in the subsequent synthesis of VP-U-2.

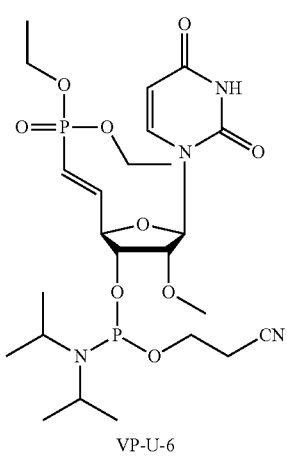

VP-U-6

(1-3-1) Synthesis of VP-U-2

VP-U-2 molecule was synthesized according to the following method:

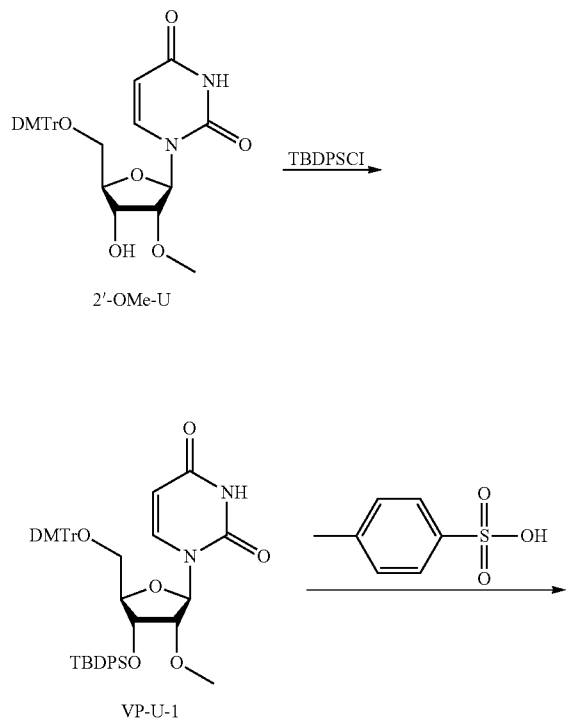

The crude product VP-U-1 was dissolved in 100 ml of dichloromethane, and then stirred for 10 minutes in an ice bath. 450 ml of 2% p-toluenesulfonic acid solution (with a mixed solvent of methanol and dichloromethane in a volume ratio of 3:7) pre-cooled in a refrigerator at 4° C. was added to react for 10 minutes. The reaction was quenched by addition of 200 ml of saturated sodium bicarbonate. The organic phase was washed by addition of saturated sodium bicarbonate solution to pH=8. Aqueous phases were combined and extracted twice, each with 200 ml of dichloromethane. The organic phases were combined and washed once with 200 ml of saturated brine. The solvent was evaporated to dryness, and the residue was purified by using a normal phase silica gel column having 200-300 mesh. The column was packed with petroleum ether and eluted with a gradient elution of petroleum ether: ethyl acetate:dichloromethane:methanol=1:1:1:0.05-1:1:1:0.25. The eluate was collected, the solvent was evaporated to dryness under reduced pressure, and the residue was foam-dried with a vacuum oil pump to give a total of 40.00 g of pure product VP-U-2. $^1$H NMR (400 MHz, DMSO-d6) δ 7.96 (d, J=7.8 Hz, 1H), 7.64 (dtd, J=5.1, 4.0, 2.2 Hz, 4H), 7.41-7.30 (m, 6H), 6.79 (d, J=4.7 Hz, 1H), 5.73 (d, J=7.6 Hz, 1H), 4.94 (t, J=7.0 Hz, 1H), 4.12 (td, J=4.6, 3.9 Hz, 1H), 4.05 (dd, J=4.8, 4.0 Hz, 1H), 3.96 (t, J=4.7 Hz, 1H), 3.68 (ddd, J=11.8, 7.0, 4.6 Hz, 1H), 3.57-3.46 (m, 1H), 3.39 (s, 3H), 1.05 (s, 8H). MS m/z: $C_{26}H_{33}N_2O_6Si$, $[M+H]^+$, calcd: 497.21, measured: 497.45.

(1-3-2) Synthesis of Synthesis of VP-U-4:

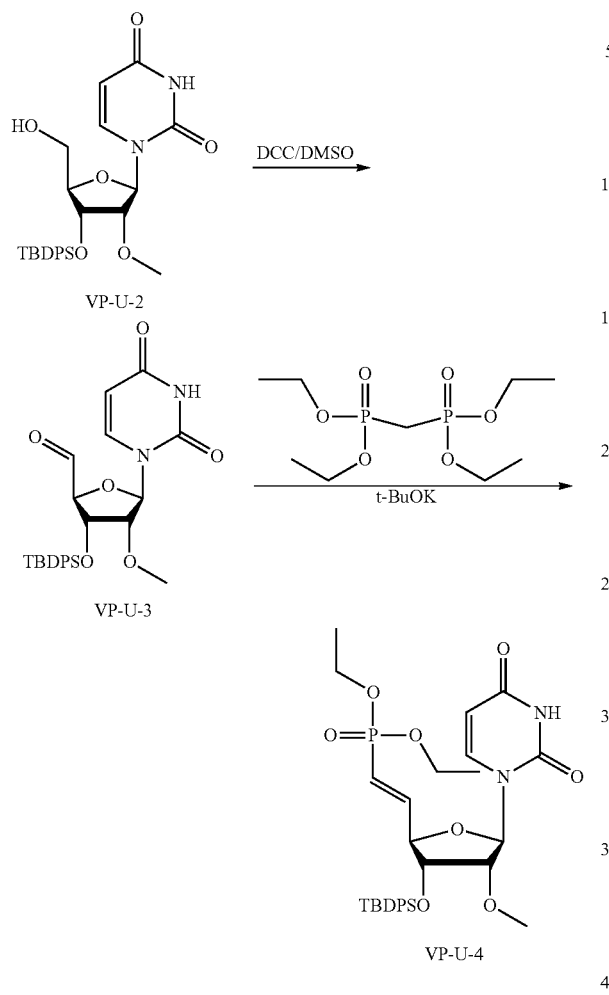

residue was foam-dried with a vacuum oil pump to give a total of 14.00 g of pure product VP-U-4. $^1$H NMR (400 MHz, DMSO-d6) δ 7.96 (d, J=7.8 Hz, 1H), 7.64 (dtd, J=5.1, 4.0, 2.2 Hz, 4H), 7.41-7.30 (m, 6H), 6.82-6.71 (m, 2H), 5.90 (ddd, J=25.9, 15.0, 1.0 Hz, 1H), 5.73 (d, J=7.6 Hz, 1H), 4.36-4.21 (m, 3H), 4.18 (t, J=4.9 Hz, 1H), 4.05 (ddq, J=9.7, 8.5, 6.9 Hz, 2H), 3.87 (t, J=4.8 Hz, 1H), 3.39 (s, 3H), 1.32 (td, J=6.9, 0.7 Hz, 6H), 1.05 (s, 8H). MS m/z: $C_{31}H_{42}N_2O_8Psi$, $[M+H]^+$, calcd: 629.24, measured: 629.51.

(1-3-3) Synthesis of VP-U-5

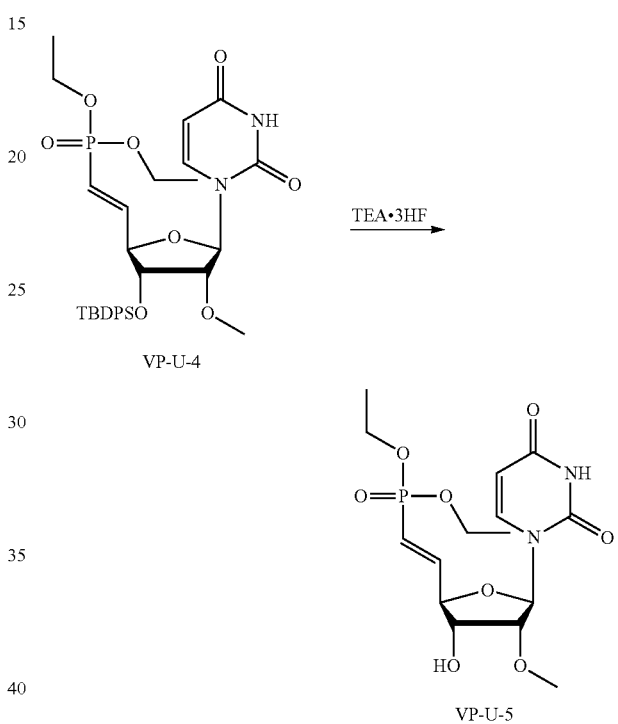

VP-U-2 (19.84 g, 40.0 mmol), dicyclohexylcarbodiimide (DCC, 16.48 g, 80.0 mmol), pyridine (4.20 g, 53.2 mmol), and trifluoroacetic acid (6.61 g, 53.2 mmol) were mixed and dissolved in 200 ml of dimethyl sulfoxide (DMSO) to react for 20 hours under stirring at room temperature. In addition, tetraethyl methylenediphosphate (21.44 g, 74.4 mmol) was dissolved in 120 ml of THF, cooled in an ice bath, added with t-BuOK (11.36 g, 101.2 mmol) at a temperature of the ice bath to react for 10 min, warmed to room temperature to react for 0.5 h and added into the above reaction liquid over about 1 h. The reaction was carried out for 1 h at a temperature of the ice bath and then warmed to room temperature to react for 18 h. The reaction was quenched by addition of water. The aqueous phase was extracted three times, each with 200 ml of dichloromethane. The organic phases were combined and washed once with 200 ml of saturated brine. The solvent was evaporated to dryness, and the residue was purified by using a normal phase silica gel column having 200-300 mesh. The column was packed with petroleum ether and eluted with a gradient elution of petroleum ether: ethyl acetate=1:1-1:4. The eluate was collected, the solvent was evaporated under reduced pressure, and the VP-U-4 (14.00 g, 22.29 mmol) was dissolved in 100 ml of tetrahydrofuran, added with triethylamine trihydrofluoride (17.96 g, 111.45 mmol), and stirred at room temperature for 20 hours to react completely. The solvent was directly evaporated to dryness and the residue was dissolved in dichoromethane; the above evaporation and dissolution steps were additionally repeated twice, each with 50 ml of dichloromethane, to give a crude product. The crude product was purified by using a normal phase silica gel column having 200-300 mesh. The column was packed with petroleum ether and eluted with a gradient elution of petroleum ether: ethyl acetate:dichloromethane:methanol=1:1:1:0.05-1:1:1:0.25. The eluate of product was collected, the solvent was evaporated to dryness under reduced pressure, and the residue was foam-dried with a vacuum oil pump to give a total of 6.70 g of pure product VP-U-5. $^1$H NMR (400 MHz, DMSO-d6) δ 7.96 (d, J=7.8 Hz, 1H), 6.77 (dd, J=15.0, 6.2 Hz, 1H), 5.99-5.82 (m, 2H), 5.73 (d, J=7.6 Hz, 1H), 5.27 (d, J=5.1 Hz, 1H), 5.10 (dd, J=5.3, 4.7 Hz, 1H), 4.29 (ddq, J=9.8, 8.6, 7.0 Hz, 2H), 4.17 (ddd, J=6.2, 5.2, 1.0 Hz, 1H), 4.12-3.98 (m, 3H), 3.39 (s, 2H), 1.32 (td, J=6.9, 0.6 Hz, 6H). MS m/z: $C_{15}H_{24}N_2O_8P$, $[M+H]^+$, calcd: 391.13, measured: 391.38.

(1-3-4) Synthesis of VP-U-6:

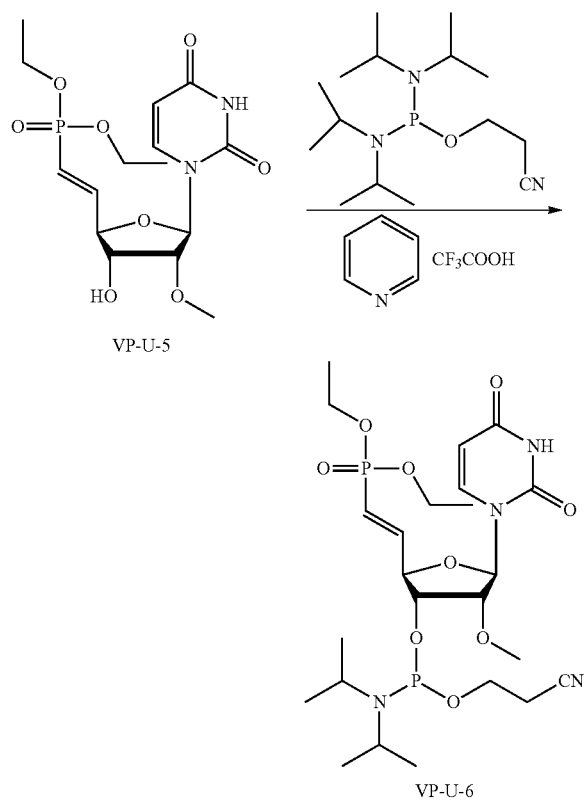

VP-U-5 (391 mg, 1.0 mmol), pyridine trifluoroacetate (0.232 g, 1.2 mmol), N-methylimidazole (0.099 g, 1.2 mmol), and bis(diisopropylamino)(2-cyanoethoxy)phosphine (0.452 g, 1.5 mmol) were added to 10 ml of anhydrous dichloromethane in argon atmosphere to react for 5 hours under stirring at room temperature. The solvent was evaporated to dryness, and then the residue was purified by column chromatography (200-300 mesh normal phase silica gel, with a gradient elution of dichloromethane: acetonitrile (containing 0.5 wt % triethylamine)=3:1-1:3). The eluate of product was collected and concentrated to remove the solvent to give a total of 508 mg of target product VP-U-6. $^{31}$P NMR (161 MHz, DMSO-d6) δ 150.34, 150.29, 17.07, 15.50. MS m/z: $C_{24}H_{41}N_4O_9P_2$, $[M+H]^+$, calcd: 591.23, measured: 591.55. This showed that VP-U-6 is target product VP-Um, which was involved in the synthesis of RNA strand as a nucleoside monomer.

(1-3B) Preparation of an Antisense Strand of Conjugate 2:

The antisense strand of conjugate 2 differs from the antisense strand of conjugate 1 only in the first nucleotide modification at the 5' terminal. In the preparation of an antisense strand according to solid-phase phosphoramidite method, the finally linked nucleoside monomer is 2'-methoxy modified uracil nucleoside monomer (Um), and the CPR-I monomer (purchased from Suzhou GenePharma Inc. as Cat #13-2601-XX) was linked to the 5' terminal of the antisense strand through a four-step reaction of deprotection, coupling, capping and oxydization to form 5'-phosphoate modification.

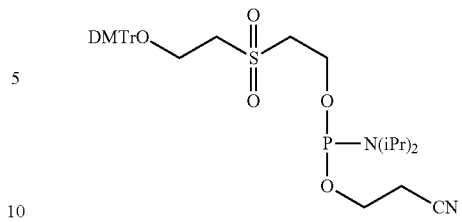

(CPR-I)

In the synthesis, the universal solid phase support and the conditions of deprotection, coupling, capping, and oxidization or sulfuration, the cleavage and deprotection, and purification and desalting are the same as those in the synthesis of sense strand.

The purity was determined by IEX-HPLC, and the molecular weight was analyzed by LC-MS, with a calculated value of 7011.47 and a measured value of 7011.3. The measured value was in conformity with the calculated value, indicating that antisense strand AS having target sequence was synthesized.

(1-3C) Synthesis of the Antisense Strand of Conjugate 3

It was expected that the antisense strand of conjugate 3 with a 5'-phosphorothioate modification was prepared by employing the same process as that in the synthesis of the antisense strand of conjugate 2, except that: when CPR-I is linked, the above oxidization reaction condition was replaced with a sulfuration reaction condition.

(1-3D) Synthesis of the Antisense Strand of Conjugate 4

The antisense strand of conjugate 4 and the antisense strand of conjugate 1 differ only in the first nucleotide modification at the 5' terminal. In the preparation of an antisense strand according to solid-phase phosphoramidite method, the finally linked nucleoside monomer is 2'-methoxy modified uracil nucleoside monomer (Um).

The purity was determined by IEX-HPLC, and the molecular weight was analyzed by LC-MS, with a calculated value of 6931.47 and a measured value of 6930.9. The measured value was in conformity with the calculated value, indicating that antisense strand AS having target sequence was synthesized.

(1-4) Synthesis of Conjugates 1-4

For conjugate 1, the S strand and the AS strand were dissolved in water for injection to give a solution of 40 mg/mL, respectively. They are mixed in an equimolar ratio, heated for 15 min at 50° C., and then cooled to room temperature to form a double stranded structure via hydrogen bonds. The conjugate was diluted to a concentration of 0.2 mg/mL by using ultra-pure water (homemade by Milli-Q ultra-pure water instrument, with resistivity of 18.2MΩ*cm (25° C.)). The molecular weight was measured by LC-MS (Liquid Chromatography-Mass Spectrometry) (purchased from Waters Corp., model: LCT Premier). The measured value was in conformity with the calculated value, indicating that the synthesized conjugate 1 was the designed target double stranded nucleic acid sequence with the L9 conjugating molecule.

For conjugates 2-4, they were prepared by the same method and their molecular weight was measured by the same method. The measured values were in conformity with the calculated values, indicating that the synthesized conjugates were the designed target double stranded nucleic acid sequences with the L9 conjugating molecules. Conjugates 1-4 have the structure as shown by Formula (403).

Preparation Example 2. Preparation of Conjugates 5-21 and Comparative Conjugate 1

Conjugates 5, 6 and 7 and comparative conjugate 1 were synthesized, and conjugates 8-11 were expected to be prepared by using the same method as that in Preparation Example 1, except that: 1) the siRNAs respectively have the sequences as shown in Table 3 corresponding to comparative conjugate 1 and conjugates 5-21; 2) when the target sequence comprises unmodified nucleotides, in the cleavage and deprotection conditions, after treatment with aqueous ammonia, the product was dissolved in N-methylpyrrolidone in an amount of 0.4 ml/µmol, followed by addition of 0.3 ml/µmol of triethylamine and 0.6 ml/µmol of triethylamine trihydrofluoride, with respect to the amount of the single strand nucleic acid, thereby removing the 2'-TBDMS protection on ribose.

TABLE 3 siRNA Conjugates

| Conjugate | NO. | | Sequence Direction 5'-3' | SEQ ID NO |
|---|---|---|---|---|
| Conjugate1 | L10-siAN1 M3SVP | S | CmsCmsAmAmGmAmGfCfAfCmCmAmAmGmAmAmCmUmAm | 26 |
| | | AS | VP-UmsAfsGmUmUmCfUmUmGmUmGmCmCmfCmUfUmGmGmsCmsUm | 36 |
| Conjugate2 | L10-siAN1 M3SP | S | CmsCmsAmAmGmAmGfCfAfCmCmAmAmGmAmAmCmUmAm | 26 |
| | | AS | P-UmsAfsGmUmUmCfUmUmGmUmGmCmCmfCmUfUmGmGmsCmsUm | 37 |
| Conjugate3 | L10-siAN1 M3SPs | S | CmsCmsAmAmGmAmGfCfAfCmCmAmAmGmAmAmCmUmAm | 26 |
| | | AS | Ps-UmsAfsGmUmUmCfUmUmGmUmGmCmCmfCmUfUmGmGmsCmsUm | 38 |
| Conjugate4 | L10-sAN1 M3S | S | CmsCmsAmAmGmAmGfCfAfCmCmAmAmGmAmAmCmUmAm | 26 |
| | | AS | UmsAfsGmUmUmCfUmUmGmGmUmGmCmCmfCmUfUmGmGmsCmsUm | 24 |
| Conjugate5 | L10-sAN1 M1SVP | S | CmsCmsAmAmGfAmGfCfAfCmCmAmAmGmAmAmCmUmAm | 20 |
| | | AS | VP-UmsAfsGmUmUmCfUmUfGfGmUmGmCmUfCmUfUmGmGmsCmsUm | 39 |
| Conjugate6 | L10-siAN1 M1SP | S | CmsCmsAmAmGfAmGfCfAfCmCmAmAmGmAmAmCmUmAm | 20 |
| | | AS | P-UmsAfsGmUmUmCfUmUfGfGmUmGmCmUfCmUfUmGmGmsCmsUm | 40 |
| Conjugate7 | L10-siAN1 M1S | S | CmsCmsAmAmGfAmGfCfAfCmCmAmAmGmAmAmCmUmAm | 20 |
| | | AS | UmsAfsGmUmUmCfUmUfGfGmUmGmCmUfCmUfUmGmGmsCmsUm | 21 |
| Conjugate8 | L10-siAN1 | S | CCAAGAGCACCAAGAACUA | 8 |
| | | AS | UAGUUCUUGGUGCUCUUGGCU | 9 |
| Conjugate9 | L10-siAN2 | S | AGCCAAGAGCACCAAGAACUA | 10 |
| | | AS | UAGUUCUUGGUGCUCUUGGCUUG | 11 |
| Conjugate10 | L10-siAN1 M1 | S | CmCmAmAmGfAmGfCfAfCmCmAmAmGmAmAmCmUmAm | 12 |
| | | AS | UmAfGmUmUmCfUmUfGfGmUmGmCmUfCmUfUmGmGmCmUm | 13 |
| Conjugate11 | L10-siAN2 M1 | S | AmGmCmCmAmAmGfAmGfCfAfCmCmAmAmGmAmAmCmUmAm | 14 |
| | | AS | UmAfGmUmUmCfUmUfGfGmUmGmCmUfCmUfUmGmGmCmUmUmGm | 15 |
| Conjugate12 | L10-siAN1 M2 | S | CmCmAmAmGfAmGfCfAfCmCmAmAmGmAmAmCmUmAm | 12 |
| | | AS | UmAfGmUmUmCfUmUmGmUmGmCmUfCmUfUmGmGmCmUm | 16 |
| Conjugate13 | L10-siAN1 M3 | S | CmCmAmAmGmAmGfCfAfCmCmAmAmGmAmAmCmUmAm | 18 |
| | | AS | UmAfGmUmUmCfUmUmGmUmGmCmUfCmUfUmGmGmCmUm | 16 |
| Conjugate14 | L10-siAN2 M2S | S | AmsGmsCmCmAmAmGfAmGfCfAfCmCmAmAmGmAmAmCmUmAm | 22 |
| | | AS | UmsAfsGmUmUmCfUmUmGmGmUmGmCmUfCmUfUmGmGmCmUmsUmsGm | 25 |
| Conjugate15 | L10-siAN1 M1VP | S | CmCmAmAmGfAmGfCfAfCmCmAmAmGmAmAmCmUmAm | 12 |
| | | AS | VP-UmAfGmUmUmCfUmUfGfGmUmGmCmUfCmUfUmGmGmCmUm | 41 |
| Conjugate16 | L10-siAN1 M2VP | S | CmCmAmAmGfAmGfCfAfCmCmAmAmGmAmAmCmUmAm | 12 |
| | | AS | VP-UmAfGmUmUmCfUmUmGmUmGmCmUfCmUfUmGmGmCmUm | 42 |
| Conjugate17 | L10-siAN2 M2VP | S | AmGmCmCmAmAmGfAmGfCfAfCmCmAmAmGmAmAmCmUmAm | 14 |
| | | AS | VP-UmAfGmUmUmCfUmUmGmGmUmGmCmUfCmUfUmGmGmCmUmUmGm | 43 |
| Conjugate18 | L10-siAN1 M3VP | S | CmCmAmAmGmAmGfCfAfCmCmAmAmGmAmAmCmUmAm | 18 |
| | | AS | VP-UmAfGmUmUmCfUmUmGmUmGmCmUfCmUfUmGmGmCmUm | 42 |

TABLE 3-continued siRNA Conjugates

| Conjugate | NO. | | Sequence Direction 5'-3' | SEQ ID NO |
|---|---|---|---|---|
| Conjugate19 | L10-siAN2 M1SVP | S | AmsGmsCmCmAmAmGfAm GfCfAfCmCmAmAmGmAm AmCmUmAm | 22 |
| | | AS | VP-UmsAfsGmUmUmCf UmUfGfGmUmGmCmUfCm UfUmGmGmCmUmsUmsGm | 44 |
| Conjugate20 | L10-siAN1 M2SVP | S | CmsCmsAmAmGfAmGfCf AfCmCmAmAmGmAmAmCm UmAm | 20 |
| | | AS | VP-UmsAfsGmUmUmCf UmUmGmGmUmGmCmUfCm UfUmGmGmsCmsUm | 36 |
| Conjugate21 | L10-siAN2 M3SVP | S | AmsGmsCmCmAmAmGmAm GfCfAfCmCmAmAmGmAm AmCmUmAm | 27 |
| | | AS | VP-UmsAfsGmUmUmCf UmUmGmGmUmGmCmUfCm UfUmGmGmCmUmsUmsGm | 45 |
| Conjugate22 | P10-siAN1 M3SVP | S | CmsCmsAmAmGmAmGfCf AfCmCmAmAmGmAmAmCm UmAm | 26 |
| | | AS | VP-UmsAfsGmUmUmCf UmUmGmGmUmGmCmUfCm UfUmGmGmsCmsUm | 36 |
| Conjugate23 | R5-siAN1 M3SVP | S | CmsCmsAmAmGmAmGfCf AfCmCmAmAmGmAmAmCm UmAm | 26 |
| | | AS | VP-UmsAfsGmUmUmCf UmUmGmGmUmGmCmUfCm UfUmGmGmsCmsUm | 36 |
| Conjugate24 | LA5-siAN1 M3SVP | S | CmsCmsAmAmGmAmGfCf AfCmCmAmAmGmAmAmCm UmAm | 26 |
| | | AS | VP-UmsAfsGmUmUmCf UmUmGmGmUmGmCmUfCm UfUmGmGmsCmsUm | 36 |
| Conjugate25 | LB5-siAN1 M3SVP | S | CmsCmsAmAmGmAmGfCf AfCmCmAmAmGmAmAmCm UmAm | 26 |
| | | AS | VP-UmsAfsGmUmUmCf UmUmGmGmUmGmCmUfCm UfUmGmGmsCmsUm | 36 |
| Conjugate26 | V8-siAN1 M3SVP | S | CmsCmsAmAmGmAmGfCf AfCmCmAmAmGmAmAmCm UmAm | 26 |
| | | AS | VP-UmsAfsGmUmUmCf UmUmGmGmUmGmCmUfCm UfUmGmGmsCmsUm | 36 |
| Conjugate27 | W8-siAN1 M3SVP | S | CmsCmsAmAmGmAmGfCf AfCmCmAmAmGmAmAmCm UmAm | 26 |
| | | AS | VP-UmsAfsGmUmUmCf UmUmGmGmUmGmCmUfCm UfUmGmGmsCmsUm | 36 |
| Conjugate28 | X8-siAN1 M3SVP | S | CmsCmsAmAmGmAmGfCf AfCmCmAmAmGmAmAmCm UmAm | 26 |
| | | AS | VP-UmsAfsGmUmUmCf UmUmGmGmUmGmCmUfCm UfUmGmGmsCmsUm | 36 |
| Conjugate29 | Z5-siAN1 M3SVP | S | CmsCmsAmAmGmAmGfCf AfCmCmAmAmGmAmAmCm UmAm | 26 |
| | | AS | VP-UmsAfsGmUmUmCf UmUmGmGmUmGmCmUfCm UfUmGmGmsCmsUm | 36 |
| ConjugateF1 | FIN-siAN1 | S | CCAAGAGCACCAAGAAC UA | 8 |
| | | AS | ASUAGUUCUUGGUGCUCU UGGCU | 9 |
| ConjugateF2 | FIN-siAN1 M1SVP | S | CmsCmsAmAmGfAmGfCf AfCmCmAmAmGmAmAmCm UmAm | 20 |
| | | AS | VP-UmsAfsGmUmUmCf UmUfGfGmUmGmCmUfCm UfUmGmGmsCmsUm | 39 |
| ConjugateF3 | FIN-siAN1 M2SVP | S | CmsCmsAmAmGfAmGfCf AfCmCmAmAmGmAmAmCm UmAm | 20 |
| | | AS | VP-UmsAfsGmUmUmCf UmUmGmGmUmGmCmUfCm UfUmGmGmsCmsUm | 36 |
| ConjugateF4 | FIN-siAN1 M3SVP | S | CmsCmsAmAmGmAmGfCf AfCmCmAmAmGmAmAmCm UmAm | 26 |
| | | AS | VP-UmsAfsGmUmUmCf UmUmGmGmUmGmCmUfCm UfUmGmGmsCmsUm | 36 |
| ConjugateF5 | FIN-siAN1 M4SVP | S | CmsCmsAmAmGmAmGfCf AfCmCmAmAmGmAmAmCm UmAm | 26 |
| | | AS | VP-UmsAfsGmUmUmCf UmUfGmUmGmCmUfCm UfUmGmGmsCmsUm | 46 |
| ConjugateF6 | FIN-siAN2 | S | AGCCAAGAGCACCAAGAA CUA | 10 |
| | | AS | UAGUUCUUGGUGCUCUUG GCUUG | 11 |
| ConjugateF7 | FIN-siAN2 M1SVP | S | AmsGmsCmCmAmAmGfAm GfCfAfCmCmAmAmGmAm AmCmUmAm | 22 |
| | | AS | VP-UmsAfsGmUmUmCf UmUfGfGmUmGmCmUfCm UfUmGmGmCmUmsUmsGm | 44 |
| ConjugateF8 | FIN-siAN2 M2SVP | S | AmsGmsCmCmAmAmGfAm GfCfAfCmCmAmAmGmAm AmCmUmAM | 22 |
| | | AS | VP-UmsAfsGmUmUmCf UmUmGmGmUmGmCmUfCm UfUmGmGmCmUmsUmsGm | 45 |
| ConjugateF9 | FIN-siAN2 M3SVP | S | AmsGmsCmCmAmAmGmAm GfCfAfCmCmAmAmGmAm AmCmUmAm | 27 |
| | | AS | VP-UmsAfsGmUmUmCf UmUmGmGmUmGmCmUfCm UfUmGmGmCmUmsUmsGm | 45 |
| ConjugateF10 | FIN-siAN2 M5SVP | S | AmsGmsCmCmAmAmGfAm GfCfAfCmCmAmAmGmAm AmCmUmAm | 47 |
| | | AS | VP-UmsAfsGmUmUmCf UmUmGmGmUmGmCmUfCm UfUmGmGmCmUmsUmsGm | 45 |

TABLE 3-continued siRNA Conjugates

| Conjugate | NO. | Sequence Direction 5'-3' | | SEQ ID NO |
|---|---|---|---|---|
| ConjugateF11 | FIN-siAN2 M4SVP | S | AmsGmsCmCmAmAmGmAm GfCfAfCmCmAmAmGmAm AmCmUmAm | 27 |
| | | AS | VP-UmsAfsGmUmUmCf UmUfGmGmUmGmCmUfCm UfUmGmGmCmUmsUmsGm | 48 |
| ConjugateF12 | FIN-siAN1 M3S | S | CmsCmsAmAmGmAmGfCf AfCmCmAmAmGmAmAmCm UmAm | 26 |
| | | AS | UmsAfsGmUmUmCfUmUm GmGmUmGmCmUfCmUfUm GmGmsCmsUm | 24 |
| ConjugateF13 | FIN-siAN1 M1S | S | CmsCmsAmAmGfAmGfCf AfCmCmAmAmGmAmAmCm UmAm | 20 |
| | | AS | UmsAfsGmUmUmCfUmUf GfGmUmGmCmUfCmUfUm GmGmsCmsUm | 21 |

TABLE 3-continued siRNA Conjugates

| Conjugate | NO. | Sequence Direction 5'-3' | | SEQ ID NO |
|---|---|---|---|---|
| Comparative Conjugate1 | L10-siHBX1S M1SVP | S | CmsCmsUmUmGfAmGfGf CfAmUmAmCmUmUmCmAm AmAm | 49 |
| | | AS | VP-UmsUfsUmGmAmAf GmUfAfUmGmCmCmUfCm AfAmGmGmsUmsUm | 50 |
| Comparative Conjugate2 | (GalNAc)₃-S 65695 | S | AmsCmsAmUmAmUmUfUm GfAfUfCmAmGmUmCmUm UmUmUmUm | 51 |
| | | AS | AmsAfsAmAmAmGfAmCm UmGmAmUmCmAfAmAfUm AmUmGmUmsUmsGm | 52 |

Preparation Example 3. Preparation of P10-siAN1M3SVP Conjugate (Conjugate 22)

(3-1) Synthesis of Compound P-10

Compound P-10 was synthesized according to the following method:

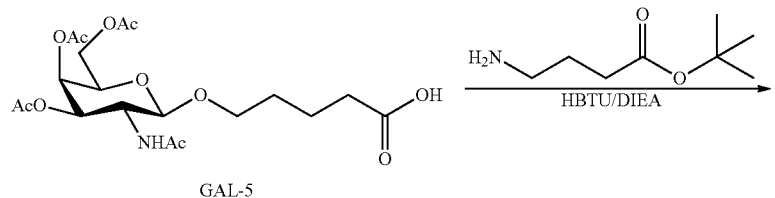

GAL-5

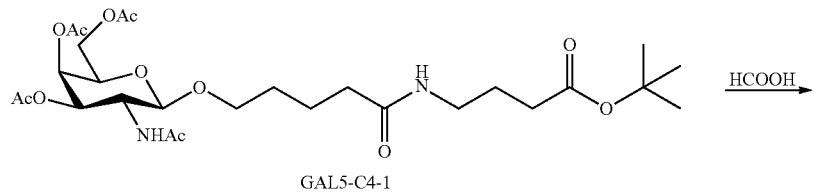

GAL5-C4-1

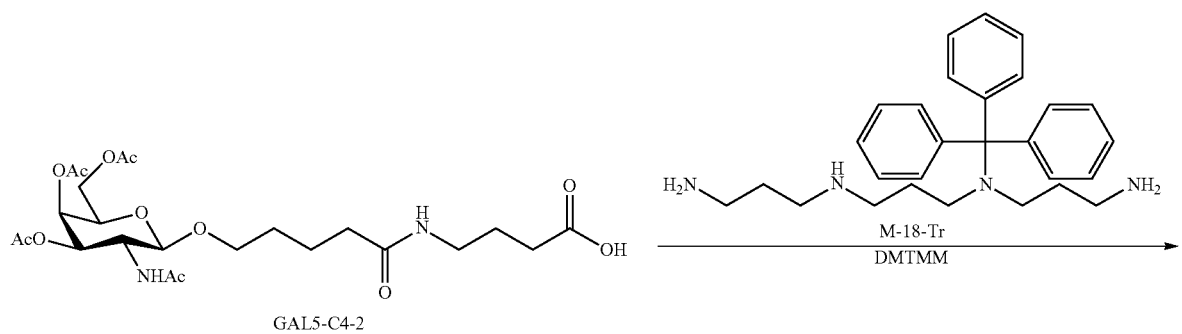

GAL5-C4-2

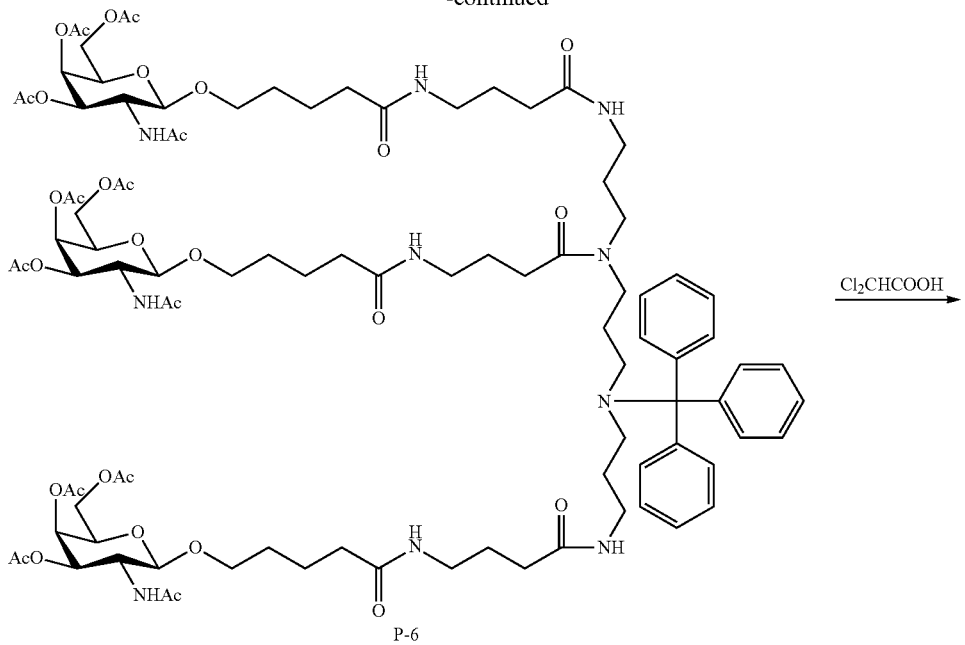
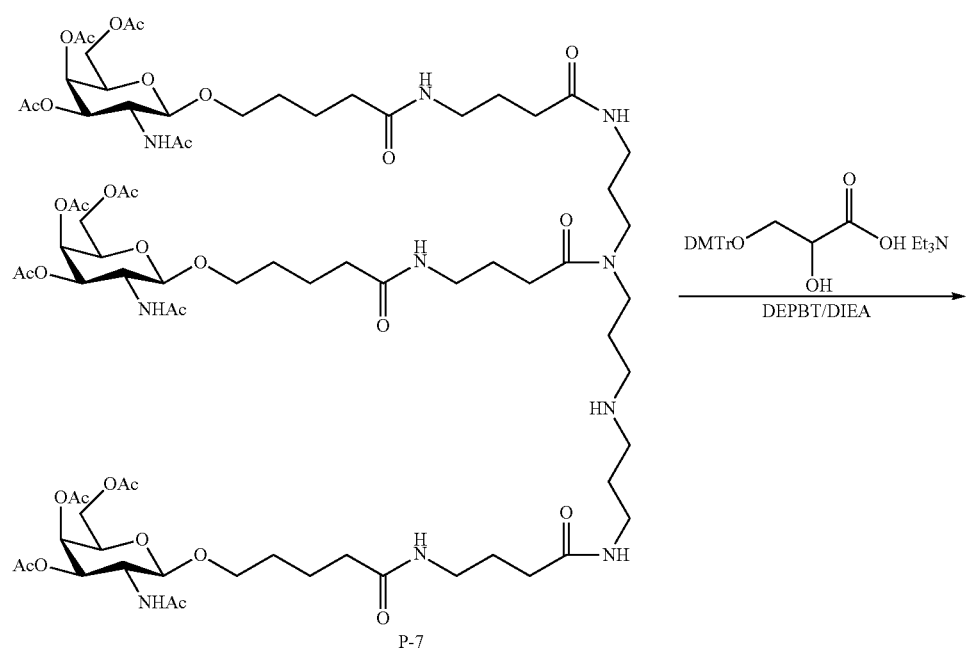

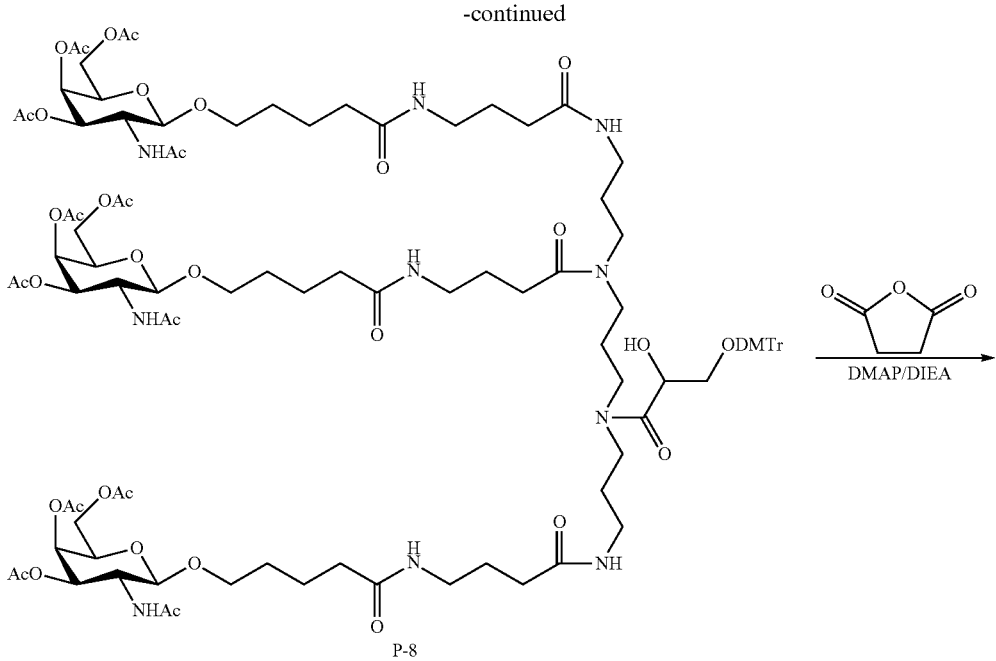
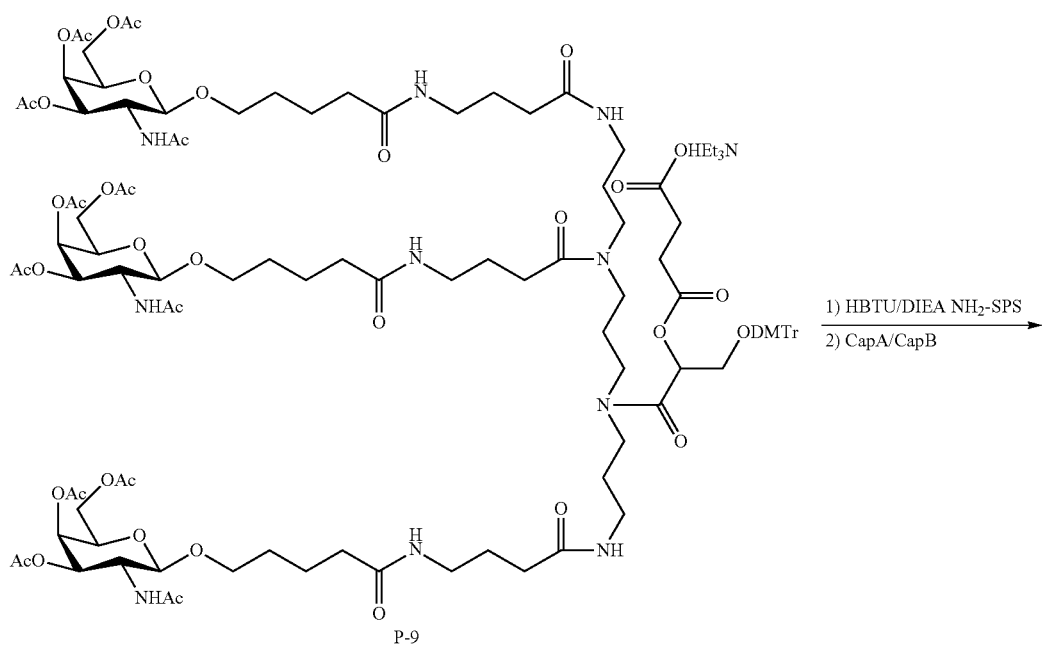

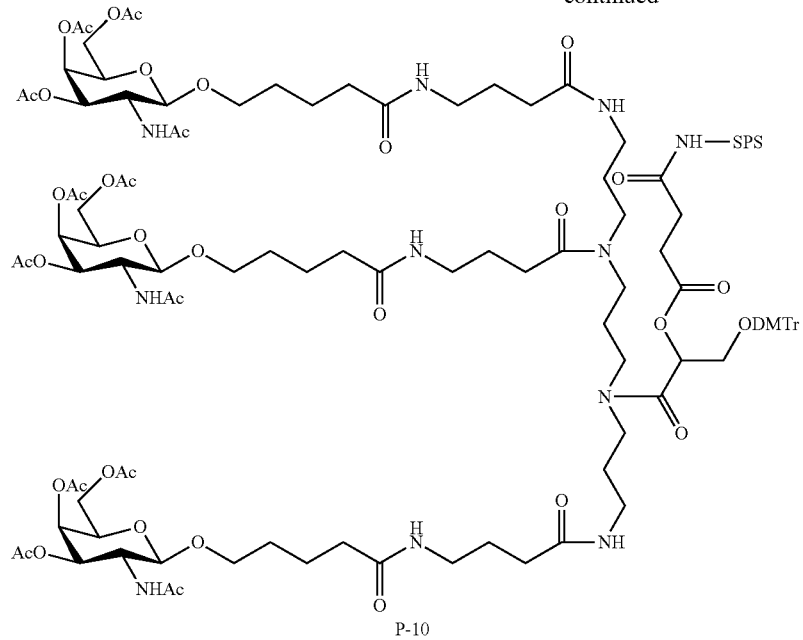

P-10

(3-1-1) Synthesis of GAL5-C4-1

GAL-5 (13.43 g, 30.0 mmol) obtained according to the method described in (1-1-1) above, t-butyl 4-aminobutyrate hydrochloride (5.87 g, 30.0 mmol), O-benzotriazol-tetramethyluronium hexafluorophosphate (13.65 g, 36.0 mmol) and diisopropylethylamine (11.63 g, 90.0 mmol) were added to 40 ml of N,N-dimethylformamide, dissolved uniformly and then stirred at room temperature to react for 5 hours. 300 ml of saturated aqueous sodium bicarbonate solution was added to the reaction solution, and then extracted three times, each with 200 ml of ethyl acetate. The organic phases were combined and washed once with 200 ml of saturated brine. The organic phase was isolated and dried with anhydrous sodium sulfate. The solvent was evaporated to dryness under reduced pressure to give 30.3 g of crude product GAL5-C4-1 as oil, which was directly used in the next reaction.

(3-1-2) Synthesis of GAL5-C4-2

The crude product GAL5-C4-1 (30.3 g, 30 mmol) obtained in step (3-1-1) was dissolved in 180 ml of formic acid and stirred at room temperature to react for 16 hours. The solvent was evaporated to dryness. The residue was purified by column chromatography (200-300 mesh normal phase silica gel, with a gradient elution of dichloromethane:methanol=100:18-100:20). The eluate was collected and concentrated to remove the solvents to give a total of 14.84 g of target product GAL5-C4-2.

(3-1-3) Synthesis of P-6:

M-18-Tr (2.02 g, 4.69 mmol) obtained according to the method described in step (1-1-4) and GAL5-C4-2 (8.24 g, 15.48 mmol, combination of 2 batches) obtained in step (3-1-2) were mixed and dissolved in 47 ml of acetonitrile, added with N-methylmorpholine (3.13 g, 30.96 mmol) followed by 4-(4,6-dimethoxytriazin-2-yl)-4-methylmorpholine hydrochloride (DMTMM, 4.28 g, 15.48 mmol) to react for 2 hours under stirring at room temperature. The resulting reaction solution was diluted with 20 ml of dichloromethane. The organic phase was washed with 10 ml of saturated sodium bicarbonate solution and 10 ml of saturated brine, respectively. All organic phases were combined, dried with anhydrous sodium sulfate, and filtered. The solvent was evaporated to dryness under reduced pressure to give a crude product, which was purified by using a normal phase silica gel column having 200-300 mesh. The column was packed with petroleum ether, added with 1 wt % triethylamine for neutralizing the acidity of silica gel, and eluted with a gradient elution of dichloromethane:methanol=100:5-100:7. The eluate of product was collected, and the solvent was evaporated to dryness under reduced pressure to give a total of 8.27 g of pure product P-6.

(3-1-4) Synthesis of P-7:

P-6 (6.82 g, 3.456 mmol) obtained in (3-1-3) above was dissolved in 69 ml of dichloromethane, and added with dichloroacetic acid (13.367 g, 103.67 mmol) to react for 2 hours at room temperature. The resulting reaction solution was diluted by adding 100 ml of dichloromethane, washed and adjusted to pH 7-8 with saturated sodium bicarbonate solution. The aqueous phase was extracted six times, each with 30 ml of dichloromethane. The organic phases were combined, dried with anhydrous sodium sulfate, and filtered. Then the solvent was evaporated to dryness under reduced pressure to give a crude product. The crude product was purified by using a normal phase silica gel column having 200-300 mesh. The column was added with 10 wt % triethylamine for neutralizing the acidity of silica gel. The column was equilibrated with 1 wt ‰ triethylamine and eluted with a gradient elution of dichloromethane:methanol=100:30-100:40. The eluate of product was collected, and the solvent was evaporated under reduced pressure to give a total of 4.82 g of P-7. MS m/z: $C_{78}H_{127}N_{10}O_{33}$, $[M+H]^+$, calcd: 1732.91, measured: 1735.73.

(3-1-5) Synthesis of P-8:

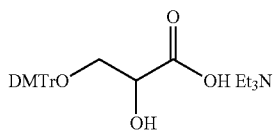

(A-1)

P-7 (2.653 g, 1.532 mmol) and A-1 (2.342 g, 4.596 mmol) were mixed and dissolved in 16 ml of dichloromethane, and added with 3-diethoxyphosphoryl-1,2,3-benzotriazol 4(3H)-one (DEPBT) (1.375 g, 4.596 mmol) followed by diisopropylethylamine (1.188 g, 9.191 mmol) to react for 2 hours under stirring at 25° C. The organic phase was washed with 10 ml of saturated sodium bicarbonate. The aqueous phase was extracted three times, each with 10 ml of dichloromethane. The organic phase was washed with 10 ml of saturated brine. The aqueous phase was extracted twice, each with 10 ml of dichloromethane. All the organic phases were combined, dried with anhydrous sodium sulfate and filtered. The solvent was evaporated to dryness under reduced pressure, and the residue was foam-dried overnight with a vacuum oil pump to give a crude product. The crude product was subjected to a column purification. The column was filled with 120 g of normal phase silica gel having 200-300 mesh, and added with 20 ml triethylamine for neutralizing the acidity of silica gel. The column was equilibrated with petroleum ether containing 1 wt % triethylamine and eluted with a gradient elution of petroleum ether: ethyl acetate: dichloromethane: N,N-dimethylformamide=1:1:1:0.5-1:1:1:0.6. The eluate of product was collected, and the solvent was evaporated to dryness under reduced pressure to give a total of 2.793 g of pure product P-8.

(3-1-6) Synthesis of P-9:

P-8 (490 mg, 0.231 mmol), succinic anhydride (69 mg, 0.693 mmol) and 4-dimethylaminopyridine (DMAP, 68 mg, 0.554 mmol) were mixed and dissolved in 2.3 ml of dichloromethane, and added with diisopropylethylamine (DIPEA, 149 mg, 1.155 mmol) to react for 21 hours under stirring at 25° C. 50 ml dichloromethane was added to the resulting reaction solution for dilution, and then washed with 100 ml of 0.5 M triethylamine phosphate. The aqueous phase was extracted three times, each with 10 ml of dichloromethane. The organic phases were combined, and the solvent was evaporated to dryness under reduced pressure to give a crude product. The crude product was subjected to a column purification. The column was filled with 80 g of normal phase silica gel having 200-300 mesh, and added with 1 wt % triethylamine for neutralizing the acidity of silica gel. The column was equilibrated with dichloromethane and eluted with a gradient elution of dichloromethane containing 1 wt ‰ triethylamine:methanol=100:18-100:20. The eluate of product was collected, and the solvent was evaporated to dryness under reduced pressure to give a total of 200 mg of pure product, P-9 conjugating molecule. MS m/z: $C_{106}H_{153}N_{10}O_{41}$, $[M-DMTr]^+$, calcd: 1921.05, measured: 1920.97.

(3-1-7) Synthesis of P-10:

P-10 was prepared by the same method as that in step (1-1-9) of Preparation Example 1, except that L-9 conjugating molecule was replaced with P-9 conjugating molecule to produce P-9 conjugating molecule linked to the solid phase support.

(3-2) Synthesis of P10-siAN1M3SVP Conjugate

Conjugate 22 was prepared by the same method as that in steps (1-2), (1-3A) and (1-4) of Preparation Example 1, except that compound L-10 was replaced with compound P-10 to start the synthesis of a sense strand. P10-siAN1M3SVP conjugate having the structure represented by Formula (404) was obtained.

Preparation Example 4. Preparation of R5-siAN1M3SVP Conjugate (Conjugate 23)

(4-1) Synthesis of Compound R-5

Compound R-5 was synthesized according to the following method:

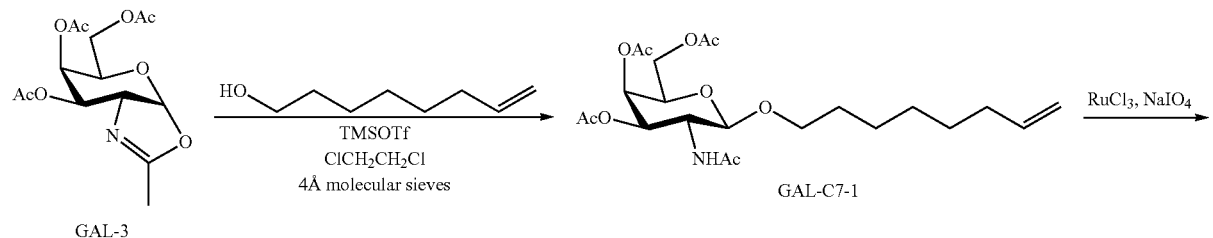

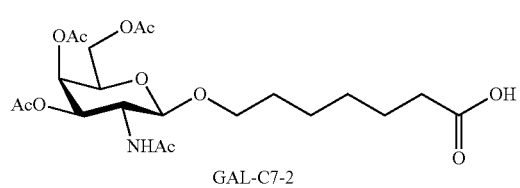

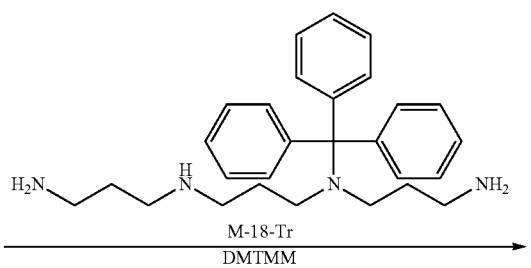

-continued
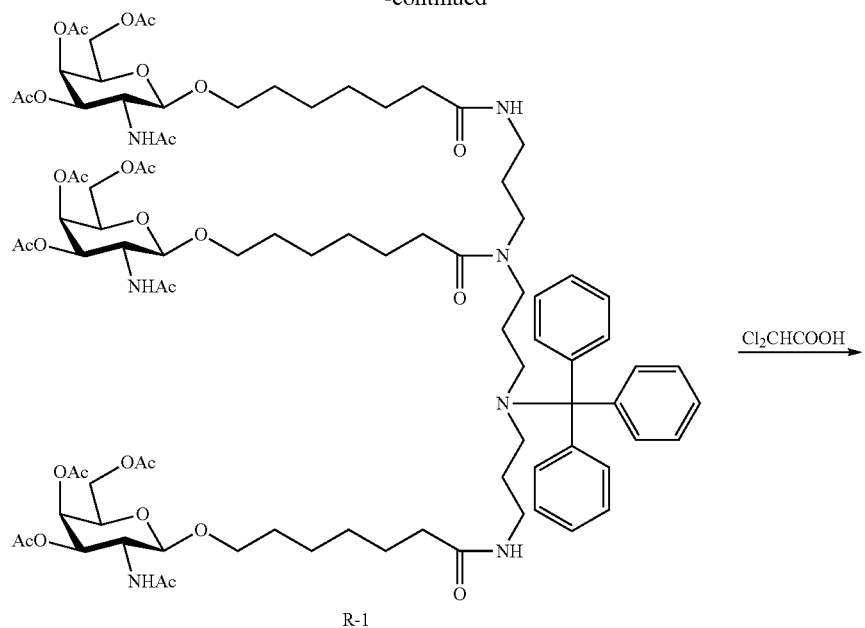
R-1
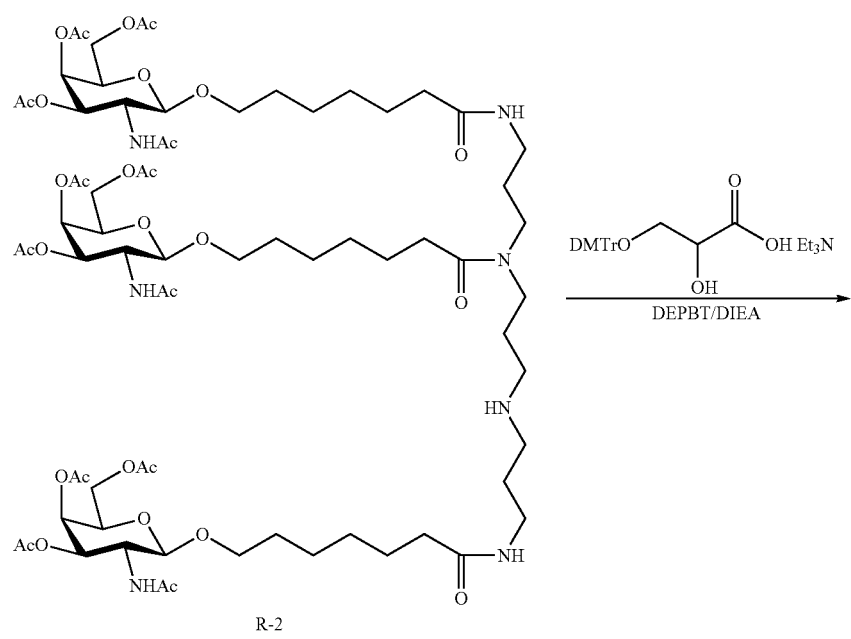
R-2

-continued
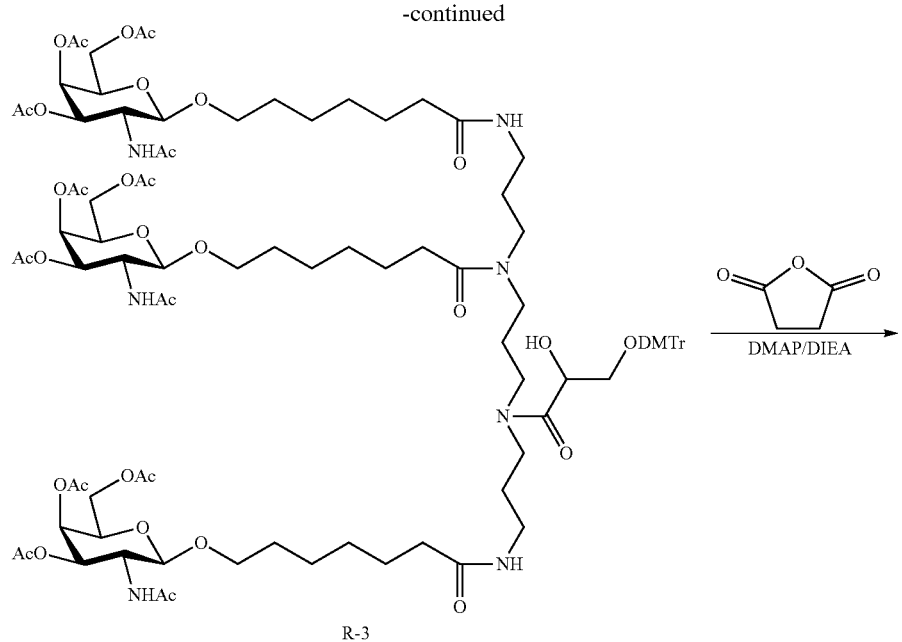
R-3
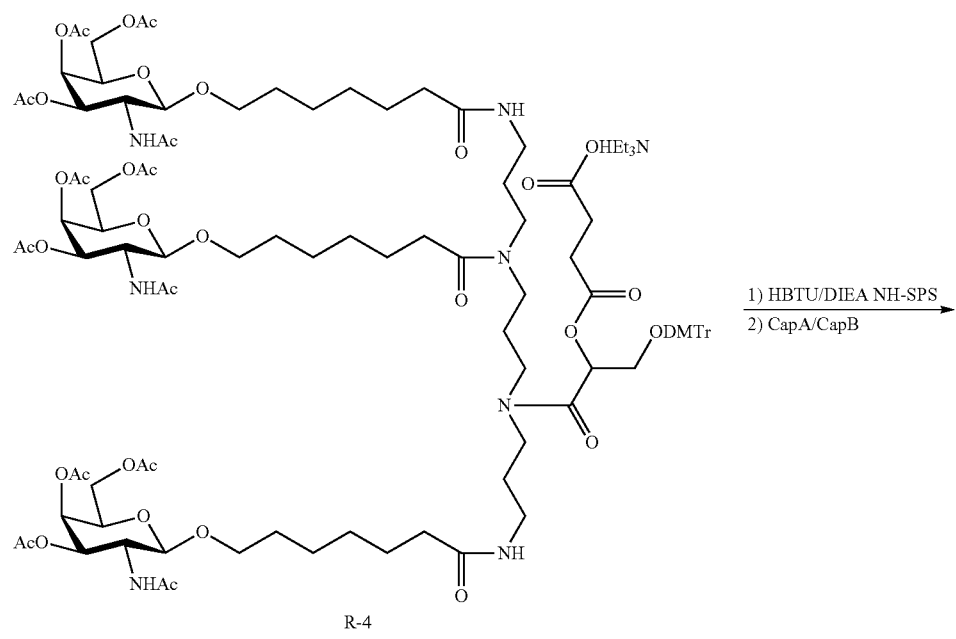
R-4

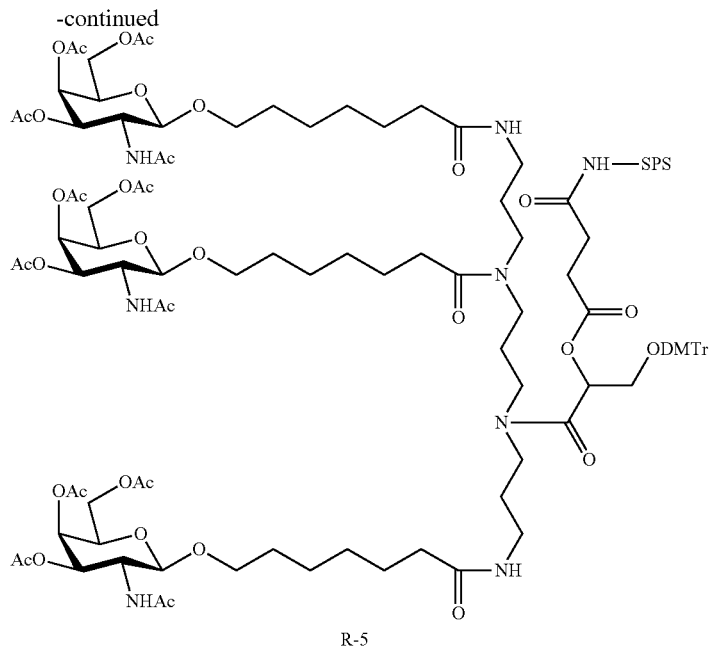

R-5

(4-1-1) Synthesis of GAL-C7-1

GAL-3 (26.4 g, 80.2 mmol) obtained according to the method described in step (1-1-1b) was dissolved in 134 ml of anhydrous 1,2-dichloroethane, and added with 60 g of 4 Å molecular sieve as a powder followed by 7-octen-1-ol (11.3 g, 88.2 mmol) to react for 10 minutes under stirring at room temperature. Trimethylsilyl trifluoromethanesulphonate (TMSOTf, 8.9 g, 40.1 mmol) was added in an ice bath and nitrogen atmosphere to react for 24 hours under stirring at room temperature. The 4 Å molecular sieve powder was removed by filtration. 500 ml of saturated aqueous sodium bicarbonate solution was added to the filtrate for washing. The organic phase was isolated. The aqueous phase was extracted once with 100 ml of dichloromethane. The organic phases were combined and washed once with 250 ml of saturated brine. The organic phase was isolated and dried with anhydrous sodium sulfate. The solvent was evaporated to dryness under reduced pressure to give 33.3 g of product GAL-C7-1 as yellow syrup, which was directly used in the next oxidation reaction without purification.

(4-1-2) Synthesis of GAL-C7-2

GAL-C7-1 (33.3 g, 72.8 mmol) obtained in step (4-1-1) was dissolved in a mixed solvent of 160 ml of dichloromethane and 160 ml of acetonitrile, added with 216 ml of water and sodium periodate solid (62.3 g, 291.2 mmol) respectively, stirred in an ice water bath for 10 minutes, and added with a catalyst ruthenium trichloride (498 mg, 2.4 mmol). The reaction was naturally warmed to room temperature and stirred for 23 hours. The resulting reaction solution was diluted by adding 200 ml of water, stirred, and adjusted to pH 7.5 by adding saturated sodium bicarbonate. The organic phase was isolated and discarded. The aqueous phase was extracted three times, each with dichloromethane. The organic phase was discarded. The aqueous phase was adjusted to a pH of about 3 with citric acid solid, extracted three times, each with 200 ml of dichloromethane. All the organic phases were combined, dried with anhydrous sodium sulfate. The solvent was evaporated under reduced pressure, and then the residue was purified by column chromatography (200-300 mesh normal phase silica gel, with a gradient elution of dichloromethane:methanol=100:18-100:20) to give 22.4 g of product GAL-C7-2 as a white foamy solid. MS m/z: $C_{21}H_{32}NO_{11}$, $[M+H]^+$, calcd: 476.50, measured: 475.94.

(4-1-3) Synthesis of R-1:

M-18-Tr (2.02 g, 4.69 mmol) obtained according to the method described in step (1-1-4) and GAL-C7-2 (7.36 g, 15.48 mmol) were mixed and dissolved in 47 ml of acetonitrile, added with N-methylmorpholine (3.13 g, 30.96 mmol) followed by 4-(4,6-dimethoxytriazin-2-yl)-4-methylmorpholine hydrochloride (DMTMM, 4.28 g, 15.48 mmol) to react for 2 hours under stirring at room temperature. The resulting reaction solution was diluted with 200 ml of dichloromethane. The organic phase was washed with 100 ml of saturated sodium bicarbonate solution and 100 ml of saturated brine, respectively. The organic phases were combined, dried with anhydrous sodium sulfate, and filtered. The solvent was evaporated to dryness under reduced pressure to give a crude product, which was purified by using a normal phase silica gel column having 200-300 mesh. The column was packed with petroleum ether, added with 1 wt % triethylamine for neutralizing the acidity of silica gel, and eluted with a gradient elution of dichloromethane:methanol=100:5-100:7. The eluate of product was collected and evaporated to dryness under reduced pressure to give 7.82 g of pure product R-1.

(4-1-4) Synthesis of R-2:

R-1 (6.23 g, 3.456 mmol) was dissolved in 69 ml of dichloromethane, and added with dichloroacetic acid (13.367 g, 103.67 mmol) to react for 2 hours at room temperature. The resulting reaction solution was diluted by adding 100 ml of dichloromethane, washed and adjusted to pH 7-8 with saturated sodium bicarbonate solution. The aqueous phase was extracted six times, each with 30 ml of dichloromethane. The organic phases were combined, dried with anhydrous sodium sulfate, and filtered. Then the solvent was evaporated to dryness under reduced pressure to give a crude product. The crude product was purified by using a normal phase silica gel column having 200-300 mesh. The column was added with 10 wt % triethylamine for neutralizing the acidity of silica gel. The column was equilibrated with 1 wt ‰ triethylamine and eluted with a gradient elution of dichloromethane:methanol=100:30-100:40. The solvent was evaporated to dryness under reduced pressure to give 4.49 g of pure product R-2.

(4-1-5) Synthesis of R-3:

R-2 (2.391 g, 1.532 mmol) and A-1 (2.342 g, 4.596 mmol) were mixed and dissolved in 16 ml of dichloromethane, and added with 3-(diethoxyphosphoryloxy)-1,2,3-benzotrizin-4 (3H)-one (DEPBT, 1.375 g, 4.596 mmol) followed by diisopropylethylamine (1.188 g, 9.191 mmol) to react for 2 hours under stirring at 25° C. The organic phase was washed with 10 ml of saturated sodium bicarbonate. The aqueous phase was extracted three times, each with 10 ml of dichloromethane. The organic phase was washed with 10 ml of saturated brine. The aqueous phase was extracted twice, each with 10 ml of dichloromethane. All the organic phases were combined, dried with anhydrous sodium sulfate, and filtered. The solvent was evaporated to dryness under reduced pressure, and the residue was foam-dried overnight with a vacuum oil pump to give a crude product. The crude product was subjected to a column purification. The column was filled with 120 g of normal phase silica gel having 200-300 mesh, and added with 20 ml triethylamine for neutralizing the acidity of silica gel. The column was equilibrated with petroleum ether containing 1 wt % triethylamine and eluted with a gradient elution of petroleum ether: ethyl acetate: dichloromethane: N,N-dimethylformamide=1:1:1:0.5-1:1:1:0.6. The solvent was evaporated to dryness under reduced pressure to give 2.642 g of pure product R-3.

(4-1-6) Synthesis of R-4:

R-3 (795 mg, 0.4074 mmol), succinic anhydride (82 mg, 0.8148 mmol) and 4-dimethylaminopyridine (DMAP, 100 mg, 0.8148 mmol) were mixed and dissolved in 4 ml of dichloromethane, and added with diisopropylethylamine (DIPEA, 100 mg, 0.8148 mmol) to react for 18 hours under stirring at 25° C. The resulting reaction solution was washed with 5 ml of 0.5 M triethylamine phosphate. The aqueous phase was extracted three times, each with 5 ml of dichloromethane. The organic phases were combined, and evaporated to dryness under reduced pressure to give a crude product. The crude product was subjected to a column purification. The column was filled with 30 g of normal phase silica gel having 200-300 mesh, and added with 1 wt % triethylamine for neutralizing the acidity of silica gel. The column was equilibrated with dichloromethane and eluted with a gradient elution of dichloromethane containing 1 wt ‰ triethylamine:methanol=100:18-100:20. The eluate of product was collected, and the solvent was evaporated to dryness under reduced pressure to give 505 mg of pure product of R-4 conjugating molecule.

(4-1-7) Synthesis of R-5 Conjugating Molecule

R-5 was prepared by a method the same as that in step (1-1-9) of Preparation Example 1, except that L-9 conjugating molecule was replaced with R-4 conjugating molecule to produce R-4 conjugating molecule linked to the solid phase support.

(4-2) Synthesis of R5-siAN1M3SVP Conjugate

Conjugate 23 was prepared by the same method as those in steps (1-2), (1-3A) and (1-4) in Preparation Example 1, except that R-10 compound was replaced with R-5 compound to start the synthesis of sense strand. It was expected that R5-siAN1M3SVP conjugate having the structure represented by Formula (407) can be produced.

Preparation Example 5. Preparation of LA5-siAN1M3SVP Conjugate (Conjugate 24)

It was expected that LA-5 compound can be synthesized according to following process route.

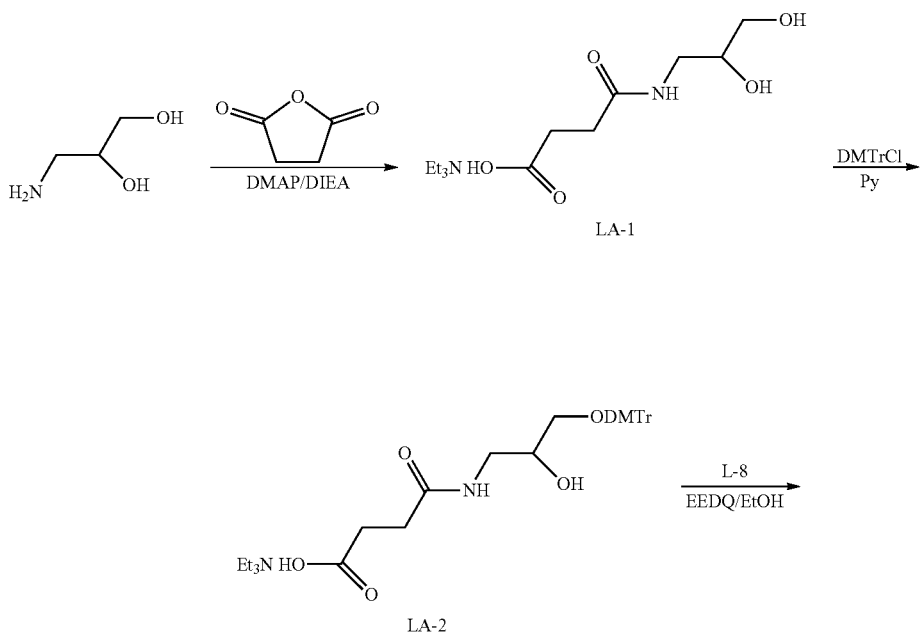

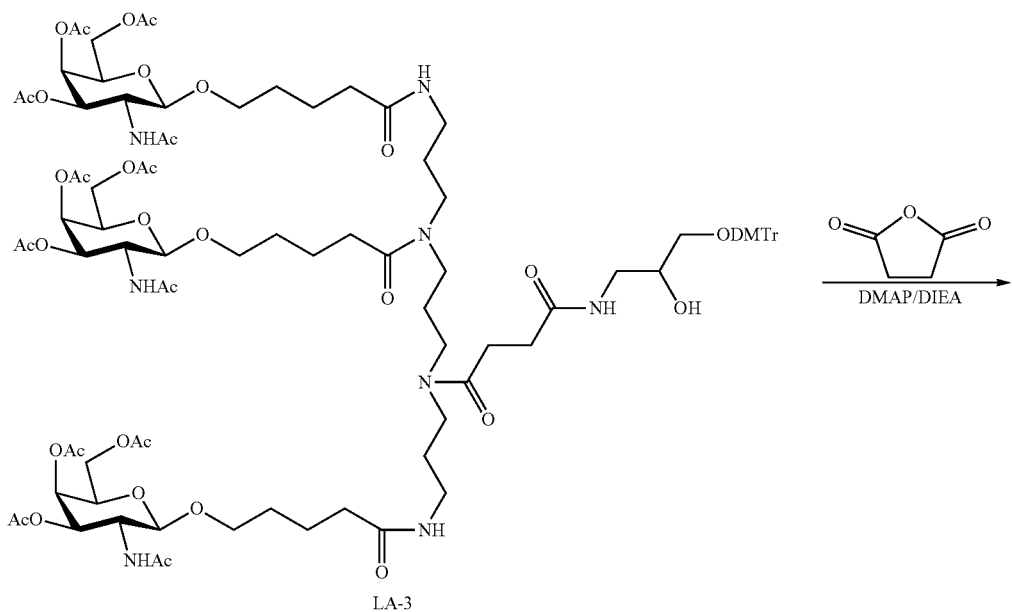
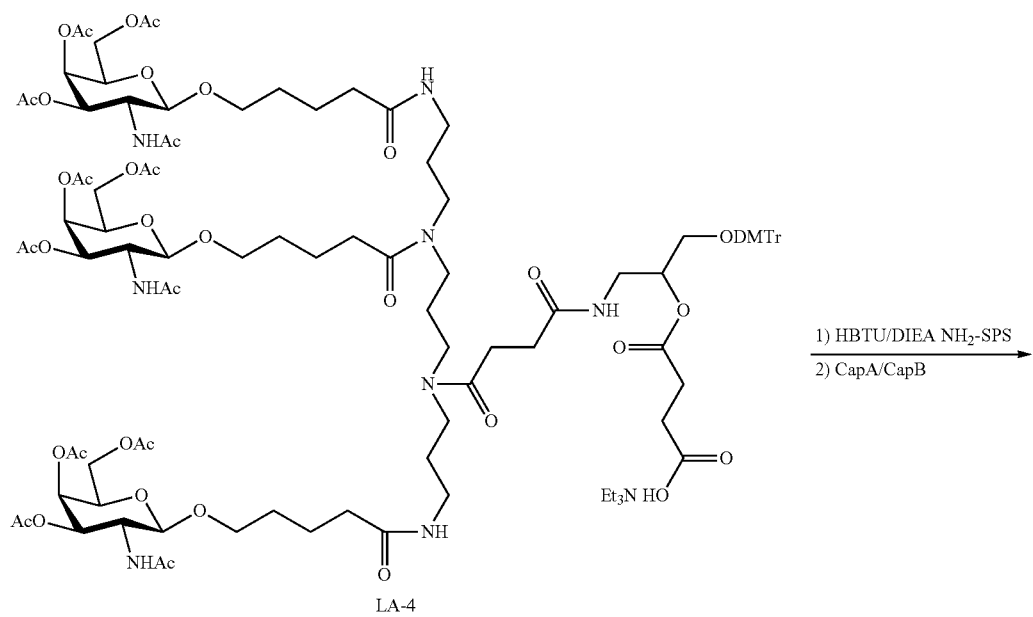

-continued

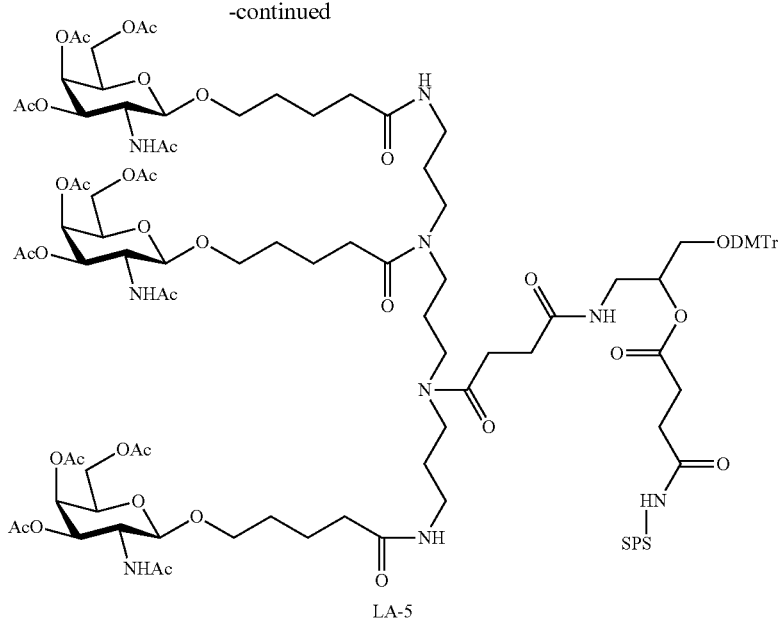

LA-5

Conjugate 24 was prepared by the same method as those in steps (1-2), (1-3A) and (1-4) of Preparation Example 1, except that L-10 compound was replaced with LA-5 compound to start the synthesis of the sense strand. It was expected that LA5-siAN1M3SVP conjugate having the structure represented by Formula (412) can be produced.

Preparation Example 6. Preparation of LB5-siAN1M3SVP Conjugate (Conjugate 25)

(6-1) Synthesis of LB-5 Compound

LB-5 compound was synthesized according to the following method:

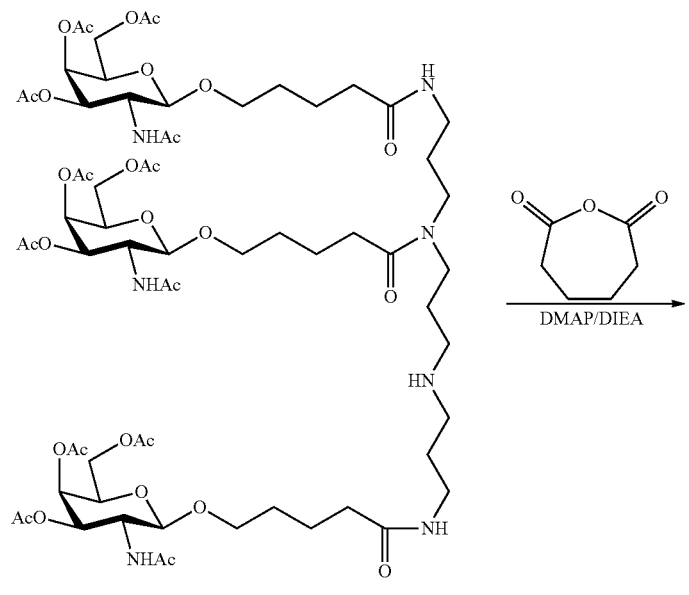

L-8

-continued
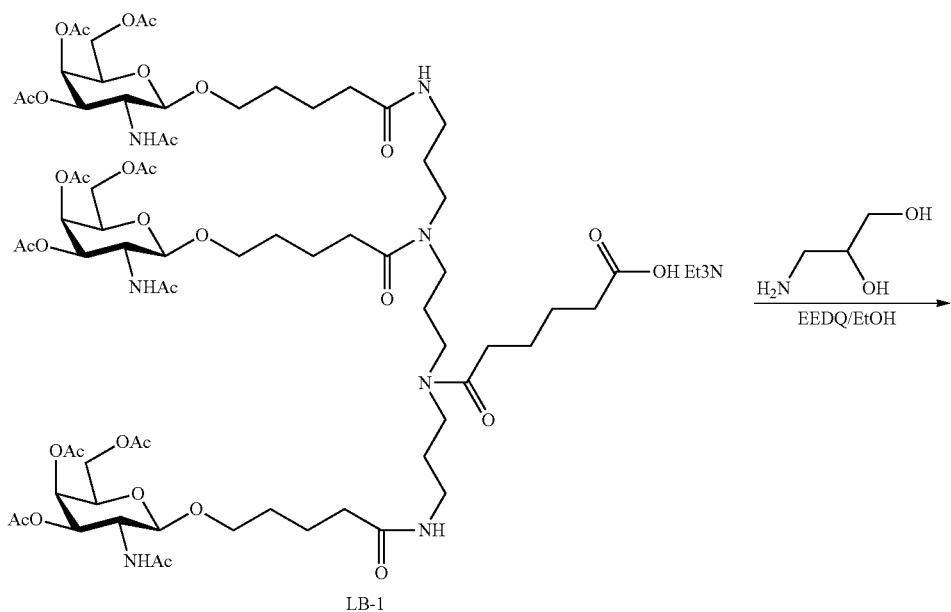
LB-1
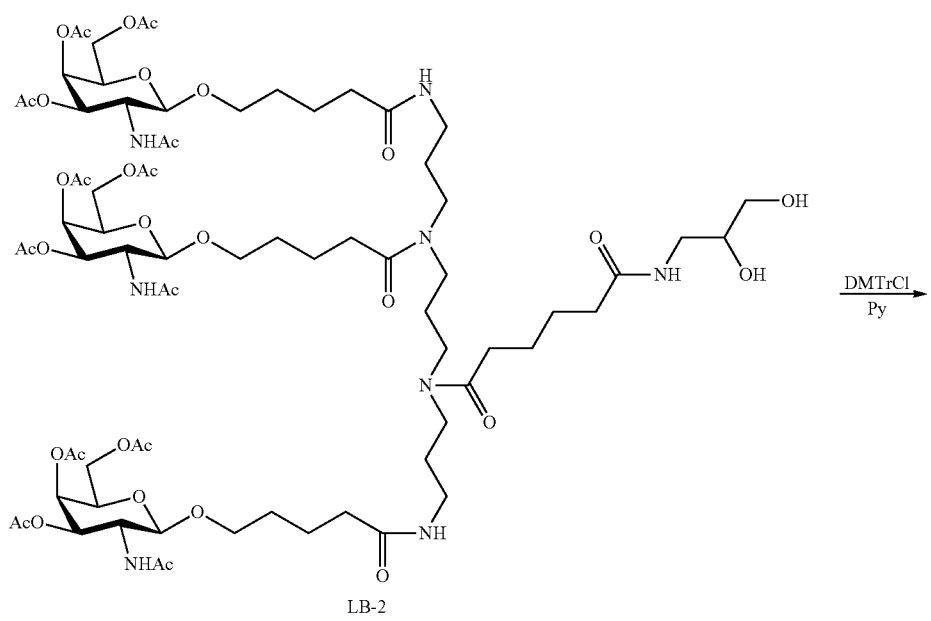
LB-2

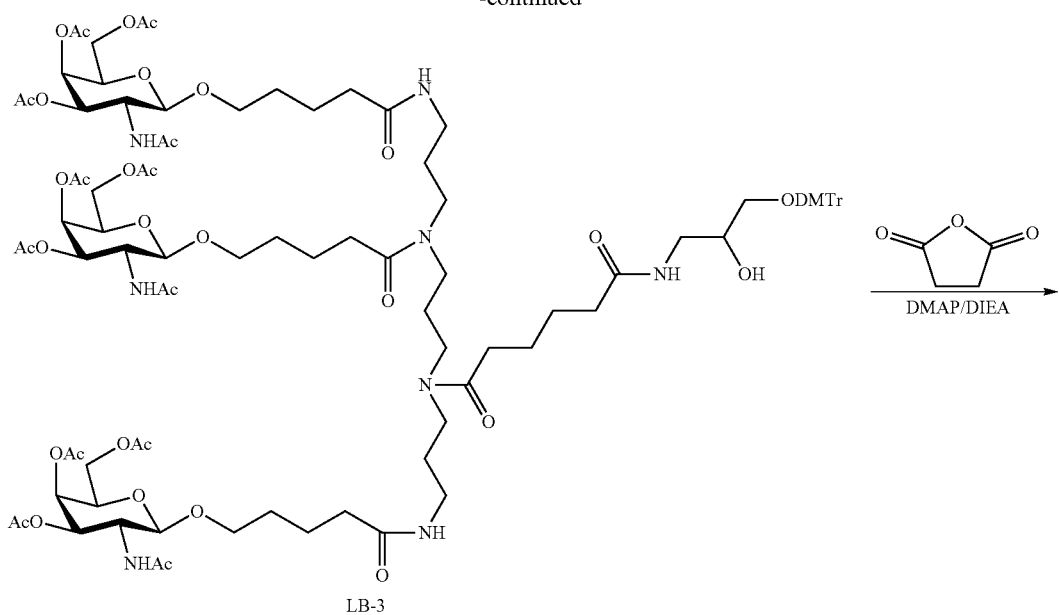
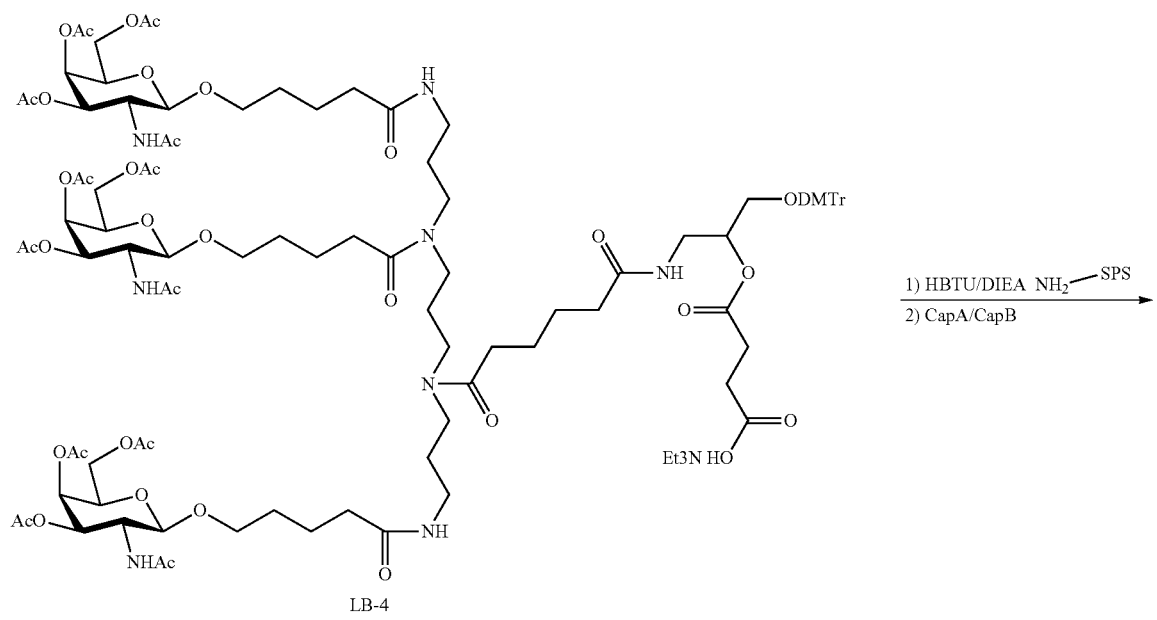

-continued

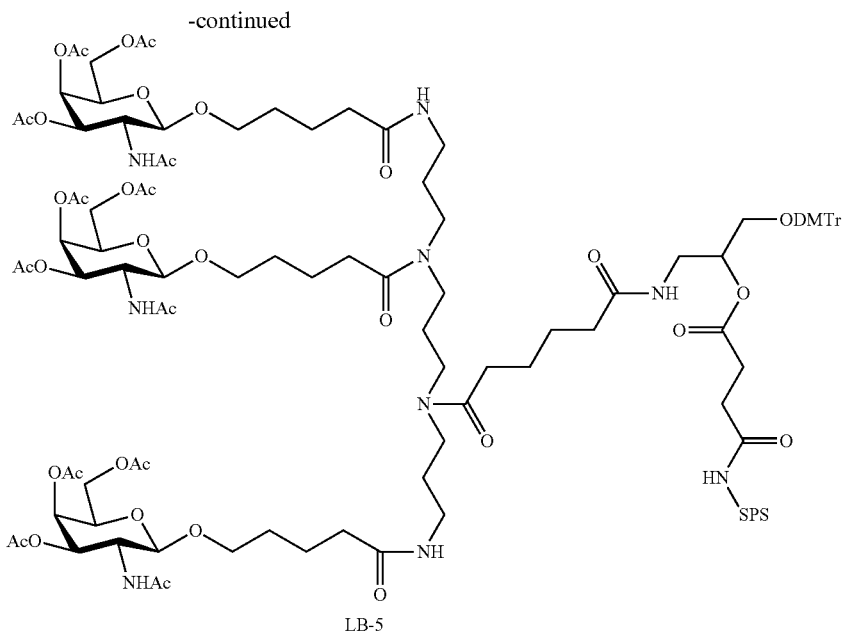

LB-5

(6-1-1) Synthesis of LB-1:

L-8 (5.0 g, 3.386 mmol) obtained according to the method described in step (1-1-6), adipic anhydride (870 mg, 6.772 mmol) and 4-dimethylaminopyridine (DMAP, 827 mg, 6.772 mmol) were mixed and dissolved in 130 ml of dichloromethane, and added with diisopropylethylamine (DIPEA, 2.2 g, 16.931 mmol) to react for 4 hours under stirring at 25° C. The resulting reaction solution was diluted by adding 70 ml dichloromethane, and then washed with 0.5 M triethylamine phosphate. The aqueous phase was extracted four times, each with 10 ml of dichloromethane. The organic phases were combined, and evaporated to dryness under reduced pressure to give a crude product. The crude product was subjected to a column purification. The column was filled with 120 g of normal phase silica gel having 200-300 mesh, and added with 1 wt % triethylamine for neutralizing the acidity of silica gel. The column was equilibrated with dichloromethane and eluted with a gradient elution of petroleum ether:ethyl acetate:dichloromethane:methanol=1:1:1:0.2-1:1:1:1. The solvent was evaporated to dryness under reduced pressure to give 4.267 g of pure product LB-1.

(6-1-2) Synthesis of LB-2:

LB-1 (4.697 g, 2.753 mmol, combination of 2 batches) obtained according to the method described in step (6-1-1), 3-amino-1,2-propanediol (313 mg, 3.442 mmol), 4-(4,6-dimethoxytriazin-2-yl)-4-methylmorpholine hydrochloride (DMTMM, 953 mg, 3.442 mmol) and N-methylmorpholine (700 mg, 6.884 mmol) were sequentially added to the mixture of 30 ml of acetonitrile and 3 ml of methanol to react overnight under stirring at room temperature. The solvent was evaporated to dryness, and the residue was purified by column chromatography (200-300 mesh normal phase silica gel, with a gradient elution of dichloromethane:methanol=1: 0.07-1:0.5). The eluate of product was collected and concentrated to remove the solvent to give 3.27 g of target product LB-2.

(6-1-3) Synthesis of LB-3:

LB-2 (2.27 g, 1.353 mmol) was dissolved in 14 ml of anhydrous pyridine, and added with 4,4'-dimethoxytrityl chloride (688 mg, 2.03 mmol) to react overnight under stirring at room temperature. The reaction was quenched by addition of 150 ml of methanol. The solvent was evaporated to dryness, and the residue was purified by column chromatography (200-300 mesh normal phase silica gel, with a gradient elution of dichloromethane:methanol=1:0.05-1: 0.2). The eluate of product was collected and concentrated to remove the solvent to give 1.647 g of target product LB-3.

(6-1-4) Synthesis of LB-4:

LB-3 (822 mg, 0.415 mmol), succinic anhydride (83 g, 0.83 mmol) and 4-dimethylaminopyridine (DMAP, 102 mg, 0.83 mmol) were mixed and dissolved in 4 ml of dichloromethane, added with DIPEA (270 mg, 2.075 mmol), and stirred at 25° C. to react overnight. The resulting reaction liquid was washed with 0.5 M triethylamine phosphate for three times. The aqueous phase was extracted three times, each with 2 ml of dichloromethane. The organic phases were combined, and the solvent was evaporated to dryness under reduced pressure to give a crude product. The crude product was subjected to a column purification. The column was filled with normal phase silica gel having 200-300 mesh, and added with 5 wt % triethylamine for neutralizing the acidity of silica gel. The column was equilibrated with petroleum ether and eluted with a gradient elution of 1 wt ‰ triethylamine-containing dichloromethane:methanol=100:5-100: 20. The solvent was evaporated to dryness under reduced pressure to give 787 mg of pure product, LB-4 conjugating molecule.

(6-1-5) Synthesis of LB-5:

LB-5 was prepared by the same method as that in step (1-1-9) of Preparation Example 1, except that L-9 conjugating molecule was replaced with LB-4 conjugating molecule to produce the LB-4 conjugating molecule linked to the solid support.

(6-2) Synthesis of LB5-siAN1M3SVP Conjugate

Conjugate 25 was prepared by the same methods as those in steps (1-2), (1-3A) and (1-4) of Preparation Example 1, except that L-10 compound was replaced with LB-5 compound to start the synthesis of the sense strand. It was expected that LB5-siAN1M3SVP having the structure represented by Formula (413) can be produced.

Preparation Example 7. Synthesis of V8-siAN1M3SVP Conjugate (Conjugate 26)

It was expected that V-8 compound can be synthesized according to the following process route:

-continued
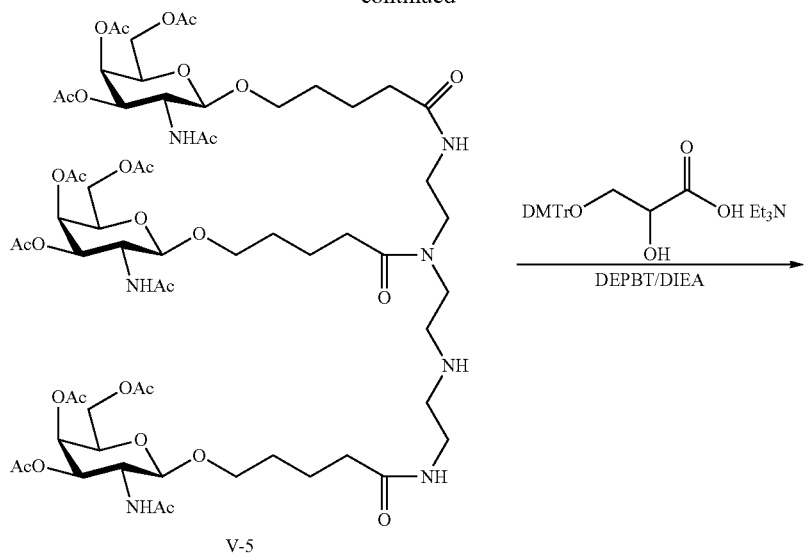
V-5
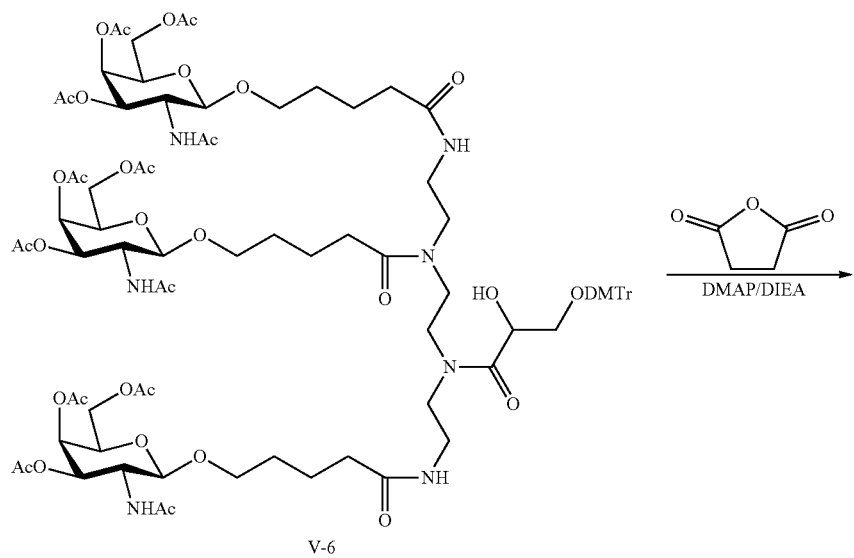
V-6
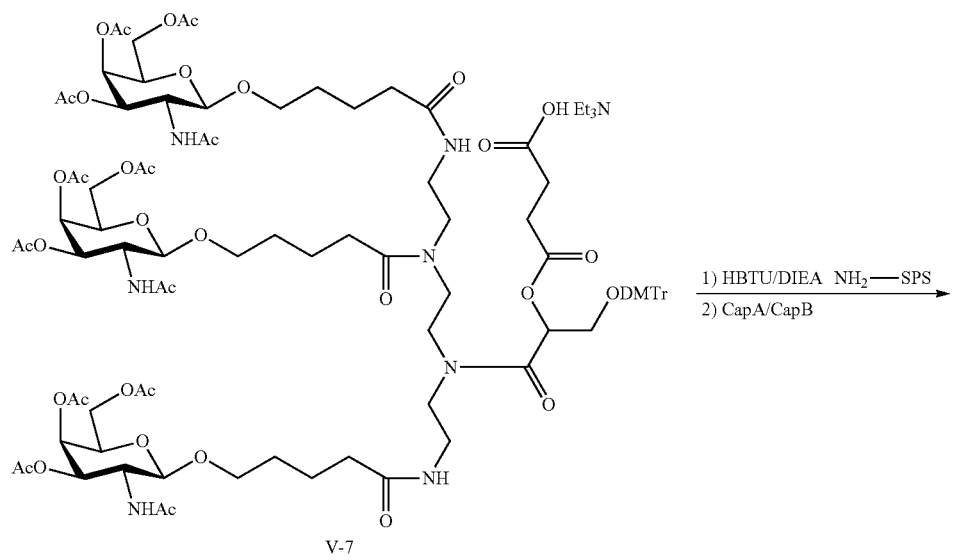
V-7

-continued

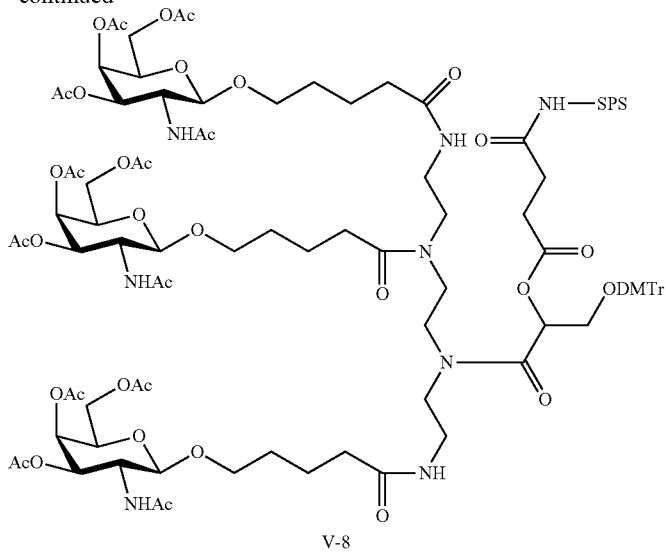

V-8

Conjugate 26 was prepared according to the same methods as those in steps (1-2), (1-3A) and (1-4) of Preparation Example 1, except that L-10 compound was replaced with V-8 compound to start the synthesis of the sense strand. It was expected that V8-siAN1M3SVP having the structure represented by Formula (414) can be obtained.

Preparation Example 8. Synthesis of W8-siAN1M3SVP Conjugate (Conjugate 27)

(8-1) Synthesis of W-8 Compound

W-8 compound was synthesized according to the following method:

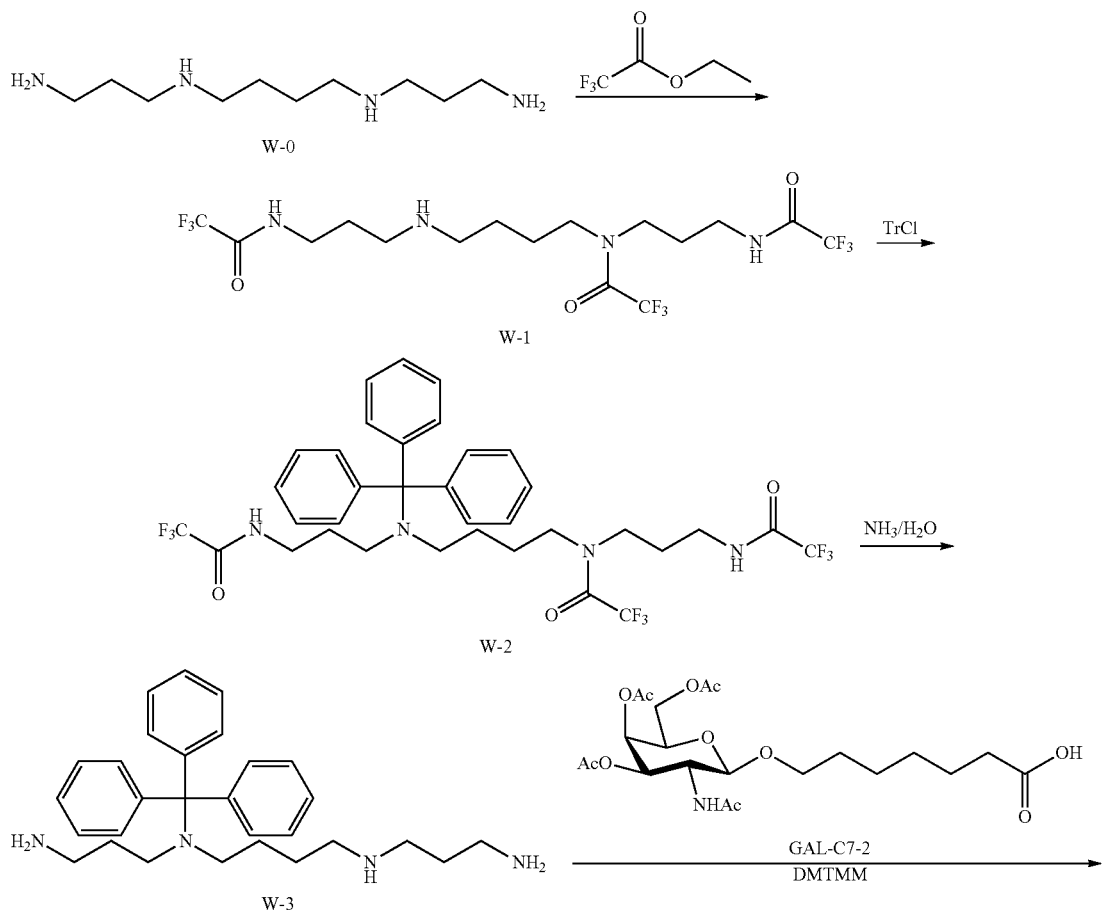

-continued
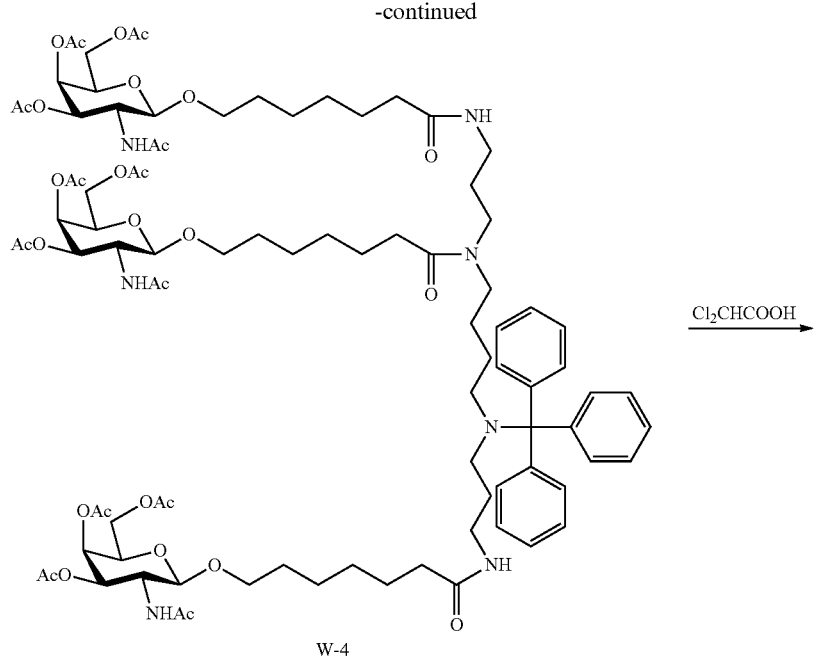
W-4
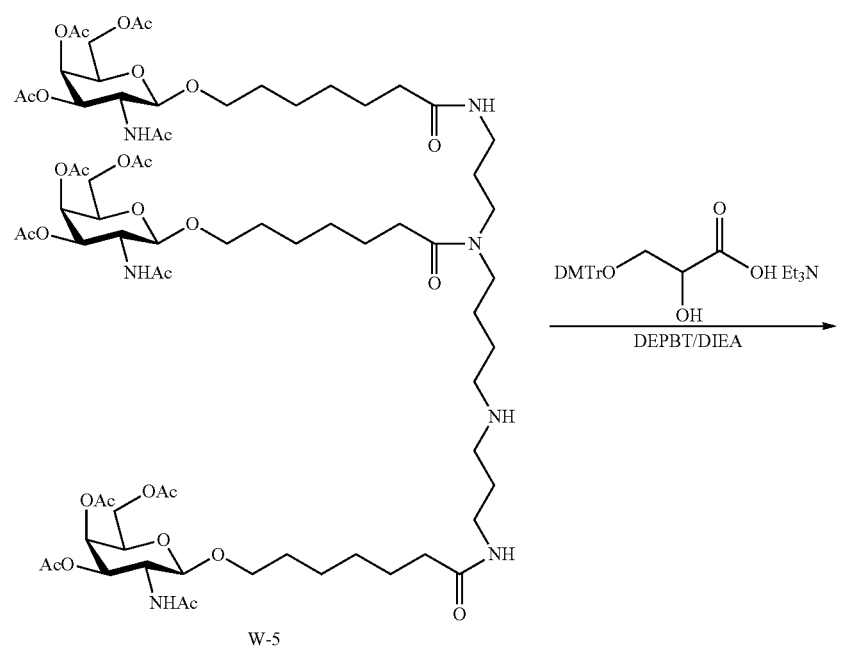
W-5

-continued
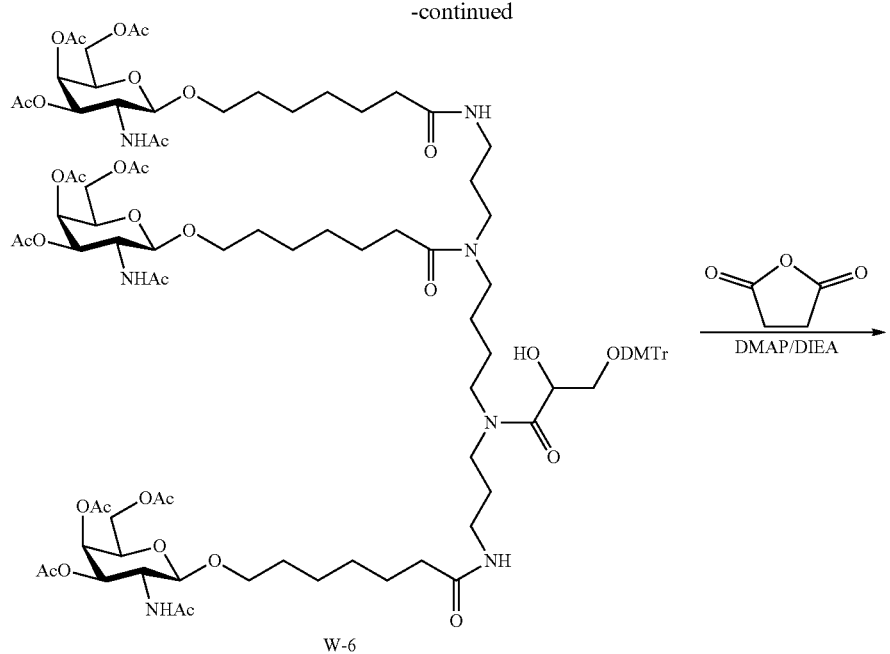
W-6
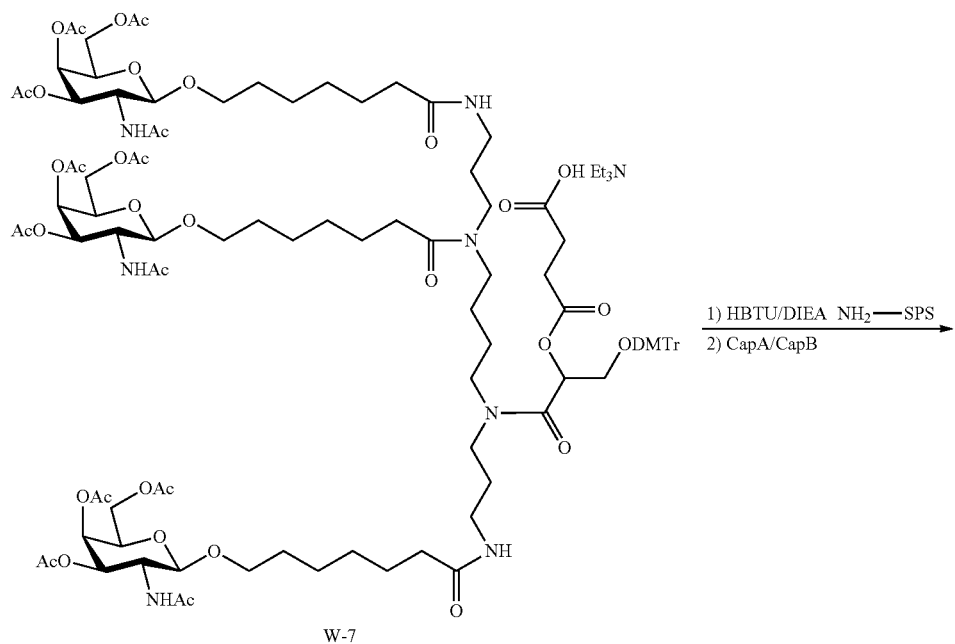
W-7

-continued

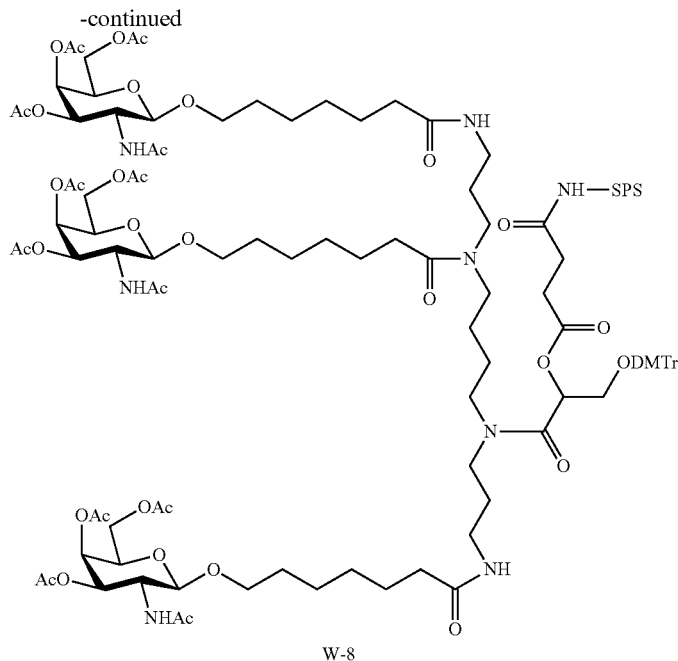

W-8

(8-1-1) Synthesis of W-1:

W-0 (2.024 g, 10 mmol) was dissolved in 25 ml of acetonitrile, added with triethylamine (4.048 g, 40 mmol), and cooled to about 0° C. in an ice water bath. Ethyl trifluoroacetate (5.683 g, 40 mmol) was added to react for 22 hours at room temperature. The solvent was evaporated to dryness under reduced pressure, and the residue was foam-dried with a vacuum oil pump for 18 hours to give 5.835 g of crude solid product W-1.

(8-1-2) Synthesis of W-2:

The crude product W-1 (5.835 g, 10 mmol) was dissolved in 50 ml of dichloromethane. TrCl (3.345 g, 12 mmol) and triethylamine (1.518 g, 15 mmol) were added to react for 20 hours under stirring at room temperature. The resulting reaction solution was washed twice with 20 ml of saturated sodium bicarbonate and once with 20 ml of saturated brine. The organic phases were combined, dried with anhydrous sodium sulfate, and filtered. The organic solvent was evaporated to dryness under reduced pressure, and the residue was foam-dried with a vacuum oil pump overnight to give 8.012 g of crude solid product W-2. The crude solid product W-2 was used in the next deprotection reaction without treatment.

(8-1-3) Synthesis of W-3:

The crude product W-2 (8.012 g, 10 mmol) was dissolved in 100 ml of methanol, and added with 100 ml of aqueous methylamine solution (40 wt %) to react for 23 hours under stirring at 50° C. Insoluble particles were removed by filtration. The solvent was evaporated to dryness under reduced pressure. The residue was added with 200 ml of mixed solvent of DCM: methanol in a volume ratio of 1:1. The organic phase was washed with 50 ml of saturated sodium bicarbonate. The aqueous phase was extracted three times, each with 50 ml of dichloromethane. The organic phases were combined, dried with anhydrous sodium sulfate, and filtered. The solvent was evaporated to dryness under reduced pressure. The residue was foam-dried with a vacuum oil pump overnight, and purified by using a normal phase silica gel column having 200-300 mesh. The column was packed with petroleum ether, added with 1 wt % triethylamine for neutralizing the acidity of silica gel, and eluted with a gradient elution of dichloromethane: methanol: aqueous ammonia (25 wt %)=1:1:0.05-1:1:0.25. The eluate of product was collected. The solvent was evaporated to dryness under reduced pressure, and the residue was foam-dried with a vacuum oil pump to give 3.062 g of pure product W-3.

(8-1-4) Synthesis of W-4:

W-3 (0.675 g, 1.517 mmol) and GAL-C7-2 (2.60 g, 5.46 mmol) were mixed and dissolved in 47 ml of acetonitrile, added with diisopropylethylamine (1.57 g, 12.14 mmol) followed by 3-(diethoxyphosphoryloxy)-1,2,3-benzotrizin-4 (3H)-one (DEPBT, 1.816 g, 6.04 mmol) to react for 2.5 hours under stirring at room temperature. The resulting reaction solution was diluted with 100 ml of dichloromethane. The organic phase was washed with 80 ml of saturated sodium bicarbonate solution and 80 ml of saturated brine, respectively. The organic phases were combined, dried with anhydrous sodium sulfate, and filtered. The solvent was evaporated to dryness under reduced pressure to give a crude product, which was purified by using a normal phase silica gel column having 200-300 mesh. The column was packed with petroleum ether, added with 1 wt % triethylamine for neutralizing the acidity of silica gel, and eluted with a gradient elution of dichloromethane:methanol=100:5-100:7. The eluate of product was collected, and evaporated to dryness under reduced pressure to give 1.610 g of pure product W-4.

(8-1-5) Synthesis of W-5:

W-4 (1.61 g, 0.886 mmol) was dissolved in 125 ml of dichloromethane, and added with dichloroacetic acid (3.5 ml, 42.43 mmol) to react for 1 hour at room temperature. The resulting reaction solution was neutralized by adding 150 ml of pyridine. The solvent was evaporated to dryness under reduced pressure to give a crude product. The crude product was purified by using a normal phase silica gel column having 200-300 mesh. The column was added with 10 wt % triethylamine for neutralizing the acidity of silica gel. The column was equilibrated with 1 wt ‰ triethylamine and eluted with a gradient elution of dichloromethane:methanol=100:30-100:40. The eluate of product was collected, and the solvent was evaporated to dryness under reduced pressure to give 1.26 g of pure product W-5.

(8-1-6) Synthesis of W-6:

W-5 (1.25 g, 0.793 mmol) and A-1 (1.21 g, 2.38 mmol) obtained according to the method described in step (1-1-7a) were mixed and dissolved in 12 ml of dichloromethane, and added with 3-(diethoxyphosphoryloxy)-1,2,3-benzotrizin-4(3H)-one (DEPBT, 0.712 g, 2.38 mmol) followed by diisopropylethylamine (0.615 g, 4.76 mmol) to react for 3 hours under stirring at 25° C. The organic phase was washed with 80 ml of saturated sodium bicarbonate. The aqueous phase was extracted three times, each with 10 ml of dichloromethane. The organic phases were combined and washed with 10 ml of saturated brine. The organic phases were combined, dried with anhydrous sodium sulfate, and filtered. The solvent was evaporated to dryness under reduced pressure, and the residue was foam-dried overnight with a vacuum oil pump to give a crude product. The crude product was subjected to a column purification. The column was filled with 185 g of normal phase silica gel having 200-300 mesh, and added with 20 ml triethylamine for neutralizing the acidity of silica gel. The column was equilibrated with petroleum ether containing 1 wt % triethylamine and eluted with a gradient elution of petroleum ether: ethyl acetate: dichloromethane: N,N-dimethylformamide=1:1:1:0.1-1:1:1:0.7. The eluate of product was collected, and the solvent was evaporated to dryness under reduced pressure to give 1.57 g of pure product W-6.

(8-1-7) Synthesis of W-7:

W-6 (1.238 g, 0.63 mmol), succinic anhydride (0.189 g, 1.89 mmol) and 4-dimethylaminopyridine (DMAP, 0.231 g, 1.89 mmol) were mixed and dissolved in 7 ml of dichloromethane, and added with DIEA (0.407 g, 3.15 mmol) to react for 24 hours under stirring at 25° C. The resulting reaction solution was washed with 5 ml of 0.5 M triethylamine phosphate. The aqueous phase was extracted three times, each with 5 ml of dichloromethane. The organic phases were combined, and evaporated to dryness under reduced pressure to give a crude product. The crude product was subjected to a column purification. The column was filled with 30 g of normal phase silica gel having 200-300 mesh, and added with 1 wt % triethylamine for neutralizing the acidity of silica gel. The column was equilibrated with dichloromethane and eluted with a gradient elution of 1 wt ‰ triethylamine-containing dichloromethane:methanol=100:18-100:20. The eluate of product was collected, and the solvent was evaporated to dryness under reduced pressure to give 1.033 g of pure product, W-7 conjugating molecule. MS m/z: $C_{101}H_{146}N_7O_{38}$, $[M-DMTr]^+$, calcd: 1763.92, measured: 1763.21.

(8-1-8) Synthesis of W-8:

W-8 was prepared by the same method as that in step (1-1-9) of Preparation Example 1, except that L-9 conjugating molecule was replaced with W-7 conjugating molecule to produce the W-7 conjugating molecule linked to the solid support.

(8-2) Synthesis of W8-siAN1M3SVP Conjugate

Conjugate 27 was prepared by the same methods as those in steps (1-2), (1-3A) and (1-4) of Preparation Example 1, except that L-10 compound was replaced with W-8 compound to start the synthesis of the sense strand. W8-siAN1M3SVP having the structure represented by Formula (415) was obtained.

Preparation Example 9. Preparation of X8-siAN1M3SVP Conjugate (Conjugate 28)

It was expected that X-8 compound can be synthesized according to the following process route:

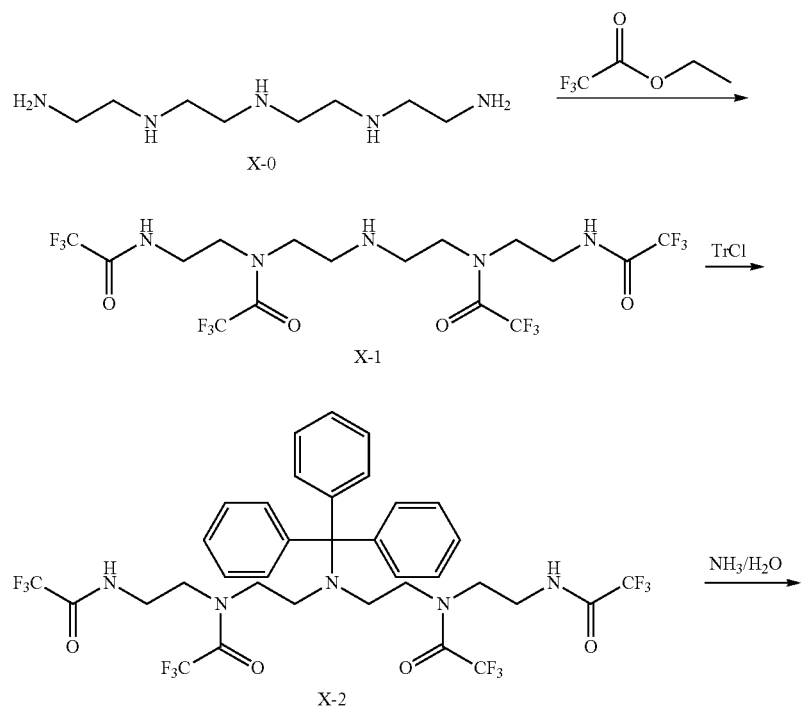

-continued
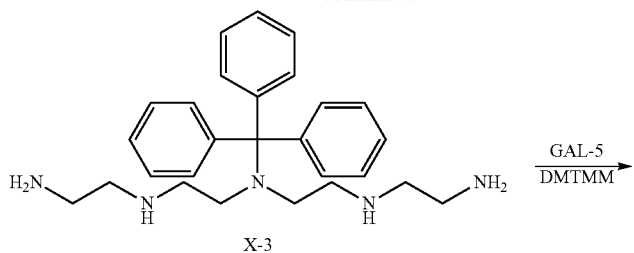
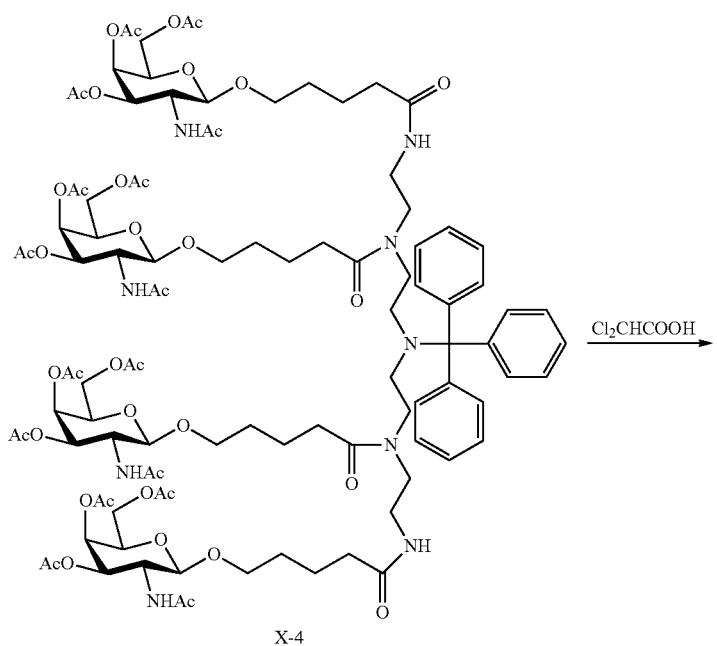
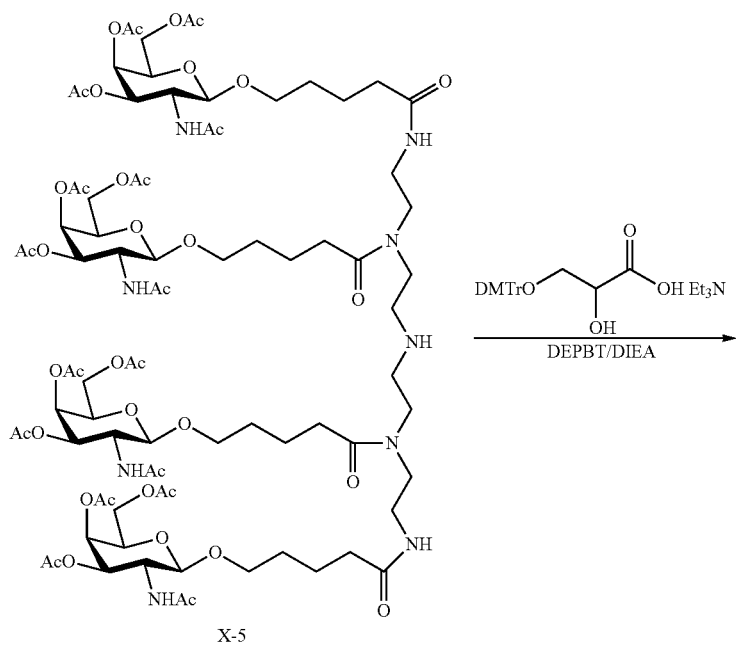

-continued
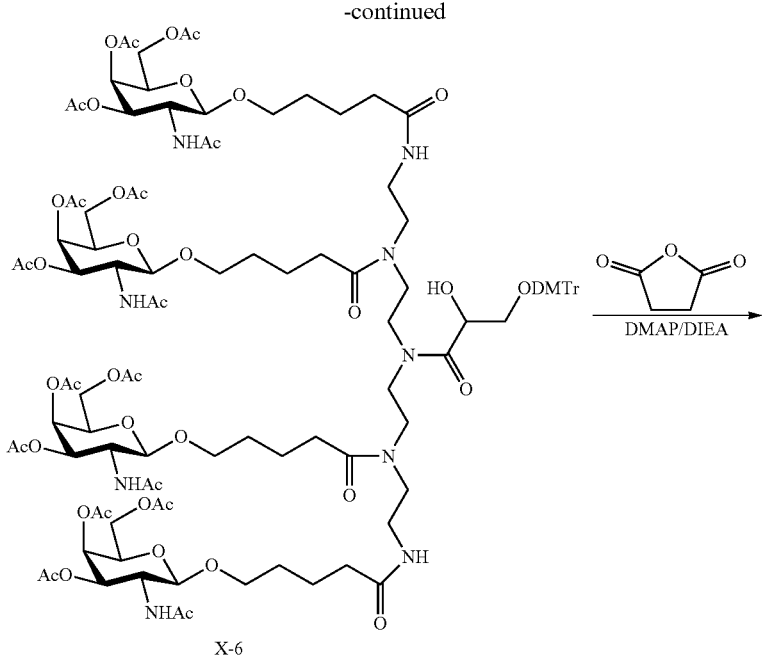
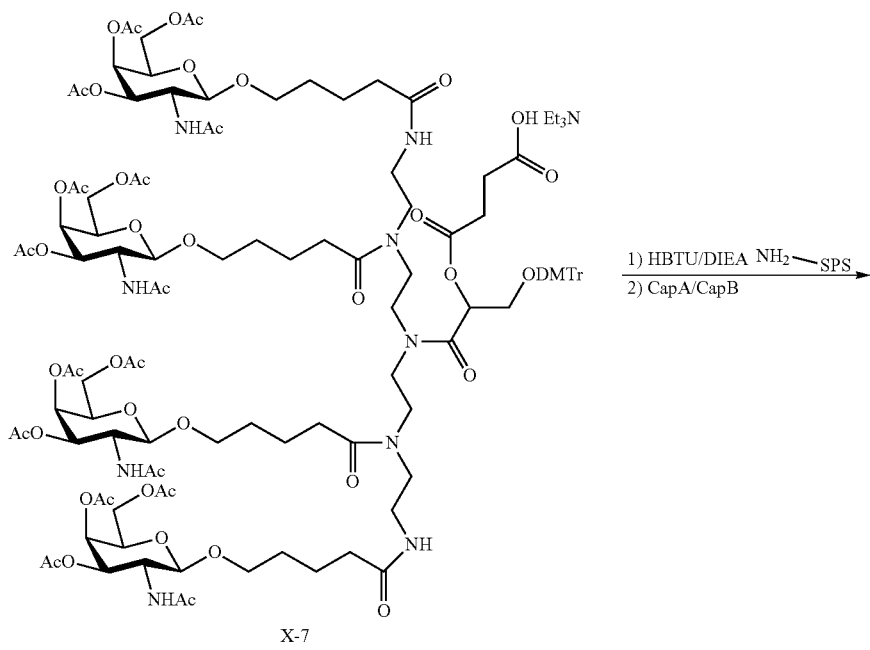

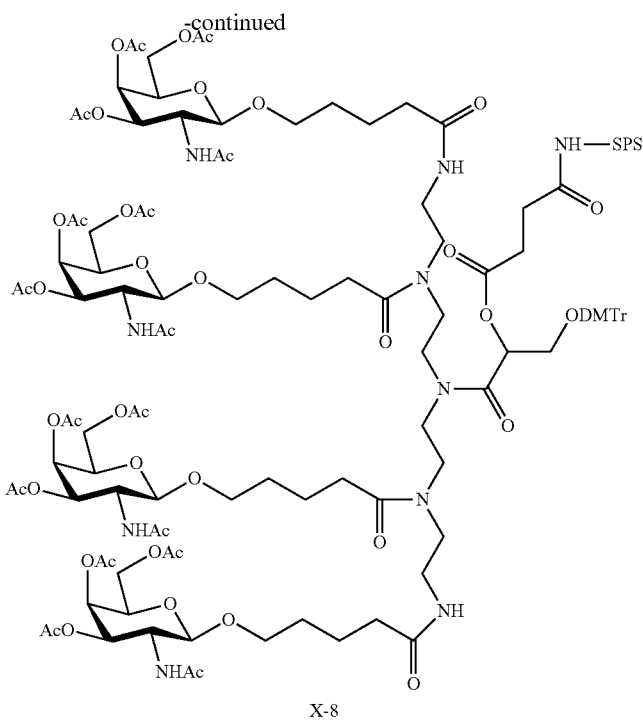

X-8

Conjugate 28 was prepared by the same methods as those in steps (1-2), (1-3A) and (1-4) of Preparation Example 1, except that L-10 compound was replaced with X-8 compound to start the synthesis of the sense strand. It was expected that X8-siAN1M3SVP having the structure represented by Formula (421) can be produced.

Preparation Example 10. Preparation of Z5-siAN1M3SVP Conjugate (Conjugate 29)

(10-1) Synthesis of Z-5 Compound

Z-5 compound was synthesized according to the following method:

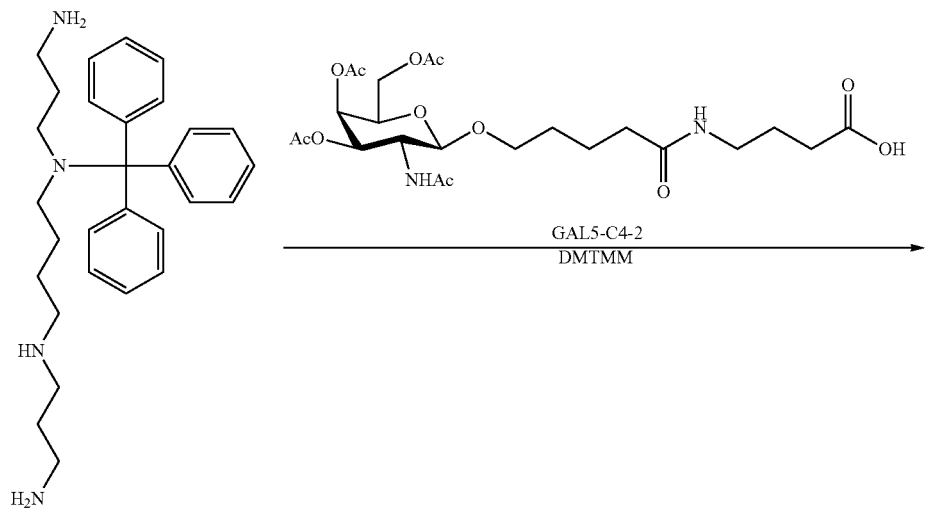

W-3

-continued
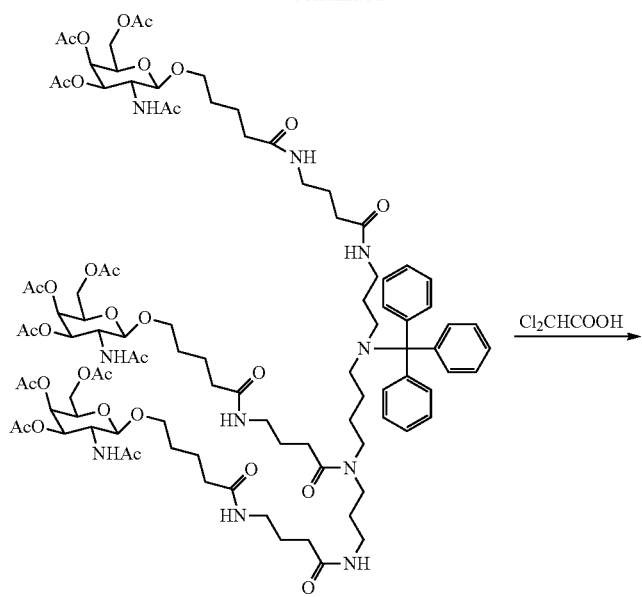
Z-1
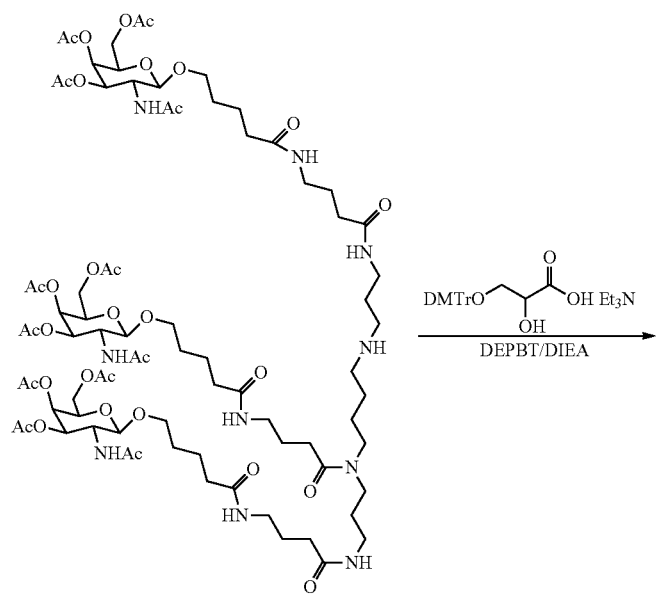
Z-2

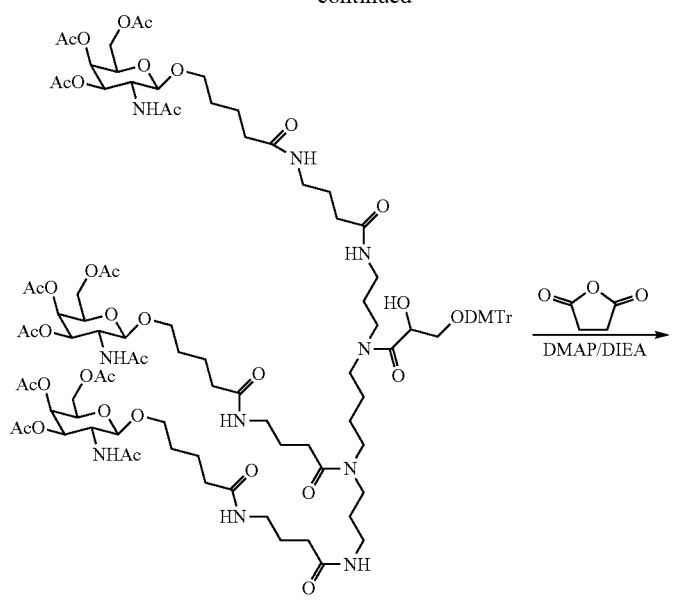
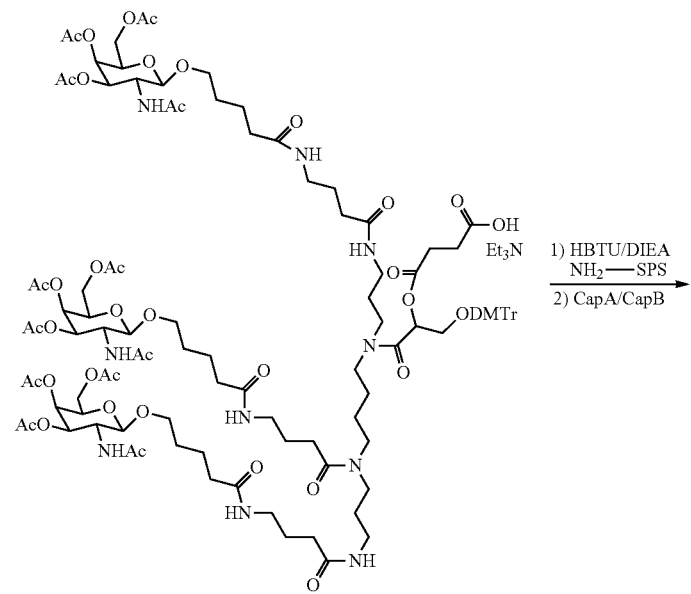

-continued

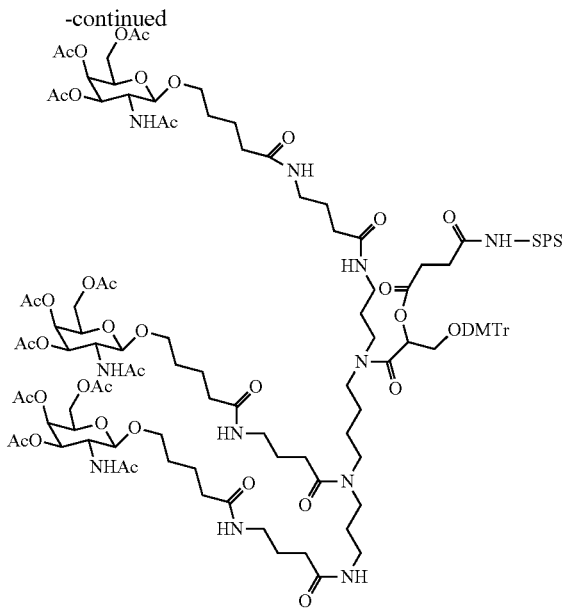

Z-5

(10-1-1) Synthesis of Z-1:

W-3 (1.50 g, 3.37 mmol) obtained according to the method described in step (8-1-3) and GAL5-C4-2 (7.18 g, 13.48 mmol) obtained according to the method described in step (3-1-2) were mixed and dissolved in 34 ml of dichloromethane, added with diisopropylethylamine (3.48 g, 26.96 mmol) followed by 3-(diethoxyphosphoryloxy)-1,2,3-benzotrizin-4(3H)-one (DEPBT, 4.04 g, 13.48 mmol) to react for 4.5 hours under stirring at room temperature. The resulting liquid solution was diluted with 100 ml of dichloromethane. The organic phase was washed with 80 ml of saturated sodium bicarbonate solution and 80 ml of saturated brine, respectively. The organic phases were combined, dried with anhydrous sodium sulfate, and filtered. The solvent was evaporated to dryness under reduced pressure to give a crude product, which was purified by using a normal phase silica gel column having 200-300 mesh. The column was packed with petroleum ether, added with 1 wt % triethylamine for neutralizing the acidity of silica gel, and eluted with a gradient elution of dichloromethane:methanol=30:1-15:1. The eluate of product was collected and evaporated to dryness under reduced pressure to give 3.97 g of pure product Z-1. MS m/z: $C_{98}H_{143}N_{10}O_{33}$, $[M+H]^+$, calcd: 1987.98, measured: 1987.90.

(10-1-2) Synthesis of Z-2:

Z-1 (3.97 g, 2.00 mmol) was dissolved in 250 ml of dichloromethane, and added with dichloroacetic acid (10.941 g, 84.85 mmol) to react for 1 hour at room temperature. The resulting reaction solution was neutralized to neutral by adding pyridine. The solvent was evaporated to dryness under reduced pressure to give a crude product. The column was filled with 220 g 200-300 mesh normal phase silica gel, and added with 10 wt % pyridine for neutralizing the acidity of silica gel. The column was equilibrated with 1 wt ‰ pyridine and eluted with a gradient elution of dichloromethane:methanol=10:1-2:1. The eluate of product was collected, and the solvent was evaporated to dryness under reduced pressure to give 3.49 g of pure product Z-2. MS m/z: $C_{79}H_{129}N_{10}O_{33}$, $[M+H]^+$, calcd: 1746.94, measured: 1746.90.

(10-1-3) synthesis of Z-3:

Z-2 (3.49 g, 2.0 mmol) and A-1 (3.06 g, 6.0 mmol) obtained according to the method described in step (1-1-7a) were mixed and dissolved in 30 ml of dichloromethane, and added with 3-(diethoxyphosphoryloxy)-1,2,3-benzotrizin-4 (3H)-one (DEPBT, 1.80 g, 6.0 mmol) followed by diisopropylethylamine (1.55 g, 12.0 mmol) to react for 3 hours under stirring at 25° C. 100 ml dichloromethane was added to the resulting reaction solution for dilution. The organic phase was washed twice, each with 30 ml of saturated sodium bicarbonate. The aqueous phase was extracted with 10 ml of dichloromethane. The organic phases were combined and washed with 50 ml of saturated brine. All the organic phases were combined and dried with anhydrous sodium sulfate, and filtered. The solvent was evaporated to dryness under reduced pressure, and the residue was foam-dried overnight with a vacuum oil pump to give a crude product. The crude product was subjected to a column purification. The column was filled with 200 g of normal phase silica gel having 200-300 mesh, and added with 20 ml triethylamine for neutralizing the acidity of silica gel. The column was equilibrated with petroleum ether containing 1 wt % triethylamine and eluted with a gradient elution of dichloromethane:methanol=25:1-15:1. The eluate of product was collected, and the solvent was evaporated to dryness under reduced pressure to give 2.2 g of pure product Z-3. MS m/z: $C_{103}H_{151}N_{10}O_{38}$, $[M+H]^+$, calcd: 2136.02, measured: 2136.20.

(10-1-4) Synthesis of Z-4:

Z-3 (2.10 g, 0.983 mmol) was dissolved in 14.8 ml of dichloromethane containing DIEA (0.635 g, 4.915 mmol). The resulting solution was added with 4-dimethylaminopyridine (DMAP, 240 mg, 1.966 mmol) and stirred to clarity. Succinic anhydride (197 mg, 1.966 mmol) was added to react for 18 hours under stirring at 25° C. The resulting reaction solution was diluted by adding 50 ml dichloromethane, and then washed with 80 ml of 0.5 M triethylamine phosphate. The aqueous phase was extracted twice, each with 50 ml of dichloromethane. The organic phases were combined, and evaporated to dryness under reduced pressure to give a crude product. The crude product was subjected to a column purification. The column was filled with 188 g of normal phase silica gel having 200-300 mesh, and added with 1 wt % triethylamine for neutralizing the acidity of silica gel. The column was equilibrated with dichloromethane and eluted with a gradient elution of dichloromethane containing 1 wt ‰ triethylamine:methanol=10:1-3:1. The eluate of product was collected, and the solvent was evaporated to dryness under reduced pressure to give 1.95 g of pure product, Z-4 conjugating molecule. MS m/z: $C_{107}H_{155}N_{10}O_{41}$, $[M+H]^+$, calcd: 1935.07, measured: 1935.29.

(10-1-5) Synthesis of Z-5

Z-5 was prepared by the same method as that in step (1-1-9) of Preparation Example 1, except that L-9 conjugating molecule was replaced with Z-4 conjugating molecule to produce Z-4 Conjugating Molecule linked to the solid support.

(10-2) Synthesis of Z5-siAN1M3SVP Conjugate

Conjugate 29 was prepared by the same method as those in steps (1-2), (1-3A) and (1-4) of Preparation Example 1, except that L-10 compound was replaced with Z-5 compound to start the synthesis of the sense strand. Z5-siAN1M3SVP conjugate having the structure represented by Formula (422) was produced.

Preparation Example 11. Preparation of Conjugates F1-F13

In this Preparation Example, conjugates F1-F13 were synthesized. The sequences of the conjugated siRNAs in the conjugates are shown in Table 3

(11-1) Synthesis of FIN-2 Conjugating Molecule

FIN-2 conjugating molecule was synthesized with reference to the preparation method described in Rajeev et al., ChemBioChem 2015, 16, 903-908 according to the following process route.

(11-1-1) Synthesis of Compound PRO-10

(11-1-1-a) Synthesis of PRO-7

2.93 g of PRO-6 (L-hydroxyproline, CAS No.: 51-35-4, purchased from Energy Chemical, 22.4 mmol) was dissolved in 22.5 ml of 1,4-dioxane (CAS No.: 123-91-1) and added with 34 ml of 10% (w/w) aqueous $Na_2CO_3$ solution, to form a suspension. 6.95 g of Fmoc-Cl (9-fluorenylmethyl chloroformate, CAS No.: 28920-43-6, purchased from Energy Chemical, 26.8 mmol) was dissolved in 34 ml of 1,4-dioxane, added into the above suspension in an ice bath, and naturally warmed to room temperature for reacting overnight. The reaction liquid was poured into 150 ml of ice water, and extracted three times, each with 100 ml of methyl t-butyl ether. The organic phase was discarded. The aqueous phase was adjusted to pH≤5 with concentrated hydrochloric acid, extracted twice with 100 ml of ethyl acetate. All the organic phases were combined and dried with anhydrous sodium sulfate. The solvent was evaporated to dryness under reduced pressure to give 7.83 g of product PRO-7 as a white foamy solid. $^1$H NMR (400 MHz, DMSO-$d_6$) δ 7.91 (t, J=7.2 Hz, 2H), 7.67 (d, J=7.5 Hz, 2H), 7.48-7.39 (m, 2H), 7.38-7.27 (m, 2H), 5.17 (s, 1H), 4.27 (s, 2H), 4.23-4.11 (m, 2H), 3.55-3.41 (m, 3H), 2.31-2.10 (m, 1H), 2.08-1.88 (m, 1H). HRMS (ESI) m/z calcd for $C_{20}H_{19}NO_5$ $[M–H]^-$ 352.1190, measured: 352.1033.

(11-1-1b) Synthesis of PRO-8

7.83 g of PRO-7 (22.2 mmol) was dissolved in 80 ml of THF (CAS No.: 109-99-9), heated to 65° C. in an oil bath, added with 36.6 ml of 2 mol/L solution of $BH_3$-$Me_2S$ in THF (CAS No. 13292-87-0, purchased from J&K Scientific Ltd., 73.2 mmol) under reflux, and refluxed continually to react for 3 hours. The reaction liquid was poured out, and the remaining solid was dissolved in methanol. To the resulting reaction liquid, methanol was added under stirring until no gas emitted, and stirred continually for 30 minutes. The solvent was evaporated under reduced pressure, and then the residue was purified three times with petroleum ether to give

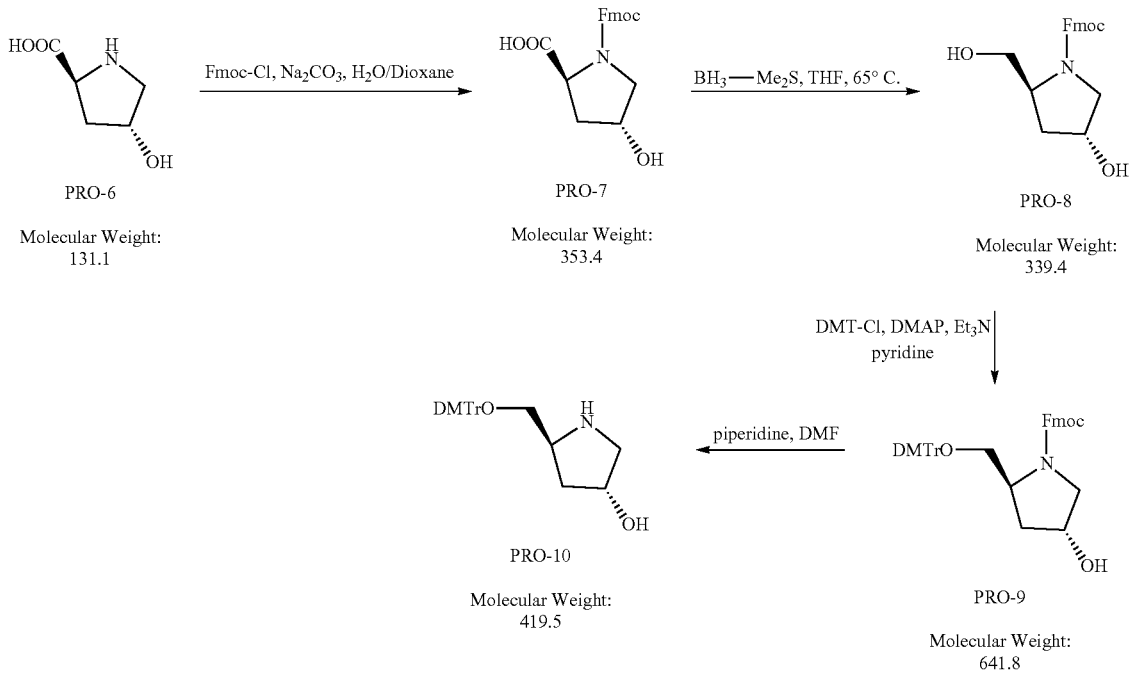

7.1 g of product PRO-8 as a white solid. $^1$H NMR (400 MHz, DMSO-$d_6$) δ 7.91 (t, J=6.7 Hz, 2H), 7.67 (d, J=7.2 Hz, 2H), 7.49-7.39 (m, 2H), 7.38-7.26 (m, 2H), 5.18 (dd, J=6.1, 3.8 Hz, 1H), 4.28 (s, 2H), 4.23-4.13 (m, 2H), 3.55-3.38 (m, 2H), 2.32-2.11 (m, 1H), 2.08-1.89 (m, 1H). HRMS (ESI) m/z calcd for $C_{20}H_{21}NO_4$ [M+Na]$^+$ 362.1368, measured: 362.1012.

(11-1-1c) Synthesis of PRO-9

7.1 g of PRO-8 (21 mmol) was dissolved in 100 ml of pyridine, and added with 14.2 g of DMTr-Cl (4,4'-dimethoxytrityl chloride, 42 mmol) to react for 5 hours under stirring at room temperature. The solvent was removed by evaporation under reduced pressure. The resulting crude product was dissolved in ethyl acetate and filtered to remove salt impurities. The solvent was evaporated under reduced pressure, and then the residue was purified by using a silica gel column. For purification, the crude product dissolved in DCM was loaded onto the silica gel column that was alkalified with pyridine beforehand. DMTr-Cl was eluted with DCM containing 1% (v/v) pyridine, and then the product was eluted with ethyl acetate. The eluate of product was collected, and the solvent was evaporated to dryness under reduced pressure to give 8.2 g of product PRO-9 as a white solid. HRMS (ESI) m/z calcd for $C_{41}H_{39}NO_6$ [M+Na]$^+$ 664.2675, measured: 664.2348; C18 RP-HPLC (Lot Number: JJS160324-1); purity: 94.20%.

(11-1-1d) Synthesis of PRO-10

8.2 g of PRO-9 (12.8 mmol) was dissolved in 64 ml of DMF (N,N-dimethylformamide) and added with 40 ml of piperidine (384 mmol) to react for 30 minutes under stirring at room temperature. The reaction liquid was poured into 300 ml of ice water and extracted three times, each with 150 ml of ethyl acetate. The organic phases were combined, washed with 200 ml of saturated brine, and then dried with anhydrous sodium sulfate. The solvent was evaporated to dryness under reduced pressure, and then the residue was purified by using a silica gel column. For purification, the crude product dissolved in DCM was loaded onto the silica gel column that was alkalified with pyridine beforehand. Fmoc was eluted with DCM containing 1% (v/v) pyridine, and then the product was eluted with ethyl acetate. The eluate of product was collected, and the solvent was evaporated to dryness under reduced pressure to give 4.65 g of product PRO-10 as a white solid. $^1$H NMR (400 MHz, DMSO-$d_6$) δ 7.40 (d, J=7.2 Hz, 2H), 7.35-7.18 (m, 7H), 6.93-6.84 (m, 4H), 4.56 (d, J=3.9 Hz, 1H), 4.12 (s, 1H), 3.74 (s, 6H), 3.46-3.37 (m, 1H), 2.88 (ddd, J=18.5, 10.0, 5.5 Hz, 2H), 2.75 (dd, J=8.7, 5.8 Hz, 1H), 2.62 (dd, J=11.0, 2.7 Hz, 1H), 1.74-1.65 (m, 1H), 1.40 (ddd, J=12.9, 8.5, 5.9 Hz, 1H); FIRMS (ESI) m/z calcd for $C_{26}H_{29}NO_4$ [M+Na]$^+$ 442.1994, measured: 442.1999; C18 RP-HPLC (Lot Number: JJS160329-1), purity: 97.07%.

(11-1-2) Synthesis of FIN-1

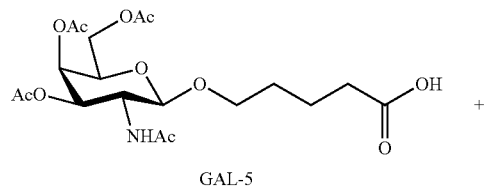

GAL-5

Molecular Weight:
447.4

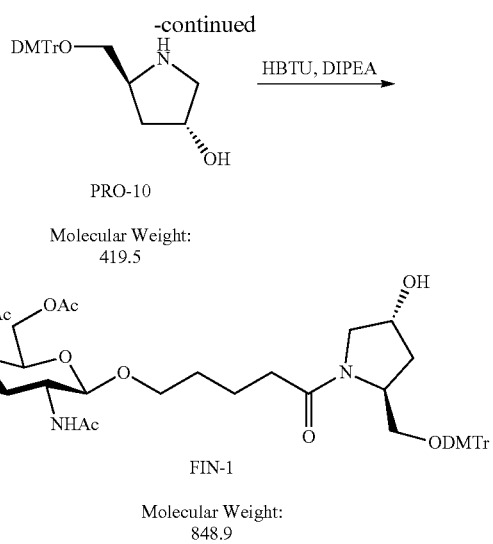

PRO-10

Molecular Weight:
419.5

FIN-1

Molecular Weight:
848.9

GAL-5 (4.5 g, 10 mmol) obtained according to the method described in (1-1-1) was dissolved in 40 ml of DMF, sequentially added with 3.9 g of DIPEA (N,N-diisopropylethylamine, CAS No.: 7087-68-5, purchased from Aladdin Inc., 30 mmol) and 3.8 g of HBTU (benzotriazol-N,N,N', N'-tetramethyluronium hexafluorophosphate, CAS No.: 94790-37-2, purchased from Aladdin Inc., 11 mmol), and stirred at room temperature for 10 minutes. PRO-10 (4.2 g, 10 mmol) obtained in step (11-1-1d) was dissolved in 40 ml of DMF, and then added into the above reaction liquid. The resulting reaction liquid was dried by addition of anhydrous sodium sulfate and stirred at room temperature for 2 hours. The reaction liquid was poured into 120 ml of ice water and extracted three times, each with 60 ml of ethyl acetate. The organic phases were combined, washed with 20 ml of water and 20 ml of saturated brine, respectively. The organic phase was isolated, dried with anhydrous sodium sulfate. The solvent was evaporated under reduced pressure, and then the residue was purified by using a silica gel column. For purification, a sample was loaded onto the silica gel column that was alkalified with pyridine beforehand, and was eluted with dichloromethane (DCM) solution containing 1% (v/v) triethylamine and 1% (v/v) methanol. The eluate of product was collected, and the solvent was evaporated to dryness under reduced pressure to give 6.5 g of product FIN-1 as a light yellow foamy solid. $^1$H NMR (400 MHz, DMSO-$d_6$) δ 7.83 (d, J=9.2 Hz, 1H), 7.32 (t, J=6.6 Hz, 4H), 7.20 (td, J=8.9, 3.5 Hz, 5H), 6.93-6.84 (m, 4H), 5.21 (d, J=3.2 Hz, 1H), 5.04-4.90 (m, 2H), 4.49 (s, 1H), 4.40 (d, J=4.4 Hz, 0.8H), 4.31 (d, J=5.0 Hz, 0.2H), 4.15 (s, 1H), 4.03 (s, 3H), 3.93 (s, 1H), 3.74 (s, 7H), 3.59 (dt, J=12.0, 6.0 Hz, 1H), 3.50-3.40 (m, 1H), 3.39-3.25 (m, 3H), 3.13 (dd, J=8.9, 5.2 Hz, 1H), 3.00 (dq, J=9.3, 5.3, 4.3 Hz, 1H), 2.22 (s, 2H), 2.07 (s, 3H), 1.99 (s, 3H), 1.90 (s, 4H), 1.74 (s, 3H), 1.50 (s, 3H), 1.36 (s, 1H). C18 RP-HPLC (Lot Number: LJ160422), purity: 95.45%.

(11-1-3) Synthesis of FIN-2

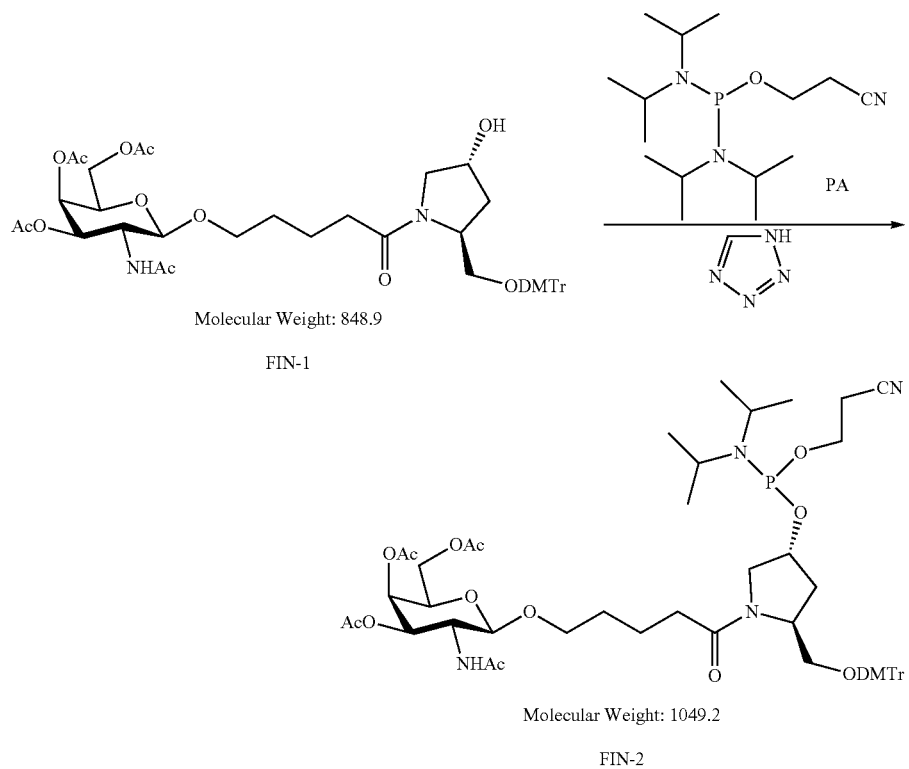

FIN-1 (3.0 g, 3.53 mmol) obtained in step (11-1-2) was azeotropically dehydrated with acetonitrile, and subjected to suction to dryness under reduced pressure. The resulting residue was dissolved in 10 ml of DMF, added with 2.13 g of PA (bis(diisopropylamino)(2-cyanoethoxy)phosphine, purchased from Adamas Inc., product No. 11356B, 7.06 mmol) and 346 mg tetrazole (CAS No.: 288-94-8, purchased from Aladdin Inc., 4.94 mmol) in nitrogen atmosphere, and stirred to react at room temperature. The reaction was added with a further 10 ml of DMF and continually stirred to react for 1 hour. The solvent was removed by evaporation under reduced pressure, and then the residue was purified by silica gel column chromatography. For purification, the crude product dissolved in DCM was loaded onto the silica gel column that alkalified with pyridine beforehand, and eluted with ethyl acetate. The eluate of product was collected, and the solvent was evaporated under reduced pressure to give 4.5 g of crude product as a colorless syrup. The crude product was completely dissolved in 50% (v/v) aqueous acetonitrile solution and purified by using a medium pressure purification column (C-18, 330 g, 300 Å) that was alkalified with a solution of 1% (v/v) pyridine in acetonitrile beforehand. The product peak was collected by gradient elution and the solvent was evaporated under reduced pressure to give 2.2 g of product as a white powder, FIN-2 conjugating molecule. $^{31}$P NMR (162 MHz, CDCl3) δ 148.04, 147.94, 147.62, 147.19, purity of $^{31}$P NMR: 92%; purity of C18 RP-HPLC: 90.54%.

(11-2) Linking FIN-2 Conjugating Molecule to a Solid Phase Support

The conjugating group (FIN_FIN_FIN) was linked to the 3' terminal of the sense strand of RNA by linking the FIN-2 conjugating molecule obtained in step (11-1-3) to a universal solid phase support (UnyLinker™ loaded NittoPhase®HL Solid Supports) according to the nucleic acid solid phase synthesis method through three reaction cycles.

The above linking was proceeded according to the preparation method described in Rajeev et al., Chem Bio Chem 2015, 16, 903-908. Specifically, started from the above-mentioned universal solid phase support, the hydroxy protecting group was firstly removed from the above-mentioned universal solid phase support, and the solid phase support was subsequently brought into contact and coupled with the FIN-2 conjugating molecule under the coupling condition in the presence of a coupling agent, and a FIN conjugating molecule connected to the solid phase support was obtained after the capping and oxidation reaction. Moreover, the hydroxy protecting group DMTr was removed from the FIN conjugating molecule connected to the solid phase support, and the solid phase support was further brought into contact and coupled with another FIN-2 conjugating molecule, followed by capping and oxidation reaction. By repeating the above steps of Deprotection-Coupling-Capping-Oxidation, a third FIN-2 conjugating molecule was connected, and a conjugating group (FIN_FIN_FIN) connected to the solid phase support was thus obtained.

In the above reactions, the reaction conditions for deprotection, coupling, capping and oxidization, as well as the amounts of solvents and reagents are the same as those in the solid phase synthesis of nucleic acid described in the above step (1-2).

(11-3) Synthesis of Conjugates F1-F13

Conjugates F1-F13 were prepared by the same methods as those in steps (1-2), (1-3) and (1-4) of Preparation Example 1, except that 1) the sense strand was synthesized starting from the compound produced in step (11-2); and 2) the conjugated siRNA had the sequences corresponding to conjugates F1-F13 shown in Table 3.

The molecular weight was measured by LC-MS (Liquid Chromatography-Mass Spectrometry, purchased from Waters Corp., model: LCT Premier). The result showed that the measured values were in conformity with the calculated values, and thus it was confirmed that the synthesized conjugates were the designed target compounds having the structure represented by Formula (307).

Preparation Example 12. Preparation of Comparative Conjugate 2

In the present preparation example, comparative conjugate 2 was synthesized. The conjugated siRNA in this conjugate has the sequence shown in Table 3. This conjugate has the same structure as compound AD-65695 in WO 2016168286A1.

(12-1) Synthesis of (GalNAc)$_3$ Conjugating Molecule

Compound 30, i.e., the conjugating molecule containing the above mentioned linker -(L$^A$)$_3$-trihydroxymethylaminomethane-L$^B$- and N-acetylgalactosamine molecule as a targeting group (wherein each L$^A$ can be linked to one N-acetylgalactosamine molecule so that one linker can be linked to three N-acetylgalactosamine molecules), was synthesized according to the preparation method described in WO2014025805A1. This conjugating molecule can also be referred to herein as (GalNAc)$_3$ conjugating molecule, and the structure of compound 30 was as follows:

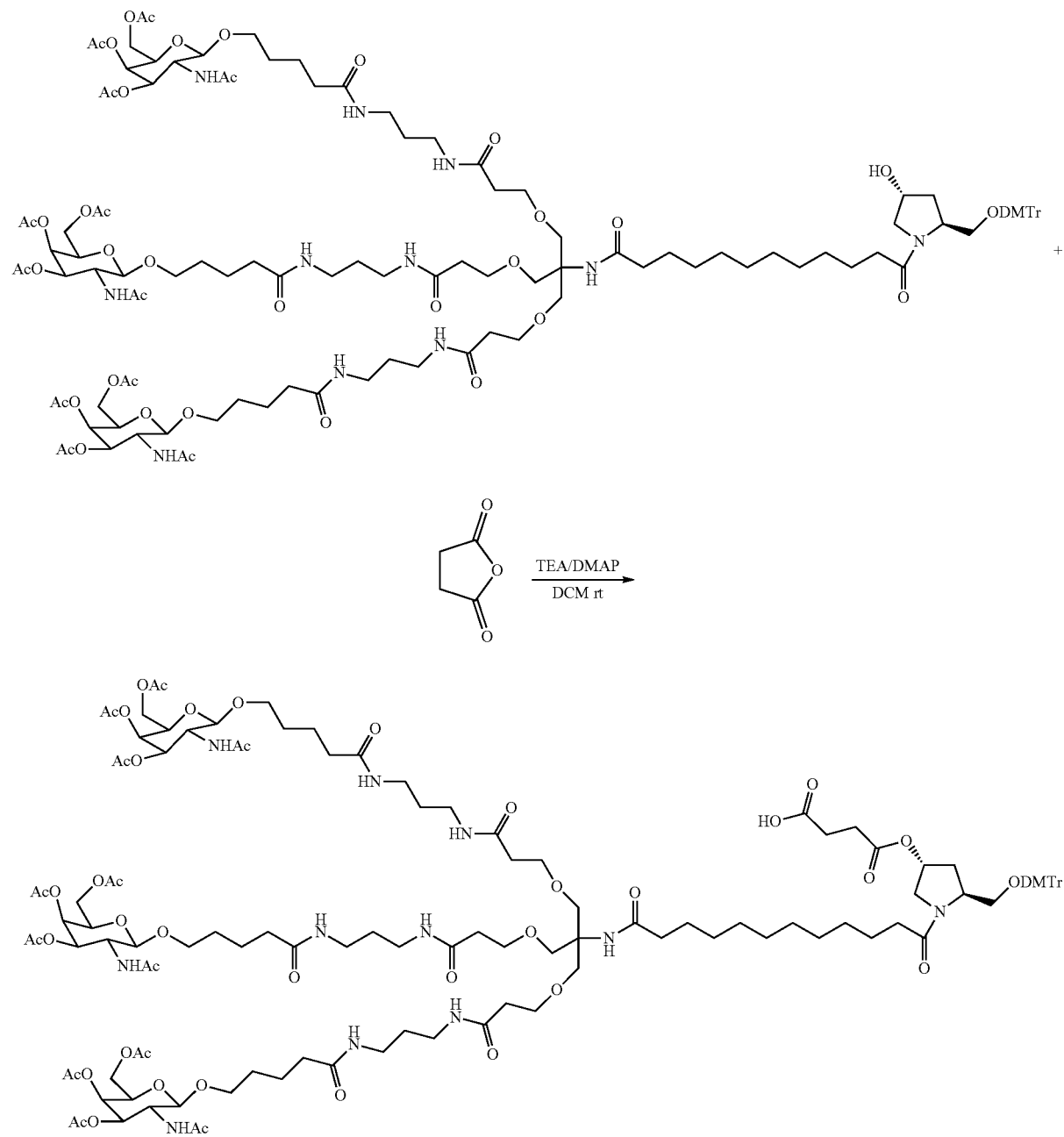

(12-2) Linking (GalNAc)₃ Conjugating Molecule to a Solid Phase Support

The (GalNAc)₃ conjugating molecule was linked to the solid phase support by the same method as that in step (1-1-9) of Preparation Example 1, thereby obtaining (GalNAc)₃ conjugating molecule linked to a solid phase support.

(12-3) Synthesis of Comparative Conjugate 2

Comparative conjugate 2 was prepared by the same methods as those in steps (1-2), (1-3D) and (1-4) of Preparation Example 1, except that 1) the sense strand was synthesized starting from the compound produced in step (12-2); and 2) the conjugated siRNA had sequences represented by No. AD-65695 as shown in Table 3. The molecular weight was measured by LC-MS (Liquid Chromatography-Mass Spectrometry, purchased from Waters Corp., model: LCT Premier). For sense strand, calcd: 8625.32, measured: 8623.7; for antisense strand, calcd: 7726.15, measured: 7725.2. The result showed that the measured values were in conformity with the theoretical values, and thus it was confirmed that the synthesized conjugate was the designed target compound having structure represented by Formula (305).

Preparation Example 13. Synthesis of siRNA Sequence

The siRNA sequences of the present disclosure listed in Table 4 were obtained by conventional solid phase synthesis method. Mixtures of equimolar amounts of the sense strand and the antisense strand were dissolved with a DEPC-treated water followed by conventional annealing to form a siRNA duplex.

TABLE 4 siRNA sequences

| siRNA | No. | | Sequence Direction 5'-3' | SEQ ID NO |
|---|---|---|---|---|
| SiRNA1 | siAN1M3SVP | S | CmsCmsAmAmGmAmGfCfAf CmCmAmAmGmAmAmCmUmAm | 26 |
| | | AS | VP-UmsAfsGmUmUmCfUm UmGmGmUmGmCmUfCmUfUm GmGmsCmsUm | 36 |
| siRNA2 | siAN1M3SP | S | CmsCmsAmAmGmAmGfCfAf CmCmAmAmGmAmAmCmUmAm | 26 |
| | | AS | P-UmsAfsGmUmUmCfUmUm GmGmUmGmCmUfCmUfUmGm GmsCmsUm | 37 |
| siRNA3 | siAN1M3SPs | S | CmsCmsAmAmGmAmGfCfAf CmCmAmAmGmAmAmCmUmAm | 26 |
| | | AS | Ps-UmsAfsGmUmUmCfUm UmGmGmUmGmCmUfCmUfUm GmGmsCmsUm | 38 |
| siRNA4 | siAN1M3S | S | CmsCmsAmAmGmAmGfCfAf CmCmAmAmGmAmAmCmUmAm | 26 |
| | | AS | UmsAfsGmUmUmCfUmUmGm GmUmGmCmUfCmUfUmGm GmsCmsUm | 24 |
| siRNA5 | siAN1M1SVP | S | CmsCmsAmAmGfAmGfCfAf CmCmAmAmGmAmAmCmUmAm | 20 |
| | | AS | VP-UmsAfsGmUmUmCfUm UfGfGmUmGmCmUfCmUfUm GmGmsCmsUm | 39 |

TABLE 4-continued siRNA sequences

| siRNA | No. | | Sequence Direction 5'-3' | SEQ ID NO |
|---|---|---|---|---|
| siRNA6 | siAN1M1SP | S | CmsCmsAmAmGfAmGfCfAf CmCmAmAmGmAmAmCmUmAm | 20 |
| | | AS | P-UmsAfsGmUmUmCfUmUf GfGmUmGmCmUfCmUfUmGm GmsCmsUm | 40 |
| siRNA7 | siAN1M1S | S | CmsCmsAmAmGfAmGfCfAf CmCmAmAmGmAmAmCmUmAm | 20 |
| | | AS | UmsAfsGmUmUmCfUmUfGf GmUmGmCmUfCmUfUmGm GmsCmsUm | 21 |
| siRNA8 | siAN1 | S | CCAAGAGCACCAAGAACUA | 8 |
| | | AS | UAGUUCUUGGUGCUCUUGG CU | 9 |
| si65695 | si65695 | S | AmsCmAmUmAmUmUfUmGf AfUfCmAmGmUmCmUmUmUm UmUm | 51 |
| | | AS | AmsAfsAmAmAmGfAmCmUm GmAmUmCmAfAmAfUmAmUm GmUmsUmsGm | 52 |

After the preparation of the siRNAs or the conjugates of the present disclosure, they were lyophilized to solid powder via standard process and stored until used. When used, they can be resolved with such as water for injection to a solution at a desired concentration.

Experimental Example 1. Detection of Inhibitory Activity and Off-Target Effect of siRNA in psiCHECK System In Vitro In this experimental example, siRNAs 1, 4, 5, 7 and 8 were investigated in psiCHECK system in vitro for the on-target activity and off-target effect, i.e., five siRNA sequences were tested for the activity of targeting completely matching target sequence or targeting seed region matching target sequence.

According to the method described by Kumico Ui-Tei et. al., Functional dissection of siRNA sequence by systematic DNA substitution: modified siRNA with a DNA seed arm is a powerful tool for mammalian gene silencing with significantly reduced off-target effect. Nucleic Acids Research, 2008.36(7), 2136-2151, plasmids for detection were constructed and co-transfected with the siRNA conjugates to be detected into HEK293A cells. The on-target activity and off-target effect of the siRNAs were reflected by the expression level of a dual-luciferase reporter gene. Specific steps are as follows:

[1] Construction of plasmids for detection

Four recombinant plasmids were constructed using psi-CHECK™-2 (Promega™) plasmid. In the recombinant plasmids, GSCM represents the on-target plasmid; and PSCM, GSSM, and PSSM represent the off-target plasmids:

(1) GSCM, containing a target sequence; the target sequence is completely complementary to all 21 nucleotide sequences of the antisense strand in the siRNA to be detected;

(2) PSCM, containing a target sequence; the target sequence is completely the same as all 21 nucleotide sequences of the antisense strand in the siRNA to be detected;

(3) GSSM, containing a target sequence; the target sequence is completely complementary to the nucleotide sequence at positions 1-8 counting from the 5' terminal of the antisense strand in the siRNA to be detected. The rest of the target sequence corresponds to the nucleotide sequence at positions 9-21 counting from the 5' terminal of antisense strand in the siRNA to be detected, and completely mispaired with the latter. Thus, when the nucleotide at any position between 9 and 21 counting from the 5' terminal of antisense strand in the siRNA to be detected is G, C, A or U, the nucleotide at the corresponding position in the target sequence is T, A, C or G.

(4) PSSM, containing a target sequence; the target sequence is completely complementary to the nucleotide sequence at positions 1-8 counting from the 5' terminal of sense strand in the siRNA to be detected. The rest of the target sequence corresponds to the nucleotide sequence at positions 9-19 counting from the 5' terminal of sense strand in the siRNA to be detected, and completely mispaired with the latter. Thus, when the nucleotide at any position between 9 and 19 counting from the 5' terminal of sense strand in the siRNA to be detected is G, C, A or U, the nucleotide at the corresponding position of the target sequence is T, A, C or G. In order that the target sequence has the same length as GSSM target sequence, nucleotides T and C are sequentially added to the 3' terminal of the target sequence.

The target sequence was cloned into the Xho I/Not I site of the psiCHECK™-2 plasmid.

[2] Transfection

In a 96-well plate, siRNA and each of the above plasmids were co-transfected according to the instructions of Lipofectamine™ 2000 (Invitrogen) respectively, wherein each plasmid corresponds to 11 groups of siRNA concentrations. In particular, 10 ng of plasmid was transfected per well, by using 0.2 μL of Lipofectamine™ 2000. The concentrations of siRNA1, siRNA4, siRNA5 and siRNA8 were 3-fold diluted from 5 nM to 0.00008 nM, with a total of 11 concentrations. The concentration of siRNA7 was double diluted from 0.5 nm to 0.00005 nM, with a total of 11 concentrations. 3 replicate wells were used for each group.

[3] Detection 24 hours post co-transfection, the HEK293A cells were lysed by using a dual luciferase reporter gene assay kit (Promega, cat. E2940) according to the instruction manual to detect the expression level of the dual luciferase reporter gene. For the test group of each specific concentration of the siRNA, the group untreated with the siRNA are used as control (con.). The Renilla luciferase protein level (Ren) was normalized to the firefly luciferase protein level (Fir).

The inhibition effect of siRNA 8 on the expression of 4 recombinant plasmids is shown in FIGS. 1A-1D. The inhibition effect of siRNA 1 on the expression of 4 recombinant plasmids is shown in FIGS. 2A-2D. Thus, when the unmodified siRNA 8 was at a concentration of 5 nM, an inhibition rate against the expressions of GSSM and PSCM was about 20%, the fact which showed the off-target effect of a few seed regions of the antisense strand and the off-target effect of the sense strand. Nevertheless, the modified siRNA 1 of the present disclosure did not show any off-target effect. The siRNAs 4, 5 and 7 also showed no off-target effect, that was the same as siRNA 1.

The dose-response curves were fitted according to the activity results measured at different siRNA concentrations, by using Function log(inhibitor) vs. response—Variable slope of Graphpad 5.0 software. Further, the $IC_{50}$ value of the siRNA to be detected that targets GSCM was calculated on the basis of the does-response curve according to the following equation. The result is shown in FIG. 5.

$$Y = Bot + \frac{Top - Bot}{1 + 10^{(log IC_{50} - X) \times HillSlope}}$$

wherein

Y is the expression level of remaining mRNA,

X is the logarithm of the concentration of transfected siRNA,

Bot is the Y value at the bottom of the steady-state phase,

Top is the Y value at the top of the steady-state phase, $LogIC_{50}$ is the X value when Y is the median value between the bottom and the top, and HillSlope is the slope of the curve.

TABLE 5

$IC_{50}$ of 5 siRNAs against GSCM

| siRNA | No. | $IC_{50}$ against GSCM |
| --- | --- | --- |
| siRNA 1 | siAN1M3SVP | 0.017 nM |
| siRNA 4 | siAN1M3S | 0.024 nM |
| siRNA 5 | siAN1M1SVP | 0.0078 nM |
| siRNA 7 | siAN1M1S | 0.027 nM |
| siRNA 8 | siAN1 | 0.0028 nM |

This experiment demonstrated that the modified siRNA of the present disclosure showed very high inhibitory activity in psiCHECK system in vitro, with $IC_{50}$ between 3 and 30 pM. Meanwhile, even at a concentration of 5 nM, no off-target effect was detected for the modified siRNAs to be detected.

Experimental Example 2. Detection of Inhibitory Activity of siRNA and siRNA Conjugate in Cell System In Vitro Experimental Example 2-1. Detection of the Inhibitory Efficiency of siRNA Against the Expression Amount of ANGPTL 3 mRNA in Huh7 Cells The siRNAs (siRNA 1, 2, 4, 5, 6, and 7) to be detected were transfected to Huh7 human hepatoma cell strain by using Lipofectamine™ 2000. The final concentrations of siRNAs were 5 nM, 0.25 nM and 0.05 nM respectively. 2 replicate wells were used for each concentration. Cells untreated with any siRNA were used as blank controls (marked as "blank" in FIG. 3A).

The expression amount of ANGPTL3 mRNA in Huh7 cells transfected with various concentrations of siRNAs were detected by Quantitative Real-Time PCR. Specific steps are as follows: 24 hours post cultivation of the transfected cells, the total RNA was extracted and obtained by using Trizol (Thermo Fisher) according to the standard procedure for total RNA extraction; 1 μg of total RNA were individually reverse transcribed into cDNA by using reverse transcription kit (Promega, Cat.A3500) according to the operation method in the instructions thereof. The expression amount of ANGPTL3 mRNA was detected by using the template cDNA according to the steps in the instructions by using 2× Ultra SYBR Mixture (with ROX) (Beijing Cowin Biosicences Co., Ltd, Cat. CW0956). In this case, the PCR primers used for amplifying ANGPTL3 and GAPDH as an internal control gene are shown in Table 6.

TABLE 6

Information of Primers

| Genes | Primer types | Nucleotide sequences (5'→3') | SEQ ID No. |
|---|---|---|---|
| human ANGPTL3 | Upstream Primer | ACCAACTATACGCTACAT | 53 |
| | Downstream Primer | CCTCCTGAATAACCCTCT | 54 |
| human GAPDH | Upstream Primer | GGTCGGAGTCAACGGATTT | 55 |
| | Downstream Primer | CCAGCATCGCCCCACTTGA | 56 |

The expression amount of ANGPTL3 mRNA was calculated by the following equation: the expression amount of ANGPTL3 mRNA=(the expression amount of ANGPTL3 mRNA in the test group/the expression amount of GAPDH mRNA in the test group)/(the expression amount of ANGPTL3 mRNA in the control group/the expression amount of GAPDH mRNA in the control group)×100%.

The inhibition rate of siRNA against ANGPTL3 mRNA is (1−the expression amount of ANGPTL3 mRNA)×100%. In particular, the test groups are Huh7 cells treated with the siRNA at various concentrations, and the control group is Huh7 cells untreated with the siRNA. The results are shown in FIG. 3A.

Figure 3A:
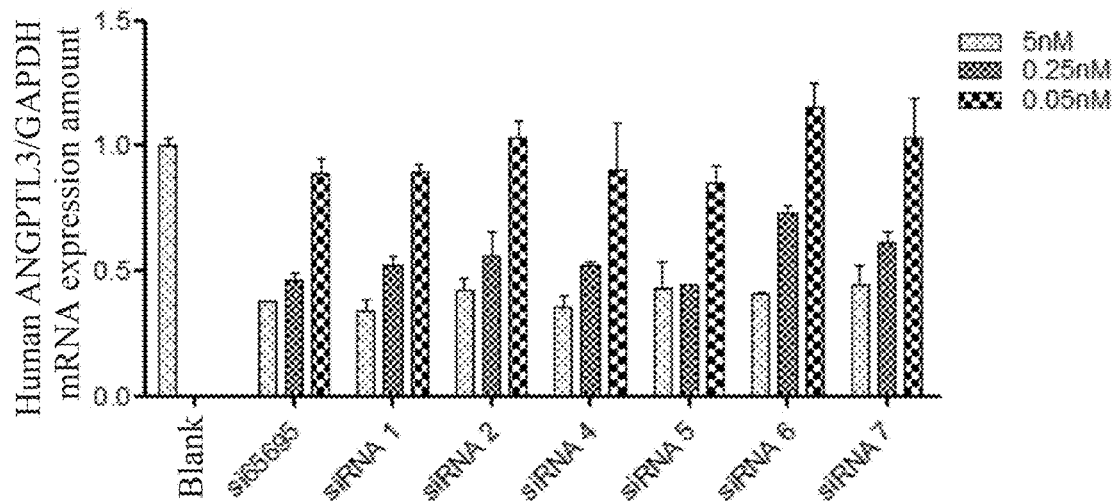
FIG. 3A shows the inhibition effect of the siRNA of the present disclosure on the expression level of ANGPTL3 mRNA in Huh 7 cell lines.

As can be seen from FIG. 3A, the modified siRNAs of the present disclosure showed higher inhibitory activity in the Huh7 cell lines, comparable to the activity of the positive control si65695.

Figure 3B:
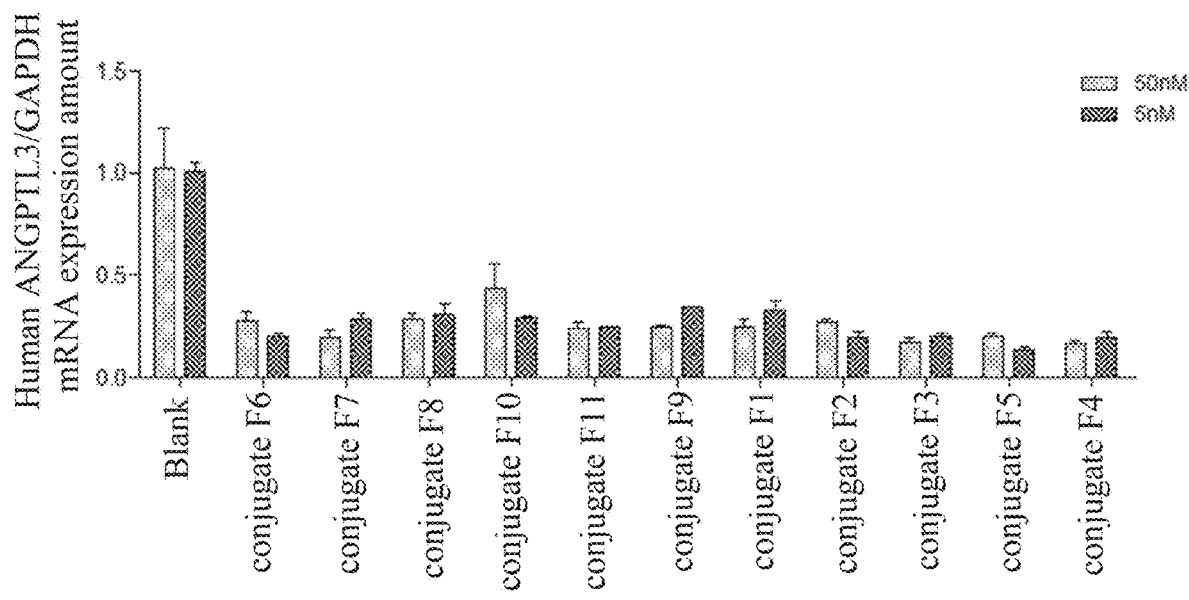
FIG. 3B shows the inhibition effect of the siRNA conjugate of the present disclosure on the expression level of ANGPTL3 mRNA in Huh 7 cell lines.

Experimental Example 2-2. Detection of the Inhibitory Efficiency of the siRNA Conjugates Against the Expression Amount of ANGPTL3 mRNA in Huh7 Cells Detection was conducted by the same method as that in Experimental Example 2-1, except that the samples to be detected were conjugates F1-F11, and the final concentrations of the conjugates (based on the amount of siRNAs) were 50 nM and 5 nM. The in vitro inhibitory activities of various conjugates are shown in FIG. 3B. From FIG. 3B, it can be seen that the siRNA conjugates of the present disclosure showed higher inhibitory activity in Huh7 cell lines, and the conjugate at a concentration of 5 nM showed an inhibition rate of 60-80% against the expression amount of ANGPTL3 mRNA.

Experimental Example 2-3. Detection of $IC_{50}$ of siRNA Conjugates Against ANGPTL3 mRNA in Huh7 Cells Detection was conducted by the same method as that in Experimental Example 2-1, except that the samples to be detected were conjugates F3, F4, F8 and F9; the concentrations of the conjugates (based on the amount of siRNAs) were five-fold diluted from 50 nM to 0.016 nM, with the lowest concentration being set at 0.00001 nM and a total of 7 concentrations. 3 replicate wells were used for each group.

In further experiments, the sample to be detected was conjugate 2. The final concentration of the conjugate (based on the amount of siRNA) was double diluted from 2 nM to 0.0078 nM, with a total of 9 concentrations. 2 replicate wells were used for each group.

In still further experiments, the samples to be detected were conjugates 1, 4, 5 and 7. The final concentrations of the conjugates (based on the amount of siRNAs) were double diluted from 0.5 nM to 0.03125 nM, with the highest concentration being set at 5 nM and a total of 6 concentrations. 2 replicate wells were used for each group. The $IC_{50}$ was calculated by the same method as that in Experimental Example 1 according to the detected inhibition rate of the siRNA conjugates at different concentration against the expression amount of ANGPTL3 mRNA, so as to obtain the $IC_{50}$ of the conjugates to be detected in Huh7 cells in vitro. The results are shown in Table 7.

TABLE 7

$IC_{50}$ of the siRNA conjugates against ANGPTL3 mRNA

| Conjugate | No. | $IC_{50}$ |
|---|---|---|
| Conjugate F3 | FIN-siAN1M2SVP | 0.1458 nM |
| Conjugate F4 | FIN-siAN1M3SVP | 0.0851 nM |
| Conjugate F8 | FIN-siAN2M2SVP | 0.4618 nM |
| Conjugate F9 | FIN-siAN2M3SVP | 0.1419 nM |
| Conjugate 2 | L10-siAN1M3SP | 0.1271 nM |
| Conjugate 1 | L10-siAN1M3SVP | 0.2137 nM |
| Conjugate 4 | L10-siAN1M3S | 0.3833 nM |
| Conjugate 5 | L10-siAN1M1SVP | 0.1961 nM |
| Conjugate 7 | L10-siAN1M1S | 0.1417 nM |

As can be seen from Table 7, the siRNA conjugates of the present disclosure have very high inhibitory activity in in vitro cell lines, with $IC_{50}$ being from 0.085 to 0.462 nM.

Experimental Example 3. Detection of the Stability of siRNAs and siRNA Conjugates in Plasma and Lysosome Experimental Example 3-1. Detection of the Stability of siRNAs in Lysosome The stability of siRNAs 1, 2, 4, 5, 6, and 7 in rat-origined lysosome lysate was investigated in this experimental example.

Preparation of test samples treated with lysosome lysate: All the siRNAs (20 μM) 6 μL were individually mixed well with 27.2 μL of sodium citrate aqueous solution (pH 5.0), 4.08 μL of deionized water and 2.72 μL of Rat lysosome lysates (Rat Liver Tritosomes, purchased from Xenotech Inc., Cat. R0610.LT, No. 1610069), with acid phosphatase being at a final concentration of 0.2 mU/μL. The mixture was incubated at a constant temperature of 37° C. 5 μL mixed liquids were taken at each time point of 0 h, 1 h, 2 h, 4 h, 6 h and 24 h respectively, and then added to 15 μL of 9 M urea solution for denaturation, followed by the addition of 4 μL of 6× loading buffer (purchased from Solarbio Inc., Cat. 20160830), and then the mixture was immediately cryopreserved in a −80° C. freezer to quench the reaction. 0 h represents the moment when the samples to be detected are mixed well with the lysosome lysate and immediately taken out.

As for samples untreated with the lysosome lysate, 1.5 µL of each of the siRNAs above at equal moles (20 µM) was mixed well with 7.5 µL of sodium citrate aqueous solution (pH 5.0) and 1 µL of deionized water, and then added to 30 µL of 9 M urea aqueous solution for denaturation, followed by the addition of 8 µL of 6× loading buffer, and then the mixture was immediately cryopreserved in a −80° C. freezer to quench the reaction. The control sample for each siRNA is marked as M in the electrophoretogram.

16 wt % of non-denatured polyacrylamide gel was prepared. 20 µL of the test samples and 20 µL control samples described above were loaded into the gel to perform electrophoresis for 10 minutes under 20 mA constant current and then 30 minutes under 40 mA constant current. After finishing the electrophoresis, the gel was placed on the shaker and stained with Gelred dye (BioTium, Cat. 13G1203) for 10 minutes. The gel was imaged, observed and photographed. The results are shown in FIG. 4. As can be seen from FIG. 4, the modified siRNAs of the present disclosure can be stable for at least 24 hours in rat-origined lysosome.

Experimental Example 3-2. Detection of the Stability of siRNA Conjugates in Lysosome The stability of conjugates 1, 4, 5 and 7 in rat-origined lysosome lysate was investigated in this experimental example.

Figure 4A:
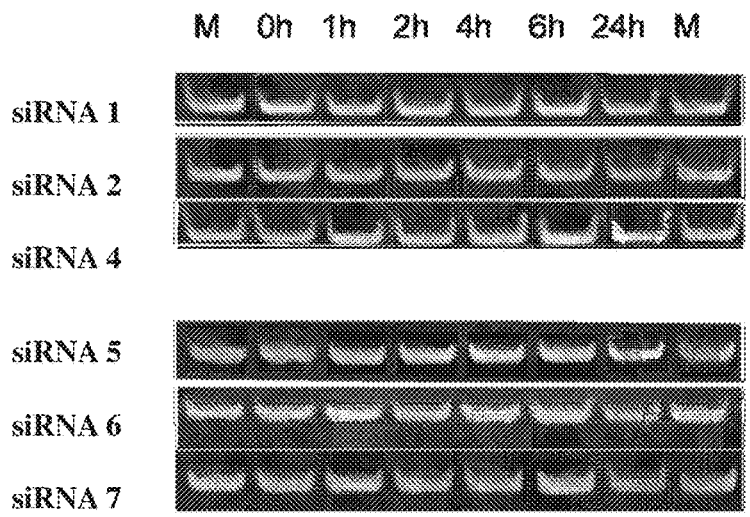
FIG. 4A shows the semiquantitative result of the stability test of the siRNA of the present disclosure in a rat-origined lysosome lysate in vitro.
Figure 4B:
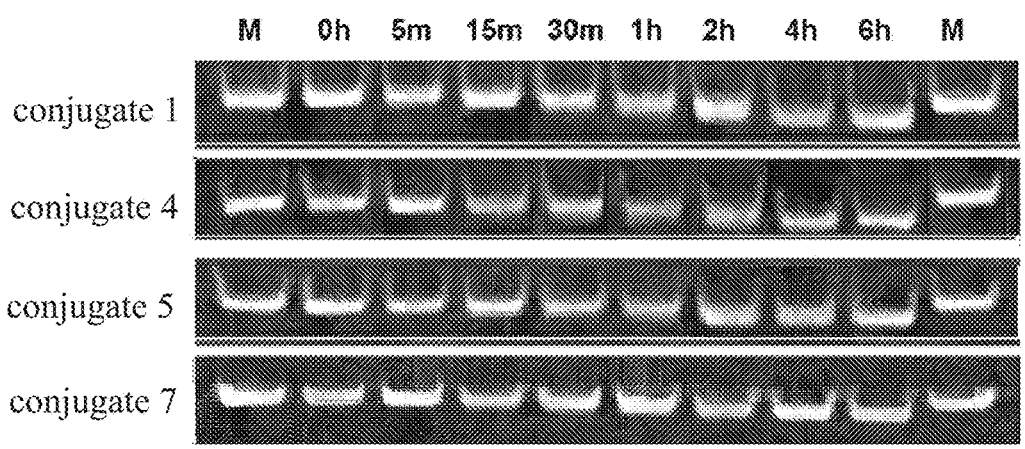
FIG. 4B shows the semiquantitative result of the stability test of the siRNA conjugate of the present disclosure in a rat-origined lysosome lysate in vitro.

Detection was performed by the same methods as that in experimental example 3-1, except that the samples to be detected were conjugates 1, 4, 5 and 7, and the concentration of the conjugates was based on the amount of siRNAs, and the detection was conducted at 0 h, 5 minutes, 15 minutes, 30 minutes, 1 h, 2 h, 4 h and 6 h. Gel imaging is shown in FIG. 4B.

From FIG. 4B, it can be seen that the siRNA conjugates of the present disclosure can remain undegraded for at least 1 hour in rat-origined lysosome, subsequently resulting in only slight downward shifting of the major band of electrophoresis. The fact of the high stability of the corresponding siRNAs in the lysosome lysate reveals that the downward shifting of the band may be caused by cleavage of the monosaccharide on the conjugating group. The siRNA conjugates of the present disclosure showed satisfactory stability.

Experimental Example 3-3. Detection of the Stability of siRNA Conjugate in Plasma The stability of conjugates 1, 4, 5 and 7 in human plasma was investigated in this experimental example.

Conjugates 1, 4, 5 and 7 and control siRNA8 (both of the concentration of siRNA and siRNA conjugate is 20 µM or 12 µM, and the siRNA conjugate is calculated on the basis of the amount of siRNA) were individually mixed well with 108 µL of 90% human plasma (diluted in PBS) and incubated at a constant temperature of 37° C. 10 µL samples were taken at each time point of 0 h, 2 h, 4 h, 6 h, 8 h, 24 h, 48 h and 72 h respectively, then immediately frozen in liquid nitrogen, and finally cryopreserved in a −80° C. freezer for use. After sampling at each time point, each sample was diluted 5-fold with 1×PBS (pH 7.4) and then taken in a volume of 10 µL for use. Meanwhile, the siRNA (2 µM, 2 µL) or the siRNA conjugate (with the siRNA concentration of 2 µM, 2 µL) at equal moles was mixed well with 8 µL of 1×PBS (pH 7.4), thus obtaining 10 µL of samples untreated with human plasma (marked as M). 20 wt % of non-denatured polyacrylamide gel was prepared. The above samples were all mixed with 4 µL of loading buffer (20 mM EDTA, 36 wt % glycerol, and 0.06 wt % bromophenol blue) and then loaded on the gel to perform electrophoresis for 60 minutes under 80 mA constant current. After finishing the electrophoresis, the gel was placed on the shaker and stained with 1× Sybr Gold dye (Invitrogen, Cat. 11494) for 15 minutes. The gel was imaged, observed and photographed. The results are shown in FIG. 4C.

Figure 4C:
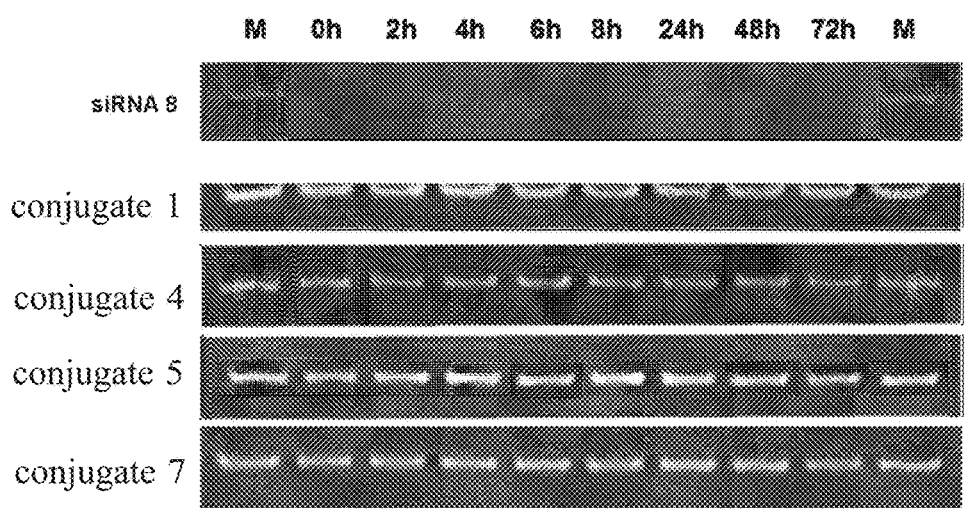
FIG. 4C shows the semiquantitative result of the stability test of the siRNA conjugate of the present disclosure in human plasma in vitro.

As can be seen from FIG. 4C, the siRNA conjugates of the present disclosure remain undegraded over a period of 72 hours in human plasma, showing good stability in human plasma.

Figure 4D:
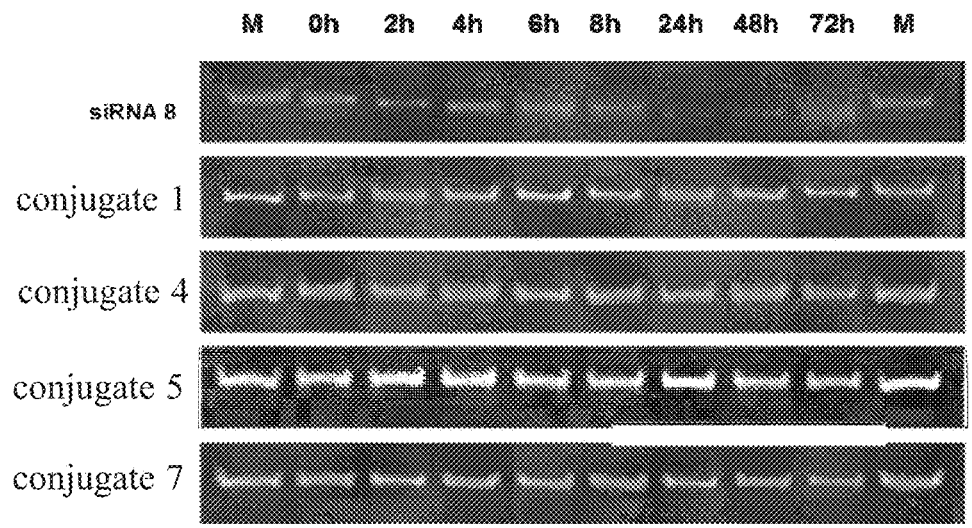
FIG. 4D shows the semiquantitative result of the stability test of the siRNA conjugate of the present disclosure in monkey plasma in vitro.

In further experiments, the stability of conjugates 1, 4, 5 and 7 in monkey plasma (purchased form HONGQUAN Bio, Cat. HQ70082, diluted in PBS) was detected by using the same method mentioned above. The results are shown in FIG. 4D.

The results demonstrate that the siRNA conjugates of the present disclosure remain stable for at least 72 hours in both human plasma and monkey plasma, showing excellent stability.

Experimental Example 4. Detection of the Inhibitory Efficiency of siRNA Conjugates Against the Expression Amount of ANGPTL3 mRNA in Mice, and Detection of the Inhibitory Effect on Blood Lipid Experimental Example 4-1. Detection of ED50 of siRNA Conjugates Against ANGPTL3 mRNA in Normal Mice C57

The inhibitory activity of conjugates F3, F4, F8, and F9 in normal mice C57 was investigated in this experimental example.

Normal mice c57 of 6-8 week old were randomly divided into groups (5 mice in each group). Conjugates F3, F4, F8, F9 and PBS were individually administrated to the mice in each group. The drug dosages for all animals were calculated according to the body weight. A single dose was injected subcutaneously, with the dosage for each siRNA conjugate (based on the amount of siRNA) of 10 mg/kg, 3 mg/kg, 1 mg/kg, 0.3 mg/kg and 0.1 mg/kg respectively. Moreover, the lowest dosage for conjugate F3 is 0.005 mg/kg, for conjugates F4 and F9 is 0.003 mg/kg, and for conjugate F8 is 0.01 mg/kg. Each test group was administered with a total of 6 dosages and the dose volume was 10 ml/kg. Each of the siRNA conjugates was administered in the form of PBS aqueous solution. The concentration of the conjugate to be formulated was calculated according to administered dosage and volume. Mice were sacrificed at day 3 after administration. The liver was collected and kept with RNA later (Sigma Aldrich), and the liver tissue was homogenized with a tissue homogenizer. Then the total RNA in the liver tissue was extracted and obtained by using Trizol (Thermo Fisher) according to the standard procedure for total RNA extraction.

The expression amount of ANGPTL3 mRNA in liver tissue was measured by real-time fluorescent qPCR. Specifically, cDNA was obtained by reverse transcription using reverse transcription kit (Promega, Cat.A3500) according to the operation method in the instruction thereof. The expression amount of ANGPTL3 mRNA was detected by taking cDNA as the template according to the steps in the instruction by using 2× Ultra SYBR Mixture (with ROX) (Beijing Cowin Biosicences Co., Ltd, Cat. CW 0956). In this case, the PCR primers used for amplifying ANGPTL3 and GAPDH as an internal control gene are shown in Table 8.

TABLE 8 sequences of primers

| genes | SEQ ID NO | Nucleotide sequence(5'→3') |
|---|---|---|
| Mouse ANGPTL3 | 57 | GAGGAGCAGCTAACCAACTTAAT |
| | 58 | TCTGCATGTGCTGTTGACTTAAT |
| Mouse GAPDH | 59 | AACTTTGGCATTGTGGAAGGGCTC |
| | 60 | TGGAAGAGTGGGAGTTGCTGTTGA |

The expression amount of ANGPTL3 mRNA in liver and the inhibition rate of the conjugates against ANGPTL3 mRNA are calculated by the same method as that in Experimental Example 2-1. In particular, the control group was a group of control mice administrated with PBS in this experiment, and each of the test groups was a group of mice administrated with different siRNA conjugate, respectively. ED50 was calculated by the same method as that in Experimental Example 1 according to the measured inhibition rates of the siRNA conjugates at different concentrations against the expression amount of ANGPTL3 mRNA, so as to obtain ED50 of the conjugates in normal mice. The results are shown in FIG. 9.

TABLE 9

ED50 of the siRNA conjugates against the ANGPTL3 mRNA in liver tissue of normal mice c57

| Conjugate | No. | ED50 |
|---|---|---|
| Conjugate F3 | FIN-siAN1M2SVP | 0.2099 nM |
| Conjugate F4 | FIN-siAN1M3SVP | 0.1403 nM |
| Conjugate F8 | FIN-siAN2M2SVP | 0.4258 nM |
| Conjugate F9 | FIN-siAN2M3SVP | 0.1595 nM |

As can be seen from Table 9, the inhibitory activity of the tested conjugates in normal mice is highly consistent with the inhibitory activity of the corresponding conjugates in in vitro cell lines in Experimental Example 2-3, with ED50 being from 0.1403 to 0.4258 nM, which demonstrates that the siRNA conjugates of the present disclosure show very high inhibitory activity in normal mice.

Experimental Example 4-2. Inhibitory Efficiency of the siRNA Conjugates in Normal Mice BALB/c Against the Expression Amount of ANGPTL3 mRNA, and Effect Thereof on Blood Lipid The inhibition rate of conjugates F4, F12 and F13 against ANGPTL3 mRNA in liver tissue of normal mice BALC/c, and the effect thereof on blood lipid, were investigated in this experimental example.

Normal mice BALB/c of 6-8 week old were randomly divided into groups (10 mice in each group). Conjugates F4, F12, F13, comparative conjugate 2, and PBS were individually administrated to the mice in each group. The drug dosages for all animals were calculated according to the body weight. A single dose was injected subcutaneously, with two dosage groups for the siRNA conjugates (based on the amount of siRNA) of 3 mg/kg (also marked as 3 mpk) and 0.3 mg/kg (also marked as 0.3 mpk), and the dose volume was 10 ml/kg. Each of the siRNA conjugates was administered in the form of PBS aqueous solution. The concentration of the conjugate to be formulated was calculated according to administered dosage and volume. The blood was taken from mouse orbital vein before administration and at days 7 and 14 after administration, the lipid level in serum was tested at each time point. Five mice were respectively sacrificed at days 7 and 14 after administration, and the liver tissue was collected to detect the expression amount of ANGPTL3 mRNA in liver.

The blood taken from the orbital vein was about 100 μl each time, and the serum was obtained after centrifugation. The contents of total cholesterol (CHO) and triglyceride (TG) in serum were further measured by using a PM1P000/3 full-automatic serum biochemical analyzer (SABA, Italy).

Normalized blood lipid levels=(the content of blood lipid in the test group after administration/the content of blood lipid in the test group before administration)×100%

Inhibition rate against blood lipid levels=(1−the content of blood lipid in the test group after administration/the content of blood lipid in the test group before administration)×100%

Blood lipid refers to total cholesterol (CHO) or triglyceride (TG).

Figure 5A:
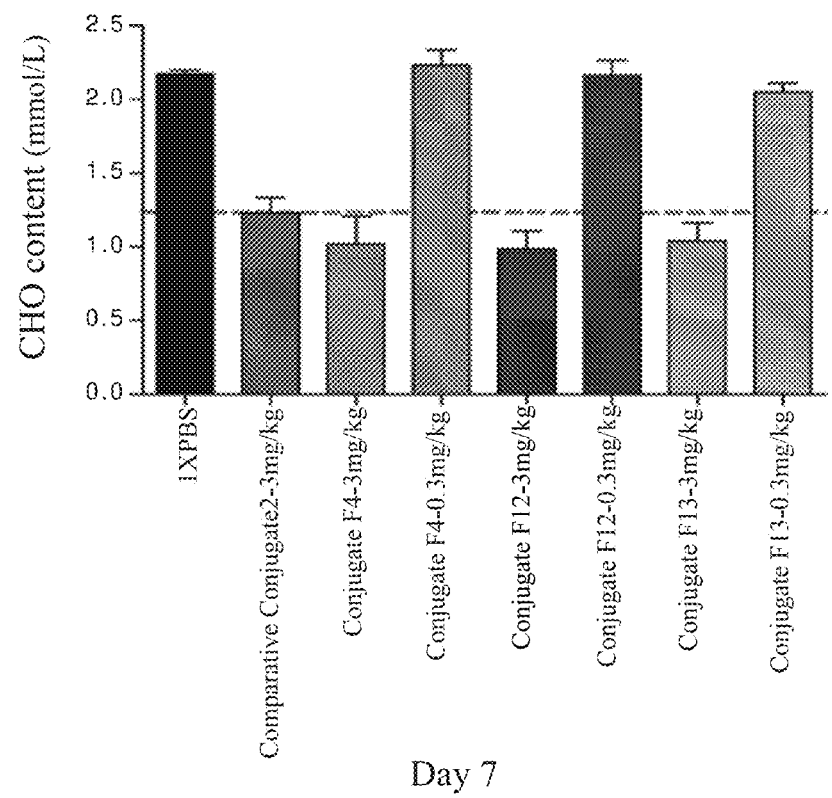
FIGS. 5A-5D show the inhibition effect of the siRNA conjugate of the present disclosure on the blood lipid level in a normal mice BALB/c.
Figure 5B:
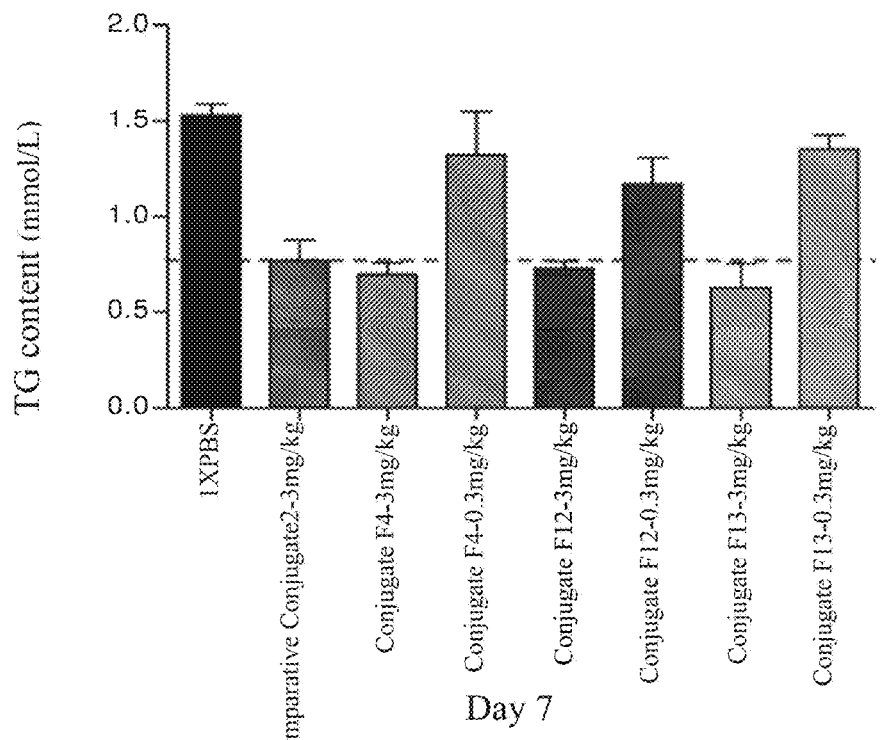
Figure 5C:
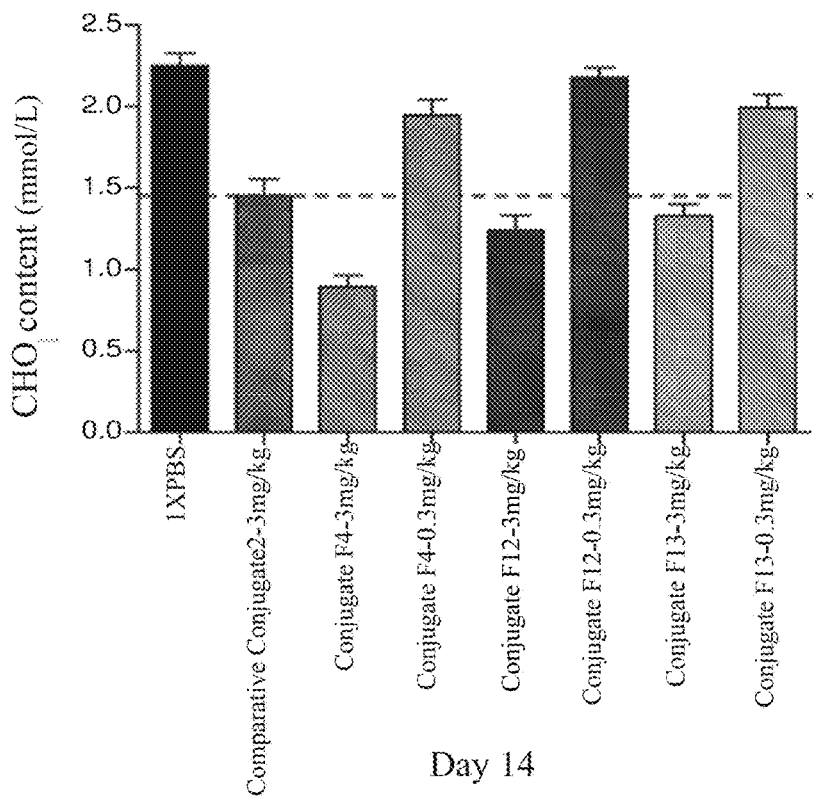
Figure 5D:
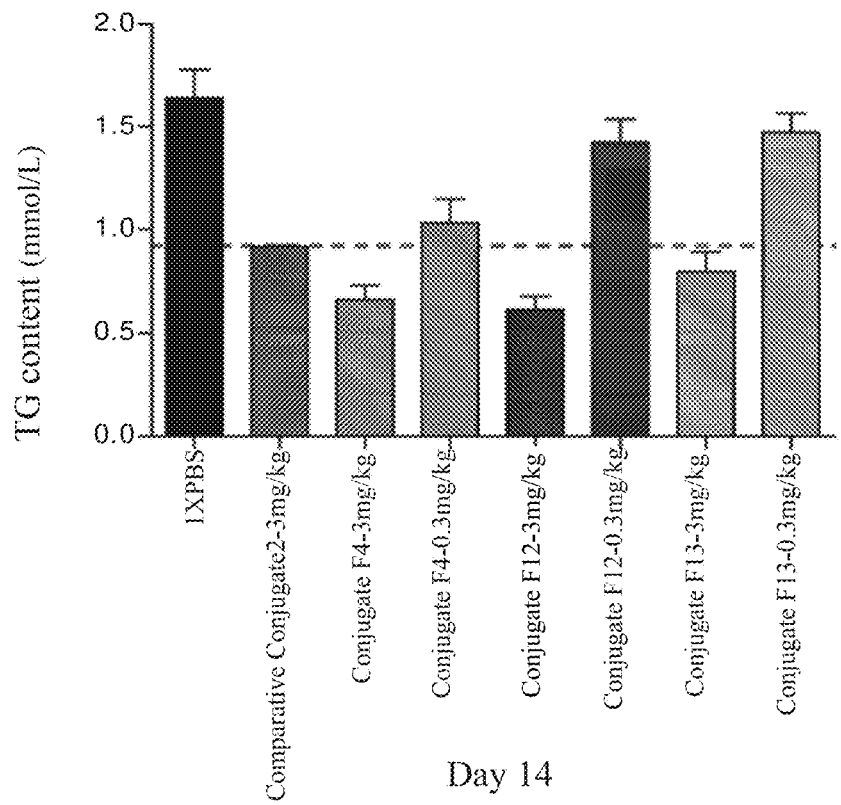
Figure 6A:
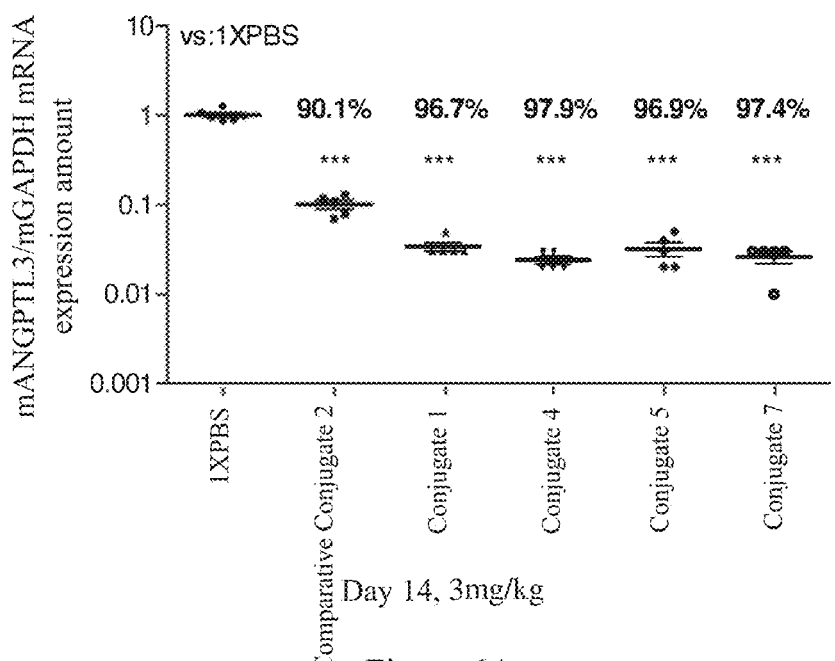
FIGS. 6A-6D show the inhibition effect of the siRNA conjugate of the present disclosure on the expression amount of ANGPTL3 mRNA in liver of a normal mice BALB/c.
Figure 6B:
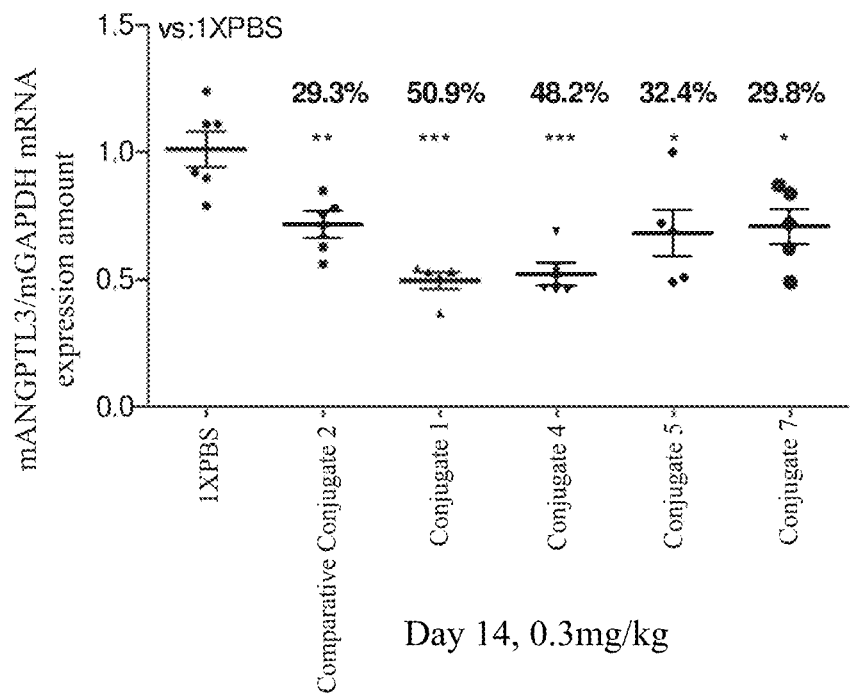
Figure 6C:
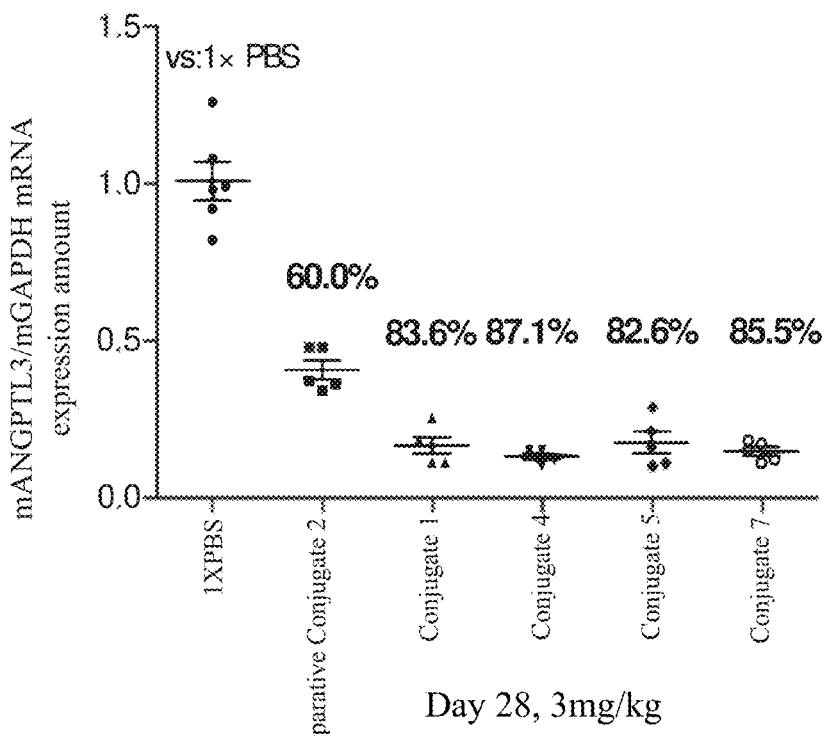
Figure 6D:
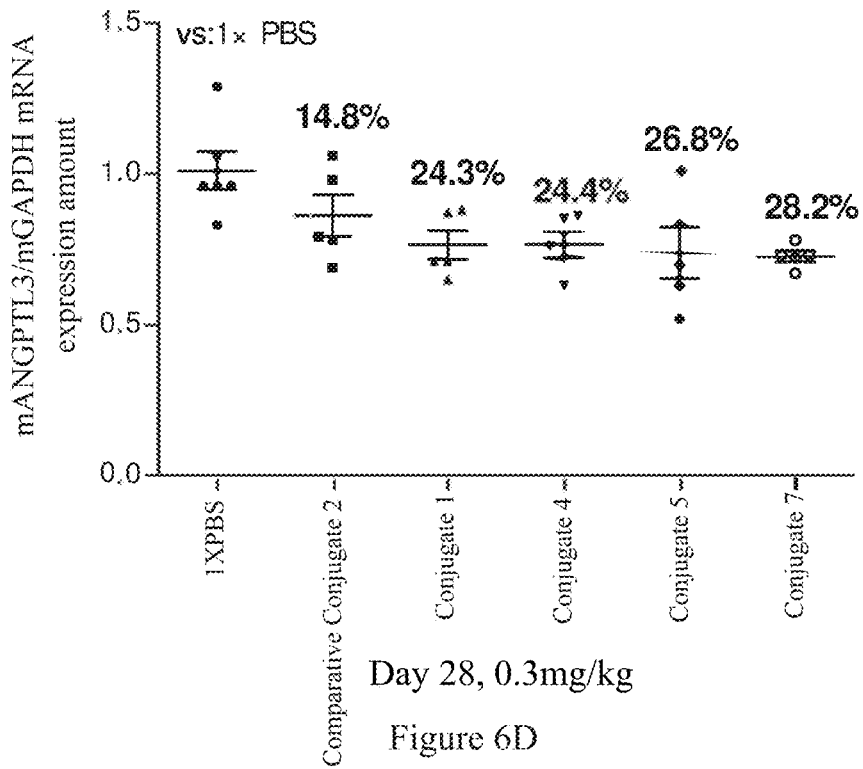
Figure 7A:
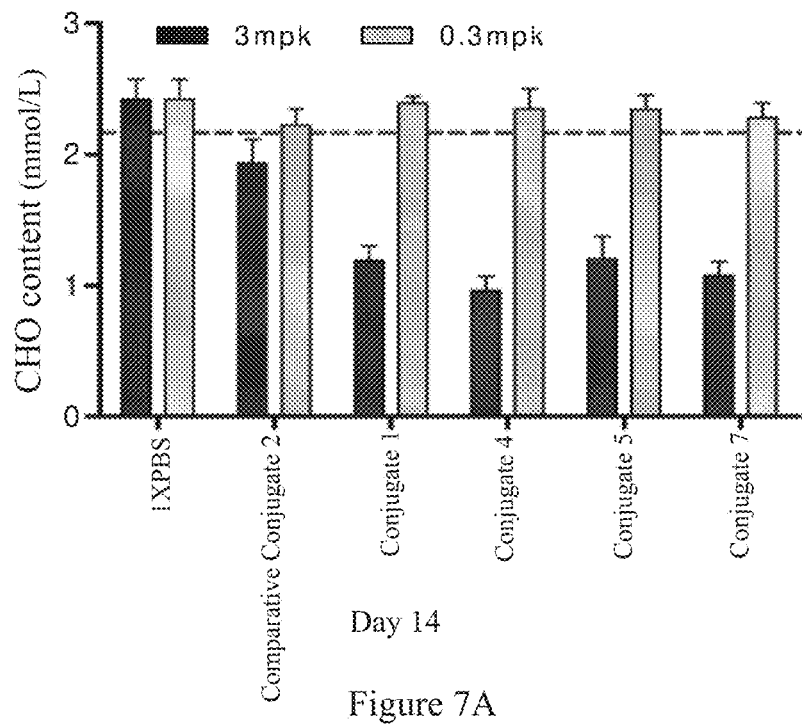
FIGS. 7A-7D show the inhibition effect of the siRNA conjugate of the present disclosure on the blood lipid level in a normal mice BALB/c.
Figure 7B:
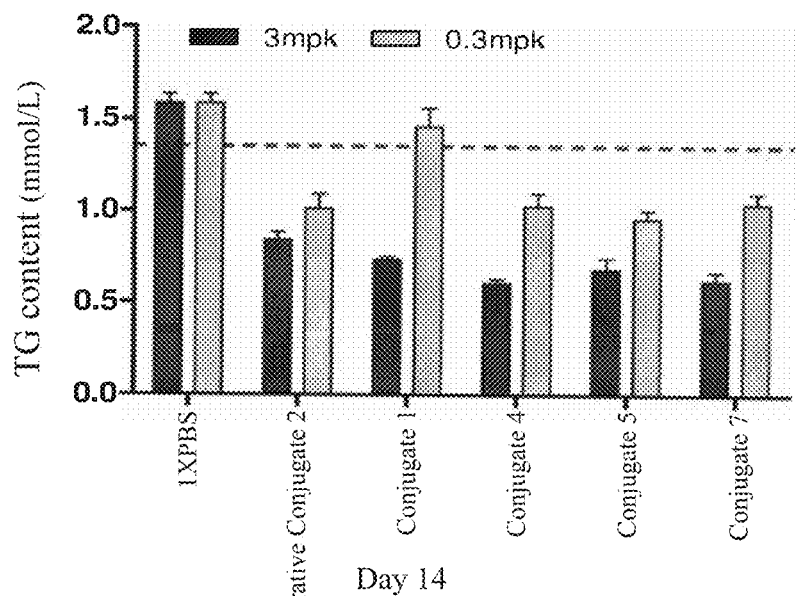
Figure 7C:
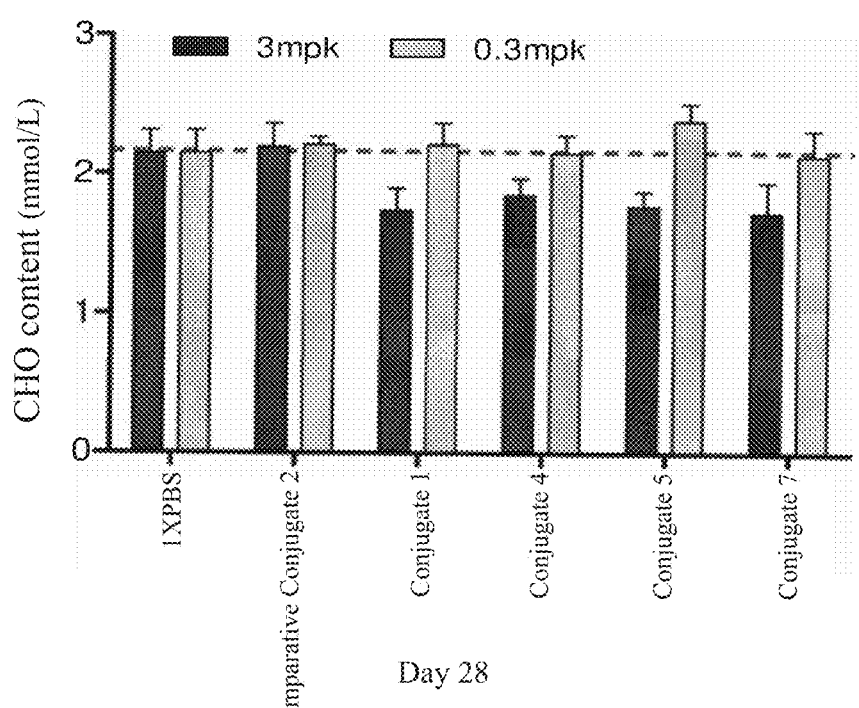
Figure 7D:
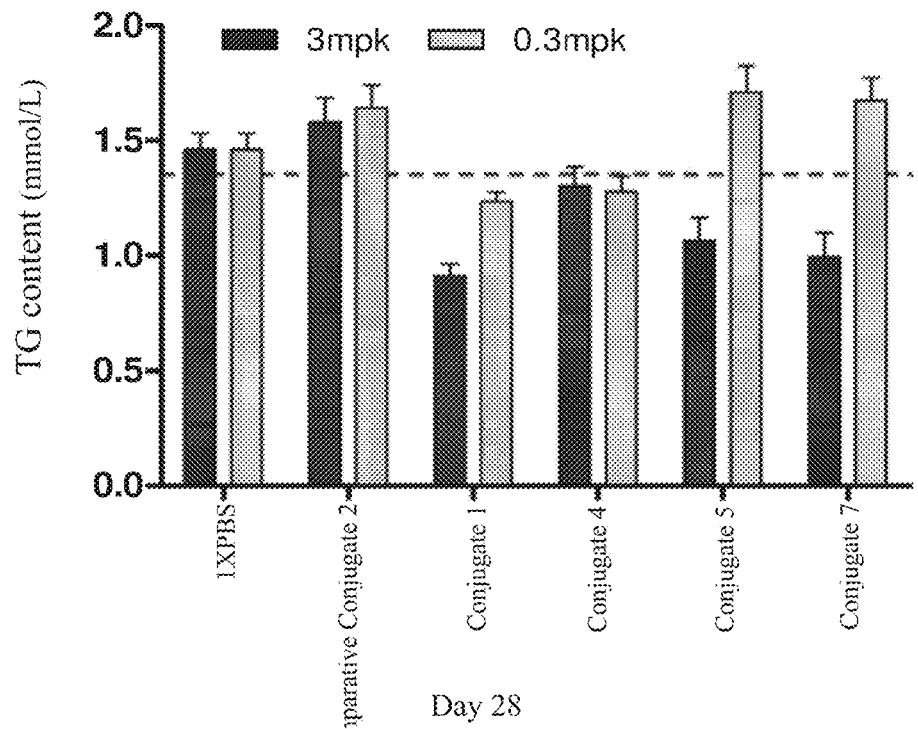

The content of blood lipid in mice at day 7 after administration is shown in FIGS. 5A-5B, and the content of blood lipid in mice at day 14 after administration is shown in FIGS. 5C-5D.

From FIGS. 5A-5D, it can be seen that the tested siRNA conjugates could significantly reduce the blood lipid level in normal mice. 14 days after administration, 3 mg/kg of the siRNA conjugates of the present disclosure showed stronger ability of reducing blood lipid level as compared with the positive control (comparative conjugate 2). The inhibitory efficiency of the siRNA conjugates against the expression amount of ANGPTL3 mRNA in liver was measured by real-time fluorescent qPCR using the same method as that in Experimental Example 4-1. The results are shown in FIG. 10.

TABLE 10 inhibitory efficiency of the siRNA conjugates against ANGPTL3 mRNA in liver tissue of normal mice

| Conjugate | No. | Dose (mg/kg) | Day 7 mRNA inhibition rate(%) | Day 14 mRNA inhibition rate(%) |
|---|---|---|---|---|
| Comparative conjugate 2 | (GalNAc)3-65695 | 3 | 96.6 | 91.2 |
| Conjugate F4 | FIN-siAN1M3SVP | 3 | 96.7 | 97.4 |
| Conjugate F12 | FIN-siAN1M3S | 3 | 98.3 | 95.8 |
| Conjugate F13 | FIN-siAN1M1S | 3 | 97.0 | 94.0 |
| Conjugate F4 | FIN-siAN1M3SVP | 0.3 | 70.6 | 46.5 |
| Conjugate F12 | FIN-siAN1M3S | 0.3 | 68.0 | 34.0 |
| Conjugate F13 | FIN-siAN1M1S | 0.3 | 67.1 | 39.7 |

In further experiments, the blood lipid and the expression amount of ANGPTL3 mRNA were detected by the same method as mentioned above, except that the administered conjugates were conjugates 1, 4, 5 and 7 and comparative conjugate 2; and the detection time was days 14 and 28 after administration. The inhibitory effect of each conjugate against ANGPTL3 mRNA is shown in FIGS. 6A-6D, and the inhibitory effect on blood lipid is shown in FIGS. 7A-7D.

As can be seen from FIGS. 6A-6D, at day 14 after administration, the siRNA conjugates of the present disclosure at high dose showed inhibition rate of up to 95% against ANGPTL 3 mRNA, i.e. showing inhibitory strength significantly higher than comparative conjugate 2. For the inventive siRNA conjugates at low doses, the tested siRNA conjugates, observed at delayed time of day 28 after administration, showed strong inhibitory effect against ANGPTL3 mRNA in liver tissue of normal mice, and showed inhibitory strength significantly higher than the comparative conjugate. As can be seen from FIGS. 7A-7D, in the serum of the mice treated with the siRNA conjugates of the present disclosure, both of the contents of CHO and TG were reduced significantly, and the reduced level of blood lipid was observed until at least 28 days after administration. The inventive siRNA conjugates in a dose of 3 mg/kg showed stronger ability of reducing blood lipid level than positive control (comparative conjugate 2).

Experimental Example 4-3. Inhibitory Efficiency of siRNA Conjugates on the Expression Amount of ANGPTL3 mRNA in Obese Mice and the Effect Thereof on Blood Lipid The inhibition rate of conjugates F2 and F4 against ANGPTL3 mRNA in liver tissue of ob/ob mice, and the effect thereof on blood lipid, were investigated in this experimental example.

The expression amount of ANGPTL3 mRNA and the blood lipid in ob/ob mice were detected by the same method as that in experimental example 4-2, except that ob/ob mice of 6-8 week (6 mice in each group) were employed; conjugates F2 and F4 were administered in a dose of 3 mg/kg, 1 mg/kg and 0.3 mg/kg; and blood was taken at two days before administration (marked as −2 days) and day 7, 14, 21, 28 and 34 after administration; the mice were sacrificed at day 34. The detection results of blood lipids were normalized, and calculated by the same method as that in Experimental Example 4-2.

Figure 8A:
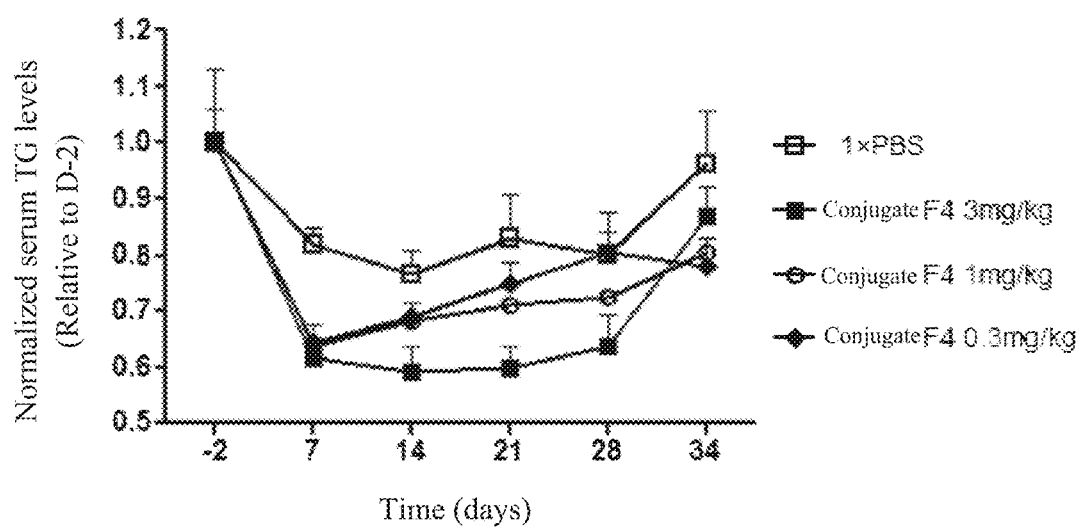
FIGS. 8A and 8B show the inhibition effect of the siRNA conjugate of the present disclosure on the blood lipid level in ob/ob mice.
Figure 8B:
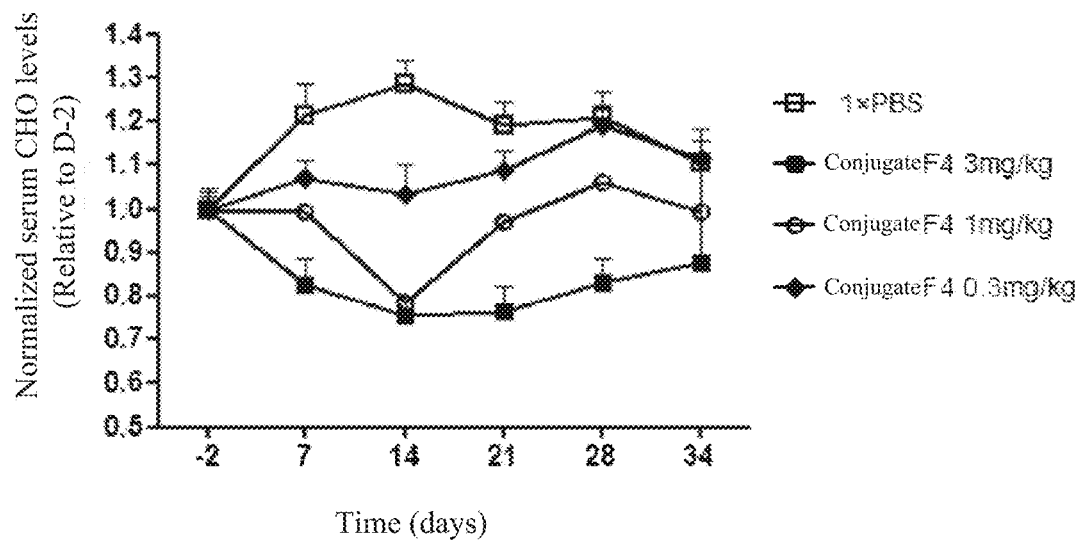
Figure 8C:
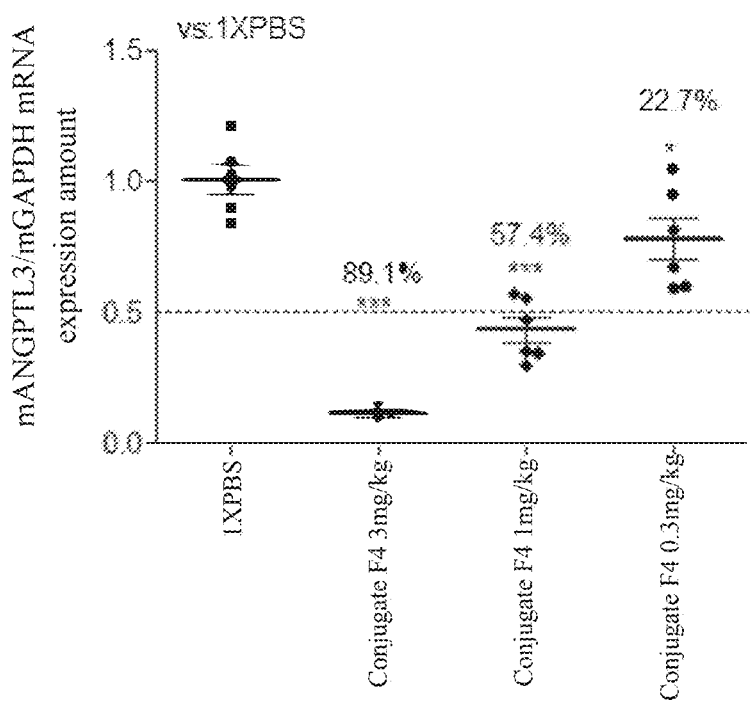
FIG. 8C shows the inhibition effect of the siRNA conjugate of the present disclosure on the expression level of ANGPTL3 mRNA in liver of ob/ob mice.
Figure 9A:
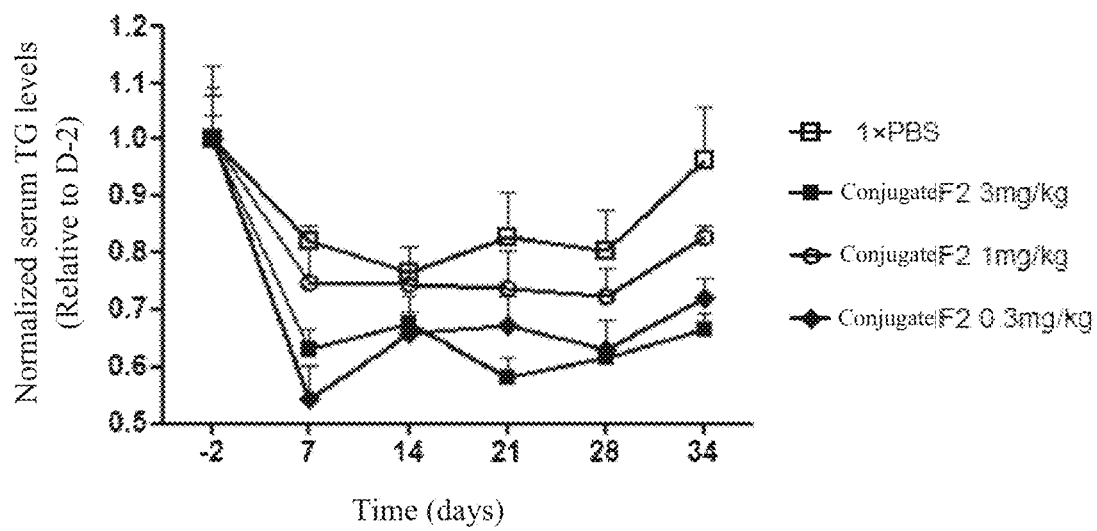
FIGS. 9A and 9B show the inhibition effect of the siRNA conjugate of the present disclosure on the blood lipid level in ob/ob mice.
Figure 9B:
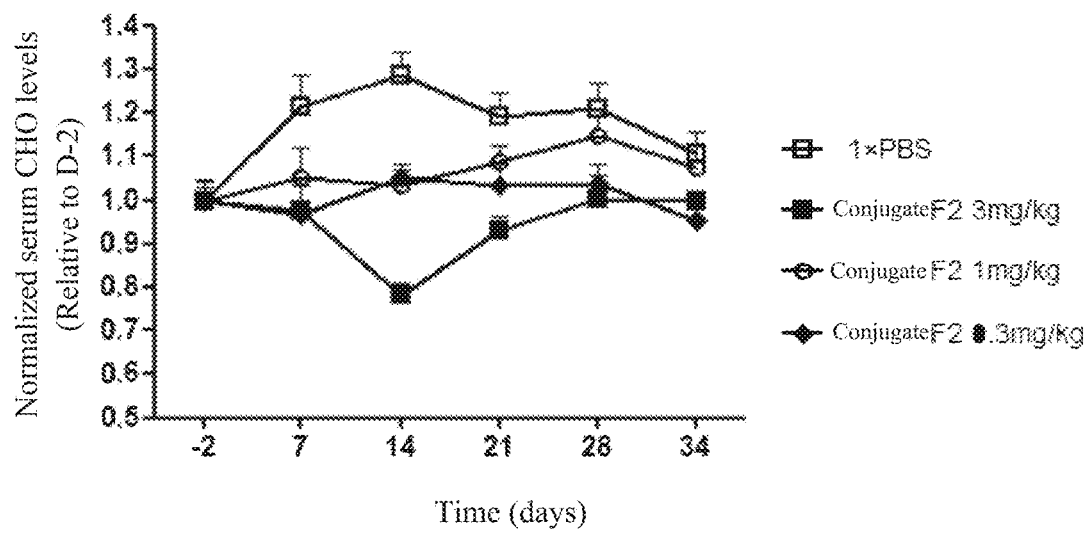
Figure 9C:
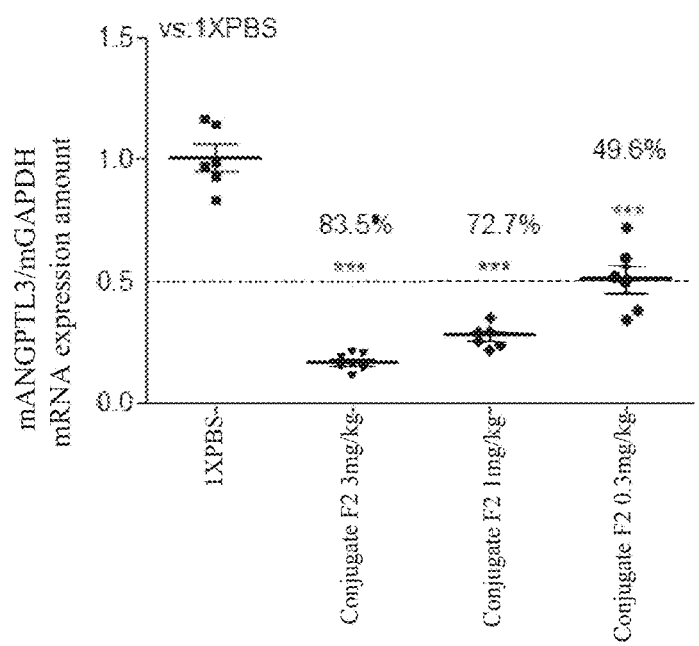
FIG. 9C shows the inhibition effect of the siRNA conjugate of the present disclosure on the expression level of ANGPTL3 mRNA in liver of ob/ob mice.

For conjugate F4, its inhibitory effect on blood lipid is shown in FIGS. 8A-8B, and its inhibitory effect on ANGPTL3 mRNA is shown in FIG. 8C. For conjugate F2, its inhibitory effect on blood lipid is shown in FIGS. 9A-9B, and its inhibitory effect on ANGPTL3 mRNA is shown in FIG. 9C.

As can be seen from the Figures, in the serum of the mice treated with siRNA conjugates of the present disclosure, both of the contents of CHO and TG were reduced significantly, and the reduced level of blood lipid was observed until at least 34 days after administration. Meanwhile, 34 days after administration, all the siRNA conjugates still could effectively inhibit the expression of ANGPTL3 mRNA.

Experimental Example 4-4. Effect of siRNA Conjugates on Blood Lipid in High-Fat Model Mice The inhibition rate of conjugate 1 against ANGPTL3 mRNA in liver tissue of human APOC3 transgenic mice, and the effect thereof on blood lipid, were investigated in this experimental example.

Human APOC3 transgenic mice Tg(APOC3)3707Bre were randomly divided into groups according to TG content>2 mmol/L in serum (6 mice in each group), and conjugate 1, comparative conjugate 1 and PBS blank control were administrated to the mice in each group respectively. The drug dosages for all animals were calculated according to the body weight. A single dose was injected subcutaneously, with the dosage for the siRNA conjugates (based on the amount of siRNA) of 3 mg/kg and 1 mg/kg respectively and the dosage volume of 5 ml/kg. Each of the siRNA conjugates was provided in the form of PBS aqueous solution. The concentration of the conjugate to be formulated is calculated according to administered dosage and volume. The blood was taken from mouse orbital venous plexus before administration (marked as day −1) and at days 7, 14, 21, 28, 35, 56, 70, 84, 98, 112, 126, 140, 154, and 168 after administration, and blood lipid level was measured for each time point by using the same method as that in Experimental Example 4-3. The results are shown in FIGS. 10A and 10B.

Figure 10A:
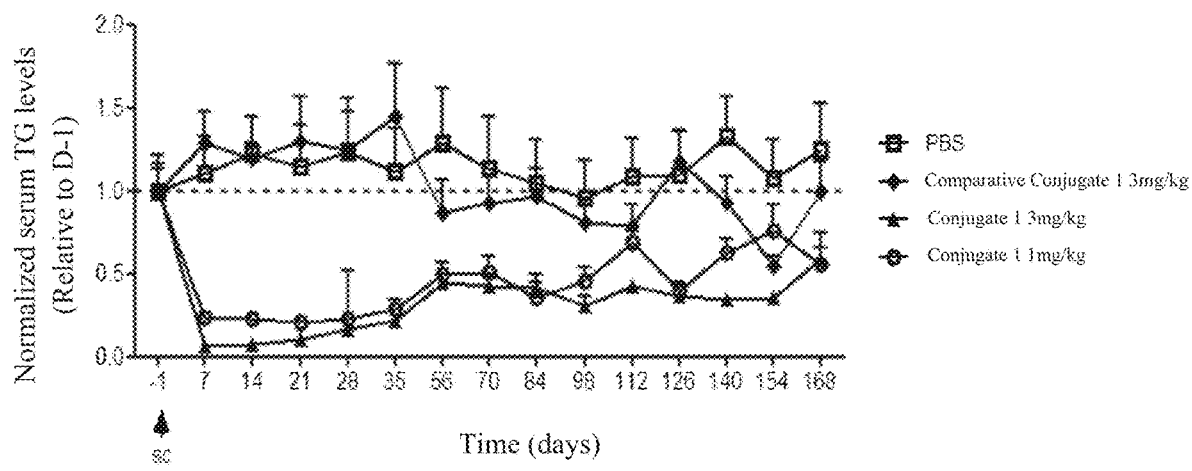
FIGS. 10A and 10B show the time-dependent inhibition effect of conjugate 1 on TG and CHO in serum of high-fat model mice.
Figure 10B:
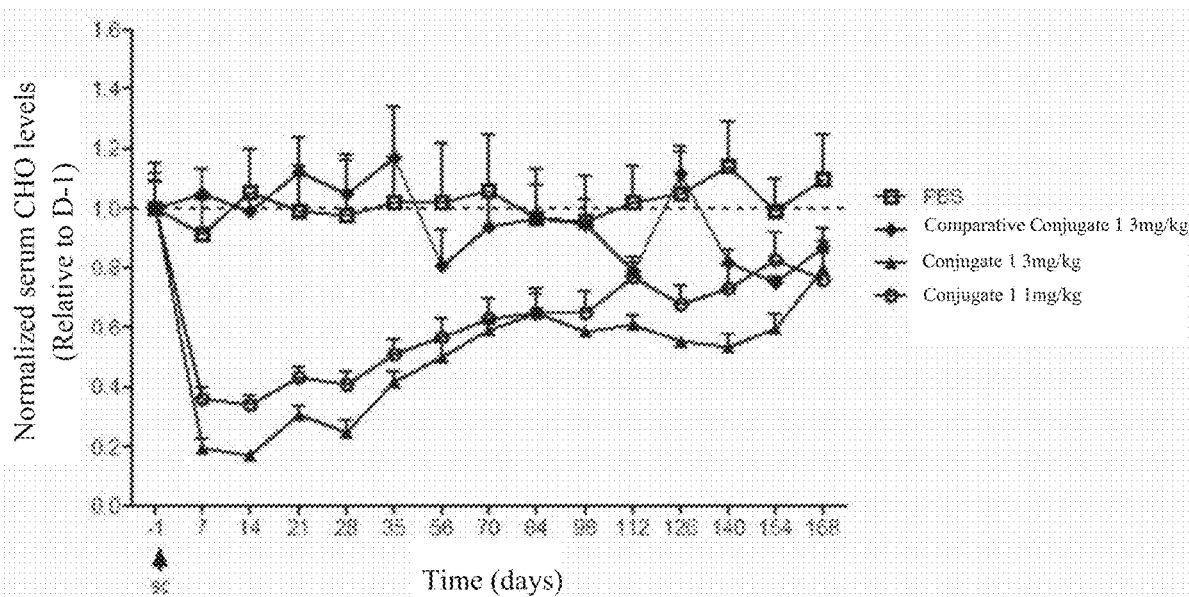

As can be seen from FIGS. 10A and 10B, the PBS blank control group and the comparative conjugate 1 negative control group show no inhibitory effect on blood lipid at different time points after administration; in contrast, conjugate 1 could significantly reduce the contents of TG and CHO. For TG, the group administered with high dose shows maximum inhibition rate, 92.9%, at day 7 after administration, and the group administered with low dose shows maximum inhibition rate, 79.1%, at day 21 after administration. The group administered with high dose consistently shows an inhibition rate over 55% against TG over a period of up to 154 days after administration of single dose; the group administered with low dose consistently shows an inhibition rate over 55% against TG over a period of up to 98 days after administration of single dose. For CHO, the group administered with high dose shows maximum inhibition rate, 82.9%, at day 14 after administration; the group administered with low dose shows maximum inhibition rate, 65.9%, at day 14 after administration. The group with high dose shows an inhibition rate over 40% against CHO over a period of up to 154 days after administration of single dose, and the group with low dose shows inhibition rate over 40% against CHO over a period of up to 56 days after administration of single dose. FIGS. 10A and 10B indicate that conjugate 1 can stably and efficiently reduce blood lipid level over a period of 168 days after administration of single dose.

In other experiments, the same experimental method as the method as described above was employed, except in that the administered conjugates were conjugate 2 and comparative conjugate 2. Blood lipid test continued until day 70 after administration, and the results are shown in FIGS. 11A-11D.

Figure 11A:
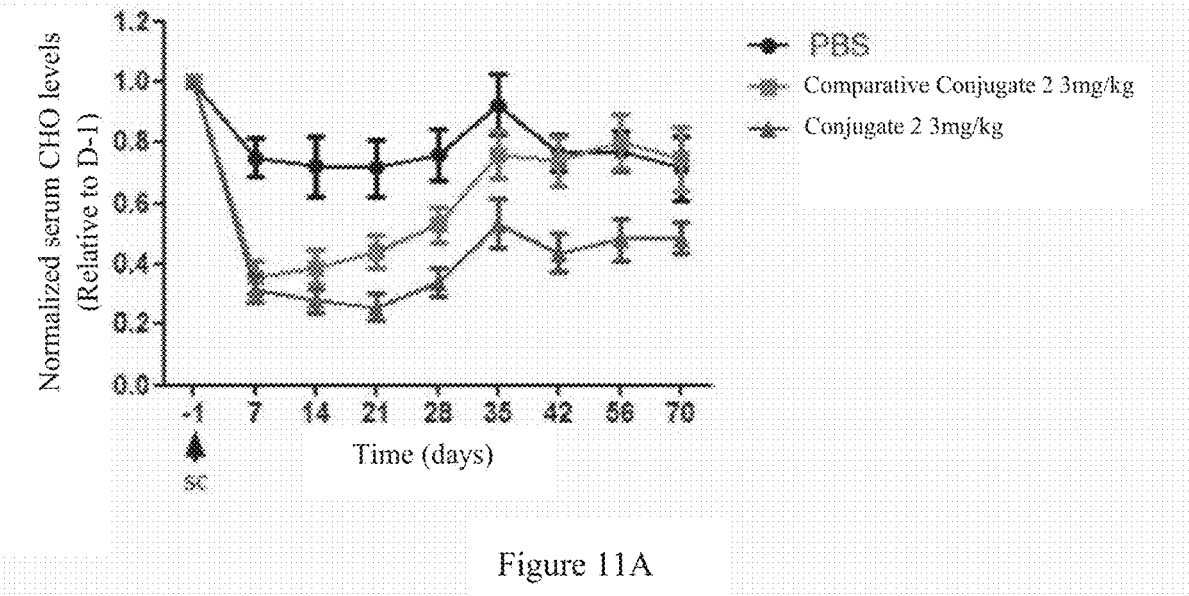
FIGS. 11A, 11B, 11C and 11D show the time-dependent inhibition effect of different doses of conjugate 2 on CHO and TG in serum of high-fat model mice.
Figure 11B:
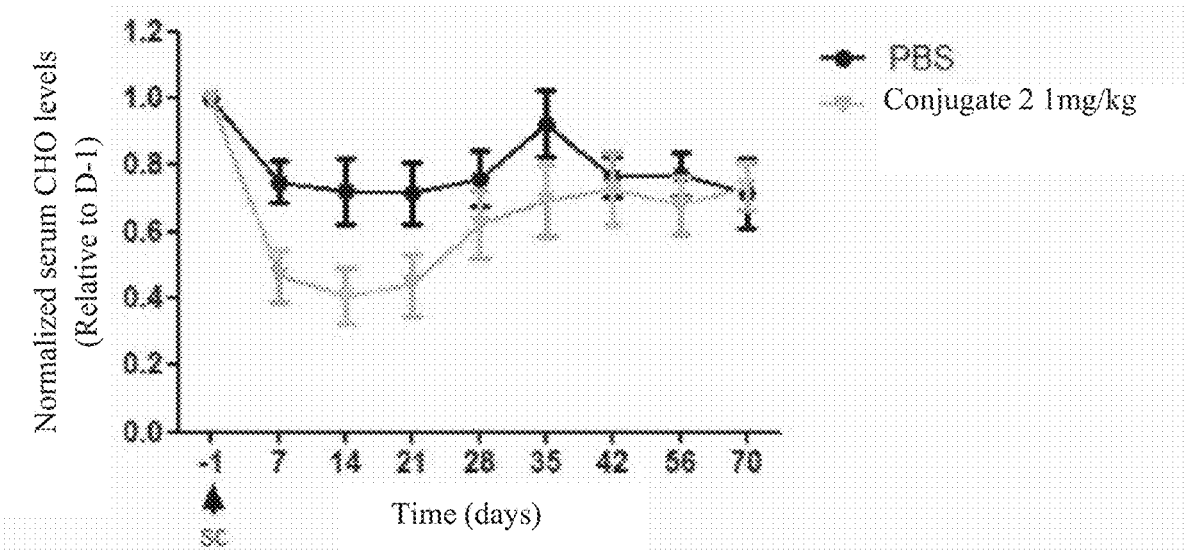
Figure 11C:
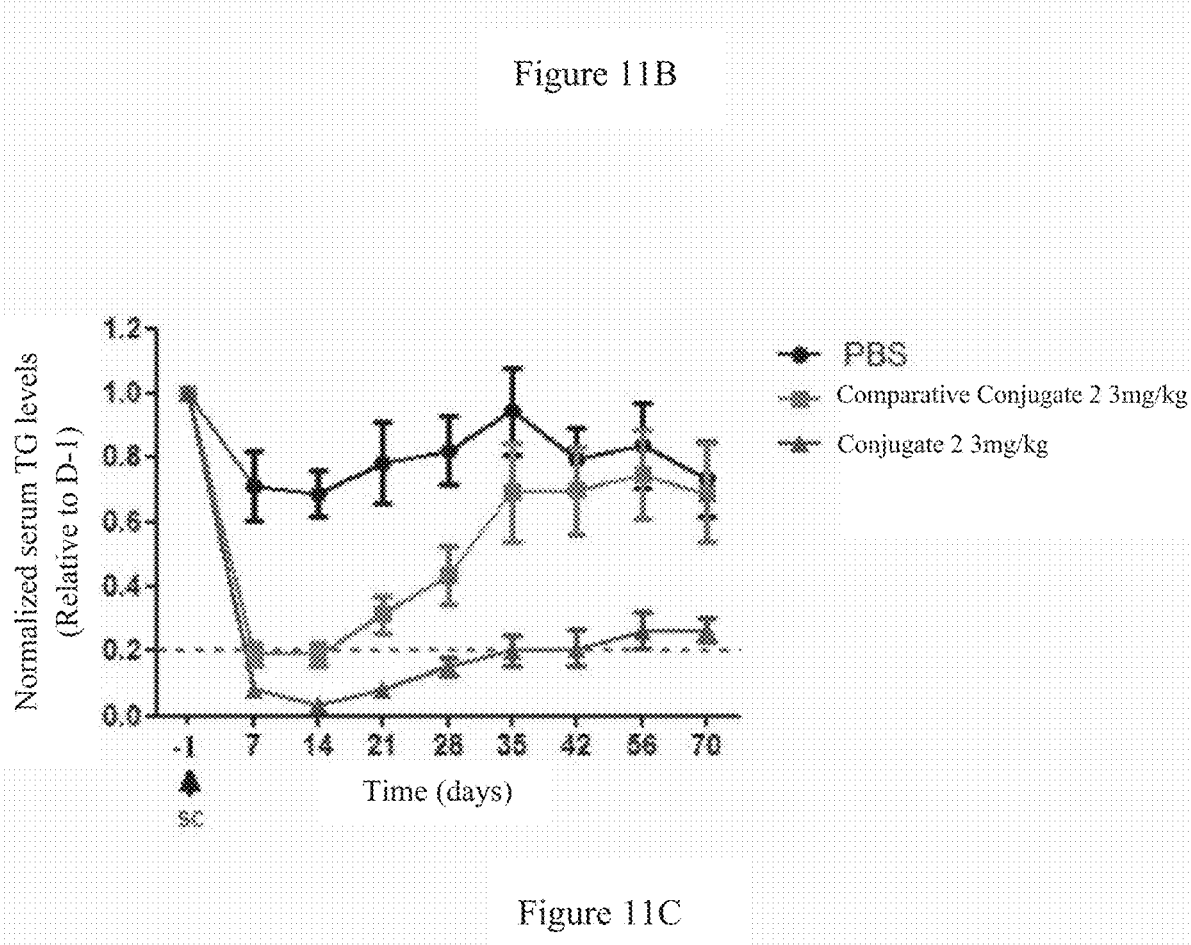
Figure 11D:
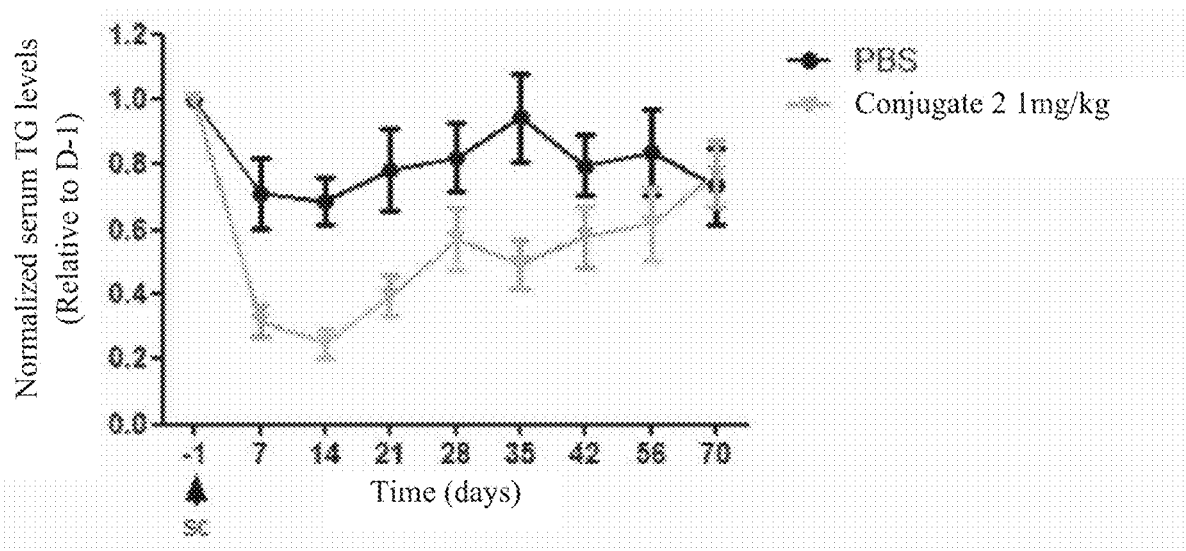

FIGS. 11A and 11B show the inhibitory effect of conjugate 2 at two doses on CHO at different time points after administration. For the group administered with high dose, the maximum inhibitory rate against CHO was 74.3% at day 21 after administration of single dose; and the inhibitory rate against CHO remained over 50% over a long period of up to 70 days after administration. For the group administered with low dose, the maximum inhibitory rate against CHO was 59.5%, at day 14 after administration. FIGS. 11C and 11D show the inhibitory effect of conjugate 2 at two doses on TG at different time points after administration. For the group administered with high dose, the maximum inhibitory rate against TG was 96.3% at day 14 after administration of single dose; and the inhibitory rate against TG remained over 70% over a long period of up to 70 days after administration. For the group administered with low dose, the maximum inhibitory rate against TG is 75.3%, at day 14 after administration.

As can be seen from FIGS. 11A-11D, conjugate 2 can continuously reduce the blood lipid level over a period of 70 days after administration of single dose, and is significantly superior to comparative conjugate 2 at equal dose.

Experimental Example 5. Detection of the Inhibitory Efficiency of siRNA Conjugate on the Expression Amount of ANGPTL3 mRNA and the Inhibitory Effect Thereof on Blood Lipid in Non-Human Primates As for monkeys with metabolic syndrome (all male), 12 animals were randomly divided into group, wherein 8 monkeys are administered with conjugate 2 and 4 monkeys are administered with comparative conjugate 1. Each of the siRNA conjugates was dissolved in normal saline for injection to a concentration (based on the amount of siRNA) of 100 mg/ml. The drug dosages for all animals were calculated according to the body weight. A single dose was injected subcutaneously, with the dosage of 9 mg/kg respectively, the injection amount of 0.09 ml/kg and the dose volume of no more than 2 ml for each administration site.

During three weeks before administration, blood was taken weekly from venous, for measuring indicators such as the blood lipid level, liver function, and blood routine. The above-mentioned indicators were re-measured at days 7, 14, 21, 28 and 35 after administration. The results of blood lipid were normalized by a calculation method the same as that in Experimental Example 4-2. The content of blood lipid before administration was the average value of the contents of blood lipid during the 3 weeks before administration, marked as the basic data at day 0 (D0). The inhibitory effect on blood lipid is shown in FIGS. 12A-12B.

Figure 12A:
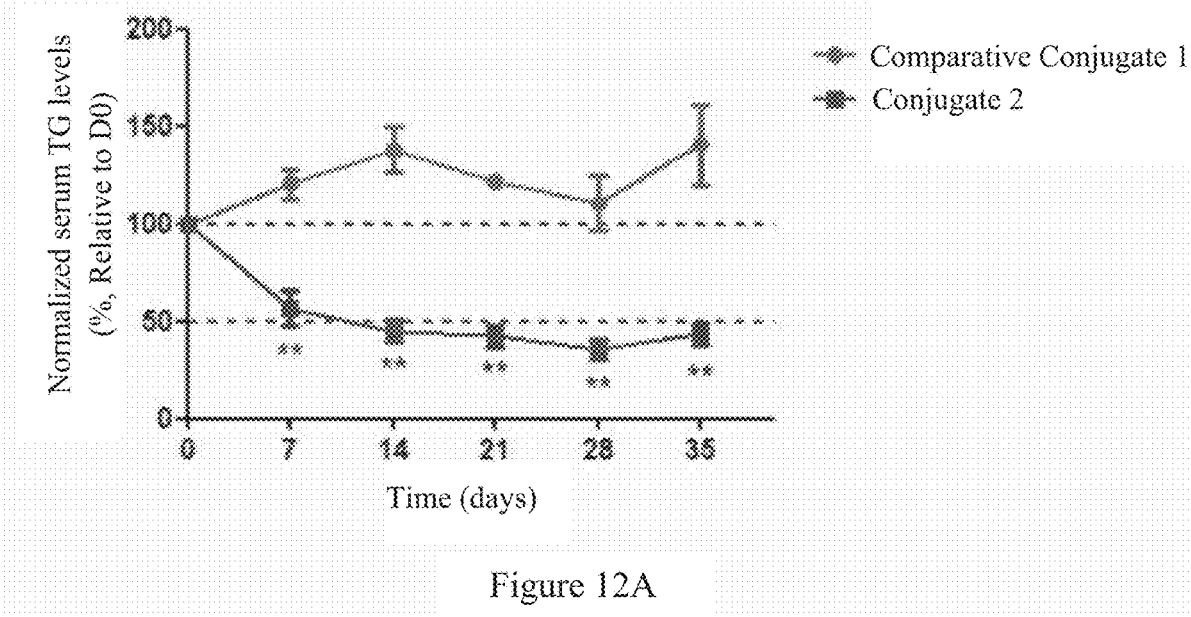
FIGS. 12A and 12B show the time-dependent inhibition effect of conjugate 2 on TG and CHO in serum of a monkey with metabolic syndrome.
Figure 12B:
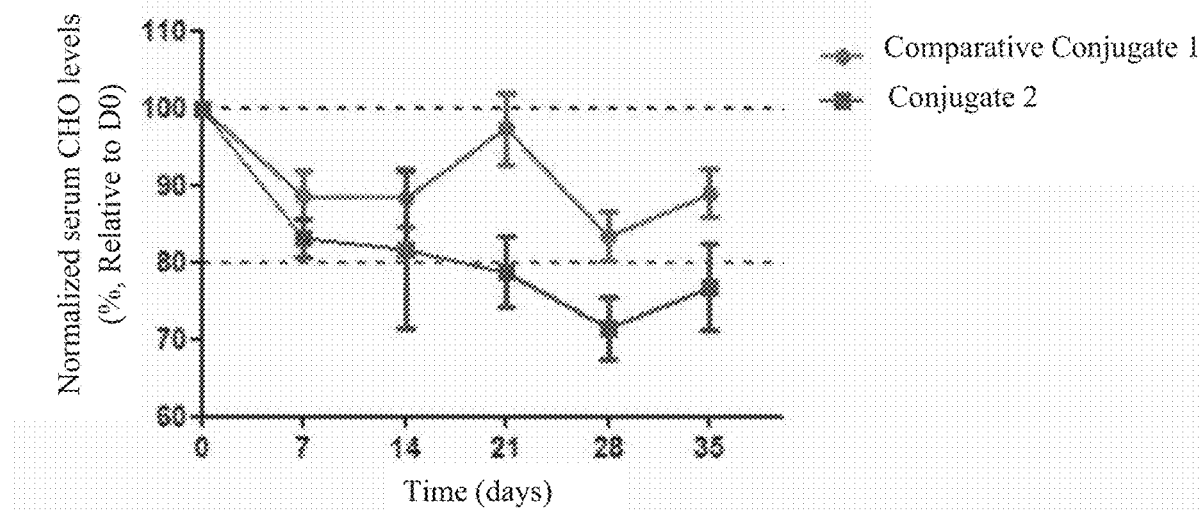

FIGS. 12A-12B show that conjugate 2 exhibits the maximum inhibitory rate against TG of 68% and the maximum inhibitory rate against CHO of 30% at day 28 after administration single dose, as compared the rate before administration.

Figure 12C:
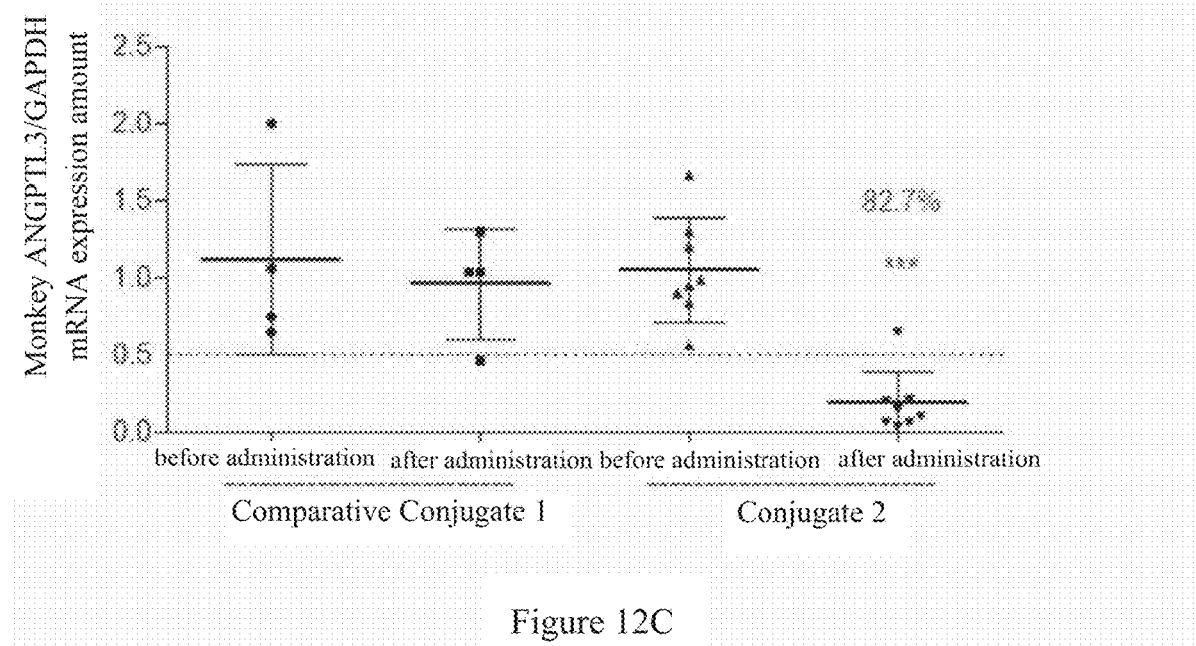
FIG. 12C shows the inhibition effect of conjugate 2 on the expression level of ANGPTL3 mRNA in a monkey with metabolic syndrome.

On the day of administration (marked as before administration) and day 28 after administration (marked as after administration), a liver puncture biopsy was proceeded to measure the expression amount of the ANGPTL3 mRNA in the liver tissue. The real-time fluorescent qPCR was the same as that in Experimental Example 4-1, except that the tested primera were different. The used primers are shown in Table 11. The inhibition rate against ANGPTL3 mRNA is shown in FIG. 12C.

TABLE 11

Sequence of Primers

| Genes | SEQ ID NO | Nucleotide sequence (5'→3') |
|---|---|---|
| Monkey | 61 | CTGGTGGTGGCATGATGAGT |
| ANGPTL3 | 62 | CTCTTCTCCGCTCTGGCTTAG |

TABLE 11-continued

Sequence of Primers

| Genes | SEQ ID NO | Nucleotide sequence (5'→3') |
|---|---|---|
| Monkey | 63 | GGGAGCCAAAAGGGTCATCA |
| GAPDH | 64 | CGTGGACTGTGGTCATGAGT |

FIG. 12C shows that the inhibition rate of conjugate 2 against ANGPTL3 mRNA at day 28 after administration of single dose is up to 83% in comparison with the rate before administration.

Other indicators were tested at all the time points after administration, and no abnormalities were found in terms of blood platelet, glutamic-pyruvic transaminase and glutamic-oxalacetic transaminase. This result indicates that conjugate 2 is relatively safe and shows no significant toxic and side effect.

As can be seen from FIG. 12A-12C, conjugate 2 shows significant effect in reducing blood lipid and inhibiting ANGPTL3 gene expression in non-human primate, and meanwhile shows relative safety.

The above results show that the siRNAs and the conjugates of the present disclosure can effectively reduce the expression amount of ANGPTL3 mRNA in liver, reduce the contents of total cholesterol and triglyceride in blood, can be used to prevent and/or treat dyslipidemia, and thus has good application prospect in clinics.

Some embodiments of the present disclosure are described in detail above, but the present disclosure is not limited to the specific details of the above-described embodiments. Various simple variations to the technical solution of the present disclosure can be made within the scope of the technical concept of the present disclosure, and these simple variations are within the scope of the present disclosure. It is to be noted that each of the specific technical features described in the above embodiments can be combined in any suitable manner as long as no contradiction is caused. In order to avoid unnecessary repetition, the various possible combination manners are no longer described in the present disclosure.

In addition, the various different embodiments of the present disclosure may also be carried out in any combination as long as it does not contravene the idea of the present disclosure, which should also be regarded as the disclosure of the present disclosure.

The invention claimed is:

1. A siRNA, comprising a sense strand and an antisense strand, wherein each nucleotide in the siRNA is independently a modified or unmodified nucleotide, wherein the sense strand comprises a nucleotide sequence I and the antisense strand comprises a nucleotide sequence II, said nucleotide sequence I and said nucleotide sequence II being reverse complementary to form a double-strand region, wherein the nucleotide sequence I comprises a nucleotide sequence represented by SEQ ID NO:3, and the nucleotide sequence II comprises a nucleotide sequence represented by SEQ ID NO:4:

```
                                        (SEQ ID NO: 3)
5'-CCAAGAGCACCAAGAACUZ_A-3';

(SEQ ID NO: 4)
5'-Z'_BAGUUCUUGGUGCUCUUGG-3',
``` wherein, $Z_A$ is selected from A, U, G, or C, and TB is the first nucleotide at the 5' terminal of the antisense strand and complementary to $Z_A$; and the sense strand and antisense strand have the same or different length, wherein the sense strand has a length of 19 to 23 nucleotides, and the antisense strand has a length of 20 to 26 nucleotides;

wherein each nucleotide in the sense strand and the antisense strand is independently a fluoro modified nucleotide or a non-fluoro modified nucleotide;

wherein the fluoro modified nucleotide is present in the nucleotide sequence represented by SEQ ID NO:3 and the nucleotide sequence represented by SEQ ID NO:4; and in a direction from 5' terminal to 3' terminal, nucleotides at positions 7, 8, 9 of the nucleotide sequence represented by SEQ ID NO:3 are fluoro modified nucleotides; and in a direction from 5' terminal to 3' terminal, nucleotides at positions 2, 6, 14 and 16 of the nucleotide sequence represented by SEQ ID NO:4 are fluoro modified nucleotides.

2. The siRNA according to claim 1, wherein the nucleotide sequence I further comprises nucleotide sequence III, the nucleotide sequence II further comprises nucleotide sequence IV, and the nucleotide sequence III and the nucleotide sequence IV each independently have a length of 1 to 4 nucleotides; the nucleotide sequence III is linked to the 5' terminal of the nucleotide sequence represented by SEQ ID NO:3, the nucleotide sequence IV is linked to the 3' terminal of the nucleotide sequence represented by SEQ ID NO:4, and the nucleotide sequence III and the nucleotide sequence IV have the same length and are reverse complementary.

3. The siRNA according to claim 2, wherein the nucleotide sequence III and the nucleotide sequence IV both have a length of one nucleotide, and the nucleotide sequence III has a base of G;

or the nucleotide sequence III and the nucleotide sequence IV both have a length of 2 nucleotides, and in the direction from 5' terminal to 3' terminal, the nucleotide sequence III has a base composition of AG;

or, the nucleotide sequence III and the nucleotide sequence IV both have a length of 3 nucleotides, and in the direction from 5' terminal to 3' terminal, the nucleotide sequence III has a base composition of AAG;

or, the nucleotide sequence III and the nucleotide sequence IV both have a length of 4 nucleotides, and in the direction from 5' terminal to 3' terminal, the nucleotide sequence III has a base composition of CAAG.

4. The siRNA according to claim 1, wherein the nucleotide sequence II further comprises a nucleotide sequence V; the nucleotide sequence V has a length of 1 to 3 nucleotides, and is linked to the 3'terminal of the antisense strand, thereby forming a 3' overhang terminal of the antisense strand.

5. The siRNA according to claim 4, wherein, the nucleotide sequence V has a length 2 nucleotides; moreover the nucleotide sequence V is 2 continuous thymine deoxyribonucleotides or 2 continuous uridine ribonucleotides, or the nucleotide sequence V is complementary to the nucleotides at the corresponding positions of the target mRNA.

6. The siRNA according to claim 1, wherein the sense strand of the siRNA comprises the nucleotide sequence represented by SEQ ID NO:3, and the antisense strand comprises the nucleotide sequence represented by SEQ ID NO:5:

```
                                        (SEQ ID NO: 3)
5'-CCAAGAGCACCAAGAACUZ_A-3';

(SEQ ID NO: 5)
5'-Z'_BAGUUCUUGGUGCUCUUGGCU-3';
``` or, the sense strand of siRNA comprises the nucleotide sequence represented by SEQ ID NO:6, and the antisense strand comprises the nucleotide sequence represented by SEQ ID NO:7:

```
                                        (SEQ ID NO: 6)
5'-AGCCAAGAGCACCAAGAACUZ_A-3';

(SEQ ID NO: 7)
5'-Z'_BAGUUCUUGGUGCUCUUGGCUUG-3';
``` wherein, $Z'_B$ is the first nucleotide at the 5'terminal of the antisense strand, $Z_A$ is selected from A, U, G or C, and $Z'_B$ is a nucleotide complementary to $Z_A$.

7. The siRNA according to claim 1, wherein the siRNA is siAN1 or siAN2:

```
siAN1
Sense strand:
                                        (SEQ ID NO: 8)
5'-CCAAGAGCACCAAGAACUA-3'

Antisense strand:
                                        (SEQ ID NO: 9)
5'-UAGUUCUUGGUGCUCUUGGCU-3' siAN2
Sense strand:
                                        (SEQ ID NO: 10)
5'-AGCCAAGAGCACCAAGAACUA-3'

Antisense strand:
                                        (SEQ ID NO: 11)
5'-UAGUUCUUGGUGCUCUUGGCUUG-3'.
```

8. The siRNA according to claim 1, wherein each non-fluoro modified nucleotide is a methoxy modified nucleotide, and the methoxy modified nucleotide refers to a nucleotide formed by replacing 2'-hydroxy of the ribose group with a methoxy group.

9. The siRNA according to claim 8, wherein in the direction from 5' terminal to 3' terminal, the nucleotides at positions 5, 7, 8 and 9 of the nucleotide sequence represented by SEQ ID NO:3 in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 8, 9, 14 and 16 of the nucleotide sequence represented by SEQ ID NO:4 in the sense strand of the siRNA are fluoro modified nucleotides, and the nucleotides at the other positions in the sense strand of siRNA are methoxy modified nucleotides;

or, in the direction from 5' terminal to 3' terminal, the nucleotides at positions 5, 7, 8 and 9 of the nucleotide sequence represented by SEQ ID NO:3 in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 14 and 16 in the nucleotide sequence represented by SEQ ID NO:4 in the antisense strand of the siRNA are fluoro modified nucleotides, and the nucleotides at the other positions in the antisense strand of the siRNA are methoxy modified nucleotides;

or, in the direction from 5' terminal to 3' terminal, the nucleotides at positions 7, 8 and 9 of the nucleotide sequence represented by SEQ ID NO:3 in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 14 and 16 of the nucleotide sequence represented by SEQ ID NO:4 in the antisense strand of the siRNA are fluoro modified nucleotides, and the nucleotides at the other positions in the antisense strand of the siRNA are methoxy modified nucleotides.

10. The siRNA according to claim 1, wherein the siRNA is any one of siAN1-M1, siAN2-M1, siAN1-M2, siAN2-M2, siAN1-M3, and siAN2-M3:

```
siAN1-M1
sense strand:
                                       (SEQ ID NO: 12)
5'-CmCmAmAmGfAmGfCfAfCmCmAmAmGmAmAmCmUmAm-3' antisense strand:
                                       (SEQ ID NO: 13)
5'-UmAfGmUmUmCfUmUfGfGmUmGmCmUfCmUfUmGmGmCmUm-3' siAN2-M1
sense strand:
                                       (SEQ ID NO: 14)
5'-AmGmCmCmAmAmGfAmGfCfAfCmCmAmAmGmAmAmCmUmAm-3' antisense strand:
                                       (SEQ ID NO: 15)
5'-UmAfGmUmUmCfUmUfGfGmUmGmCmUfCmUfUmGmGmCmUmUm
Gm-3' siAN1-M2
sense strand:
                                       (SEQ ID NO: 12)
5'-CmCmAmAmGfAmGfCfAfCmCmAmAmGmAmAmCmUmAm-3' antisense strand:
                                       (SEQ ID NO: 16)
5'-UmAfGmUmUmCfUmUmGmGmUmGmCmUfCmUfUmGmGmCmUm-3' siAN2-M2
sense strand:
                                       (SEQ ID NO: 14)
5'-AmGmCmCmAmAmGfAmGfCfAfCmCmAmAmGmAmAmCmUmAm-3' antisense strand:
                                       (SEQ ID NO: 17)
5'-UmAfGmUmUmCfUmUmGmGmUmGmCmUfCmUfUmGmGmCmUmUm
Gm-3' siAN1-M3
sense strand:
                                       (SEQ ID NO: 18)
5'-CmCmAmAmGmAmGfCfAfCmCmAmAmGmAmAmCmUmAm-3' antisense strand:
                                       (SEQ ID NO: 16)
5'-UmAfGmUmUmCfUmUmGmGmUmGmCmUfCmUfUmGmGmCmUm-3' siAN2-M3
sense strand:
                                       (SEQ ID NO: 19)
5'-AmGmCmCmAmAmGmAmGfCfAfCmCmAmAmGmAmAmCmUmAm-3' antisense strand:
                                       (SEQ ID NO: 17)
5'-UmAfGmUmUmCfUmUmGmGmUmGmCmUfCmUfUmGmGmCmUmUm
Gm-3',
``` wherein C, G, U, and A represent the base composition of the nucleotides; m represents that the nucleotide adjacent to the left side of the letter m is a methoxy modified nucleotide; and f represents that the nucleotide adjacent to the left side of the letter f is a fluoro modified nucleotide.

11. The siRNA according to claim 1, wherein in the siRNA, at least one phosphate group is a phosphorothioate group, and the phosphorothioate linkage is present at least one of the following positions:

the position between the first and second nucleotides at 5' terminal of the sense strand;

the position between the second and third nucleotides at 5' terminal of the sense strand;

the position between the first and second nucleotides at 3' terminal of the sense strand;

the position between the second and third nucleotides at 3' terminal of the sense strand;

the position between the first and second nucleotides at 5' terminal of the antisense strand;

the position between the second and third nucleotides at 5' terminal of the antisense strand;

the position between the first and second nucleotides at 3' terminal of the antisense strand; and the position between the second and third nucleotides at 3' terminal of the antisense strand.

12. The siRNA according to claim 1, wherein the siRNA is any one of siAN1-M1S, siAN2-M1S, siAN1-M2S, siAN2-M2S, siAN1-M3S, and siAN2-M3S:

```
siAN1-M1S
sense strand:
                                       (SEQ ID NO: 20)
5'-CmsCmsAmAmGfAmGfCfAfCmCmAmAmGmAmAmCmUmAm-3' antisense strand:
                                       (SEQ ID NO: 21)
5'-UmsAfsGmUmUmCfUmUfGfGmUmGmCmUfCmUfUmGmGmsCms
Um-3' siAN2-M1S
sense strand:
                                       (SEQ ID NO: 22)
5'-AmsGmsCmCmAmAmGfAmGfCfAfCmCmAmAmGmAmAmCmUm
Am-3'
```

```
anti sense strand:
                                      (SEQ ID NO: 23)
5'-UmsAfsGmUmUmCfUmUfGfGmUmGmCmUfCmUfUmGmGmCmUms UmsGm-3' siAN1-M2S
sense strand:
                                      (SEQ ID NO: 20)
5'-CmsCmsAmAmGfAmGfCfAfCmCmAmAmGmAmAmCmUmAm-3' antisense strand:
                                      (SEQ ID NO: 24)
5'-UmsAfsGmUmUmCfUmUmGmGmUmGmCmUfCmUfUmGmGmsCms Um-3' siAN2-M2S
sense strand:
                                      (SEQ ID NO: 22)
5'-AmsGmsCmCmAmAmGfAmGfCfAfCmCmAmAmGmAmAmCmUm Am-3' antisense strand:
                                      (SEQ ID NO: 25)
5'-UmsAfsGmUmUmCfUmUmGmGmUmGmCmUfCmUfUmGmGmCmUms UmsGm-3' siAN1-M3S
sense strand:
                                      (SEQ ID NO: 26)
5'-CmsCmsAmAmGmAmGfCfAfCmCmAmAmGmAmAmCmUmAm-3' antisense strand:
                                      (SEQ ID NO: 24)
5'-UmsAfsGmUmUmCfUmUmGmGmUmGmCmUfCmUfUmGmGmsCms Um-3' siAN2-M3S
sense strand:
                                      (SEQ ID NO: 27)
5'-AmsGmsCmCmAmAmGmAmGfCfAfCmCmAmAmGmAmAmCmUm Am-3' antisense strand:
                                      (SEQ ID NO: 25)
5'-UmsAfsGmUmUmCfUmUmGmGmUmGmCmUfCmUfUmGmGmCmUms UmsGm-3',
``` wherein C, G, U, and A represent the base composition of the nucleotides; m represents that the nucleotide adjacent to the left side of the letter m is a methoxy modified nucleotide; f represents that the nucleotide adjacent to the left side of the letter f is a fluoro modified nucleotide; and s represents that a phosphorothioate linkage is present between the two nucleotides adjacent to both sides of the letter s.

13. The siRNA according to claim 1, wherein the nucleotide at 5' terminal of the antisense strand is a 5'-phosphate nucleotide or a 5'-phosphate analogue modified nucleotide; or wherein the 5'-phosphate nucleotide is a nucleotide having the structure represented by Formula (2), and the 5'-phosphate analogue modified nucleotide is a nucleotide having the structure represented by any of formulae (3)-(6):

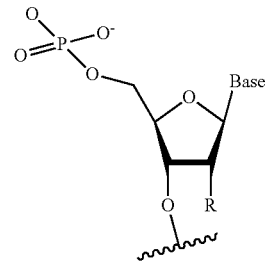

Formula (2)

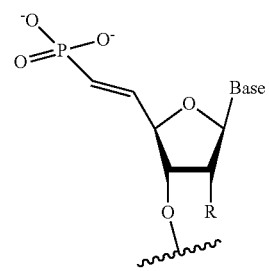

Formula (3)

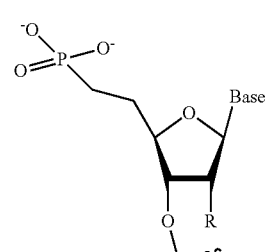

Formula (4)

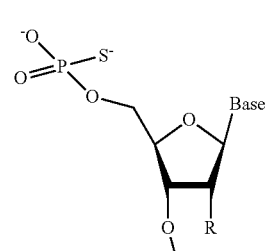

Formula (5)

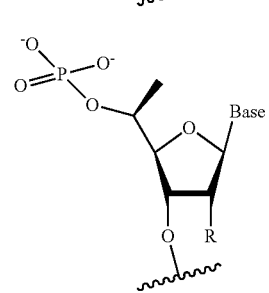

Formula (6)

wherein R is selected from H, OH, methoxy, or F; "Base" represents a base selected from A, U, C, G, or T.

14. The siRNA according to claim 1, wherein the siRNA is any one of siAN1-M1P1, siAN2-M1P1, siAN1-M2P1, siAN2-M2P1, siAN1-M3P1, siAN2-M3P1, siAN1-M1SP1, siAN2-M1SP1, siAN1-M2SP1, siAN2-M2SP1, siAN1-M3SP1, and siAN2-M3 SP1:

siAN1-M1P1
sense strand:
(SEQ ID NO: 12)
5'-CmCmAmAmGfAmGfCfAfCmCmAmAmGmAmAmCmUmAm-3' antisense strand:
(SEQ ID NO: 28)
5'-P1-UmAfGmUmUmCfUmUfGfGmUmGmCmUfCmUfUmGmGmCm
Um-3' siAN2-M1P1
sense strand:
(SEQ ID NO: 14)
5'-AmGmCmCmAmAmGfAmGfCfAfCmCmAmAmGmAmAmCmUmAm-3' antisense strand:
(SEQ ID NO: 29)
5'-P1-UmAfGmUmUmCfUmUfGfGmUmGmCmUfCmUfUmGmGmCmUmUm
Gm-3' siAN1-M2P1
sense strand:
(SEQ ID NO: 12)
5'-CmCmAmAmGfAmGfCfAfCmCmAmAmGmAmAmCmUmAm-3' antisense strand:
(SEQ ID NO: 30)
5'-P1-UmAfGmUmUmCfUmUmGmGmUmGmCmUfCmUfUmGmGmCm
Um-3' siAN2-M2P1
sense strand:
(SEQ ID NO: 14)
5'-AmGmCmCmAmAmGfAmGfCfAfCmCmAmAmGmAmAmCmUmAm-3' antisense strand:
(SEQ ID NO: 31)
5'-P1-UmAfGmUmUmCfUmUmGmGmUmGmCmUfCmUfUmGmGmCmUmUm
Gm-3' siAN1-M3P1
sense strand:
(SEQ ID NO: 18)
5'-CmCmAmAmGmAmGfCfAfCmCmAmAmGmAmAmCmUmAm-3' antisense strand:
(SEQ ID NO: 30)
5'-P1-UmAfGmUmUmCfUmUmGmGmUmGmCmUfCmUfUmGmGmCm
Um-3' siAN2-M3P1
sense strand:
(SEQ ID NO: 19)
5'-AmGmCmCmAmAmGmAmGfCfAfCmCmAmAmGmAmAmCmUmAm-3' antisense strand:
(SEQ ID NO: 31)
5'-P1-UmAfGmUmUmCfUmUmGmGmUmGmCmUfCmUfUmGmGmCmUmUm
Gm-3' siAN1-M1SP1
sense strand:
(SEQ ID NO: 20)
5'-CmsCmsAmAmGfAmGfCfAfCmCmAmAmGmAmAmCmUmAm-3' antisense strand:
(SEQ ID NO: 32)
5'-P1-UmsAfsGmUmUmCfUmUfGfGmUmGmCmUfCmUfUmGmGmsCms
Um-3' siAN2-M1SP1
sense strand:
(SEQ ID NO: 22)
5'-AmsGmsCmCmAmAmGfAmGfCfAfCmCmAmAmGmAmAmCmUmAm-3' antisense strand:
(SEQ ID NO: 33)
5'-P1-UmsAfsGmUmUmCfUmUfGfGmUmGmCmUfCmUfUmGmGmCm
UmsUmsGm-3' siAN1-M2SP1
sense strand:
(SEQ ID NO: 20)
5'-CmsCmsAmAmGfAmGfCfAfCmCmAmAmGmAmAmCmUmAm-3' antisense strand:
(SEQ ID NO: 34)
5'-P1-UmsAfsGmUmUmCfUmUmGmGmUmGmCmUfCmUfUmGmGmsCms
Um-3' siAN2-M2SP1
sense strand:
(SEQ ID NO: 22)
5'-AmsGmsCmCmAmAmGfAmGfCfAfCmCmAmAmGmAmAmCmUmAm-3' antisense strand:
(SEQ ID NO: 35)
5'-P1-UmsAfsGmUmUmCfUmUmGmGmUmGmCmUfCmUfUmGmGmCmUm
sUmsGm-3' siAN1-M3SP1
sense strand:
(SEQ ID NO: 26)
5'-CmsCmsAmAmGmAmGfCfAfCmCmAmAmGmAmAmCmUmAm-3' antisense strand:
(SEQ ID NO: 34)
5'-P1-UmsAfsGmUmUmCfUmUmGmGmUmGmCmUfCmUfUmGmGmsCms
Um-3' siAN2-M3SP1
sense strand:
(SEQ ID NO: 27)
5'-AmsGmsCmCmAmAmGmAmGfCfAfCmCmAmAmGmAmAmCmUmAm-3' antisense strand:
(SEQ ID NO: 35)
5'-P1-UmsAfsGmUmUmCfUmUmGmGmUmGmCmUfCmUfUmGmGmCm
UmsUmsGm-3' wherein C, G, U, and A represent the base composition of the nucleotides; m represents that the nucleotide adjacent to the left side of the letter m is a methoxy modified nucleotide; f represents that the nucleotide adjacent to the left side of the letter f is a fluoro modified nucleotide; s represents that a phosphorothioate linkage is present between the two nucleotides adjacent to both sides of the letter s; and P1 represents that the nucleotide adjacent to the right side of P1 is a 5'-phosphate nucleotide or a 5'-phosphate analogue modified nucleotide.

15. A pharmaceutical composition, wherein the pharmaceutical composition comprises the siRNA according to claim 1 and a pharmaceutically acceptable carrier; wherein the weight ratio of the siRNA and the pharmaceutically acceptable carrier is 1: (1-500).

16. A siRNA conjugate comprising the siRNA according to claim 1 and a conjugating group conjugated to the siRNA.

17. The siRNA conjugate according to claim 16, wherein the conjugate has the structure represented by Formula (308):

Formula (308)

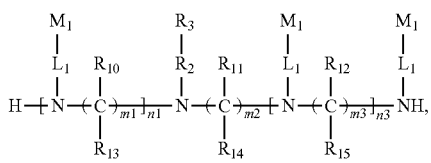

wherein, n1 is an integer of 1-3, and n3 is an integer of 0-4;

each of m1, m2, and m3 is independently an integer of 2-10;

each of $R_{10}$, $R_{11}$, $R_{12}$, $R_{13}$, $R_{14}$ and $R_{15}$ is independently H, or selected from the group consisting of $C_1$-$C_{10}$ alkyl, $C_1$-$C_{10}$ haloalkyl, and $C_1$-$C_{10}$ alkoxy;

$R_3$ is a group having the structure represented by Formula A59:

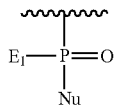

(A59)

wherein $E_1$ is OH, SH or $BH_2$, and Nu is siRNA;

$R_2$ is a linear alkylene of 1 to 20 carbon atoms in length, wherein one or more carbon atoms are optionally replaced with one or more groups selected from the group consisting of: C(O), NH, O, S, CH=N, $S(O)_2$, $C_2$-$C_{10}$ alkeylene, $C_2$-$C_{10}$ alkynylene, $C_6$-$C_{10}$ arylene, $C_3$-Cis heterocyclylene, and $C_5$-$C_{10}$ heteroarylene, and wherein $R_2$ is optionally substituted by any one or more groups selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, —S$C_1$-$C_{10}$ haloalkyl, halo, —OH, —SH, —$NH_2$, —$C_1$-$C_{10}$ alkyl-$NH_2$, —N($C_1$-$C_{10}$ alkyl)($C_1$-$C_{10}$ alkyl), —NH($C_1$-$C_{10}$ alkyl), cyano, nitro, —$CO_2H$, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2$NH($C_1$-$C_{10}$ alkyl), —$SO_2$NH(phenyl), —$NHSO_2$($C_1$-$C_{10}$ alkyl), —$NHSO_2$(phenyl), and —$NHSO_2$($C_1$-$C_{10}$ haloalkyl);

each $L_1$ is a linear alkylene of 1 to 70 carbon atoms in length, wherein one or more carbon atoms are optionally replaced with one or more groups selected from the group consisting of: C(O), NH, O, S, CH=N, $S(O)_2$, $C_2$-$C_{10}$ alkeylene, $C_2$-$C_{10}$ alkynylene, $C_6$-$C_{10}$ arylene, $C_3$-Cis heterocyclylene, and $C_5$-$C_{10}$ heteroarylene; and wherein $L_1$ is optionally substituted by any one or more groups selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, —S$C_1$-$C_{10}$ haloalkyl, halo, —OH, —SH, —$NH_2$, —$C_1$-$C_{10}$ alkyl-$NH_2$, —N($C_1$-$C_{10}$ alkyl)($C_1$-$C_{10}$ alkyl), —NH($C_1$-$C_{10}$ alkyl), cyano, nitro, —$CO_2H$, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2$NH($C_1$-$C_{10}$ alkyl), —$SO_2$NH(phenyl), —$NHSO_2$($C_1$-$C_{10}$ alkyl), —$NHSO_2$(phenyl), and —$NHSO_2$($C_1$-$C_{10}$ haloalkyl);

∿∿∿ represents a site where a group is attached to the rest of the molecule; and M1 represents a targeting group.

18. The siRNA conjugate according to claim 17, wherein each $L_1$ is independently selected from connection combinations of one or more of the groups having Formulae A1-A26:

(A1)

(A2)

(A3)

(A4)

(A5)

(A6)

(A7)

(A8)

(A9)

(A10)

(A11) 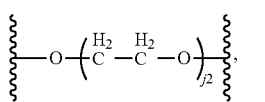
(A12) 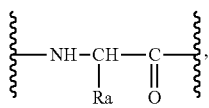
(A13) 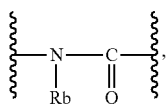
(A14) 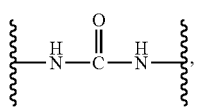
(A15) 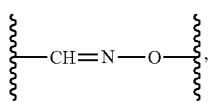
(A16) 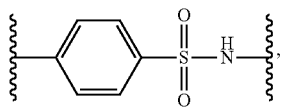
(A17) 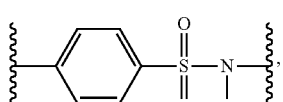
(A18) 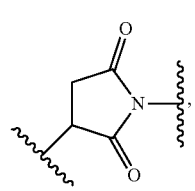
(A19) 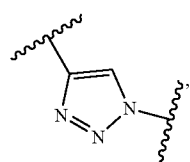
(A20) 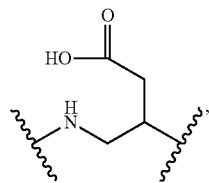
(A21) 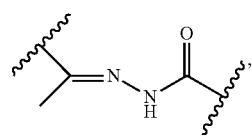
(A22) 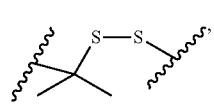
(A23) 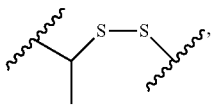
(A24) 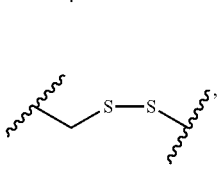
(A25) 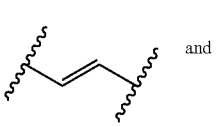
and
(A26) 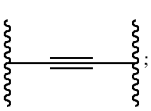
wherein, j1 is an integer of 1-20; j2 is an integer of 1-20; R' is a $C_1$-$C_{10}$ alkyl;
Ra is selected from the group consisting of Formulae A27-A45 and any combination thereof:
(A27) 
(A28) 
(A29) 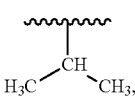
(A30) 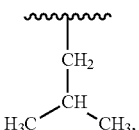
(A31) 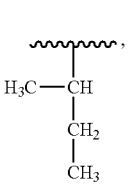
(A32) 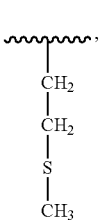

-continued (A33) 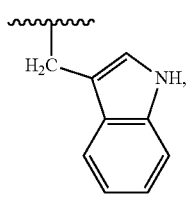

(A34) 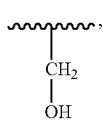

(A35) 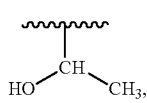

(A36) 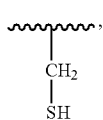

(A37) 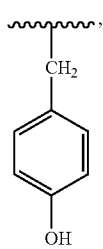

(A38) 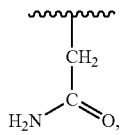

(A39) 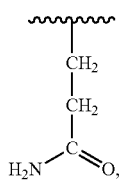

(A40) 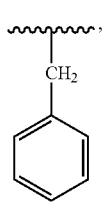

(A41) 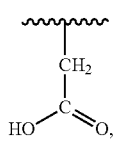

-continued (A42) 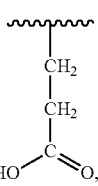

(A43) 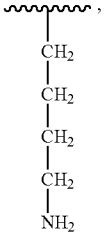

(A44) 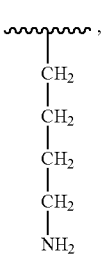 or (A45) 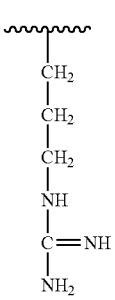

Rb is a $C_1$-$C_{10}$ alkyl.

19. The siRNA conjugate according to claim 18, wherein $L_1$ is selected from connection combinations of one or more of A1, A4, A5, A6, A8, A10, A11, A13; or $L_1$ is selected from connection combinations of at least two of A1, A4, A8, A10, and A11.

20. The siRNA conjugate according to claim 17, wherein $L_1$ is 3 to 25 atoms in length; or $L_1$ is further 4 to 15 atoms in length.

21. The siRNA conjugate according to claim 17, wherein m1, m2 and m3 are each independently an integer of 2-5; or wherein m1=m2=m3.

22. The siRNA conjugate according to claim 17, wherein each of the targeting groups is independently a ligand having affinity to asialoglycoprotein receptors on the surface of mammalian hepatocytes; or each of the targeting group is independently selected from the group consisting of D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, β-D-mannopyranose, α-D-glucopyranose, β-D-glucopyranose, α-D-glucofuranose, β-D-glucofuranose, α-D-fructofuranose, α-D-fructopyranose, α-D-galactopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-n-butyrylgalactosamine, N-isobutyrylgalactosamine, 2-amino-3-O-[(R)-1-carboxyethyl]-2-deoxy-β-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-α-neuraminic acid, 5-thio-β-D-glucopyranose, methyl 2,3,4-tris-O-acetyl-1-thio-6-O-trityl-α-D-glucopyranoside, 4-thio-β-D-galactopyranose, ethyl 3,4,6,7-tetra-O-acetyl-2-deoxy-1,5-dithio-α-D-glucoheptopyranoside, 2,5-anhydro-D-allononitrile, ribose, D-ribose, D-4-thioribose, L-ribose, and L-4-thioribose.

23. The siRNA conjugate according to claim 17, wherein $R_2$ comprises both a site linking to the N atom on the nitrogenous backbone and a site linking to the P atom in $R_3$; and in $R_2$, the site linking to the N atom on the nitrogenous backbone forms an amide bond with the N atom, and the site linking to the P in $R_3$ forms a phosphoester bond with the P; or wherein $R_2$ is selected from B5, B6, B5' or B6':

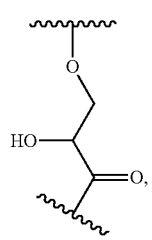

(B5)

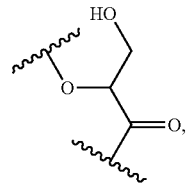

(B5')

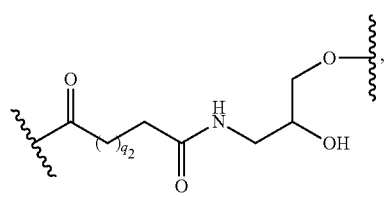

(B6)

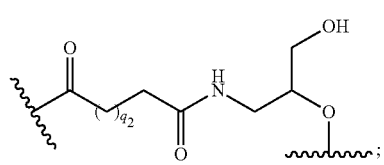

(B6')

wherein ～～ represents the site where a group is covalently linked, and $q_2$ is an integer of 1-10.

24. The siRNA conjugate according to claim 17, wherein the P atom in the Formula A59 is linked to 3' terminal of the sense strand of the siRNA.

25. The siRNA conjugate according to claim 16, wherein the conjugate has the structure represented by Formula (403), (404), (405), (406), (407), (408), (409), (410), (411), (412), (413), (414), (415), (416), (417), (418), (419), (420), (421) or (422):

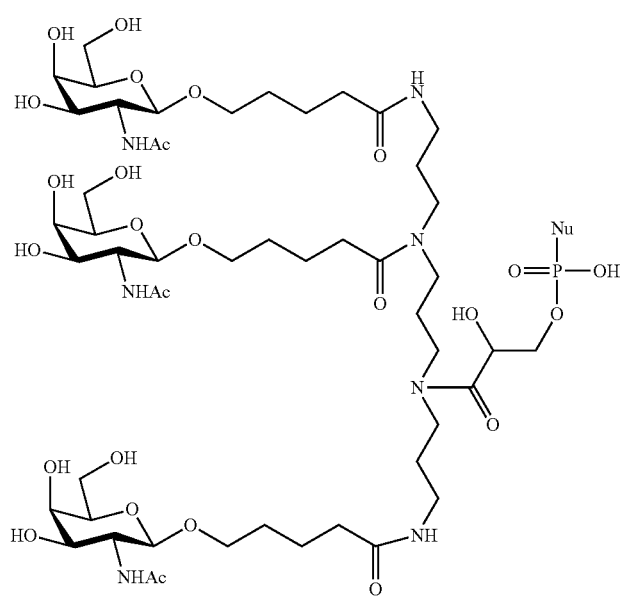

Formula (403)

-continued
Formula (404)
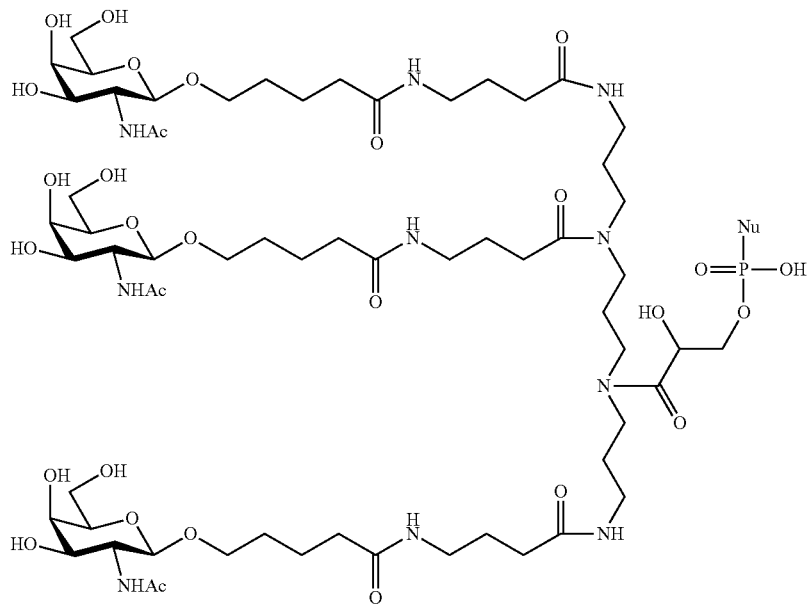
Formula (405)
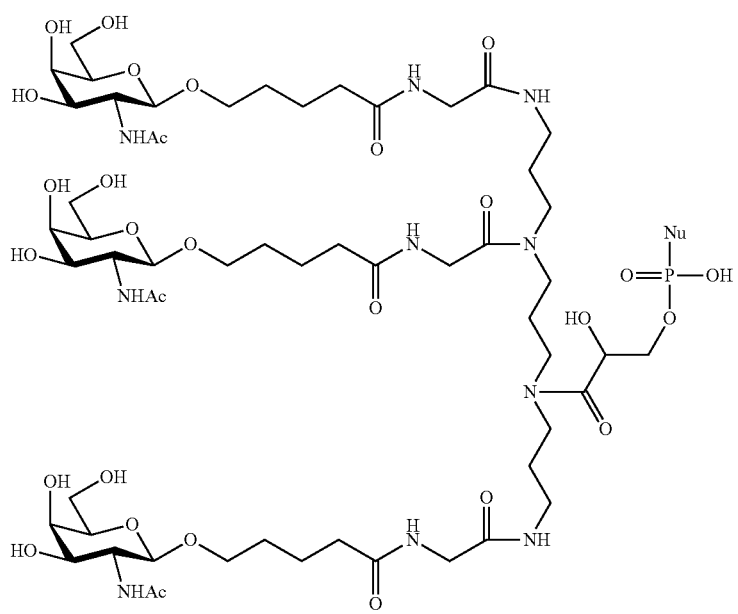

Formula (406)
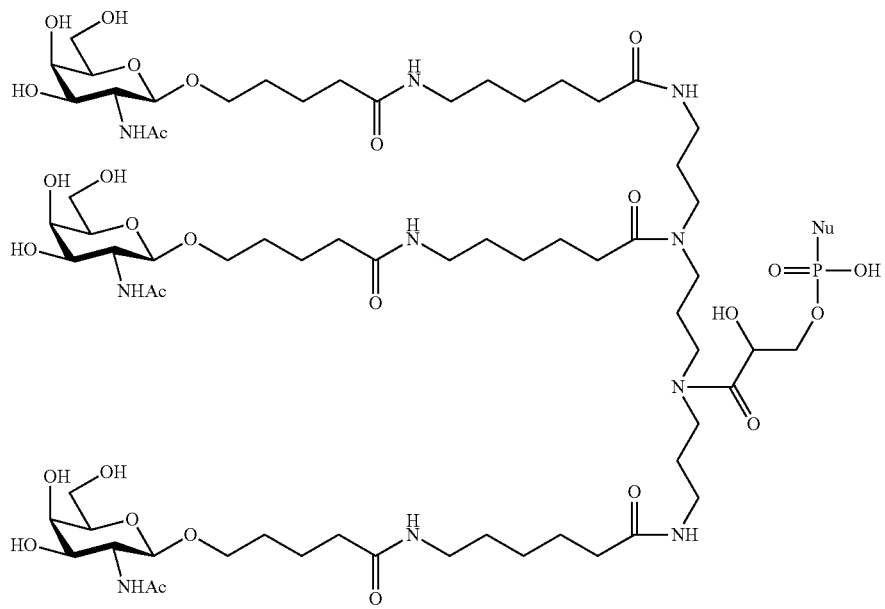
Formula (407)
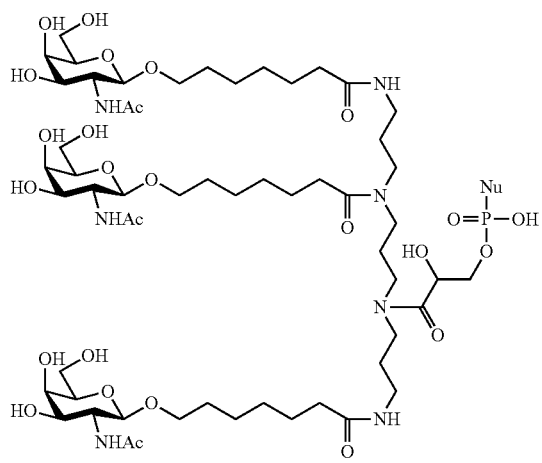
Formula (408)
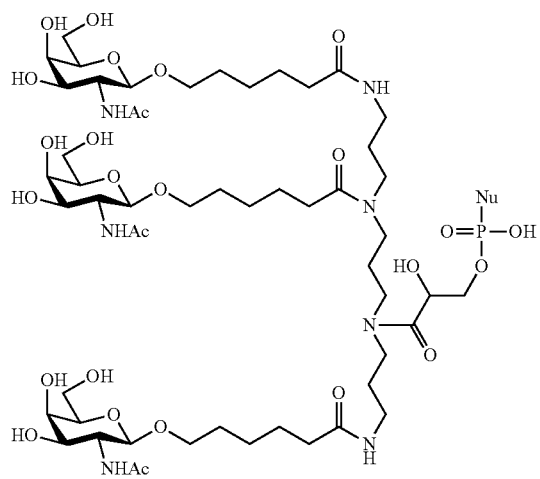
Formula (409)
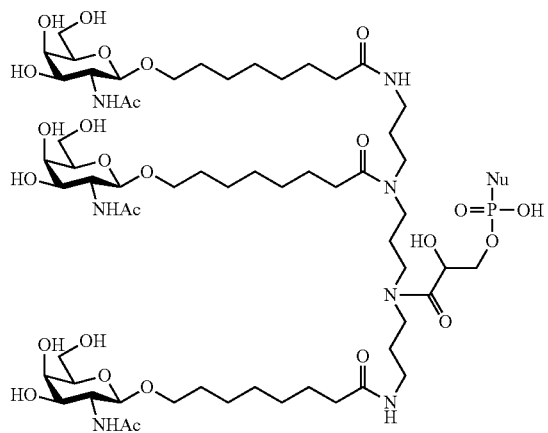
Formula (410)
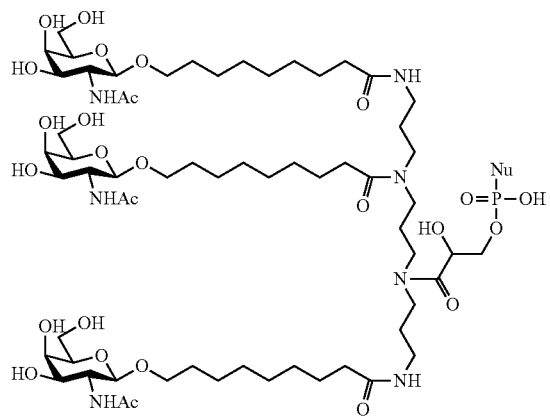

Formula (411)
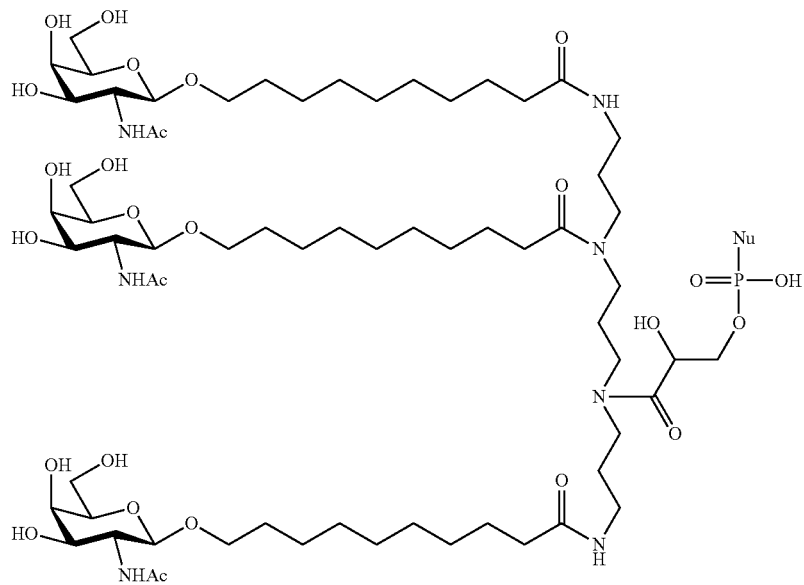
Formula (412)
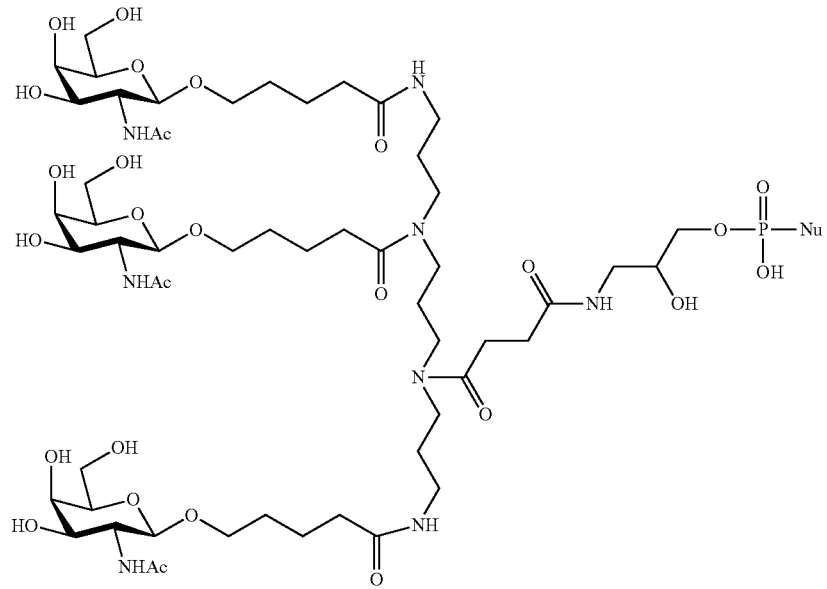

Formula (413)
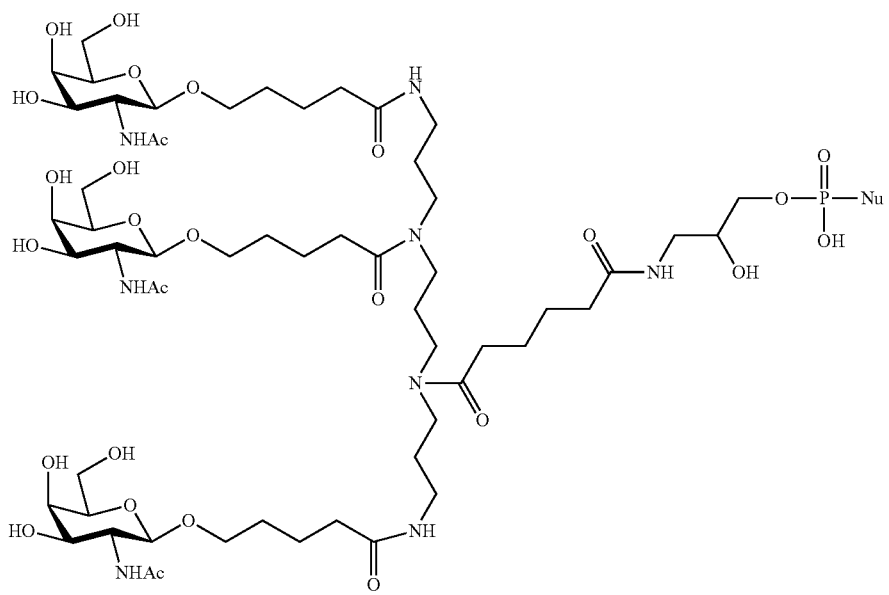
Formula (414)
Formula (415)
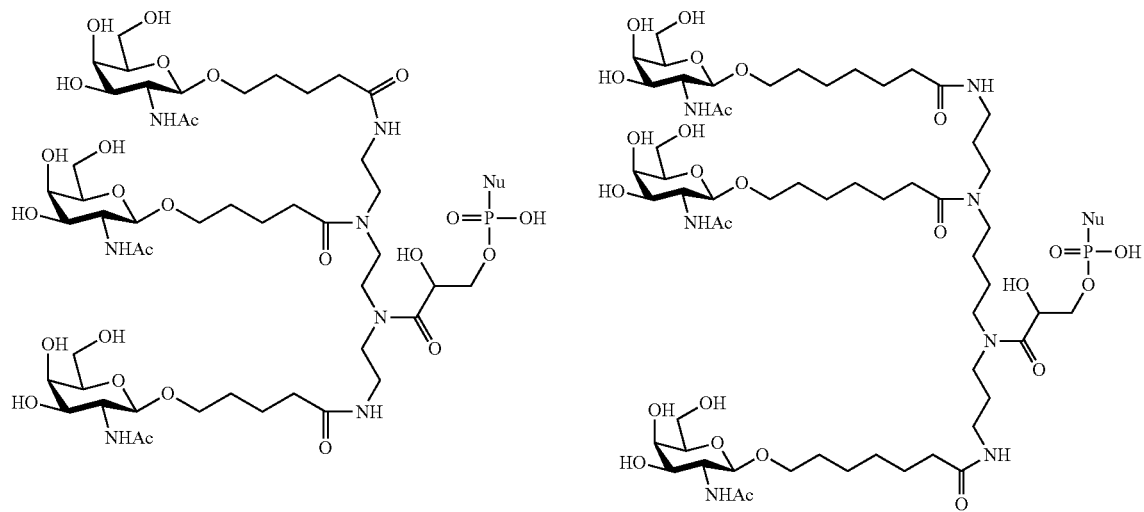

-continued
Formula (416)
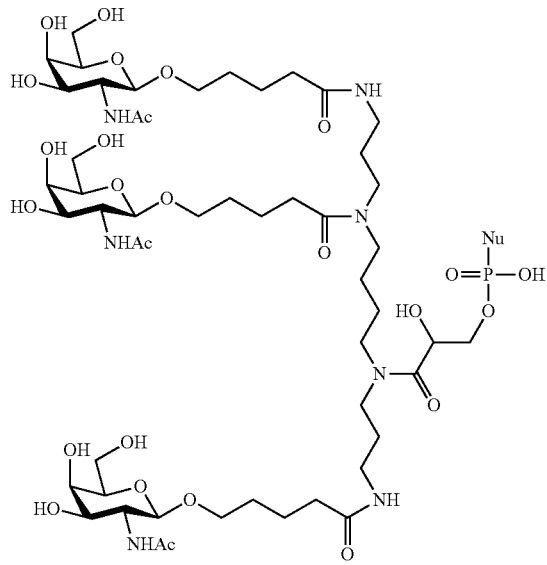
Formula (417)
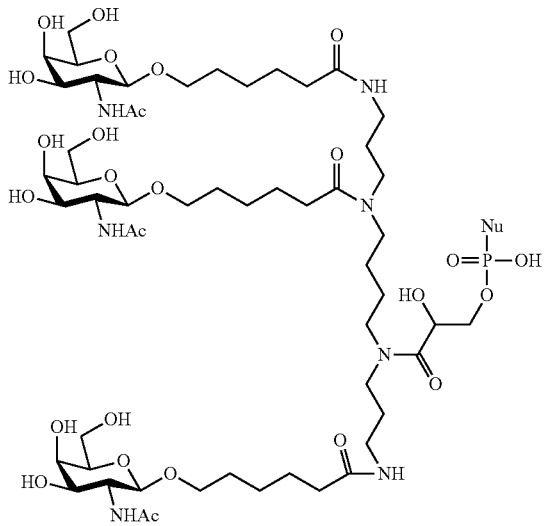
Formula (418)
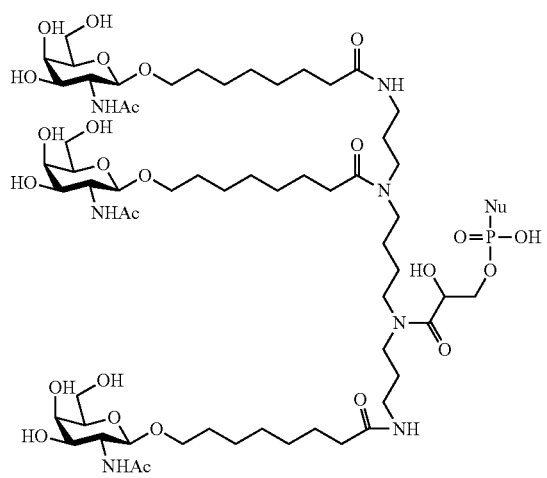
Formula (419)
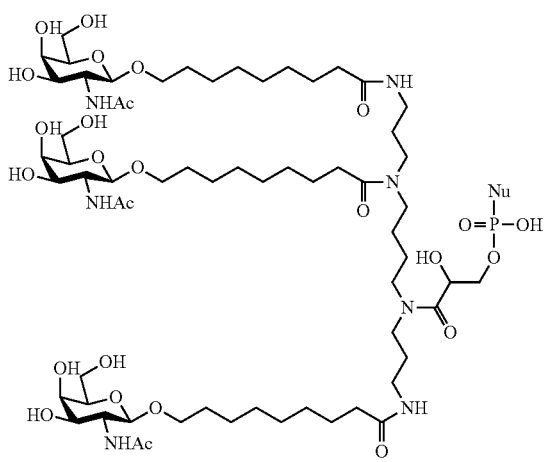
Formula (420)
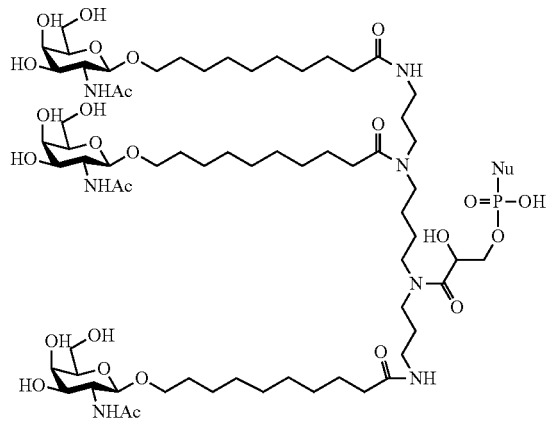
Formula (421)
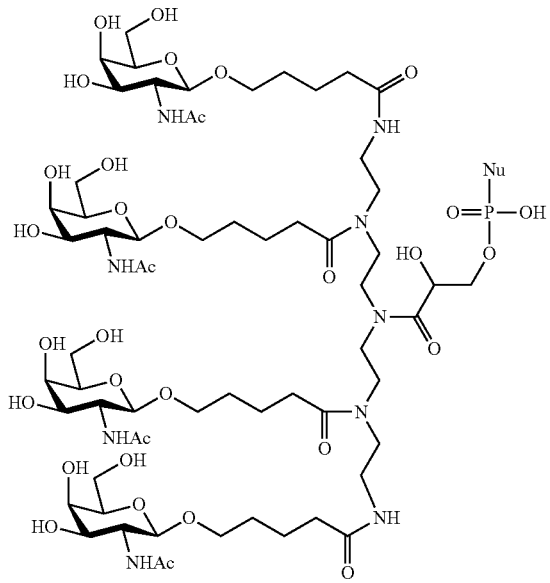

Formula (422)

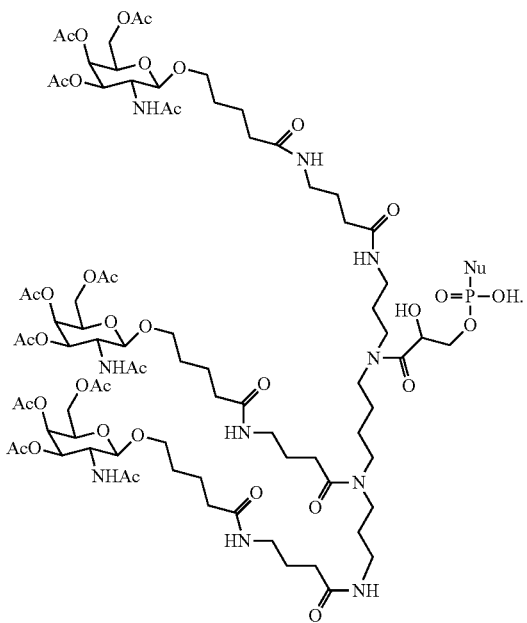

26. A method for treating dyslipidemia, wherein the method comprises administering an effective amount of the siRNA according to claim 1, and/or a siRNA conjugate to a subject suffering from dyslipidemia, wherein the siRNA conjugate comprises the siRNA according to claim 1 and a conjugating group conjugated to the siRNA.

27. The method of claim 26, wherein the dyslipidemia is hypercholesteremia, hypertriglyceridemia or atherosclerosis.

28. A method for inhibiting the expression of ANGPTL3 gene in hepatocytes, comprising contacting an effective amount of the siRNA according to claim 1 and/or a siRNA conjugate with the hepatocytes, wherein the siRNA conjugate comprises the siRNA according to claim 1 and a conjugating group conjugated to the siRNA.

* * * * *